(12) United States Patent
Behrens et al.

(10) Patent No.: US 8,178,109 B2
(45) Date of Patent: May 15, 2012

(54) COMPOSITIONS AND METHODS OF USE FOR MGD-CSF IN DISEASE TREATMENT

(75) Inventors: Dirk Behrens, San Francisco, CA (US); Elizabeth Bosch, San Francisco, CA (US); Stephen K. Doberstein, San Francisco, CA (US); Robert Forgan Halenbeck, San Francisco, CA (US); Kevin Hestir, San Francisco, CA (US); Min Mei Huang, San Francisco, CA (US); Ernestine Lee, San Francisco, CA (US); Haishan Lin, San Francisco, CA (US); Thomas Linnemann, San Francisco, CA (US); Shannon Marshall, San Francisco, CA (US); Justin G. P. Wong, San Francisco, CA (US); Ge Wu, La Canada, CA (US); Aileen Zhou, San Francisco, CA (US); Cindy Leo, San Francisco, CA (US); Lewis T. Williams, San Francisco, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 430 days.

(21) Appl. No.: 12/370,559

(22) Filed: Feb. 12, 2009

(65) Prior Publication Data

US 2011/0003384 A1    Jan. 6, 2011

Related U.S. Application Data

(63) Continuation of application No. 11/632,319, filed as application No. PCT/US2005/025941 on Jul. 21, 2005, now abandoned.

(60) Provisional application No. 60/590,565, filed on Jul. 22, 2004, provisional application No. 60/647,604, filed on Jan. 27, 2005, provisional application No. 60/664,932, filed on Mar. 24, 2005, provisional application No. 60/699,019, filed on Jul. 14, 2005.

(51) Int. Cl.
    *A61K 39/00* (2006.01)
(52) U.S. Cl. .................................. 424/198.1
(58) Field of Classification Search ............. 424/198.1
    See application file for complete search history.

(56) References Cited

U.S. PATENT DOCUMENTS

| 5,350,836 | A | * | 9/1994 | Kopchick et al. | 530/399 |
| 5,831,036 | A | * | 11/1998 | Springer et al. | 530/395 |
| 2004/0048249 | A1 | | 3/2004 | Tang et al. | |

FOREIGN PATENT DOCUMENTS

| WO | WO 96/23060 A1 | 8/1996 |
| WO | WO 01/75067 A2 | 10/2001 |
| WO | WO 02/48337 A2 | 6/2002 |
| WO | WO 02/068579 A2 | 9/2002 |
| WO | WO 2004/009834 A2 | 1/2004 |
| WO | WO 2004/080148 A2 | 9/2004 |

OTHER PUBLICATIONS

Jones (Pharmacogenomics Journal, 1:126-134, 2001).*
Tosatto et al (Current Pharmaceutical Design, 12:2067-2086, 2006).*
Skolnick et al. (Trends in Biotechnology 2000; 18: 34-39).*
Bowie et al. (Science 257: 1306-1310, 1990).*
Burgess et al. (Journal of Cell Biology 1990; 111: 2129-2138).*
Lazar et al. (Molecular and Cellular Biology, 1988, 8: 1247-1252).*
Guo et al. (Proc. Natl. Acad. Sci. USA. Jun. 22, 2004; 101 (25): 9205-9210).*
Lin et al., "Discovery of a cytokine and its receptor by functional screening of the extracellular proteome," *Science*, 320: 807-811 (2008).
Lin et al., "Regulation of Myeloid Growth and Differentiation by a Novel Cytokine, Interleukin-34 (IL-34), via the CSF-1 Receptor," Cytokines in Health and Disease, the 15th Annual Meeting of the International Cytokine Society, Oct. 26-30, 2007, Poster Presentation (1 page).
Lin et al., "A Novel Cytokine, Interleukin-34 (IL-34, FPT025), Regulates Myeloid Growth and Differentiation via the CSF-1 Receptor," 48th ASHT™ Annual Meeting and Exposition, Dec. 9-12, 2006, Orange County Convention Center, Orlando, FL, Presentation (17 pages).
Lin et al., "FPT025, a novel cytokine stimulating myeloid proliferation and differentiation," Immunology 2006, Annual Meeting of American Association of Immunologists (AAI) 2006, May 12-16, 2006, Boston, MA, Poster Presentation (1 page).
NCBI Genebank Database Accession No. NP_689669, Interleukin 34 (Jun. 6, 2008) (1 page).
Peng et al., "Multiple PCR analyses on trace amounts of DNA extracted from fresh and paraffin wax embedded tissues after random hexamer primer PCR amplification" *J. Clin. Pathol.*, 47: 605-608 (1994).
Strausberg, et al., "Generation and initial analysis of more than 15,000 full-length human and mouse cDNA sequences", *Proc. Natl. Acad. Sci. USA*, 99(26): 16899-16903 (2002).
Office Action mailed Nov. 12, 2008, in U.S. Appl. No. 11/632,319.

(Continued)

*Primary Examiner* — Misook Yu
*Assistant Examiner* — Brad Duffy
(74) *Attorney, Agent, or Firm* — Finnegan, Henderson, Farabow, Garrett, & Dunner, L.L.P.

(57) ABSTRACT

Disclosed is a newly identified secreted molecule, identified herein as "monocyte, granulocyte, and dendritic cell colony stimulating factor" (MGD-CSF), the polypeptide sequence, and polynucleotides encoding the polypeptide sequence. Also provided is a procedure for producing the polypeptide by recombinant techniques employing, for example, vectors and host cells. Additionally, procedures are described to modify the disclosed novel molecules of the invention to prepare fusion molecules. Also disclosed are methods for using the polypeptides and active fragments thereof for treatment of a variety of diseases, including, for example, cancer, autoimmune and inflammatory diseases, infectious diseases, and recurrent pregnancy loss.

12 Claims, 27 Drawing Sheets

OTHER PUBLICATIONS

Preliminary Amendment filed Oct. 29, 2008, in U.S. Appl. No. 11/632,319.
Reply to Restriction Requirement filed Oct. 14, 2008, in U.S. Appl. No. 11/632,319.
Office Action (Restriction Requirement) mailed Sep. 11, 2008, in U.S. Appl. No. 11/632,319.
Preliminary Amendment filed Mar. 20, 2007, in U.S. Appl. No. 11/632,319.
European Search Report dated Jan. 20, 2011, in European Application No. 10179665.4.
Extended European Search Report of Jan. 20, 2011, in European Patent Application No. 10179665.4—2402 (5 pages).
Communication pursuant to Article 94(3) EPC, mailed May 11, 2011, for European Patent App. No. 05 791 762.7-2402 (5 pages).
Response to Communication from the European Patent Office of May 11, 2011, for European Patent App. No. 05791762.7, submitted Jul. 7, 2011, including claims 1-21 (6 pages).
Declaration of Dr. Haishan Lin, submitted to the European Patent Office on Jul. 7, 2011, for European Patent App. No. 05791762.7 (2 pages).
Invitation pursuant to Article 94(3) and Rule 71(1) EPC mailed Jul. 29, 20011, for European Patent App. No. 05 791 762.7-2402 (3 pages).

* cited by examiner

```
MGD-CSF_exon4   ------------------------------------------------------------     0
NP_689669       MPRGFTWLRYLGIFLGVALGNEPLEMWPLTQNEECTVTGFLRDKLQYRSRLQYMKHYFPI    60
MGD-CSF         MPRGFTWLRYLGIFLGVALGNEPLEMWPLTQNEECTVTGFLRDKLQYRSRLQYMKHYFPI    60

MGD-CSF_exon4   ---------------------------------------RAQVSERELRYLWVLVSLSATESVQDVLLEGHPSWKYLQ    39
NP_689669       NYKISVPYEGVFRIANVTRLQRAQVSERELRYLWVLVSLSATESVQDVLLEGHPSWKYLQ   120
MGD-CSF         NYKISVPYEGVFRIANVTRL-RAQVSERELRYLWVLVSLSATESVQDVLLEGHPSWKYLQ   119
                                     ***************************************

MGD-CSF_exon4   EVQTLLLNVQQGLT----------------------------------------------    53
NP_689669       EVQTLLLNVQQGLTDVEVSPKVESVLSLLNAPGPNLKLVRPKALLDNCFRVMELLYCSCC   180
MGD-CSF         EVQTLLLNVQQGLTDVEVSPKVESVLSLLNAPGPNLKLVRPKALLDNCFRVMELLYCSCC   179
                **************

MGD-CSF_exon4   ------------------------------------------------------------    53
NP_689669       KQSSVLNWQDCEVPSPQSCSPEPSLQYAATQLYPPPWSPSPSSPPHSTGSVRPVRAQGEGL   240
MGD-CSF         KQSSVLNWQDCEVPSPQSCSPEPSLQYAATQLYPPPWSPSPSSPPHSTGSVRPVRAQGEGL   239

MGD-CSF_exon4   --  53
NP_689669       LP 242
MGD-CSF         LP 241
```

FIG. 1 pTT5-G:

GCCGCCACCATGAAGAGACCTGCTGGAAAATTCCAGTTTCTTTGTGTGCAGTTTCCTGGAACCCTGGGCATCT

GCAGAATTC————GGATCCgaaaacctgtattcagggcTTCGAAGGTAAGCCTATCCCTAACCCTCTCCTCGGT
EcoR1           BamH1         TEV                    V5
CTCGATTCTACGCGTgggagccaccgcagttcgagaaaACCGGTCATCATCACCATCACCATCACCATGGAGGACAGTGA
                              StreptTagII           H8 pTT5-H:

GCCGCCACCATGAAGAGACCTGCTGGAAAATTCCAGTTTCTTTGTGTGCAGTTTCCTGGAAC CCTGGGCATCT
                                SP
GCAGAAGGTCATCATCACCATCACCATCACCATGGAGGACAGTGGAGCCACCCGCAGTTCGAGAAAGGTAAGC
         H8                                   StreptTagII
CTATCCCTAACCCTCTCCTCGGTCTCGATTCTACG GAAAACCTGTATTTTCAGGGCGAATTC————GGATCC
         V5                          TEV                  EcoR1      BamH1 pTT5-I:

gaattcGCCGCCACCATG————GGATCCgaaaacctgtattcagggcTTCGAAGGTAAGCCTATCCCTAACCCTCTC
EcoR1             BamH1       TEV                    V5
CTCGGTCTCGATTCTACGCGTggagccaccgcagttcgagaaaACCGGTCATCATCACCATC ACCATCACCATGGAGG
                     StreptTagII                              H8
ACAGTGA

**FIG. 2
(cont'd)**

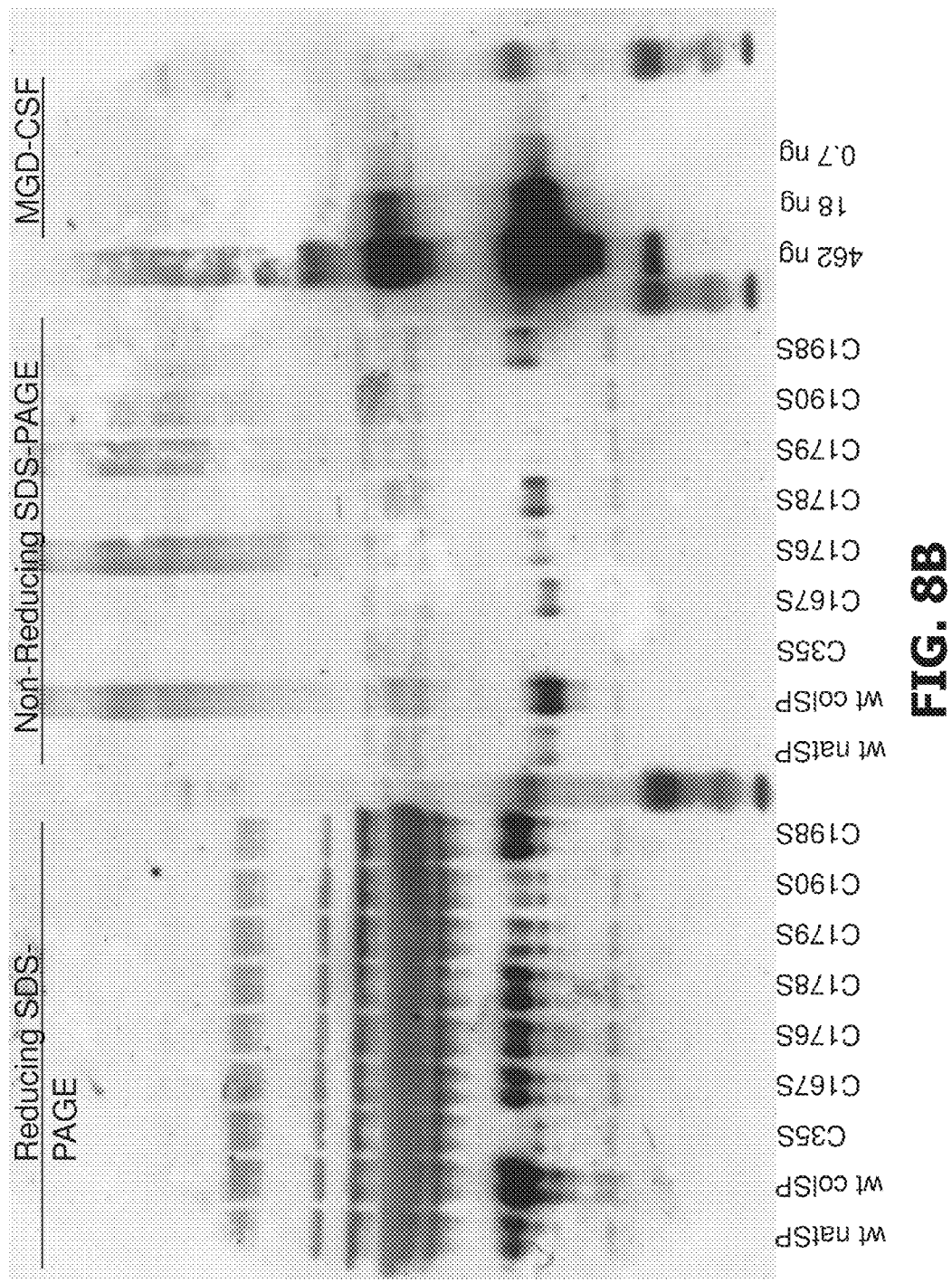

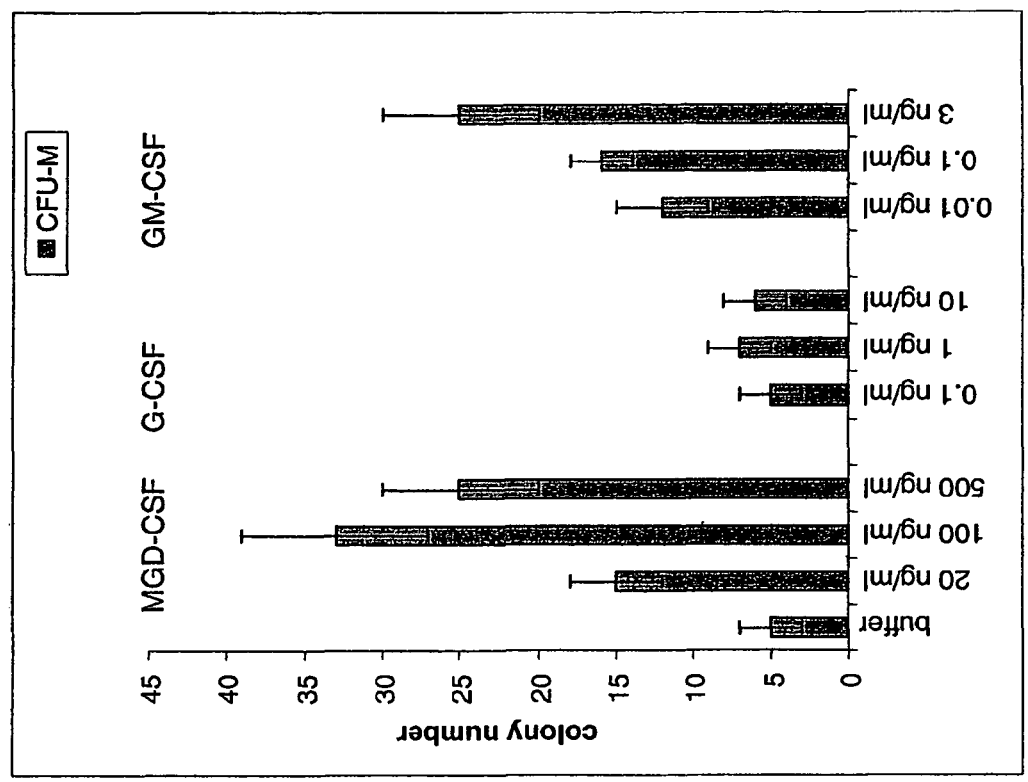
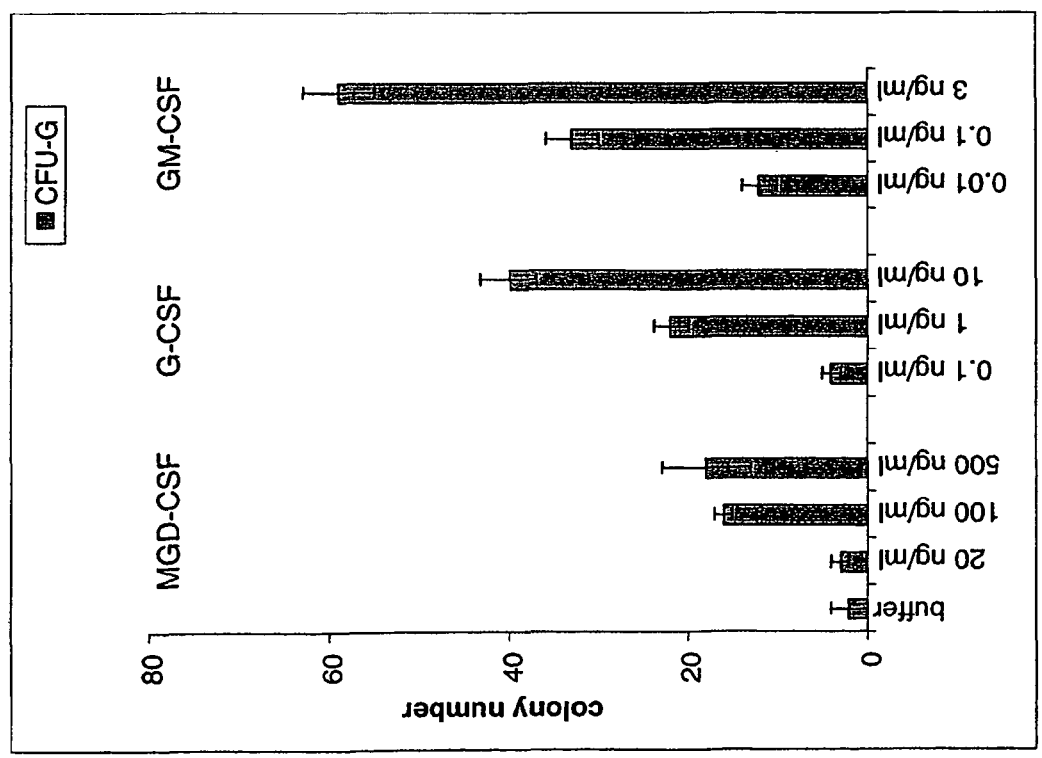
FIG. 18A

SEQUENCE LISTING

<160> NUMBER OF SEQ ID NOS: 284

<210> SEQ ID NO 1
<211> LENGTH: 726
<212> TYPE: DNA
<213> ORGANISM: Homo sapiens

<400> SEQUENCE: 1

```
atgccccggg gcttcacctg gctgcgctat cttgggatct tccttggcgt ggccttgggg      60
aatgagcctt tggagatgtg gcccttgacg cagaatgagg agtgcactgt cacgggtttt     120
ctgcgggaca agctgcagta caggagccga cttcagtaca tgaaacacta cttccccatc     180
aactacaaga tcagtgtgcc ttacgagggg gtgttcagaa tcgccaacgt caccaggctg     240
agggcccagg tgagcgagcg ggagctgcgg tatctgtggg tcttggtgag cctcagtgcc     300
actgagtcgg tgcaggacgt gctgctcgag ggccacccat cctggaagta cctgcaggag     360
gtgcagacgc tgctgctgaa tgtccagcag ggcctcacgg atgtggaggt cagccccaag     420
gtggaatccg tgttgtccct cttgaatgcc ccagggccaa acctgaagct ggtgcggccc     480
aaagccctgc tggacaactg cttccgggtc atggagctgc tgtactgctc ctgctgtaaa     540
caaagctccg tcctaaactg gcaggactgt gaggtgccaa gtcctcagtc ttgcagccca     600
gagccctcat tgcagtatgc ggccacccag ctgtaccctc cgccccgtg gtcccccagc      660 tccccgcctc actccacggg ctcggtgagg ccggtcaggg cacagggcga gggcctcttg     720
ccctag                                                                726
```

<210> SEQ ID NO 2
<211> LENGTH: 159
<212> TYPE: DNA
<213> ORGANISM: Homo sapiens

<400> SEQUENCE: 2
agggcccagg tgagcgagcg ggagctgcgg tatctgtggg tcttggtgag cctcagtgcc    60
actgagtcgg tgcaggacgt gctgctcgag ggccacccat cctggaagta cctgcaggag   120
gtgcagacgc tgctgctgaa tgtccagcag ggcctcacg                          159

<210> SEQ ID NO 3
<211> LENGTH: 663
<212> TYPE: DNA
<213> ORGANISM: Homo sapiens

<400> SEQUENCE: 3
aatgagcctt tggagatgtg gcccttgacg cagaatgagg agtgcactgt cacgggtttt    60
ctgcgggaca agctgcagta caggagccga cttcagtaca tgaaacacta cttccccatc   120
aactacaaga tcagtgtgcc ttacgagggg gtgttcagaa tcgccaacgt caccaggctg   180
agggcccagg tgagcgagcg ggagctgcgg tatctgtggg tcttggtgag cctcagtgcc   240
actgagtcgg tgcaggacgt gctgctcgag ggccacccat cctggaagta cctgcaggag   300
gtgcagacgc tgctgctgaa tgtccagcag ggcctcacgg atgtggaggt cagccccaag   360
gtggaatccg tgttgtccct cttgaatgcc cagggccaa acctgaagct ggtgcggccc    420
aaagccctgc tggacaactg cttccgggtc atggagctgc tgtactgctc ctgctgtaaa   480
caaagctccg tcctaaactg gcaggactgt gaggtgccaa gtcctcagtc ttgcagccca   540
gagccctcat tgcagtatgc ggccacccag ctgtaccctc gccccgtg gtccccagc     600 tccccgcctc actccacggg ctcggtgagg ccggtcaggg cacagggcga gggcctcttg   660
ccc                                                                  663

<210> SEQ ID NO 4
<211> LENGTH: 729
<212> TYPE: DNA
<213> ORGANISM: Homo sapiens

<400> SEQUENCE: 4
atgccccggg gcttcacctg gctgcgctat cttgggatct tccttggcgt ggccttgggg    60
aatgagcctt tggagatgtg gcccttgacg cagaatgagg agtgcactgt cacgggtttt   120
ctgcgggaca agctgcagta caggagccga cttcagtaca tgaaacacta cttccccatc   180
aactacaaga tcagtgtgcc ttacgagggg gtgttcagaa tcgccaacgt caccaggctg   240
cagagggccc aggtgagcga gcgggagctg cggtatctgt gggtcttggt gagcctcagt   300
gccactgagt cggtgcagga cgtgctgctc gagggccacc catcctggaa gtacctgcag   360
gaggtgcaga cgctgctgct gaatgtccag cagggcctca cggatgtgga ggtcagcccc   420
aaggtggaat ccgtgttgtc cctcttgaat gccccagggc caaacctgaa gctggtgcgg   480
cccaaagccc tgctggacaa ctgcttccgg gtcatggagc tgctgtactg ctcctgctgt   540
aaacaaagct ccgtcctaaa ctggcaggac tgtgaggtgc caagtcctca gtcttgcagc   600
ccagagccct cattgcagta tgcggccacc cagctgtacc ctcgccccc gtggtccccc    660 agctccccgc ctcactccac gggctcggtg aggccggtca gggcacaggg cgagggcctc   720
ttgccctga                                                          729

```
<210> SEQ ID NO 5
<211> LENGTH: 18
<212> TYPE: DNA
<213> ORGANISM: Homo sapiens

<400> SEQUENCE: 5
accaggctga gggcccag                                                   18

<210> SEQ ID NO 6
<211> LENGTH: 18
<212> TYPE: DNA
<213> ORGANISM: Homo sapiens

<400> SEQUENCE: 6
accaggctgc agagggcc                                                   18

<210> SEQ ID NO 7
<211> LENGTH: 241
<212> TYPE: PRT
<213> ORGANISM: Homo sapiens

<400> SEQUENCE: 7
```

Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
        35                  40                  45

Ser Arg Leu Gln Tyr Met Lys His Tyr Phe Pro Ile Asn Tyr Lys Ile
    50                  55                  60

Ser Val Pro Tyr Glu Gly Val Phe Arg Ile Ala Asn Val Thr Arg Leu
65                  70                  75                  80

Arg Ala Gln Val Ser Glu Arg Glu Leu Arg Tyr Leu Trp Val Leu Val
                85                  90                  95

Ser Leu Ser Ala Thr Glu Ser Val Gln Asp Val Leu Leu Glu Gly His
            100                 105                 110

Pro Ser Trp Lys Tyr Leu Gln Glu Val Gln Thr Leu Leu Leu Asn Val
        115                 120                 125

Gln Gln Gly Leu Thr Asp Val Glu Val Ser Pro Lys Val Glu Ser Val
    130                 135                 140

Leu Ser Leu Leu Asn Ala Pro Gly Pro Asn Leu Lys Leu Val Arg Pro
145                 150                 155                 160

Lys Ala Leu Leu Asp Asn Cys Phe Arg Val Met Glu Leu Leu Tyr Cys
                165                 170                 175

Ser Cys Cys Lys Gln Ser Ser Val Leu Asn Trp Gln Asp Cys Glu Val
            180                 185                 190

Pro Ser Pro Gln Ser Cys Ser Pro Glu Pro Ser Leu Gln Tyr Ala Ala
        195                 200                 205

Thr Gln Leu Tyr Pro Pro Pro Trp Ser Pro Ser Ser Pro Pro His
    210                 215                 220

Ser Thr Gly Ser Val Arg Pro Val Arg Ala Gln Gly Glu Gly Leu Leu
225                 230                 235                 240

Pro

```
<210> SEQ ID NO 8
<211> LENGTH: 53
<212> TYPE: PRT
```

<213> ORGANISM: Homo sapiens

<400> SEQUENCE: 8

Arg Ala Gln Val Ser Glu Arg Glu Leu Arg Tyr Leu Trp Val Leu Val
1               5                   10                  15

Ser Leu Ser Ala Thr Glu Ser Val Gln Asp Val Leu Leu Glu Gly His
            20                  25                  30

Pro Ser Trp Lys Tyr Leu Gln Glu Val Gln Thr Leu Leu Leu Asn Val
        35                  40                  45

Gln Gln Gly Leu Thr
    50

<210> SEQ ID NO 9
<211> LENGTH: 221
<212> TYPE: PRT
<213> ORGANISM: Homo sapiens

<400> SEQUENCE: 9

Asn Glu Pro Leu Glu Met Trp Pro Leu Thr Gln Asn Glu Glu Cys Thr
1               5                   10                  15

Val Thr Gly Phe Leu Arg Asp Lys Leu Gln Tyr Arg Ser Arg Leu Gln
            20                  25                  30

Tyr Met Lys His Tyr Phe Pro Ile Asn Tyr Lys Ile Ser Val Pro Tyr
        35                  40                  45

Glu Gly Val Phe Arg Ile Ala Asn Val Thr Arg Leu Arg Ala Gln Val
    50                  55                  60

Ser Glu Arg Glu Leu Arg Tyr Leu Trp Val Leu Val Ser Leu Ser Ala
65                  70                  75                  80

Thr Glu Ser Val Gln Asp Val Leu Leu Glu Gly His Pro Ser Trp Lys
                85                  90                  95

Tyr Leu Gln Glu Val Gln Thr Leu Leu Leu Asn Val Gln Gln Gly Leu
            100                 105                 110

Thr Asp Val Glu Val Ser Pro Lys Val Glu Ser Val Leu Ser Leu Leu
        115                 120                 125

Asn Ala Pro Gly Pro Asn Leu Lys Leu Val Arg Pro Lys Ala Leu Leu
    130                 135                 140

Asp Asn Cys Phe Arg Val Met Glu Leu Leu Tyr Cys Ser Cys Cys Lys
145                 150                 155                 160

Gln Ser Ser Val Leu Asn Trp Gln Asp Cys Glu Val Pro Ser Pro Gln
                165                 170                 175

Ser Cys Ser Pro Glu Pro Ser Leu Gln Tyr Ala Ala Thr Gln Leu Tyr
            180                 185                 190

Pro Pro Pro Pro Trp Ser Pro Ser Ser Pro Pro His Ser Thr Gly Ser
        195                 200                 205

Val Arg Pro Val Arg Ala Gln Gly Glu Gly Leu Leu Pro
    210                 215                 220

<210> SEQ ID NO 10
<211> LENGTH: 242
<212> TYPE: PRT
<213> ORGANISM: Homo sapiens

<400> SEQUENCE: 10

Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

```
Glu Glu Cys Thr Val Thr Gly Phe Leu Arg Asp Lys Leu Gln Tyr Arg
            35                  40                  45

Ser Arg Leu Gln Tyr Met Lys His Tyr Phe Pro Ile Asn Tyr Lys Ile
 50                  55                  60

Ser Val Pro Tyr Glu Gly Val Phe Arg Ile Ala Asn Val Thr Arg Leu
 65                  70                  75                  80

Gln Arg Ala Gln Val Ser Glu Arg Glu Leu Arg Tyr Leu Trp Val Leu
                 85                  90                  95

Val Ser Leu Ser Ala Thr Glu Ser Val Gln Asp Val Leu Leu Glu Gly
                100                 105                 110

His Pro Ser Trp Lys Tyr Leu Gln Glu Val Gln Thr Leu Leu Leu Asn
            115                 120                 125

Val Gln Gln Gly Leu Thr Asp Val Glu Val Ser Pro Lys Val Glu Ser
130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Lys Gln Ser Val Leu Asn Trp Gln Asp Cys Glu
            180                 185                 190

Val Pro Ser Pro Gln Ser Cys Ser Pro Glu Pro Ser Leu Gln Tyr Ala
            195                 200                 205

Ala Thr Gln Leu Tyr Pro Pro Pro Trp Ser Pro Ser Ser Pro Pro
210                 215                 220

His Ser Thr Gly Ser Val Arg Pro Val Arg Ala Gln Gly Glu Gly Leu
225                 230                 235                 240

Leu Pro

<210> SEQ ID NO 11
<211> LENGTH: 6
<212> TYPE: PRT
<213> ORGANISM: Homo sapiens

<400> SEQUENCE: 11

Thr Arg Leu Arg Ala Gln
1               5

<210> SEQ ID NO 12
<211> LENGTH: 6
<212> TYPE: PRT
<213> ORGANISM: Homo sapiens

<400> SEQUENCE: 12

Thr Arg Leu Gln Arg Ala
1               5

<210> SEQ ID NO 13
<211> LENGTH: 1652
<212> TYPE: DNA
<213> ORGANISM: Homo sapiens

<400> SEQUENCE: 13
agcagctgca gtcggaaaaa tcagagaaag cgtcacccag ccccagattc cgaggggcct      60
gccagggact ctctcctcct gctccttgga aaggaagacc ccgaaagacc cccaagccac     120
cggctcagac ctgcttctgg gctgccatgg gacttgcggc caccgccccc cggctgtcct     180
ccacgctgcc gggcagataa gggcagctgc tgccttgggc acctgctc actcccgcag      240 cccagccact cctccagggc cagccccttcc ctgactgagt gaccacctct gctgcccga    300
```

```
ggccatgtag gccgtgctta ggcctctgtg acacactgc tggggacggc gcctgagctc    360
tcaggggac gaggaacacc accatgcccc ggggcttcac ctggctgcgc tatcttggga    420
tcttccttgg cgtggccttg gggaatgagc ctttggagat gtggcccttg acgcagaatg   480
aggagtgcac tgtcacgggt tttctgcggg acaagctgca gtacaggagc cgacttcagt   540
acatgaaaca ctacttcccc atcaactaca agatcagtgt gccttacgag ggggtgttca   600
gaatcgccaa cgtcaccagg ctgcagaggg cccaggtgag cgagcgggag ctgcggtatc   660
tgtgggtctt ggtgagcctc agtgccactg agtcggtgca ggacgtgctg ctcgagggcc   720
acccatcctg gaagtacctg caggaggtgc agacgctgct gctgaatgtc cagcagggcc   780
tcacggatgt ggaggtcagc cccaaggtgg aatccgtgtt gtccctcttg aatgccccag   840
ggccaaacct gaagctggtg cggcccaaag ccctgctgga caactgcttc cgggtcatgg   900
agctgctgta ctgctcctgc tgtaaacaaa gctccgtcct aaactggcag gactgtgagg   960
tgccaagtcc tcagtcttgc agcccagagc cctcattgca gtatgcggcc acccagctgt  1020
accctccgcc cccgtggtcc cccagctccc cgcctcactc cacgggctcg gtgaggccgg  1080
tcagggcaca gggcgagggc ctcttgccct gagcaccctg gatggtgact gcggataggg  1140
gcagccagac cagctcccac aggagttcaa ctgggtctga acttcaagg ggtggtggtg   1200
ggagcccccc ttgggagagg acccctggga agggtgtttt tcctttgagg gggattctgt  1260
gccacagcag ggctcagctt cctgccttcc atagctgtca tggcctcacc tggagcggag  1320
gggacctggg gacctgaagg tggatgggga cacagctcct ggcttctcct ggtgctgccc  1380
tcactgtccc cccgcctaaa gggggtactg agcctcctgt ggcccgcagc agtgagggca  1440
cagctgtggg ttgcagggga gacagccagc acggcgtggc cattctatga cccccccagcc 1500
tggcagactg gggagctggg ggcagagggc ggtgccaagt gccacatctt gccatagtgg  1560
atgctcttcc agtttctttt ttctattaaa caccccactt cctttgaaaa aaaaaaaaa   1620
aaaaaaaaaa aaaaaaaaa aaaaaaaaa aa                                  1652

<210> SEQ ID NO 14
<211> LENGTH: 23
<212> TYPE: PRT
<213> ORGANISM: Homo sapiens

<400> SEQUENCE: 14

Met Lys Thr Cys Trp Lys Ile Pro Val Phe Phe Val Cys Ser Phe
1               5                   10                  15

Leu Glu Pro Trp Ala Ser Ala
            20

<210> SEQ ID NO 15
<211> LENGTH: 17
<212> TYPE: PRT
<213> ORGANISM: Homo sapiens

<400> SEQUENCE: 15

Met Ala Leu Leu Trp Gly Leu Leu Val Leu Ser Trp Ser Cys Leu Gln
1               5                   10                  15

Gly

<210> SEQ ID NO 16
<211> LENGTH: 13
<212> TYPE: PRT
<213> ORGANISM: Homo sapiens
```

```
<400> SEQUENCE: 16

Met Ala Leu Leu Trp Gly Leu Leu Val Leu Ser Trp Ser
1               5                   10

<210> SEQ ID NO 17
<211> LENGTH: 19
<212> TYPE: PRT
<213> ORGANISM: Homo sapiens

<400> SEQUENCE: 17

Met Ala Leu Leu Trp Gly Leu Leu Val Leu Ser Trp Ser Cys Leu Gln
1               5                   10                  15

Gly Pro Cys

<210> SEQ ID NO 18
<211> LENGTH: 16
<212> TYPE: PRT
<213> ORGANISM: Homo sapiens

<400> SEQUENCE: 18

Met Ala Leu Leu Trp Gly Leu Leu Val Leu Ser Trp Ser Cys Leu Gln
1               5                   10                  15

<210> SEQ ID NO 19
<211> LENGTH: 15
<212> TYPE: PRT
<213> ORGANISM: Homo sapiens

<400> SEQUENCE: 19

Met Ala Leu Leu Trp Gly Leu Leu Val Leu Ser Trp Ser Cys Leu
1               5                   10                  15

<210> SEQ ID NO 20
<211> LENGTH: 30
<212> TYPE: PRT
<213> ORGANISM: Homo sapiens

<400> SEQUENCE: 20

Met Asp Ser Met Pro Glu Pro Ala Ser Arg Cys Leu Leu Leu Leu Pro
1               5                   10                  15

Leu Leu Leu Leu Leu Leu Leu Leu Leu Pro Ala Pro Glu Leu
            20                  25                  30

<210> SEQ ID NO 21
<211> LENGTH: 25
<212> TYPE: PRT
<213> ORGANISM: Homo sapiens

<400> SEQUENCE: 21

Met Asp Ser Met Pro Glu Pro Ala Ser Arg Cys Leu Leu Leu Leu Pro
1               5                   10                  15

Leu Leu Leu Leu Leu Leu Leu Leu Leu
            20                  25

<210> SEQ ID NO 22
<211> LENGTH: 33
<212> TYPE: PRT
<213> ORGANISM: Homo sapiens

<400> SEQUENCE: 22

Met Asp Ser Met Pro Glu Pro Ala Ser Arg Cys Leu Leu Leu Leu Pro
1               5                   10                  15

Leu Leu Leu Leu Leu Leu Leu Leu Leu Pro Ala Pro Glu Leu Gly Pro
```

Ser

<210> SEQ ID NO 23
<211> LENGTH: 24
<212> TYPE: PRT
<213> ORGANISM: Homo sapiens

<400> SEQUENCE: 23

Met Asp Ser Met Pro Glu Pro Ala Ser Arg Cys Leu Leu Leu Leu Pro
1               5                   10                  15

Leu Leu Leu Leu Leu Leu Leu Leu
            20

<210> SEQ ID NO 24
<211> LENGTH: 26
<212> TYPE: PRT
<213> ORGANISM: Homo sapiens

<400> SEQUENCE: 24

Met Asp Ser Met Pro Glu Pro Ala Ser Arg Cys Leu Leu Leu Leu Pro
1               5                   10                  15

Leu Leu Leu Leu Leu Leu Leu Leu Leu Pro
            20                  25

<210> SEQ ID NO 25
<211> LENGTH: 32
<212> TYPE: PRT
<213> ORGANISM: Homo sapiens

<400> SEQUENCE: 25

Met Asp Ser Met Pro Glu Pro Ala Ser Arg Cys Leu Leu Leu Leu Pro
1               5                   10                  15

Leu Leu Leu Leu Leu Leu Leu Leu Leu Pro Ala Pro Glu Leu Gly Pro
            20                  25                  30

<210> SEQ ID NO 26
<211> LENGTH: 27
<212> TYPE: PRT
<213> ORGANISM: Homo sapiens

<400> SEQUENCE: 26

Met Asp Ser Met Pro Glu Pro Ala Ser Arg Cys Leu Leu Leu Leu Pro
1               5                   10                  15

Leu Leu Leu Leu Leu Leu Leu Leu Leu Pro Ala
            20                  25

<210> SEQ ID NO 27
<211> LENGTH: 23
<212> TYPE: PRT
<213> ORGANISM: Homo sapiens

<400> SEQUENCE: 27

Met Asp Ser Met Pro Glu Pro Ala Ser Arg Cys Leu Leu Leu Leu Pro
1               5                   10                  15

Leu Leu Leu Leu Leu Leu Leu
            20

<210> SEQ ID NO 28
<211> LENGTH: 35
<212> TYPE: PRT
<213> ORGANISM: Homo sapiens

<400> SEQUENCE: 28

Met Asp Ser Met Pro Glu Pro Ala Ser Arg Cys Leu Leu Leu Pro
1               5                   10                  15

Leu Leu Leu Leu Leu Leu Leu Leu Leu Pro Ala Pro Glu Leu Gly Pro
            20                  25                  30

Ser Gln Ala
        35

<210> SEQ ID NO 29
<211> LENGTH: 24
<212> TYPE: PRT
<213> ORGANISM: Homo sapiens

<400> SEQUENCE: 29

Met Arg Arg Met Trp Ala Thr Gln Gly Leu Ala Val Ala Leu Ala Leu
1               5                   10                  15

Ser Val Leu Pro Gly Ser Arg Ala
            20

<210> SEQ ID NO 30
<211> LENGTH: 21
<212> TYPE: PRT
<213> ORGANISM: Homo sapiens

<400> SEQUENCE: 30

Met Arg Arg Met Trp Ala Thr Gln Gly Leu Ala Val Ala Leu Ala Leu
1               5                   10                  15

Ser Val Leu Pro Gly
            20

<210> SEQ ID NO 31
<211> LENGTH: 19
<212> TYPE: PRT
<213> ORGANISM: Homo sapiens

<400> SEQUENCE: 31

Met Asp Leu Arg Gln Phe Leu Met Cys Leu Ser Leu Cys Thr Ala Phe
1               5                   10                  15

Ala Leu Ser

<210> SEQ ID NO 32
<211> LENGTH: 15
<212> TYPE: PRT
<213> ORGANISM: Homo sapiens

<400> SEQUENCE: 32

Met Asp Leu Arg Gln Phe Leu Met Cys Leu Ser Leu Cys Thr Ala
1               5                   10                  15

<210> SEQ ID NO 33
<211> LENGTH: 17
<212> TYPE: PRT
<213> ORGANISM: Homo sapiens

<400> SEQUENCE: 33

Met Asp Leu Arg Gln Phe Leu Met Cys Leu Ser Leu Cys Thr Ala Phe
1               5                   10                  15

Ala

<210> SEQ ID NO 34
<211> LENGTH: 23
<212> TYPE: PRT

```
<213> ORGANISM: Homo sapiens

<400> SEQUENCE: 34

Met Lys Thr Cys Trp Lys Ile Pro Val Phe Phe Val Cys Ser Phe
1               5                   10                  15

Leu Glu Pro Trp Ala Ser Ala
            20

<210> SEQ ID NO 35
<211> LENGTH: 21
<212> TYPE: PRT
<213> ORGANISM: Homo sapiens

<400> SEQUENCE: 35

Met Met Leu Arg Val Leu Val Gly Ala Val Leu Pro Ala Met Leu Leu
1               5                   10                  15

Ala Ala Pro Pro Pro
            20

<210> SEQ ID NO 36
<211> LENGTH: 17
<212> TYPE: PRT
<213> ORGANISM: Homo sapiens

<400> SEQUENCE: 36

Met Met Leu Arg Val Leu Val Gly Ala Val Leu Pro Ala Met Leu Leu
1               5                   10                  15

Ala

<210> SEQ ID NO 37
<211> LENGTH: 19
<212> TYPE: PRT
<213> ORGANISM: Homo sapiens

<400> SEQUENCE: 37

Met Arg Leu Ser Leu Pro Leu Leu Leu Leu Leu Gly Ala Trp Ala
1               5                   10                  15

Ile Pro Gly

<210> SEQ ID NO 38
<211> LENGTH: 22
<212> TYPE: PRT
<213> ORGANISM: Homo sapiens

<400> SEQUENCE: 38

Met Arg Leu Ser Leu Pro Leu Leu Leu Leu Leu Gly Ala Trp Ala
1               5                   10                  15

Ile Pro Gly Gly Leu Gly
            20

<210> SEQ ID NO 39
<211> LENGTH: 18
<212> TYPE: PRT
<213> ORGANISM: Homo sapiens

<400> SEQUENCE: 39

Met Arg Leu Ser Leu Pro Leu Leu Leu Leu Leu Gly Ala Trp Ala
1               5                   10                  15

Ile Pro

<210> SEQ ID NO 40
<211> LENGTH: 16
```

-continued

```
<212> TYPE: PRT
<213> ORGANISM: Homo sapiens

<400> SEQUENCE: 40

Met Arg Leu Ser Leu Pro Leu Leu Leu Leu Leu Gly Ala Trp Ala
1               5                   10                  15

<210> SEQ ID NO 41
<211> LENGTH: 14
<212> TYPE: PRT
<213> ORGANISM: Homo sapiens

<400> SEQUENCE: 41

Met Arg Leu Ser Leu Pro Leu Leu Leu Leu Leu Gly Ala
1               5                   10

<210> SEQ ID NO 42
<211> LENGTH: 20
<212> TYPE: PRT
<213> ORGANISM: Homo sapiens

<400> SEQUENCE: 42

Met Ser Met Leu Val Val Phe Leu Leu Trp Gly Val Thr Trp Gly
1               5                   10                  15

Pro Val Thr Glu
            20

<210> SEQ ID NO 43
<211> LENGTH: 16
<212> TYPE: PRT
<213> ORGANISM: Homo sapiens

<400> SEQUENCE: 43

Met Ser Met Leu Val Val Phe Leu Leu Leu Trp Gly Val Thr Trp Gly
1               5                   10                  15

<210> SEQ ID NO 44
<211> LENGTH: 21
<212> TYPE: PRT
<213> ORGANISM: Homo sapiens

<400> SEQUENCE: 44

Met Ser Met Leu Val Val Phe Leu Leu Trp Gly Val Thr Trp Gly
1               5                   10                  15

Pro Val Thr Glu Ala
            20

<210> SEQ ID NO 45
<211> LENGTH: 24
<212> TYPE: PRT
<213> ORGANISM: Homo sapiens

<400> SEQUENCE: 45

Met Arg Ala Leu Arg Asp Arg Ala Gly Leu Leu Leu Cys Val Leu Leu
1               5                   10                  15

Leu Ala Ala Leu Leu Glu Ala Ala
            20

<210> SEQ ID NO 46
<211> LENGTH: 20
<212> TYPE: PRT
<213> ORGANISM: Homo sapiens

<400> SEQUENCE: 46
```

Met Arg Ala Leu Arg Asp Arg Ala Gly Leu Leu Cys Val Leu Leu
1               5                   10                  15

Leu Ala Ala Leu
            20

<210> SEQ ID NO 47
<211> LENGTH: 26
<212> TYPE: PRT
<213> ORGANISM: Homo sapiens

<400> SEQUENCE: 47

Met Arg Ala Leu Arg Asp Arg Ala Gly Leu Leu Cys Val Leu Leu
1               5                   10                  15

Leu Ala Ala Leu Leu Glu Ala Ala Leu Gly
            20                  25

<210> SEQ ID NO 48
<211> LENGTH: 21
<212> TYPE: PRT
<213> ORGANISM: Homo sapiens

<400> SEQUENCE: 48

Met Arg Ala Leu Arg Asp Arg Ala Gly Leu Leu Cys Val Leu Leu
1               5                   10                  15

Leu Ala Ala Leu Leu
            20

<210> SEQ ID NO 49
<211> LENGTH: 23
<212> TYPE: PRT
<213> ORGANISM: Homo sapiens

<400> SEQUENCE: 49

Met Arg Ala Leu Arg Asp Arg Ala Gly Leu Leu Cys Val Leu Leu
1               5                   10                  15

Leu Ala Ala Leu Leu Glu Ala
            20

<210> SEQ ID NO 50
<211> LENGTH: 24
<212> TYPE: PRT
<213> ORGANISM: Homo sapiens

<400> SEQUENCE: 50

Met Arg Ala Pro Gly Cys Gly Arg Leu Val Leu Pro Leu Leu Leu
1               5                   10                  15

Ala Ala Ala Ala Leu Ala Glu Gly
            20

<210> SEQ ID NO 51
<211> LENGTH: 19
<212> TYPE: PRT
<213> ORGANISM: Homo sapiens

<400> SEQUENCE: 51

Met Arg Ala Pro Gly Cys Gly Arg Leu Val Leu Pro Leu Leu Leu
1               5                   10                  15

Ala Ala Ala

<210> SEQ ID NO 52
<211> LENGTH: 22
<212> TYPE: PRT
<213> ORGANISM: Homo sapiens

<400> SEQUENCE: 52

Met Arg Ala Pro Gly Cys Gly Arg Leu Val Leu Pro Leu Leu Leu Leu
1               5                   10                  15

Ala Ala Ala Ala Leu Ala
            20

<210> SEQ ID NO 53
<211> LENGTH: 20
<212> TYPE: PRT
<213> ORGANISM: Homo sapiens

<400> SEQUENCE: 53

Met Arg Ala Pro Gly Cys Gly Arg Leu Val Leu Pro Leu Leu Leu Leu
1               5                   10                  15

Ala Ala Ala Ala
            20

<210> SEQ ID NO 54
<211> LENGTH: 26
<212> TYPE: PRT
<213> ORGANISM: Homo sapiens

<400> SEQUENCE: 54

Met Arg Ala Pro Gly Cys Gly Arg Leu Val Leu Pro Leu Leu Leu Leu
1               5                   10                  15

Ala Ala Ala Ala Leu Ala Glu Gly Asp Ala
            20                  25

<210> SEQ ID NO 55
<211> LENGTH: 21
<212> TYPE: PRT
<213> ORGANISM: Homo sapiens

<400> SEQUENCE: 55

Met Arg Ala Pro Gly Cys Gly Arg Leu Val Leu Pro Leu Leu Leu Leu
1               5                   10                  15

Ala Ala Ala Ala Leu
            20

<210> SEQ ID NO 56
<211> LENGTH: 24
<212> TYPE: PRT
<213> ORGANISM: Homo sapiens

<400> SEQUENCE: 56

Met Arg Leu Arg Arg Leu Ala Leu Phe Pro Gly Val Ala Leu Leu Leu
1               5                   10                  15

Ala Ala Gly Arg Leu Val Ala Ala
            20

<210> SEQ ID NO 57
<211> LENGTH: 23
<212> TYPE: PRT
<213> ORGANISM: Homo sapiens

<400> SEQUENCE: 57

Met Arg Leu Arg Arg Leu Ala Leu Phe Pro Gly Val Ala Leu Leu Leu
1               5                   10                  15

Ala Ala Gly Arg Leu Val Ala
            20

```
<210> SEQ ID NO 58
<211> LENGTH: 24
<212> TYPE: PRT
<213> ORGANISM: Homo sapiens

<400> SEQUENCE: 58

Met Pro Ser Ser Val Ser Trp Gly Ile Leu Leu Leu Ala Gly Leu Cys
1               5                   10                  15

Cys Leu Val Pro Val Ser Leu Ala
            20

<210> SEQ ID NO 59
<211> LENGTH: 18
<212> TYPE: PRT
<213> ORGANISM: Homo sapiens

<400> SEQUENCE: 59

Met Pro Ser Ser Val Ser Trp Gly Ile Leu Leu Leu Ala Gly Leu Cys
1               5                   10                  15

Cys Leu

<210> SEQ ID NO 60
<211> LENGTH: 23
<212> TYPE: PRT
<213> ORGANISM: Homo sapiens

<400> SEQUENCE: 60

Met Pro Ser Ser Val Ser Trp Gly Ile Leu Leu Leu Ala Gly Leu Cys
1               5                   10                  15

Cys Leu Val Pro Val Ser Leu
            20

<210> SEQ ID NO 61
<211> LENGTH: 17
<212> TYPE: PRT
<213> ORGANISM: Homo sapiens

<400> SEQUENCE: 61

Met Pro Ser Ser Val Ser Trp Gly Ile Leu Leu Leu Ala Gly Leu Cys
1               5                   10                  15

Cys

<210> SEQ ID NO 62
<211> LENGTH: 23
<212> TYPE: PRT
<213> ORGANISM: Homo sapiens

<400> SEQUENCE: 62

Met Gln Ser Leu Met Gln Ala Pro Leu Leu Ile Ala Leu Gly Leu Leu
1               5                   10                  15

Leu Ala Thr Pro Ala Gln Ala
            20

<210> SEQ ID NO 63
<211> LENGTH: 18
<212> TYPE: PRT
<213> ORGANISM: Homo sapiens

<400> SEQUENCE: 63

Met Gln Ser Leu Met Gln Ala Pro Leu Leu Ile Ala Leu Gly Leu Leu
1               5                   10                  15

Leu Ala
```

```
<210> SEQ ID NO 64
<211> LENGTH: 25
<212> TYPE: PRT
<213> ORGANISM: Homo sapiens

<400> SEQUENCE: 64

Met Gln Ser Leu Met Gln Ala Pro Leu Leu Ile Ala Leu Gly Leu Leu
1               5                   10                  15

Leu Ala Thr Pro Ala Gln Ala His Leu
            20                  25

<210> SEQ ID NO 65
<211> LENGTH: 20
<212> TYPE: PRT
<213> ORGANISM: Homo sapiens

<400> SEQUENCE: 65

Met Gln Ser Leu Met Gln Ala Pro Leu Leu Ile Ala Leu Gly Leu Leu
1               5                   10                  15

Leu Ala Thr Pro
            20

<210> SEQ ID NO 66
<211> LENGTH: 21
<212> TYPE: PRT
<213> ORGANISM: Homo sapiens

<400> SEQUENCE: 66

Met Gln Ser Leu Met Gln Ala Pro Leu Leu Ile Ala Leu Gly Leu Leu
1               5                   10                  15

Leu Ala Thr Pro Ala
            20

<210> SEQ ID NO 67
<211> LENGTH: 23
<212> TYPE: PRT
<213> ORGANISM: Homo sapiens

<400> SEQUENCE: 67

Met Gly Arg Pro Leu His Leu Val Leu Leu Ser Ala Ser Leu Ala Gly
1               5                   10                  15

Leu Leu Leu Leu Gly Glu Ser
            20

<210> SEQ ID NO 68
<211> LENGTH: 19
<212> TYPE: PRT
<213> ORGANISM: Homo sapiens

<400> SEQUENCE: 68

Met Gly Arg Pro Leu His Leu Val Leu Leu Ser Ala Ser Leu Ala Gly
1               5                   10                  15

Leu Leu Leu

<210> SEQ ID NO 69
<211> LENGTH: 20
<212> TYPE: PRT
<213> ORGANISM: Homo sapiens

<400> SEQUENCE: 69

Met Gly Arg Pro Leu His Leu Val Leu Leu Ser Ala Ser Leu Ala Gly
1               5                   10                  15
```

Leu Leu Leu Leu
            20

<210> SEQ ID NO 70
<211> LENGTH: 15
<212> TYPE: PRT
<213> ORGANISM: Homo sapiens

<400> SEQUENCE: 70

Met Gly Arg Pro Leu His Leu Val Leu Leu Ser Ala Ser Leu Ala
1               5                   10                  15

<210> SEQ ID NO 71
<211> LENGTH: 21
<212> TYPE: PRT
<213> ORGANISM: Homo sapiens

<400> SEQUENCE: 71

Met Gly Arg Pro Leu His Leu Val Leu Leu Ser Ala Ser Leu Ala Gly
1               5                   10                  15

Leu Leu Leu Leu Gly
            20

<210> SEQ ID NO 72
<211> LENGTH: 17
<212> TYPE: PRT
<213> ORGANISM: Homo sapiens

<400> SEQUENCE: 72

Met Gly Arg Pro Leu His Leu Val Leu Leu Ser Ala Ser Leu Ala Gly
1               5                   10                  15

Leu

<210> SEQ ID NO 73
<211> LENGTH: 18
<212> TYPE: PRT
<213> ORGANISM: Homo sapiens

<400> SEQUENCE: 73

Met Arg Ile Ala Val Ile Cys Phe Cys Leu Leu Gly Ile Thr Cys Ala
1               5                   10                  15

Ile Pro

<210> SEQ ID NO 74
<211> LENGTH: 16
<212> TYPE: PRT
<213> ORGANISM: Homo sapiens

<400> SEQUENCE: 74

Met Arg Ile Ala Val Ile Cys Phe Cys Leu Leu Gly Ile Thr Cys Ala
1               5                   10                  15

<210> SEQ ID NO 75
<211> LENGTH: 15
<212> TYPE: PRT
<213> ORGANISM: Homo sapiens

<400> SEQUENCE: 75

Met Arg Ile Ala Val Ile Cys Phe Cys Leu Leu Gly Ile Thr Cys
1               5                   10                  15

<210> SEQ ID NO 76
<211> LENGTH: 16
<212> TYPE: PRT

<213> ORGANISM: Homo sapiens

<400> SEQUENCE: 76

Met Lys Arg Val Leu Val Leu Leu Ala Val Ala Phe Gly His Ala
1               5                   10                  15

<210> SEQ ID NO 77
<211> LENGTH: 14
<212> TYPE: PRT
<213> ORGANISM: Homo sapiens

<400> SEQUENCE: 77

Met Lys Arg Val Leu Val Leu Leu Ala Val Ala Phe Gly
1               5                   10

<210> SEQ ID NO 78
<211> LENGTH: 25
<212> TYPE: PRT
<213> ORGANISM: Homo sapiens

<400> SEQUENCE: 78

Met Asn Ser Phe Ser Thr Ser Ala Phe Gly Pro Val Ala Phe Ser Leu
1               5                   10                  15

Gly Leu Leu Leu Val Leu Pro Ala Ala
            20                  25

<210> SEQ ID NO 79
<211> LENGTH: 24
<212> TYPE: PRT
<213> ORGANISM: Homo sapiens

<400> SEQUENCE: 79

Met Asn Ser Phe Ser Thr Ser Ala Phe Gly Pro Val Ala Phe Ser Leu
1               5                   10                  15

Gly Leu Leu Leu Val Leu Pro Ala
            20

<210> SEQ ID NO 80
<211> LENGTH: 27
<212> TYPE: PRT
<213> ORGANISM: Homo sapiens

<400> SEQUENCE: 80

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro
            20                  25

<210> SEQ ID NO 81
<211> LENGTH: 18
<212> TYPE: PRT
<213> ORGANISM: Homo sapiens

<400> SEQUENCE: 81

Met Ala Leu Ser Trp Val Leu Thr Val Leu Ser Leu Leu Pro Leu Leu
1               5                   10                  15

Glu Ala

<210> SEQ ID NO 82
<211> LENGTH: 19
<212> TYPE: PRT
<213> ORGANISM: Homo sapiens

<400> SEQUENCE: 82

```
Met Ala Arg Val Leu Gly Ala Pro Val Ala Leu Gly Leu Trp Ser Leu
1               5                   10                  15

Cys Trp Ser
```

<210> SEQ ID NO 83
<211> LENGTH: 25
<212> TYPE: PRT
<213> ORGANISM: Homo sapiens

<400> SEQUENCE: 83

```
Met Ala Arg Val Leu Gly Ala Pro Val Ala Leu Gly Leu Trp Ser Leu
1               5                   10                  15

Cys Trp Ser Leu Ala Ile Ala Thr Pro
            20                  25
```

<210> SEQ ID NO 84
<211> LENGTH: 21
<212> TYPE: PRT
<213> ORGANISM: Homo sapiens

<400> SEQUENCE: 84

```
Met Ala Arg Val Leu Gly Ala Pro Val Ala Leu Gly Leu Trp Ser Leu
1               5                   10                  15

Cys Trp Ser Leu Ala
            20
```

<210> SEQ ID NO 85
<211> LENGTH: 23
<212> TYPE: PRT
<213> ORGANISM: Homo sapiens

<400> SEQUENCE: 85

```
Met Ala Arg Val Leu Gly Ala Pro Val Ala Leu Gly Leu Trp Ser Leu
1               5                   10                  15

Cys Trp Ser Leu Ala Ile Ala
            20
```

<210> SEQ ID NO 86
<211> LENGTH: 31
<212> TYPE: PRT
<213> ORGANISM: Homo sapiens

<400> SEQUENCE: 86

```
Met Ala Arg Val Leu Gly Ala Pro Val Ala Leu Gly Leu Trp Ser Leu
1               5                   10                  15

Cys Trp Ser Leu Ala Ile Ala Thr Pro Leu Pro Pro Thr Ser Ala
            20                  25                  30
```

<210> SEQ ID NO 87
<211> LENGTH: 26
<212> TYPE: PRT
<213> ORGANISM: Homo sapiens

<400> SEQUENCE: 87

```
Met Asp Tyr Tyr Arg Lys Tyr Ala Ala Ile Phe Leu Val Thr Leu Ser
1               5                   10                  15

Val Phe Leu His Val Leu His Ser Ala Pro
            20                  25
```

<210> SEQ ID NO 88
<211> LENGTH: 24
<212> TYPE: PRT

<213> ORGANISM: Homo sapiens

<400> SEQUENCE: 88

Met Asp Tyr Tyr Arg Lys Tyr Ala Ala Ile Phe Leu Val Thr Leu Ser
1               5                   10                  15

Val Phe Leu His Val Leu His Ser
            20

<210> SEQ ID NO 89
<211> LENGTH: 18
<212> TYPE: PRT
<213> ORGANISM: Homo sapiens

<400> SEQUENCE: 89

Met Lys Leu Ile Thr Ile Leu Phe Leu Cys Ser Arg Leu Leu Leu Ser
1               5                   10                  15

Leu Thr

<210> SEQ ID NO 90
<211> LENGTH: 19
<212> TYPE: PRT
<213> ORGANISM: Homo sapiens

<400> SEQUENCE: 90

Met Lys Leu Ile Thr Ile Leu Phe Leu Cys Ser Arg Leu Leu Leu Ser
1               5                   10                  15

Leu Thr Gln

<210> SEQ ID NO 91
<211> LENGTH: 16
<212> TYPE: PRT
<213> ORGANISM: Homo sapiens

<400> SEQUENCE: 91

Met Lys Leu Ile Thr Ile Leu Phe Leu Cys Ser Arg Leu Leu Leu Ser
1               5                   10                  15

<210> SEQ ID NO 92
<211> LENGTH: 23
<212> TYPE: PRT
<213> ORGANISM: Homo sapiens

<400> SEQUENCE: 92

Met Lys Leu Ile Thr Ile Leu Phe Leu Cys Ser Arg Leu Leu Leu Ser
1               5                   10                  15

Leu Thr Gln Glu Ser Gln Ser
            20

<210> SEQ ID NO 93
<211> LENGTH: 17
<212> TYPE: PRT
<213> ORGANISM: Homo sapiens

<400> SEQUENCE: 93

Met Leu Arg Arg Ala Leu Leu Cys Leu Ala Val Ala Ala Leu Val Arg
1               5                   10                  15

Ala

<210> SEQ ID NO 94
<211> LENGTH: 23
<212> TYPE: PRT
<213> ORGANISM: Homo sapiens -continued

```
<400> SEQUENCE: 94

Met Pro Arg Ser Cys Cys Ser Arg Ser Gly Ala Leu Leu Leu Ala Leu
1               5                   10                  15

Leu Leu Gln Ala Ser Met Glu
            20

<210> SEQ ID NO 95
<211> LENGTH: 26
<212> TYPE: PRT
<213> ORGANISM: Homo sapiens

<400> SEQUENCE: 95

Met Pro Arg Ser Cys Cys Ser Arg Ser Gly Ala Leu Leu Leu Ala Leu
1               5                   10                  15

Leu Leu Gln Ala Ser Met Glu Val Arg Gly
            20                  25

<210> SEQ ID NO 96
<211> LENGTH: 23
<212> TYPE: PRT
<213> ORGANISM: Homo sapiens

<400> SEQUENCE: 96

Met Ala Thr His His Thr Leu Trp Met Gly Leu Ala Leu Leu Gly Val
1               5                   10                  15

Leu Gly Asp Leu Gln Ala Ala
            20

<210> SEQ ID NO 97
<211> LENGTH: 22
<212> TYPE: PRT
<213> ORGANISM: Homo sapiens

<400> SEQUENCE: 97

Met Ala Thr His His Thr Leu Trp Met Gly Leu Ala Leu Leu Gly Val
1               5                   10                  15

Leu Gly Asp Leu Gln Ala
            20

<210> SEQ ID NO 98
<211> LENGTH: 18
<212> TYPE: PRT
<213> ORGANISM: Homo sapiens

<400> SEQUENCE: 98

Met Ala Thr His His Thr Leu Trp Met Gly Leu Ala Leu Leu Gly Val
1               5                   10                  15

Leu Gly

<210> SEQ ID NO 99
<211> LENGTH: 18
<212> TYPE: PRT
<213> ORGANISM: Homo sapiens

<400> SEQUENCE: 99

Met Val Arg Met Val Pro Val Leu Leu Ser Leu Leu Leu Leu Leu Gly
1               5                   10                  15

Pro Ala

<210> SEQ ID NO 100
<211> LENGTH: 20
<212> TYPE: PRT
```

<213> ORGANISM: Homo sapiens

<400> SEQUENCE: 100

Met Val Arg Met Val Pro Val Leu Leu Ser Leu Leu Leu Leu Leu Gly
1               5                   10                  15

Pro Ala Val Pro
            20

<210> SEQ ID NO 101
<211> LENGTH: 21
<212> TYPE: PRT
<213> ORGANISM: Homo sapiens

<400> SEQUENCE: 101

Met Val Arg Met Val Pro Val Leu Leu Ser Leu Leu Leu Leu Leu Gly
1               5                   10                  15

Pro Ala Val Pro Gln
            20

<210> SEQ ID NO 102
<211> LENGTH: 17
<212> TYPE: PRT
<213> ORGANISM: Homo sapiens

<400> SEQUENCE: 102

Met Val Arg Met Val Pro Val Leu Leu Ser Leu Leu Leu Leu Leu Gly
1               5                   10                  15

Pro

<210> SEQ ID NO 103
<211> LENGTH: 18
<212> TYPE: PRT
<213> ORGANISM: Homo sapiens

<400> SEQUENCE: 103

Met Arg Ser Ala Ala Val Leu Ala Leu Leu Leu Cys Ala Gly Gln Val
1               5                   10                  15

Thr Ala

<210> SEQ ID NO 104
<211> LENGTH: 15
<212> TYPE: PRT
<213> ORGANISM: Homo sapiens

<400> SEQUENCE: 104

Met Arg Ser Ala Ala Val Leu Ala Leu Leu Leu Cys Ala Gly Gln
1               5                   10                  15

<210> SEQ ID NO 105
<211> LENGTH: 14
<212> TYPE: PRT
<213> ORGANISM: Homo sapiens

<400> SEQUENCE: 105

Met Arg Ser Ala Ala Val Leu Ala Leu Leu Leu Cys Ala Gly
1               5                   10

<210> SEQ ID NO 106
<211> LENGTH: 26
<212> TYPE: PRT
<213> ORGANISM: Homo sapiens

<400> SEQUENCE: 106

Met Ala Arg Ser Asn Leu Pro Leu Ala Leu Gly Leu Ala Leu Val Ala
1               5                   10                  15

Phe Cys Leu Leu Ala Leu Pro Arg Asp Ala
            20                  25

<210> SEQ ID NO 107
<211> LENGTH: 18
<212> TYPE: PRT
<213> ORGANISM: Homo sapiens

<400> SEQUENCE: 107

Met Ala Arg Ser Asn Leu Pro Leu Ala Leu Gly Leu Ala Leu Val Ala
1               5                   10                  15

Phe Cys

<210> SEQ ID NO 108
<211> LENGTH: 20
<212> TYPE: PRT
<213> ORGANISM: Homo sapiens

<400> SEQUENCE: 108

Met Ala Arg Ser Asn Leu Pro Leu Ala Leu Gly Leu Ala Leu Val Ala
1               5                   10                  15

Phe Cys Leu Leu
            20

<210> SEQ ID NO 109
<211> LENGTH: 28
<212> TYPE: PRT
<213> ORGANISM: Homo sapiens

<400> SEQUENCE: 109

Met Ala Arg Ser Asn Leu Pro Leu Ala Leu Gly Leu Ala Leu Val Ala
1               5                   10                  15

Phe Cys Leu Leu Ala Leu Pro Arg Asp Ala Arg Ala
            20                  25

<210> SEQ ID NO 110
<211> LENGTH: 21
<212> TYPE: PRT
<213> ORGANISM: Homo sapiens

<400> SEQUENCE: 110

Met Ala Arg Ser Asn Leu Pro Leu Ala Leu Gly Leu Ala Leu Val Ala
1               5                   10                  15

Phe Cys Leu Leu Ala
            20

<210> SEQ ID NO 111
<211> LENGTH: 23
<212> TYPE: PRT
<213> ORGANISM: Homo sapiens

<400> SEQUENCE: 111

Met Ala Arg Ser Asn Leu Pro Leu Ala Leu Gly Leu Ala Leu Val Ala
1               5                   10                  15

Phe Cys Leu Leu Ala Leu Pro
            20

<210> SEQ ID NO 112
<211> LENGTH: 22
<212> TYPE: PRT
<213> ORGANISM: Homo sapiens

```
<400> SEQUENCE: 112

Met Met Lys Thr Leu Leu Leu Phe Val Gly Leu Leu Leu Thr Trp Glu
1               5                   10                  15

Ser Gly Gln Val Leu Gly
            20

<210> SEQ ID NO 113
<211> LENGTH: 18
<212> TYPE: PRT
<213> ORGANISM: Homo sapiens

<400> SEQUENCE: 113

Met Met Lys Thr Leu Leu Leu Phe Val Gly Leu Leu Leu Thr Trp Glu
1               5                   10                  15

Ser Gly

<210> SEQ ID NO 114
<211> LENGTH: 14
<212> TYPE: PRT
<213> ORGANISM: Homo sapiens

<400> SEQUENCE: 114

Met Met Lys Thr Leu Leu Leu Phe Val Gly Leu Leu Leu Thr
1               5                   10

<210> SEQ ID NO 115
<211> LENGTH: 24
<212> TYPE: PRT
<213> ORGANISM: Homo sapiens

<400> SEQUENCE: 115

Met Asp Gly Ala Met Gly Pro Arg Gly Leu Leu Leu Cys Met Tyr Leu
1               5                   10                  15

Val Ser Leu Leu Ile Leu Gln Ala
            20

<210> SEQ ID NO 116
<211> LENGTH: 29
<212> TYPE: PRT
<213> ORGANISM: Homo sapiens

<400> SEQUENCE: 116

Met Asp Gly Ala Met Gly Pro Arg Gly Leu Leu Leu Cys Met Tyr Leu
1               5                   10                  15

Val Ser Leu Leu Ile Leu Gln Ala Met Pro Ala Leu Gly
            20                  25

<210> SEQ ID NO 117
<211> LENGTH: 30
<212> TYPE: PRT
<213> ORGANISM: Homo sapiens

<400> SEQUENCE: 117

Met Asp Gly Ala Met Gly Pro Arg Gly Leu Leu Leu Cys Met Tyr Leu
1               5                   10                  15

Val Ser Leu Leu Ile Leu Gln Ala Met Pro Ala Leu Gly Ser
            20                  25                  30

<210> SEQ ID NO 118
<211> LENGTH: 23
<212> TYPE: PRT
<213> ORGANISM: Homo sapiens
```

```
<400> SEQUENCE: 118

Met Asp Gly Ala Met Gly Pro Arg Gly Leu Leu Leu Cys Met Tyr Leu
1               5                   10                  15
Val Ser Leu Leu Ile Leu Gln
            20

<210> SEQ ID NO 119
<211> LENGTH: 31
<212> TYPE: PRT
<213> ORGANISM: Homo sapiens

<400> SEQUENCE: 119

Met Asp Gly Ala Met Gly Pro Arg Gly Leu Leu Leu Cys Met Tyr Leu
1               5                   10                  15
Val Ser Leu Leu Ile Leu Gln Ala Met Pro Ala Leu Gly Ser Ala
            20                  25                  30

<210> SEQ ID NO 120
<211> LENGTH: 22
<212> TYPE: PRT
<213> ORGANISM: Homo sapiens

<400> SEQUENCE: 120

Met Lys Val Leu Ala Ala Gly Val Val Pro Leu Leu Leu Val Leu His
1               5                   10                  15
Trp Lys His Gly Ala Gly
            20

<210> SEQ ID NO 121
<211> LENGTH: 23
<212> TYPE: PRT
<213> ORGANISM: Homo sapiens

<400> SEQUENCE: 121

Met Lys Val Leu Ala Ala Gly Val Val Pro Leu Leu Leu Val Leu His
1               5                   10                  15
Trp Lys His Gly Ala Gly Ser
            20

<210> SEQ ID NO 122
<211> LENGTH: 18
<212> TYPE: PRT
<213> ORGANISM: Homo sapiens

<400> SEQUENCE: 122

Met Ser Leu Ser Ala Phe Thr Leu Phe Leu Ala Leu Ile Gly Gly Thr
1               5                   10                  15
Ser Gly

<210> SEQ ID NO 123
<211> LENGTH: 15
<212> TYPE: PRT
<213> ORGANISM: Homo sapiens

<400> SEQUENCE: 123

Met Ser Leu Ser Ala Phe Thr Leu Phe Leu Ala Leu Ile Gly Gly
1               5                   10                  15

<210> SEQ ID NO 124
<211> LENGTH: 17
<212> TYPE: PRT
<213> ORGANISM: Homo sapiens
```

```
<400> SEQUENCE: 124

Met Ser Leu Ser Ala Phe Thr Leu Phe Leu Ala Leu Ile Gly Gly Thr
1               5                   10                  15
Ser

<210> SEQ ID NO 125
<211> LENGTH: 14
<212> TYPE: PRT
<213> ORGANISM: Homo sapiens

<400> SEQUENCE: 125

Met Ser Leu Ser Ala Phe Thr Leu Phe Leu Ala Leu Ile Gly
1               5                   10

<210> SEQ ID NO 126
<211> LENGTH: 18
<212> TYPE: PRT
<213> ORGANISM: Homo sapiens

<400> SEQUENCE: 126

Met Lys Leu Leu Met Val Leu Met Leu Ala Ala Leu Ser Gln His Cys
1               5                   10                  15
Tyr Ala

<210> SEQ ID NO 127
<211> LENGTH: 30
<212> TYPE: PRT
<213> ORGANISM: Homo sapiens

<400> SEQUENCE: 127

Met Gln Ser Val Gln Ser Thr Ser Phe Cys Leu Arg Lys Gln Cys Leu
1               5                   10                  15
Cys Leu Thr Phe Leu Leu Leu His Leu Leu Gly Gln Val Ala
            20                  25                  30

<210> SEQ ID NO 128
<211> LENGTH: 32
<212> TYPE: PRT
<213> ORGANISM: Homo sapiens

<400> SEQUENCE: 128

Met Gln Ser Val Gln Ser Thr Ser Phe Cys Leu Arg Lys Gln Cys Leu
1               5                   10                  15
Cys Leu Thr Phe Leu Leu Leu His Leu Leu Gly Gln Val Ala Ala Thr
            20                  25                  30

<210> SEQ ID NO 129
<211> LENGTH: 28
<212> TYPE: PRT
<213> ORGANISM: Homo sapiens

<400> SEQUENCE: 129

Met Gln Ser Val Gln Ser Thr Ser Phe Cys Leu Arg Lys Gln Cys Leu
1               5                   10                  15
Cys Leu Thr Phe Leu Leu Leu His Leu Leu Gly Gln
            20                  25

<210> SEQ ID NO 130
<211> LENGTH: 27
<212> TYPE: PRT
<213> ORGANISM: Homo sapiens
```

```
<400> SEQUENCE: 130

Met Gln Ser Val Gln Ser Thr Ser Phe Cys Leu Arg Lys Gln Cys Leu
1               5                   10                  15

Cys Leu Thr Phe Leu Leu Leu His Leu Leu Gly
            20                  25

<210> SEQ ID NO 131
<211> LENGTH: 31
<212> TYPE: PRT
<213> ORGANISM: Homo sapiens

<400> SEQUENCE: 131

Met Gln Ser Val Gln Ser Thr Ser Phe Cys Leu Arg Lys Gln Cys Leu
1               5                   10                  15

Cys Leu Thr Phe Leu Leu Leu His Leu Leu Gly Gln Val Ala Ala
            20                  25                  30

<210> SEQ ID NO 132
<211> LENGTH: 26
<212> TYPE: PRT
<213> ORGANISM: Homo sapiens

<400> SEQUENCE: 132

Met Ala Arg Gly Gly Arg Gly Arg Arg Leu Gly Leu Ala Leu Gly Leu
1               5                   10                  15

Leu Leu Ala Leu Val Leu Ala Pro Arg Val
            20                  25

<210> SEQ ID NO 133
<211> LENGTH: 22
<212> TYPE: PRT
<213> ORGANISM: Homo sapiens

<400> SEQUENCE: 133

Met Ala Arg Gly Gly Arg Gly Arg Arg Leu Gly Leu Ala Leu Gly Leu
1               5                   10                  15

Leu Leu Ala Leu Val Leu
            20

<210> SEQ ID NO 134
<211> LENGTH: 29
<212> TYPE: PRT
<213> ORGANISM: Homo sapiens

<400> SEQUENCE: 134

Met Ala Arg Gly Gly Arg Gly Arg Arg Leu Gly Leu Ala Leu Gly Leu
1               5                   10                  15

Leu Leu Ala Leu Val Leu Ala Pro Arg Val Leu Arg Ala
            20                  25

<210> SEQ ID NO 135
<211> LENGTH: 24
<212> TYPE: PRT
<213> ORGANISM: Homo sapiens

<400> SEQUENCE: 135

Met Ala Arg Gly Gly Arg Gly Arg Arg Leu Gly Leu Ala Leu Gly Leu
1               5                   10                  15

Leu Leu Ala Leu Val Leu Ala Pro
            20

<210> SEQ ID NO 136
```

```
<211> LENGTH: 23
<212> TYPE: PRT
<213> ORGANISM: Homo sapiens

<400> SEQUENCE: 136

Met Ala Arg Gly Gly Arg Gly Arg Arg Leu Gly Leu Ala Leu Gly Leu
1               5                   10                  15

Leu Leu Ala Leu Val Leu Ala
            20

<210> SEQ ID NO 137
<211> LENGTH: 25
<212> TYPE: PRT
<213> ORGANISM: Homo sapiens

<400> SEQUENCE: 137

Met Arg Leu Gly Pro Arg Thr Ala Ala Leu Gly Leu Leu Leu Leu Cys
1               5                   10                  15

Ala Ala Ala Ala Gly Ala Gly Lys Ala
            20                  25

<210> SEQ ID NO 138
<211> LENGTH: 19
<212> TYPE: PRT
<213> ORGANISM: Homo sapiens

<400> SEQUENCE: 138

Met Arg Leu Gly Pro Arg Thr Ala Ala Leu Gly Leu Leu Leu Leu Cys
1               5                   10                  15

Ala Ala Ala

<210> SEQ ID NO 139
<211> LENGTH: 22
<212> TYPE: PRT
<213> ORGANISM: Homo sapiens

<400> SEQUENCE: 139

Met Arg Leu Gly Pro Arg Thr Ala Ala Leu Gly Leu Leu Leu Leu Cys
1               5                   10                  15

Ala Ala Ala Ala Gly Ala
            20

<210> SEQ ID NO 140
<211> LENGTH: 18
<212> TYPE: PRT
<213> ORGANISM: Homo sapiens

<400> SEQUENCE: 140

Met Arg Leu Gly Pro Arg Thr Ala Ala Leu Gly Leu Leu Leu Leu Cys
1               5                   10                  15

Ala Ala

<210> SEQ ID NO 141
<211> LENGTH: 20
<212> TYPE: PRT
<213> ORGANISM: Homo sapiens

<400> SEQUENCE: 141

Met Arg Leu Gly Pro Arg Thr Ala Ala Leu Gly Leu Leu Leu Leu Cys
1               5                   10                  15

Ala Ala Ala Ala
            20
```

<210> SEQ ID NO 142
<211> LENGTH: 21
<212> TYPE: PRT
<213> ORGANISM: Homo sapiens

<400> SEQUENCE: 142

Met Arg Leu Gly Pro Arg Thr Ala Ala Leu Gly Leu Leu Leu Leu Cys
1               5                   10                  15

Ala Ala Ala Ala Gly
            20

<210> SEQ ID NO 143
<211> LENGTH: 23
<212> TYPE: PRT
<213> ORGANISM: Homo sapiens

<400> SEQUENCE: 143

Met Arg Leu Gly Pro Arg Thr Ala Ala Leu Gly Leu Leu Leu Leu Cys
1               5                   10                  15

Ala Ala Ala Ala Gly Ala Gly
            20

<210> SEQ ID NO 144
<211> LENGTH: 19
<212> TYPE: PRT
<213> ORGANISM: Homo sapiens

<400> SEQUENCE: 144

Met Ala Trp Phe Ala Leu Tyr Leu Leu Ser Leu Leu Trp Ala Thr Ala
1               5                   10                  15

Gly Thr Ser

<210> SEQ ID NO 145
<211> LENGTH: 18
<212> TYPE: PRT
<213> ORGANISM: Homo sapiens

<400> SEQUENCE: 145

Met Ala Trp Phe Ala Leu Tyr Leu Leu Ser Leu Leu Trp Ala Thr Ala
1               5                   10                  15

Gly Thr

<210> SEQ ID NO 146
<211> LENGTH: 20
<212> TYPE: PRT
<213> ORGANISM: Homo sapiens

<400> SEQUENCE: 146

Met Ala Trp Phe Ala Leu Tyr Leu Leu Ser Leu Leu Trp Ala Thr Ala
1               5                   10                  15

Gly Thr Ser Thr
            20

<210> SEQ ID NO 147
<211> LENGTH: 24
<212> TYPE: PRT
<213> ORGANISM: Homo sapiens

<400> SEQUENCE: 147

Met Ala Trp Phe Ala Leu Tyr Leu Leu Ser Leu Leu Trp Ala Thr Ala
1               5                   10                  15

Gly Thr Ser Thr Gln Thr Gln Ser

-continued

```
                20

<210> SEQ ID NO 148
<211> LENGTH: 16
<212> TYPE: PRT
<213> ORGANISM: Homo sapiens

<400> SEQUENCE: 148

Met Ala Trp Phe Ala Leu Tyr Leu Leu Ser Leu Leu Trp Ala Thr Ala
1               5                   10                  15

<210> SEQ ID NO 149
<211> LENGTH: 17
<212> TYPE: PRT
<213> ORGANISM: Homo sapiens

<400> SEQUENCE: 149

Met Ala Trp Phe Ala Leu Tyr Leu Leu Ser Leu Leu Trp Ala Thr Ala
1               5                   10                  15

Gly

<210> SEQ ID NO 150
<211> LENGTH: 14
<212> TYPE: PRT
<213> ORGANISM: Homo sapiens

<400> SEQUENCE: 150

Met Ala Trp Phe Ala Leu Tyr Leu Leu Ser Leu Leu Trp Ala
1               5                   10

<210> SEQ ID NO 151
<211> LENGTH: 17
<212> TYPE: PRT
<213> ORGANISM: Homo sapiens

<400> SEQUENCE: 151

Met His Leu Leu Leu Phe Gln Leu Leu Val Leu Leu Pro Leu Gly Lys
1               5                   10                  15

Thr

<210> SEQ ID NO 152
<211> LENGTH: 18
<212> TYPE: PRT
<213> ORGANISM: Homo sapiens

<400> SEQUENCE: 152

Met Pro Leu Gly Leu Leu Trp Leu Gly Leu Ala Leu Leu Gly Ala Leu
1               5                   10                  15

His Ala

<210> SEQ ID NO 153
<211> LENGTH: 20
<212> TYPE: PRT
<213> ORGANISM: Homo sapiens

<400> SEQUENCE: 153

Met Pro Leu Gly Leu Leu Trp Leu Gly Leu Ala Leu Leu Gly Ala Leu
1               5                   10                  15

His Ala Gln Ala
            20

<210> SEQ ID NO 154
<211> LENGTH: 15
```

```
<212> TYPE: PRT
<213> ORGANISM: Homo sapiens

<400> SEQUENCE: 154

Met Pro Leu Gly Leu Leu Trp Leu Gly Leu Ala Leu Leu Gly Ala
1               5                   10                  15

<210> SEQ ID NO 155
<211> LENGTH: 29
<212> TYPE: PRT
<213> ORGANISM: Homo sapiens

<400> SEQUENCE: 155

Met Arg His Asn Trp Thr Pro Asp Leu Ser Pro Leu Trp Val Leu Leu
1               5                   10                  15

Leu Cys Ala His Val Val Thr Leu Leu Val Arg Ala Thr
            20                  25

<210> SEQ ID NO 156
<211> LENGTH: 24
<212> TYPE: PRT
<213> ORGANISM: Homo sapiens

<400> SEQUENCE: 156

Met Arg His Asn Trp Thr Pro Asp Leu Ser Pro Leu Trp Val Leu Leu
1               5                   10                  15

Leu Cys Ala His Val Val Thr Leu
            20

<210> SEQ ID NO 157
<211> LENGTH: 28
<212> TYPE: PRT
<213> ORGANISM: Homo sapiens

<400> SEQUENCE: 157

Met Arg His Asn Trp Thr Pro Asp Leu Ser Pro Leu Trp Val Leu Leu
1               5                   10                  15

Leu Cys Ala His Val Val Thr Leu Leu Val Arg Ala
            20                  25

<210> SEQ ID NO 158
<211> LENGTH: 19
<212> TYPE: PRT
<213> ORGANISM: Homo sapiens

<400> SEQUENCE: 158

Met Leu Pro Leu Thr Met Thr Val Leu Ile Leu Leu Leu Leu Pro Thr
1               5                   10                  15

Gly Gln Ala

<210> SEQ ID NO 159
<211> LENGTH: 18
<212> TYPE: PRT
<213> ORGANISM: Homo sapiens

<400> SEQUENCE: 159

Met Leu Pro Leu Thr Met Thr Val Leu Ile Leu Leu Leu Leu Pro Thr
1               5                   10                  15

Gly Gln

<210> SEQ ID NO 160
<211> LENGTH: 21
<212> TYPE: PRT
```

```
<213> ORGANISM: Homo sapiens

<400> SEQUENCE: 160

Met Leu Pro Leu Thr Met Thr Val Leu Ile Leu Leu Leu Pro Thr
1               5                   10                  15

Gly Gln Ala Ala Pro
            20

<210> SEQ ID NO 161
<211> LENGTH: 15
<212> TYPE: PRT
<213> ORGANISM: Homo sapiens

<400> SEQUENCE: 161

Met Thr Ser Ile Leu Thr Val Leu Ile Cys Leu Gly Leu Ser Leu
1               5                   10                  15

<210> SEQ ID NO 162
<211> LENGTH: 26
<212> TYPE: PRT
<213> ORGANISM: Homo sapiens

<400> SEQUENCE: 162

Met Glu Asn Pro Ser Pro Ala Ala Ala Leu Gly Lys Ala Leu Cys Ala
1               5                   10                  15

Leu Leu Leu Ala Thr Leu Gly Ala Ala Gly
            20                  25

<210> SEQ ID NO 163
<211> LENGTH: 25
<212> TYPE: PRT
<213> ORGANISM: Homo sapiens

<400> SEQUENCE: 163

Met Glu Asn Pro Ser Pro Ala Ala Ala Leu Gly Lys Ala Leu Cys Ala
1               5                   10                  15

Leu Leu Leu Ala Thr Leu Gly Ala Ala
            20                  25

<210> SEQ ID NO 164
<211> LENGTH: 24
<212> TYPE: PRT
<213> ORGANISM: Homo sapiens

<400> SEQUENCE: 164

Met Glu Asn Pro Ser Pro Ala Ala Ala Leu Gly Lys Ala Leu Cys Ala
1               5                   10                  15

Leu Leu Leu Ala Thr Leu Gly Ala
            20

<210> SEQ ID NO 165
<211> LENGTH: 28
<212> TYPE: PRT
<213> ORGANISM: Homo sapiens

<400> SEQUENCE: 165

Met Glu Asn Pro Ser Pro Ala Ala Ala Leu Gly Lys Ala Leu Cys Ala
1               5                   10                  15

Leu Leu Leu Ala Thr Leu Gly Ala Ala Gly Gln Pro
            20                  25

<210> SEQ ID NO 166
<211> LENGTH: 20
```

<212> TYPE: PRT
<213> ORGANISM: Homo sapiens

<400> SEQUENCE: 166

Met Lys Gly Trp Gly Trp Leu Ala Leu Leu Gly Ala Leu Leu Gly
1               5                   10                  15

Thr Ala Trp Ala
            20

<210> SEQ ID NO 167
<211> LENGTH: 18
<212> TYPE: PRT
<213> ORGANISM: Homo sapiens

<400> SEQUENCE: 167

Met Lys Gly Trp Gly Trp Leu Ala Leu Leu Gly Ala Leu Leu Gly
1               5                   10                  15

Thr Ala

<210> SEQ ID NO 168
<211> LENGTH: 16
<212> TYPE: PRT
<213> ORGANISM: Homo sapiens

<400> SEQUENCE: 168

Met Lys Gly Trp Gly Trp Leu Ala Leu Leu Gly Ala Leu Leu Gly
1               5                   10                  15

<210> SEQ ID NO 169
<211> LENGTH: 24
<212> TYPE: PRT
<213> ORGANISM: Homo sapiens

<400> SEQUENCE: 169

Met Arg Ala Pro Gly Cys Gly Arg Leu Val Leu Pro Leu Leu Leu
1               5                   10                  15

Ala Ala Ala Ala Leu Ala Glu Gly
            20

<210> SEQ ID NO 170
<211> LENGTH: 19
<212> TYPE: PRT
<213> ORGANISM: Homo sapiens

<400> SEQUENCE: 170

Met Arg Ala Pro Gly Cys Gly Arg Leu Val Leu Pro Leu Leu Leu
1               5                   10                  15

Ala Ala Ala

<210> SEQ ID NO 171
<211> LENGTH: 22
<212> TYPE: PRT
<213> ORGANISM: Homo sapiens

<400> SEQUENCE: 171

Met Arg Ala Pro Gly Cys Gly Arg Leu Val Leu Pro Leu Leu Leu
1               5                   10                  15

Ala Ala Ala Ala Leu Ala
            20

<210> SEQ ID NO 172
<211> LENGTH: 20
<212> TYPE: PRT

<213> ORGANISM: Homo sapiens

<400> SEQUENCE: 172

Met Arg Ala Pro Gly Cys Gly Arg Leu Val Leu Pro Leu Leu Leu Leu
1               5                   10                  15

Ala Ala Ala Ala
            20

<210> SEQ ID NO 173
<211> LENGTH: 26
<212> TYPE: PRT
<213> ORGANISM: Homo sapiens

<400> SEQUENCE: 173

Met Arg Ala Pro Gly Cys Gly Arg Leu Val Leu Pro Leu Leu Leu Leu
1               5                   10                  15

Ala Ala Ala Ala Leu Ala Glu Gly Asp Ala
            20                  25

<210> SEQ ID NO 174
<211> LENGTH: 21
<212> TYPE: PRT
<213> ORGANISM: Homo sapiens

<400> SEQUENCE: 174

Met Arg Ala Pro Gly Cys Gly Arg Leu Val Leu Pro Leu Leu Leu Leu
1               5                   10                  15

Ala Ala Ala Ala Leu
            20

<210> SEQ ID NO 175
<211> LENGTH: 18
<212> TYPE: PRT
<213> ORGANISM: Homo sapiens

<400> SEQUENCE: 175

Met Ser Leu Gly Gln Ser Ala Cys Leu Phe Leu Ser Ile Ala Arg Ser
1               5                   10                  15

Arg Ser

<210> SEQ ID NO 176
<211> LENGTH: 18
<212> TYPE: PRT
<213> ORGANISM: Homo sapiens

<400> SEQUENCE: 176

Met Gln Arg Leu Gly Ala Thr Leu Leu Cys Leu Leu Leu Ala Ala Ala
1               5                   10                  15

Val Pro

<210> SEQ ID NO 177
<211> LENGTH: 19
<212> TYPE: PRT
<213> ORGANISM: Homo sapiens

<400> SEQUENCE: 177

Met Gln Arg Leu Gly Ala Thr Leu Leu Cys Leu Leu Leu Ala Ala Ala
1               5                   10                  15

Val Pro Thr

<210> SEQ ID NO 178
<211> LENGTH: 22

```
<212> TYPE: PRT
<213> ORGANISM: Homo sapiens

<400> SEQUENCE: 178

Met Gln Arg Leu Gly Ala Thr Leu Leu Cys Leu Leu Leu Ala Ala Ala
1               5                   10                  15

Val Pro Thr Ala Pro Ala
            20

<210> SEQ ID NO 179
<211> LENGTH: 16
<212> TYPE: PRT
<213> ORGANISM: Homo sapiens

<400> SEQUENCE: 179

Met Gln Arg Leu Gly Ala Thr Leu Leu Cys Leu Leu Leu Ala Ala Ala
1               5                   10                  15

<210> SEQ ID NO 180
<211> LENGTH: 21
<212> TYPE: PRT
<213> ORGANISM: Homo sapiens

<400> SEQUENCE: 180

Met Gln Arg Leu Gly Ala Thr Leu Leu Cys Leu Leu Leu Ala Ala Ala
1               5                   10                  15

Val Pro Thr Ala Pro
            20

<210> SEQ ID NO 181
<211> LENGTH: 26
<212> TYPE: PRT
<213> ORGANISM: Homo sapiens

<400> SEQUENCE: 181

Met Ser Ala Ser Lys Ile Pro Leu Phe Lys Met Lys Asp Leu Ile Leu
1               5                   10                  15

Ile Leu Cys Leu Leu Glu Met Ser Phe Ala
            20                  25

<210> SEQ ID NO 182
<211> LENGTH: 28
<212> TYPE: PRT
<213> ORGANISM: Homo sapiens

<400> SEQUENCE: 182

Met Ser Ala Ser Lys Ile Pro Leu Phe Lys Met Lys Asp Leu Ile Leu
1               5                   10                  15

Ile Leu Cys Leu Leu Glu Met Ser Phe Ala Val Pro
            20                  25

<210> SEQ ID NO 183
<211> LENGTH: 18
<212> TYPE: PRT
<213> ORGANISM: Homo sapiens

<400> SEQUENCE: 183

Met Glu Met Phe Gln Gly Leu Leu Leu Leu Leu Leu Leu Ser Met Gly
1               5                   10                  15

Gly Thr

<210> SEQ ID NO 184
<211> LENGTH: 20
```

<212> TYPE: PRT
<213> ORGANISM: Homo sapiens

<400> SEQUENCE: 184

Met Glu Met Phe Gln Gly Leu Leu Leu Leu Leu Leu Ser Met Gly
1               5                   10                  15

Gly Thr Trp Ala
            20

<210> SEQ ID NO 185
<211> LENGTH: 16
<212> TYPE: PRT
<213> ORGANISM: Homo sapiens

<400> SEQUENCE: 185

Met Glu Met Phe Gln Gly Leu Leu Leu Leu Leu Leu Ser Met Gly
1               5                   10                  15

<210> SEQ ID NO 186
<211> LENGTH: 18
<212> TYPE: PRT
<213> ORGANISM: Homo sapiens

<400> SEQUENCE: 186

Met Thr Met Arg Ser Leu Leu Arg Thr Pro Phe Leu Cys Gly Leu Leu
1               5                   10                  15

Trp Ala

<210> SEQ ID NO 187
<211> LENGTH: 20
<212> TYPE: PRT
<213> ORGANISM: Homo sapiens

<400> SEQUENCE: 187

Met Thr Met Arg Ser Leu Leu Arg Thr Pro Phe Leu Cys Gly Leu Leu
1               5                   10                  15

Trp Ala Phe Cys
            20

<210> SEQ ID NO 188
<211> LENGTH: 26
<212> TYPE: PRT
<213> ORGANISM: Homo sapiens

<400> SEQUENCE: 188

Met Thr Met Arg Ser Leu Leu Arg Thr Pro Phe Leu Cys Gly Leu Leu
1               5                   10                  15

Trp Ala Phe Cys Ala Pro Gly Ala Arg Ala
            20                  25

<210> SEQ ID NO 189
<211> LENGTH: 23
<212> TYPE: PRT
<213> ORGANISM: Homo sapiens

<400> SEQUENCE: 189

Met Thr Met Arg Ser Leu Leu Arg Thr Pro Phe Leu Cys Gly Leu Leu
1               5                   10                  15

Trp Ala Phe Cys Ala Pro Gly
            20

<210> SEQ ID NO 190
<211> LENGTH: 13

```
<212> TYPE: PRT
<213> ORGANISM: Homo sapiens

<400> SEQUENCE: 190

Met Leu Leu Leu Leu Thr Leu Ala Leu Leu Gly Gly Pro
1               5                   10

<210> SEQ ID NO 191
<211> LENGTH: 16
<212> TYPE: PRT
<213> ORGANISM: Homo sapiens

<400> SEQUENCE: 191

Met Leu Leu Leu Leu Thr Leu Ala Leu Leu Gly Gly Pro Thr Trp Ala
1               5                   10                  15

<210> SEQ ID NO 192
<211> LENGTH: 14
<212> TYPE: PRT
<213> ORGANISM: Homo sapiens

<400> SEQUENCE: 192

Met Leu Leu Leu Leu Thr Leu Ala Leu Leu Gly Gly Pro Thr
1               5                   10

<210> SEQ ID NO 193
<211> LENGTH: 17
<212> TYPE: PRT
<213> ORGANISM: Homo sapiens

<400> SEQUENCE: 193

Met Leu Leu Leu Leu Thr Leu Ala Leu Leu Gly Gly Pro Thr Trp Ala
1               5                   10                  15

Gly

<210> SEQ ID NO 194
<211> LENGTH: 25
<212> TYPE: PRT
<213> ORGANISM: Homo sapiens

<400> SEQUENCE: 194

Met Glu Ala Ala Pro Ser Arg Phe Met Phe Leu Leu Phe Leu Leu Thr
1               5                   10                  15

Cys Glu Leu Ala Ala Glu Val Ala Ala
            20                  25

<210> SEQ ID NO 195
<211> LENGTH: 21
<212> TYPE: PRT
<213> ORGANISM: Homo sapiens

<400> SEQUENCE: 195

Met Glu Ala Ala Pro Ser Arg Phe Met Phe Leu Leu Phe Leu Leu Thr
1               5                   10                  15

Cys Glu Leu Ala Ala
            20

<210> SEQ ID NO 196
<211> LENGTH: 18
<212> TYPE: PRT
<213> ORGANISM: Homo sapiens

<400> SEQUENCE: 196

Met Pro Pro Phe Leu Leu Leu Thr Cys Leu Phe Ile Thr Gly Thr Ser
1               5                   10                  15
```

-continued

```
                1               5                  10                 15
Val Ser

<210> SEQ ID NO 197
<211> LENGTH: 16
<212> TYPE: PRT
<213> ORGANISM: Homo sapiens

<400> SEQUENCE: 197

Met Pro Pro Phe Leu Leu Leu Thr Cys Leu Phe Ile Thr Gly Thr Ser
1               5                   10                  15

<210> SEQ ID NO 198
<211> LENGTH: 15
<212> TYPE: PRT
<213> ORGANISM: Homo sapiens

<400> SEQUENCE: 198

Met Pro Pro Phe Leu Leu Leu Thr Cys Leu Phe Ile Thr Gly Thr
1               5                   10                  15

<210> SEQ ID NO 199
<211> LENGTH: 21
<212> TYPE: PRT
<213> ORGANISM: Homo sapiens

<400> SEQUENCE: 199

Met Gly Pro Val Arg Leu Gly Ile Leu Leu Phe Leu Phe Leu Ala Val
1               5                   10                  15

His Glu Ala Trp Ala
            20

<210> SEQ ID NO 200
<211> LENGTH: 29
<212> TYPE: PRT
<213> ORGANISM: Homo sapiens

<400> SEQUENCE: 200

Met Arg His Asn Trp Thr Pro Asp Leu Ser Pro Leu Trp Val Leu Leu
1               5                   10                  15

Leu Cys Ala His Val Val Thr Leu Leu Val Arg Ala Thr
            20                  25

<210> SEQ ID NO 201
<211> LENGTH: 24
<212> TYPE: PRT
<213> ORGANISM: Homo sapiens

<400> SEQUENCE: 201

Met Arg His Asn Trp Thr Pro Asp Leu Ser Pro Leu Trp Val Leu Leu
1               5                   10                  15

Leu Cys Ala His Val Val Thr Leu
            20

<210> SEQ ID NO 202
<211> LENGTH: 28
<212> TYPE: PRT
<213> ORGANISM: Homo sapiens

<400> SEQUENCE: 202

Met Arg His Asn Trp Thr Pro Asp Leu Ser Pro Leu Trp Val Leu Leu
1               5                   10                  15

Leu Cys Ala His Val Val Thr Leu Leu Val Arg Ala
```

```
                        20                  25

<210> SEQ ID NO 203
<211> LENGTH: 23
<212> TYPE: PRT
<213> ORGANISM: Homo sapiens

<400> SEQUENCE: 203

Met Glu Ile Cys Arg Gly Leu Arg Ser His Leu Ile Thr Leu Leu Leu
1               5                   10                  15

Phe Leu Phe His Ser Glu Thr
            20

<210> SEQ ID NO 204
<211> LENGTH: 25
<212> TYPE: PRT
<213> ORGANISM: Homo sapiens

<400> SEQUENCE: 204

Met Glu Ile Cys Arg Gly Leu Arg Ser His Leu Ile Thr Leu Leu Leu
1               5                   10                  15

Phe Leu Phe His Ser Glu Thr Ile Cys
            20                  25

<210> SEQ ID NO 205
<211> LENGTH: 32
<212> TYPE: PRT
<213> ORGANISM: Homo sapiens

<400> SEQUENCE: 205

Met Trp Ala Pro Arg Cys Arg Arg Phe Trp Ser Arg Trp Glu Gln Val
1               5                   10                  15

Ala Ala Leu Leu Leu Leu Leu Leu Leu Gly Val Pro Pro Arg Ser
            20                  25                  30

<210> SEQ ID NO 206
<211> LENGTH: 34
<212> TYPE: PRT
<213> ORGANISM: Homo sapiens

<400> SEQUENCE: 206

Met Trp Ala Pro Arg Cys Arg Arg Phe Trp Ser Arg Trp Glu Gln Val
1               5                   10                  15

Ala Ala Leu Leu Leu Leu Leu Leu Leu Gly Val Pro Pro Arg Ser
            20                  25                  30

Leu Ala

<210> SEQ ID NO 207
<211> LENGTH: 29
<212> TYPE: PRT
<213> ORGANISM: Homo sapiens

<400> SEQUENCE: 207

Met Trp Ala Pro Arg Cys Arg Arg Phe Trp Ser Arg Trp Glu Gln Val
1               5                   10                  15

Ala Ala Leu Leu Leu Leu Leu Leu Leu Gly Val Pro
            20                  25

<210> SEQ ID NO 208
<211> LENGTH: 30
<212> TYPE: PRT
<213> ORGANISM: Homo sapiens
```

<400> SEQUENCE: 208

Met Trp Ala Pro Arg Cys Arg Arg Phe Trp Ser Arg Trp Glu Gln Val
1               5                   10                  15
Ala Ala Leu Leu Leu Leu Leu Leu Leu Leu Gly Val Pro Pro
            20                  25                  30

<210> SEQ ID NO 209
<211> LENGTH: 27
<212> TYPE: PRT
<213> ORGANISM: Homo sapiens

<400> SEQUENCE: 209

Met Trp Ala Pro Arg Cys Arg Arg Phe Trp Ser Arg Trp Glu Gln Val
1               5                   10                  15
Ala Ala Leu Leu Leu Leu Leu Leu Leu Leu Gly
            20                  25

<210> SEQ ID NO 210
<211> LENGTH: 26
<212> TYPE: PRT
<213> ORGANISM: Homo sapiens

<400> SEQUENCE: 210

Met Trp Cys Ala Ser Pro Val Ala Val Val Ala Phe Cys Ala Gly Leu
1               5                   10                  15
Leu Val Ser His Pro Val Leu Thr Gln Gly
            20                  25

<210> SEQ ID NO 211
<211> LENGTH: 24
<212> TYPE: PRT
<213> ORGANISM: Homo sapiens

<400> SEQUENCE: 211

Met Trp Cys Ala Ser Pro Val Ala Val Val Ala Phe Cys Ala Gly Leu
1               5                   10                  15
Leu Val Ser His Pro Val Leu Thr
            20

<210> SEQ ID NO 212
<211> LENGTH: 726
<212> TYPE: DNA
<213> ORGANISM: Homo sapiens

<400> SEQUENCE: 212
atgccccggg gcttcacctg ctgcgctat cttgggatct tccttggcgt ggccttgggg      60
aatgagcctt tggagatgtg gcccttgacg cagaatgagg agtgcactgt cacgggtttt     120
ctgcgggaca agctgcagta caggagccga cttcagtaca tgaaacacta cttccccatc    180
aactacaaga tcagtgtgcc ttacgagggg gtgttcagaa tcgccaacgt caccaggctg    240
agggcccagg tgagcgagcg ggagctgcgg tatctgtggg tcttggtgag cctcagtgcc    300
actgagtcgg tgcaggacgt gctgctcgag ggccacccat cctggaagta cctgcaggag    360
gtgcagacgc tgctgctgaa tgtccagcag ggcctcacgg atgtggaggt cagccccaag    420
gtggaatccg tgttgtccct cttgaatgcc ccagggccaa acctgaagct ggtgcggccc    480
aaagccctgc tggacaactg cttccgggtc atggagctgc tgtactgctc ctgctgtaaa    540
caaagctccg tcctaaactg gcaggactgt gaggtgccaa gtcctcagtc ttgcagccca    600
gagccctcat tgcagtatgc ggccacccag ctgtaccctc cgccccgtgt ggtccccagc    660

| | |
|---|---:|
| tccccgcctc actccacggg ctcggtgagg ccggtcaggg cacagggcga gggcctcttg | 720 |
| ccctag | 726 |

<210> SEQ ID NO 213
<211> LENGTH: 726
<212> TYPE: DNA
<213> ORGANISM: Homo sapiens

<400> SEQUENCE: 213

| | |
|---|---:|
| atgccccggg gcttcacctg gctgcgctat cttgggatct tccttggcgt ggccttgggg | 60 |
| aatgagcctt tggagatgtg gcccttgacg cagaatgagg agtgcactgt cacgggtttt | 120 |
| ctgcgggaca agctgcagta caggagccga cttcagtaca tgaaacacta cttccccatc | 180 |
| aactacaaga tcagtgtgcc ttacgagggg gtgttcagaa tcgccaacgt caccaggctg | 240 |
| agggcccagg tgagcgagcg ggagctgcgg tatctgtggg tcttggtgag cctcagtgcc | 300 |
| actgagtcgg tgcaggacgt gctgctcgag ggccacccat cctggaagta cctgcaggag | 360 |
| gtgcagacgc tgctgctgaa tgtccagcag ggcctcacgg atgtggaggt cagccccaag | 420 |
| gtggaatccg tgttgtccct cttgaatgcc ccagggccaa acctgaagct ggtgcggccc | 480 |
| aaagccctgc tggacaactg cttccgggtc atggagctgc tgtactgctc ctgctgtaaa | 540 |
| caaagctccg tcctaaactg gcaggactgt gaggtgccaa gtcctcagtc ttgcagccca | 600 |
| gagccctcat tgcagtatgc ggccacccag ctgtaccctc cgccccgtg gtccccagc | 660 |
| tccccgcctc actccacggg ctcggtgagg ccggtcaggg cacagggcga gggcctcttg | 720 |
| ccctga | 726 |

<210> SEQ ID NO 214
<211> LENGTH: 843
<212> TYPE: DNA
<213> ORGANISM: Homo sapiens

<400> SEQUENCE: 214

| | |
|---|---:|
| atgccccggg gcttcacctg gctgcgctat cttgggatct tccttggcgt ggccttgggg | 60 |
| aatgagcctt tggagatgtg gcccttgacg cagaatgagg agtgcactgt cacgggtttt | 120 |
| ctgcgggaca agctgcagta caggagccga cttcagtaca tgaaacacta cttccccatc | 180 |
| aactacaaga tcagtgtgcc ttacgagggg gtgttcagaa tcgccaacgt caccaggctg | 240 |
| agggcccagg tgagcgagcg ggagctgcgg tatctgtggg tcttggtgag cctcagtgcc | 300 |
| actgagtcgg tgcaggacgt gctgctcgag ggccacccat cctggaagta cctgcaggag | 360 |
| gtgcagacgc tgctgctgaa tgtccagcag ggcctcacgg atgtggaggt cagccccaag | 420 |
| gtggaatccg tgttgtccct cttgaatgcc ccagggccaa acctgaagct ggtgcggccc | 480 |
| aaagccctgc tggacaactg cttccgggtc atggagctgc tgtactgctc ctgctgtaaa | 540 |
| caaagctccg tcctaaactg gcaggactgt gaggtgccaa gtcctcagtc ttgcagccca | 600 |
| gagccctcat tgcagtatgc ggccacccag ctgtaccctc cgccccgtg gtccccagc | 660 |
| tccccgcctc actccacggg ctcggtgagg ccggtcaggg cacagggcga gggcctcttg | 720 |
| ccctacccag ctttcttgta caaagtggtg atcgaaggta agcctatccc taaccctctc | 780 |
| ctcggtctcg attctacgcg taccggtcat catcaccatc accatcacca tggaggacag | 840 |
| tga | 843 |

<210> SEQ ID NO 215
<211> LENGTH: 843
<212> TYPE: DNA

-continued

<213> ORGANISM: Homo sapiens

<400> SEQUENCE: 215

```
atgccccggg gcttcacctg gctgcgctat cttgggatct tccttggcgt ggccttgggg    60
aatgagcctt tggagatgtg gcccttgacg cagaatgagg agtgcactgt cacgggtttt   120
ctgcgggaca agctgcagta caggagccga cttcagtaca tgaaacacta cttccccatc   180
aactacaaga tcagtgtgcc ttacgagggg gtgttcagaa tcgccaacgt caccaggctg   240
agggcccagg tgagcgagcg ggagctgcgg tatctgtggg tcttggtgag cctcagtgcc   300
actgagtcgg tgcaggacgt gctgctcgag ggccacccat cctggaagta cctgcaggag   360
gtgcagacgc tgctgctgaa tgtccagcag ggcctcacgg atgtggaggt cagccccaag   420
gtggaatccg tgttgtccct cttgaatgcc ccagggccaa acctgaagct ggtgcggccc   480
aaagccctgc tggacaactg cttccgggtc atggagctgc tgtactgctc ctgctgtaaa   540
caaagctccg tcctaaactg gcaggactgt gaggtgccaa gtcctcagtc ttgcagccca   600
gagccctcat tgcagtatgc ggccacccag ctgtaccctc cgccccgtg gtcccccagc    660
tccccgcctc actccacggg ctcggtgagg ccggtcaggg cacagggcga gggcctcttg   720
ccctacccag ctttcttgta caaagtggtg atcgaaggta agcctatccc taaccctctc   780
ctcggtctcg attctacgcg taccggtcat catcaccatc accatcacca tggaggacag   840
tga                                                                 843
```

<210> SEQ ID NO 216
<211> LENGTH: 843
<212> TYPE: DNA
<213> ORGANISM: Homo sapiens

<400> SEQUENCE: 216

```
atgccccggg gcttcacctg gctgcgctat cttgggatct tccttggcgt ggccttgggg    60
aatgagcctt tggagatgtg gcccttgacg cagaatgagg agtgcactgt cacgggtttt   120
ctgcgggaca agctgcagta caggagccga cttcagtaca tgaaacacta cttccccatc   180
aactacaaga tcagtgtgcc ttacgagggg gtgttcagaa tcgccaacgt caccaggctg   240
agggcccagg tgagcgagcg ggagctgcgg tatctgtggg tcttggtgag cctcagtgcc   300
actgagtcgg tgcaggacgt gctgctcgag ggccacccat cctggaagta cctgcaggag   360
gtgcagacgc tgctgctgaa tgtccagcag ggcctcacgg atgtggaggt cagccccaag   420
gtggaatccg tgttgtccct cttgaatgcc ccagggccaa acctgaagct ggtgcggccc   480
aaagccctgc tggacaactg cttccgggtc atggagctgc tgtactgctc ctgctgtaaa   540
caaagctccg tcctaaactg gcaggactgt gaggtgccaa gtcctcagtc ttgcagccca   600
gagccctcat tgcagtatgc ggccacccag ctgtaccctc cgccccgtg gtcccccagc    660
tccccgcctc actccacggg ctcggtgagg ccggtcaggg cacagggcga gggcctcttg   720
ccctacccag ctttcttgta caaagtggtg atcgaaggta agcctatccc taaccctctc   780
ctcggtctcg attctacgcg taccggtcat catcaccatc accatcacca tggaggacag   840
tga                                                                 843
```

<210> SEQ ID NO 217
<211> LENGTH: 741
<212> TYPE: DNA
<213> ORGANISM: Homo sapiens

<400> SEQUENCE: 217

```
atgaagacct gctggaaaat tccagttttc ttctttgtgt gcagtttcct ggaaccctgg      60
gcatctgcag aattcaatga gcctttggag atgtggccct tgacgcagaa tgaggagtgc     120
actgtcacgg gttttctgcg ggacaagctg cagtacagga gccgacttca gtacatgaaa     180
cactacttcc ccatcaacta caagatcagt gtgccttacg agggggtgtt cagaatcgcc     240
aacgtcacca ggctgagggc ccaggtgagc gagcgggagc tgcggtatct gtgggtcttg     300
gtgagcctca gtgccactga gtcggtgcag gacgtgctgc tcgagggcca cccatcctgg     360
aagtacctgc aggaggtgca gacgctgctg ctgaatgtcc agcagggcct cacggatgtg     420
gaggtcagcc ccaaggtgga atccgtgttg tccctcttga tgccccaggc caaacctg      480 aagctggtgc ggcccaaagc cctgctggac aactgcttcc gggtcatgga gctgctgtac     540
tgctcctgct gtaaacaaag ctccgtccta aactggcagg actgtgaggt gccaagtcct     600
cagtcttgca gcccagagcc ctcattgcag tatgcggcca cccagctgta ccctccgccc     660
ccgtggtccc ccagctcccc gcctcactcc acgggctcgg tgaggccggt cagggcacag     720
ggcgagggcc tcttgccctg a                                               741

<210> SEQ ID NO 218
<211> LENGTH: 867
<212> TYPE: DNA
<213> ORGANISM: Homo sapiens

<400> SEQUENCE: 218
atgccccggg gcttcacctg gctgcgctat cttgggatct tccttggcgt ggccttgggg      60
aatgagcctt tggagatgtg gcccttgacg cagaatgagg agtgcactgt cacgggtttt     120
ctgcgggaca agctgcagta caggagccga cttcagtaca tgaaacacta cttccccatc     180
aactacaaga tcagtgtgcc ttacgagggg gtgttcagaa tcgccaacgt caccaggctg     240
agggcccagg tgagcgagcg ggagctgcgg tatctgtggg tcttggtgag cctcagtgcc     300
actgagtcgg tgcaggacgt gctgctcgag ggccacccat cctggaagta cctgcaggag     360
gtgcagacgc tgctgctgaa tgtccagcag ggcctcacgg atgtggaggt cagccccaag     420
gtggaatccg tgttgtccct cttgaatgcc ccagggccaa acctgaagct ggtgcggccc     480
aaagccctgc tggacaactg cttccgggtc atggagctgc tgtactgctc ctgctgtaaa     540
caaagctccg tcctaaactg gcaggactgt gaggtgccaa gtcctcagtc ttgcagccca     600
gagccctcat tgcagtatgc ggccacccag ctgtaccctc cgccccgtg gtccccagc     660 tccccgcctc actccacggg ctcggtgagg ccggtcaggg cacagggcga gggcctcttg     720
cccggatccg aaaacctgta ttttcagggc ttcgaaggta agcctatccc taaccctctc     780
ctcggtctcg attctacgcg ttggagccac ccgcagttcg agaaaaccgg tcatcatcac     840
catcaccatc accatggagg acagtga                                         867

<210> SEQ ID NO 219
<211> LENGTH: 882
<212> TYPE: DNA
<213> ORGANISM: Homo sapiens

<400> SEQUENCE: 219
atgaagacct gctggaaaat tccagttttc ttctttgtgt gcagtttcct ggaaccctgg      60
gcatctgcag aattcaatga gcctttggag atgtggccct tgacgcagaa tgaggagtgc     120
actgtcacgg gttttctgcg ggacaagctg cagtacagga gccgacttca gtacatgaaa     180
cactacttcc ccatcaacta caagatcagt gtgccttacg agggggtgtt cagaatcgcc     240
```

```
aacgtcacca ggctgagggc ccaggtgagc gagcgggagc tgcggtatct gtgggtcttg      300
gtgagcctca gtgccactga gtcggtgcag gacgtgctgc tcgagggcca cccatcctgg      360
aagtacctgc aggaggtgca gacgctgctg ctgaatgtcc agcagggcct cacggatgtg      420
gaggtcagcc ccaaggtgga atccgtgttg tccctcttga atgccccagg gccaaacctg      480
aagctggtgc ggcccaaagc cctgctggac aactgcttcc gggtcatgga gctgctgtac      540
tgctcctgct gtaaacaaag ctccgtccta aactggcagg actgtgaggt gccaagtcct      600
cagtcttgca gcccagagcc ctcattgcag tatgcggcca cccagctgta ccctccgccc      660
ccgtggtccc ccagctcccc gcctcactcc acgggctcgg tgaggccggt cagggcacag      720
ggcgagggcc tcttgcccgg atccgaaaac ctgtattttc agggcttcga aggtaagcct      780
atccctaacc ctctcctcgg tctcgattct acgcgttgga gccacccgca gttcgagaaa      840
accggtcatc atcaccatca ccatcaccat ggaggacagt ga                        882

<210> SEQ ID NO 220
<211> LENGTH: 867
<212> TYPE: DNA
<213> ORGANISM: Homo sapiens

<400> SEQUENCE: 220
atgaagacct gctggaaaat tccagttttc ttctttgtgt gcagtttcct ggaaccctgg       60
gcatctgcag aaggtcatca tcaccatcac catcaccatg gaggacagtg gagccacccg      120
cagttcgaga aagtaagcc tatccctaac cctctcctcg gtctcgattc tacggaaaac      180
ctgtattttc agggcgaatt caatgagcct ttggagatgt ggcccttgac gcagaatgag      240
gagtgcactg tcacgggttt tctgcgggac aagctgcagt acaggagccg acttcagtac      300
atgaaacact acttccccat caactacaag atcagtgtgc cttacgaggg ggtgttcaga      360
atcgccaacg tcaccaggct gagggcccag gtgagcgagc gggagctgcg gtatctgtgg      420
gtcttggtga gcctcagtgc cactgagtcg gtgcaggacg tgctgctcga gggccaccca      480
tcctggaagt acctgcagga ggtgcagacg ctgctgctga atgtccagca gggcctcacg      540
gatgtggagg tcagccccaa ggtggaatcc gtgttgtccc tcttgaatgc cccagggcca      600
aacctgaagc tggtgcggcc caaagccctg ctggacaact gcttccgggt catggagctg      660
ctgtactgct cctgctgtaa acaaagctcc gtcctaaact ggcaggactg tgaggtgcca      720
agtcctcagt cttgcagccc agagccctca ttgcagtatg cggccaccca gctgtaccct      780 ccgccccgt ggtcccccag ctccccgcct cactccacgg gctcggtgag gccggtcagg      840
gcacagggcg agggcctctt gccctga                                         867

<210> SEQ ID NO 221
<211> LENGTH: 726
<212> TYPE: DNA
<213> ORGANISM: Homo sapiens

<400> SEQUENCE: 221
atgaagacct gctggaaaat tccagttttc ttctttgtgt gcagtttcct ggaaccctgg       60
gcatctgcag aattcatgtg gcccttgacg cagaatgagg agtgcactgt cacgggtttt      120
ctgcgggaca agctgcagta caggagccga cttcagtaca tgaaacacta cttccccatc      180
aactacaaga tcagtgtgcc ttacgagggg gtgttcagaa tcgccaacgt caccaggctg      240
agggcccagg tgagcgagcg ggagctgcgg tatctgtggg tcttggtgag cctcagtgcc      300
actgagtcgg tgcaggacgt gctgctcgag ggccacccat cctggaagta cctgcaggag      360
```

```
gtgcagacgc tgctgctgaa tgtccagcag ggcctcacgg atgtggaggt cagccccaag    420
gtggaatccg tgttgtccct cttgaatgcc ccagggccaa acctgaagct ggtgcggccc    480
aaagccctgc tggacaactg cttccgggtc atggagctgc tgtactgctc ctgctgtaaa    540
caaagctccg tcctaaactg gcaggactgt gaggtgccaa gtcctcagtc ttgcagccca    600
gagccctcat tgcagtatgc ggccacccag ctgtaccctc cgccccgtg gtccccagc    660 tccccgcctc actccacggg ctcggtgagg ccggtcaggg cacagggcga gggcctcttg    720
ccctga                                                               726

<210> SEQ ID NO 222
<211> LENGTH: 711
<212> TYPE: DNA
<213> ORGANISM: Homo sapiens

<400> SEQUENCE: 222
atgaagacct gctggaaaat tccagttttc ttctttgtgt gcagtttcct ggaaccctgg     60
gcatctgcag aattccagaa tgaggagtgc actgtcacgg gttttctgcg ggacaagctg    120
cagtacagga gccgacttca gtacatgaaa cactacttcc ccatcaacta caagatcagt    180
gtgccttacg agggggtgtt cagaatcgcc aacgtcacca ggctgagggc ccaggtgagc    240
gagcgggagc tgcggtatct gtgggtcttg gtgagcctca gtgccactga gtcggtgcag    300
gacgtgctgc tcgagggcca cccatcctgg aagtacctgc aggaggtgca gacgctgctg    360
ctgaatgtcc agcagggcct cacggatgtg gaggtcagcc caaggtgga atccgtgttg    420 tccctcttga atgccccagg gccaaacctg aagctggtgc ggcccaaagc cctgctggac    480
aactgcttcc gggtcatgga gctgctgtac tgctcctgct gtaaacaaag ctccgtccta    540
aactggcagg actgtgaggt gccaagtcct cagtcttgca gcccagagcc ctcattgcag    600
tatgcggcca cccagctgta ccctccgccc cgtggtccc ccagctcccc gcctcactcc    660
acgggctcgg tgaggccggt cagggcacag ggcgagggcc tcttgccctg a             711

<210> SEQ ID NO 223
<211> LENGTH: 657
<212> TYPE: DNA
<213> ORGANISM: Homo sapiens

<400> SEQUENCE: 223
atgaagacct gctggaaaat tccagttttc ttctttgtgt gcagtttcct ggaaccctgg     60
gcatctgcag aattcaatga gcctttggag atgtggccct tgacgcagaa tgaggagtgc    120
actgtcacgg gttttctgcg ggacaagctg cagtacagga gccgacttca gtacatgaaa    180
cactacttcc ccatcaacta caagatcagt gtgccttacg agggggtgtt cagaatcgcc    240
aacgtcacca ggctgagggc ccaggtgagc gagcgggagc tgcggtatct gtgggtcttg    300
gtgagcctca gtgccactga gtcggtgcag gacgtgctgc tcgagggcca cccatcctgg    360
aagtacctgc aggaggtgca gacgctgctg ctgaatgtcc agcagggcct cacggatgtg    420
gaggtcagcc caaggtgga atccgtgttg tccctcttga atgccccagg gccaaacctg    480
aagctggtgc ggcccaaagc cctgctggac aactgcttcc gggtcatgga gctgctgtac    540
tgctcctgct gtaaacaaag ctccgtccta aactggcagg actgtgaggt gccaagtcct    600
cagtcttgca gcccagagcc ctcattgcag tatgcggcca cccagctgta cccttga       657

<210> SEQ ID NO 224
<211> LENGTH: 711
<212> TYPE: DNA
```

<213> ORGANISM: Homo sapiens

<400> SEQUENCE: 224

```
atgaagacct gctggaaaat tccagttttc ttctttgtgt gcagtttcct ggaaccctgg      60
gcatctgcag aattcaatga gcctttggag atgtggccct tgacgcagaa tgaggagtgc     120
actgtcacgg gttttctgcg ggacaagctg cagtacagga gccgacttca gtacatgaaa     180
cactacttcc ccatcaacta caagatcagt gtgccttacg agggggtgtt cagaatcgcc     240
aacgtcacca ggctgagggc ccaggtgagc gagcgggagc tgcggtatct gtgggtcttg     300
gtgagcctca gtgccactga gtcggtgcag gacgtgctgc tcgagggcca cccatcctgg     360
aagtacctgc aggaggtgca gacgctgctg ctgaatgtcc agcagggcct cacggatgtg     420
gaggtcagcc ccaaggtgga atccgtgttg tccctcttga atgccccagg gccaaacctg     480
aagctggtgc ggcccaaagc cctgctggac aactgcttcc gggtcatgga gctgctgtac     540
tgctcctgct gtaaacaaag ctccgtccta actggcagg actgtgaggt gccaagtcct     600
cagtcttgca gcccagagcc ctcattgcag tatgcggcca cccagctgta ccctccgccc     660
ccgtggtccc ccagctcccc gcctcactcc acgggctcgg tgaggccgtg a              711
```

<210> SEQ ID NO 225
<211> LENGTH: 741
<212> TYPE: DNA
<213> ORGANISM: Homo sapiens

<400> SEQUENCE: 225

```
atgaagacct gctggaaaat tccagttttc ttctttgtgt gcagtttcct ggaaccctgg      60
gcatctgcag aattcaatga gcctttggag aatgagcctt tggagatgtg gcccttgacg     120
cagaatgagg agtgcactgt cacgggtttt ctgcgggaca agctgcagta caggagccga     180
cttcagtaca tgaaacacta cttccccatc aactacaaga tcagtgtgcc ttacaggggg     240
gtgttcagaa tcgccaacgt caccaggctg agggcccagg tgagcgagcg ggagctgcgg     300
tatctgtggg tcttggtgag cctcagtgcc actgagtcgg tgcaggacgt gctgctcgag     360
ggccacccat cctggaagta cctgcaggag gtgcagacgc tgctgctgaa tgtccagcag     420
ggcctcacgg atgtggaggt cagccccaag gtggaatccg tgttgtccct cttgaatgcc     480
ccagggccaa acctgaagct ggtgcggccc aaagccctgc tggacaactg cttccgggtc     540
atggagctgc tgtactgctc ctgctgtaaa caaagctccg tcctaaactg gcaggactgt     600
gaggtgccaa gtcctcagtc ttgcagccca gagccctcat tgcagtatgc ggccacccag     660
ctgtaccctc cgccccgtg gtcccccagc tccccgcctc actccacggg ctcggtgagg     720
ccggtcaggg cacagggctg a                                               741
```

<210> SEQ ID NO 226
<211> LENGTH: 696
<212> TYPE: DNA
<213> ORGANISM: Homo sapiens

<400> SEQUENCE: 226

```
atgaagacct gctggaaaat tccagttttc ttctttgtgt gcagtttcct ggaaccctgg      60
gcatctgcag aattcatgtg gcccttgacg cagaatgagg agtgcactgt cacgggtttt     120
ctgcgggaca agctgcagta caggagccga cttcagtaca tgaaacacta cttccccatc     180
aactacaaga tcagtgtgcc ttacaggggg gtgttcagaa tcgccaacgt caccaggctg     240
agggcccagg tgagcgagcg ggagctgcgg tatctgtggg tcttggtgag cctcagtgcc     300
```

| | |
|---|---|
| actgagtcgg tgcaggacgt gctgctcgag ggccacccat cctggaagta cctgcaggag | 360 |
| gtgcagacgc tgctgctgaa tgtccagcag ggcctcacgg atgtggaggt cagccccaag | 420 |
| gtggaatccg tgttgtccct cttgaatgcc ccagggccaa acctgaagct ggtgcggccc | 480 |
| aaagccctgc tggacaactg cttccgggtc atggagctgc tgtactgctc ctgctgtaaa | 540 |
| caaagctccg tcctaaactg caggactgt gaggtgccaa gtcctcagtc ttgcagccca | 600 |
| gagccctcat tgcagtatgc ggccacccag ctgtaccctc cgccccgtg gtccccagc | 660 |
| tccccgcctc actccacggg ctcggtgagg ccgtga | 696 |

<210> SEQ ID NO 227
<211> LENGTH: 660
<212> TYPE: DNA
<213> ORGANISM: Mus musculus

<400> SEQUENCE: 227

| | |
|---|---|
| atgccctggg gactcgcctg gctatactgt cttgggatcc tacttgacgt ggctttggga | 60 |
| aacgagaatt tggagatatg gactctgacc caagataagg agtgtgacct tacaggctac | 120 |
| cttcggggca agctgcagta caagaaccgg cttcagtaca tgaaacatta cttccccatc | 180 |
| aactacagga ttgctgtgcc ttatgagggg gtactcagag tggccaacat cacaaggctg | 240 |
| cagaaggctc acgtgagtga gcgagagctt cggtacctgt gggtcttggt gagtctcaat | 300 |
| gccactgagt ctgtgatgga tgtacttctc gagggccacc cgtcctggaa gtatctacag | 360 |
| gaggttcaga cattgctgga gaacgtacag cggagcctca tggccgttgg tgtacacctg | 420 |
| ccgggacacg tacttgtgac cctgctcagc cagctgcctg gcctccccag cccatgggcc | 480 |
| agatcatttg acaccagctg ggagcttctg atgatgaaag gatgtggaga ttggccctca | 540 |
| cgtggaagct gtgttatctc ttctgagtac tccaggccta agcctgaagc tggtgcggcc | 600 |
| caaagccttg ctggacaact gcttccgggt catggaactg ctgtactgtt cttgctgtaa | 660 |

<210> SEQ ID NO 228
<211> LENGTH: 801
<212> TYPE: DNA
<213> ORGANISM: Mus musculus

<400> SEQUENCE: 228

| | |
|---|---|
| atgccctggg gactcgcctg gctatactgt cttgggatcc tacttgacgt ggctttggga | 60 |
| aacgagaatt tggagatatg gactctgacc caagataagg agtgtgacct tacaggctac | 120 |
| cttcggggca agctgcagta caagaaccgg cttcagtaca tgaaacatta cttccccatc | 180 |
| aactacagga ttgctgtgcc ttatgagggg gtactcagag tggccaacat cacaaggctg | 240 |
| cagaaggctc acgtgagtga gcgagagctt cggtacctgt gggtcttggt gagtctcaat | 300 |
| gccactgagt ctgtgatgga tgtacttctc gagggccacc cgtcctggaa gtatctacag | 360 |
| gaggttcaga cattgctgga gaacgtacag cggagcctca tggccgttgg tgtacacctg | 420 |
| ccgggacacg tacttgtgac cctgctcagc cagctgcctg gcctccccag cccatgggcc | 480 |
| agatcatttg acaccagctg ggagcttctg atgatgaaag gatgtggaga ttggccctca | 540 |
| cgtggaagct gtgttatctc ttctgagtac tccaggccta agcctgaagc tggtgcggcc | 600 |
| caaagccttg ctggacaact gcttccgggt catggaactg ctgtactgtt cttgctggga | 660 |
| tccgaaaacc tgtattttca gggcttcgaa ggtaagccta tccctaaccc tctcctcggt | 720 |
| ctcgattcta cgccgtggag ccaccccgcag ttcgagaaaa ccggtcatca tcaccatcac | 780 |
| catcaccatg gaggacagtg a | 801 |

<210> SEQ ID NO 229
<211> LENGTH: 708
<212> TYPE: DNA
<213> ORGANISM: Mus musculus

<400> SEQUENCE: 229

```
atgccctggg gactcgcctg gctatactgt cttgggatcc tacttgacgt ggctttggga      60
aacgagaatt tggagatatg gactctgacc caagataagg agtgtgacct tacaggctac     120
cttcggggca agctgcagta caagaaccgg cttcagtaca tgaaacatta cttccccatc     180
aactacagga ttgctgtgcc ttatgagggg gtactcagag tggccaacat cacaaggctg     240
cagaaggctc acgtgagtga gcgagagctt cggtacctgt gggtcttggt gagtctcaat     300
gccactgagt ctgtgatgga tgtacttctc gagggccacc cgtcctggaa gtatctacag     360
gaggttcaga cattgctgga gaacgtacag cggagcctca tggatgtgga gattggccct     420
cacgtggaag ctgtgttatc tcttctgagt actccaggcc taagcctgaa gctggtgcgg     480
cccaaagcct tgctggacaa ctgcttccgg gtcatggaac tgctgtactg ttcttgctgt     540
aaacaaagcc ccatcttaaa atggcaggac tgcgagctgc ccaggctcca tccccacagt     600
ccggggtcct tgatgcaatg tacagctaca aatgtgtacc ctttgtctcg gcagaccccc     660
acctccctgc ccggatcccc aagctcaagc catggctcgt gccctga                   708
```

<210> SEQ ID NO 230
<211> LENGTH: 849
<212> TYPE: DNA
<213> ORGANISM: Mus musculus

<400> SEQUENCE: 230

```
atgccctggg gactcgcctg gctatactgt cttgggatcc tacttgacgt ggctttggga      60
aacgagaatt tggagatatg gactctgacc caagataagg agtgtgacct tacaggctac     120
cttcggggca agctgcagta caagaaccgg cttcagtaca tgaaacatta cttccccatc     180
aactacagga ttgctgtgcc ttatgagggg gtactcagag tggccaacat cacaaggctg     240
cagaaggctc acgtgagtga gcgagagctt cggtacctgt gggtcttggt gagtctcaat     300
gccactgagt ctgtgatgga tgtacttctc gagggccacc cgtcctggaa gtatctacag     360
gaggttcaga cattgctgga gaacgtacag cggagcctca tggatgtgga gattggccct     420
cacgtggaag ctgtgttatc tcttctgagt actccaggcc taagcctgaa gctggtgcgg     480
cccaaagcct tgctggacaa ctgcttccgg gtcatggaac tgctgtactg ttcttgctgt     540
aaacaaagcc ccatcttaaa atggcaggac tgcgagctgc ccaggctcca tccccacagt     600
ccggggtcct tgatgcaatg tacagctaca aatgtgtacc ctttgtctcg gcagaccccc     660
acctccctgc ccggatcccc aagctcaagc catggctcgt gcccggatc cgaaaacctg     720
tattttcagg gcttcgaagg taagcctatc cctaaccctc tcctcggtct cgattctacg     780
cgttggagcc acccgcagtt cgagaaaacc ggtcatcatc accatcacca tcaccatgga     840
ggacagtga                                                             849
```

<210> SEQ ID NO 231
<211> LENGTH: 669
<212> TYPE: DNA
<213> ORGANISM: Homo sapiens

<400> SEQUENCE: 231

```
aatgagcctt tggagatgtg gcccttgacg cagaatgagg agtgcactgt cacgggtttt      60
```

```
ctgcgggaca agctgcagta caggagccga cttcagtaca tgaaacacta cttccccatc    120
aactacaaga tcagtgtgcc ttacgagggg gtgttcagaa tcgccaacgt caccaggctg    180
cagagggccc aggtgagcga gcgggagctg cggtatctgt gggtcttggt gagcctcagt    240
gccactgagt cggtgcagga cgtgctgctc gagggccacc catcctggaa gtacctgcag    300
gaggtgcaga cgctgctgct gaatgtccag cagggcctca cggatgtgga ggtcagcccc    360
aaggtggaat ccgtgttgtc cctcttgaat gccccagggc caaacctgaa gctggtgcgg    420
cccaaagccc tgctggacaa ctgcttccgg gtcatggagc tgctgtactg ctcctgctgt    480
aaacaaagct ccgtcctaaa ctggcaggac tgtgaggtgc aagtcctca gtcttgcagc    540 ccagagccct cattgcagta tgcggccacc cagctgtacc ctccgccccc gtggtccccc    600
agctccccgc ctcactccac gggctcggtg aggccggtca gggcacaggg cgagggcctc    660
ttgccctga                                                            669

<210> SEQ ID NO 232
<211> LENGTH: 729
<212> TYPE: DNA
<213> ORGANISM: Homo sapiens

<400> SEQUENCE: 232
atgccccggg gcttcacctg gctgcgctat cttgggatct tccttggcgt ggccttgggg     60
aatgagcctt tggagatgtg gcccttgacg cagaatgagg agtgcactgt cacgggtttt    120
ctgcgggaca agctgcagta caggagccga cttcagtaca tgaaacacta cttccccatc    180
aactacaaga tcagtgtgcc ttacgagggg gtgttcagaa tcgccaacgt caccaggctg    240
cagagggccc aggtgagcga gcgggagctg cggtatctgt gggtcttggt gagcctcagt    300
gccactgagt cggtgcagga cgtgctgctc gagggccacc catcctggaa gtacctgcag    360
gaggtggaga cgctgctgct gaatgtccag cagggcctca cggatgtgga ggtcagcccc    420
aaggtggaat ccgtgttgtc cctcttgaat gccccagggc caaacctgaa gctggtgcgg    480
cccaaagccc tgctggacaa ctgcttccgg gtcatggagc tgctgtactg ctcctgctgt    540
aaacaaagct ccgtcctaaa ctggcaggac tgtgaggtgc aagtcctca gtcttgcagc    600 ccagagccct cattgcagta tgcggccacc cagctgtacc ctccgccccc gtggtccccc    660
agctccccgc ctcactccac gggctcggtg aggccggtca gggcacaggg cgagggcctc    720
ttgccctga                                                            729

<210> SEQ ID NO 233
<211> LENGTH: 669
<212> TYPE: DNA
<213> ORGANISM: Homo sapiens

<400> SEQUENCE: 233
gaatgagcct ttggagatgt ggcccttgac gcagaatgag gagtgcactg tcacgggttt     60
tctgcgggac aagctgcagt acaggagccg acttcagtac atgaaacact acttccccat    120
caactacaag atcagtgtgc cttacgaggg ggtgttcaga atcgccaacg tcaccaggct    180
gcagagggcc caggtgagcg agcgggagct gcggtatctg tgggtcttgg tgagcctcag    240
tgccactgag tcggtgcagg acgtgctgct cgagggccac ccatcctgga agtacctgca    300
ggaggtggag acgctgctgc tgaatgtcca gcagggcctc acggatgtgg aggtcagccc    360
caaggtggaa tccgtgttgt ccctcttgaa tgccccaggg ccaaacctga agctggtgcg    420
gcccaaagcc ctgctggaca actgcttccg ggtcatggag ctgctgtact gctcctgctg    480
```

```
taaacaaagc tccgtcctaa actggcagga ctgtgaggtg ccaagtcctc agtcttgcag      540
cccagagccc tcattgcagt atgcggccac cagctgtac cctccgcccc cgtggtcccc       600
cagctccccg cctcactcca cgggctcggt gaggccggtc agggcacagg gcgagggcct      660
cttgccctg                                                              669
```

<210> SEQ ID NO 234
<211> LENGTH: 9
<212> TYPE: DNA
<213> ORGANISM: Artificial Sequence
<220> FEATURE:
<223> OTHER INFORMATION: Description of Artificial Sequence: Synthetic
      Kozak sequence

<400> SEQUENCE: 234

```
gccgccacc                                                               9
```

<210> SEQ ID NO 235
<211> LENGTH: 241
<212> TYPE: PRT
<213> ORGANISM: Homo sapiens

<400> SEQUENCE: 235

```
Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
        35                  40                  45

Ser Arg Leu Gln Tyr Met Lys His Tyr Phe Pro Ile Asn Tyr Lys Ile
    50                  55                  60

Ser Val Pro Tyr Glu Gly Val Phe Arg Ile Ala Asn Val Thr Arg Leu
65                  70                  75                  80

Arg Ala Gln Val Ser Glu Arg Glu Leu Arg Tyr Leu Trp Val Leu Val
                85                  90                  95

Ser Leu Ser Ala Thr Glu Ser Val Gln Asp Val Leu Leu Glu Gly His
            100                 105                 110

Pro Ser Trp Lys Tyr Leu Gln Glu Val Gln Thr Leu Leu Leu Asn Val
        115                 120                 125

Gln Gln Gly Leu Thr Asp Val Glu Val Ser Pro Lys Val Glu Ser Val
    130                 135                 140

Leu Ser Leu Leu Asn Ala Pro Gly Pro Asn Leu Lys Leu Val Arg Pro
145                 150                 155                 160

Lys Ala Leu Leu Asp Asn Cys Phe Arg Val Met Glu Leu Leu Tyr Cys
                165                 170                 175

Ser Cys Cys Lys Gln Ser Ser Val Leu Asn Trp Gln Asp Cys Glu Val
            180                 185                 190

Pro Ser Pro Gln Ser Cys Ser Pro Glu Pro Ser Leu Gln Tyr Ala Ala
        195                 200                 205

Thr Gln Leu Tyr Pro Pro Pro Trp Ser Pro Ser Ser Pro Pro His
    210                 215                 220

Ser Thr Gly Ser Val Arg Pro Val Arg Ala Gln Gly Glu Gly Leu Leu
225                 230                 235                 240

Pro
```

<210> SEQ ID NO 236
<211> LENGTH: 241
<212> TYPE: PRT

<213> ORGANISM: Homo sapiens

<400> SEQUENCE: 236

Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
        35                  40                  45

Ser Arg Leu Gln Tyr Met Lys His Tyr Phe Pro Ile Asn Tyr Lys Ile
    50                  55                  60

Ser Val Pro Tyr Glu Gly Val Phe Arg Ile Ala Asn Val Thr Arg Leu
65                  70                  75                  80

Arg Ala Gln Val Ser Glu Arg Glu Leu Arg Tyr Leu Trp Val Leu Val
                85                  90                  95

Ser Leu Ser Ala Thr Glu Ser Val Gln Asp Val Leu Leu Glu Gly His
            100                 105                 110

Pro Ser Trp Lys Tyr Leu Gln Glu Val Gln Thr Leu Leu Leu Asn Val
        115                 120                 125

Gln Gln Gly Leu Thr Asp Val Glu Val Ser Pro Lys Val Glu Ser Val
    130                 135                 140

Leu Ser Leu Leu Asn Ala Pro Gly Pro Asn Leu Lys Leu Val Arg Pro
145                 150                 155                 160

Lys Ala Leu Leu Asp Asn Cys Phe Arg Val Met Glu Leu Leu Tyr Cys
                165                 170                 175

Ser Cys Cys Lys Gln Ser Ser Val Leu Asn Trp Gln Asp Cys Glu Val
            180                 185                 190

Pro Ser Pro Gln Ser Cys Ser Pro Glu Pro Ser Leu Gln Tyr Ala Ala
        195                 200                 205

Thr Gln Leu Tyr Pro Pro Pro Trp Ser Pro Ser Ser Pro Pro His
    210                 215                 220

Ser Thr Gly Ser Val Arg Pro Val Arg Ala Gln Gly Glu Gly Leu Leu
225                 230                 235                 240

Pro

<210> SEQ ID NO 237
<211> LENGTH: 280
<212> TYPE: PRT
<213> ORGANISM: Homo sapiens

<400> SEQUENCE: 237

Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
        35                  40                  45

Ser Arg Leu Gln Tyr Met Lys His Tyr Phe Pro Ile Asn Tyr Lys Ile
    50                  55                  60

Ser Val Pro Tyr Glu Gly Val Phe Arg Ile Ala Asn Val Thr Arg Leu
65                  70                  75                  80

Arg Ala Gln Val Ser Glu Arg Glu Leu Arg Tyr Leu Trp Val Leu Val
                85                  90                  95

Ser Leu Ser Ala Thr Glu Ser Val Gln Asp Val Leu Leu Glu Gly His
            100                 105                 110

```
Pro Ser Trp Lys Tyr Leu Gln Glu Val Gln Thr Leu Leu Leu Asn Val
        115                 120                 125

Gln Gln Gly Leu Thr Asp Val Glu Val Ser Pro Lys Val Glu Ser Val
130                 135                 140

Leu Ser Leu Leu Asn Ala Pro Gly Pro Asn Leu Lys Leu Val Arg Pro
145                 150                 155                 160

Lys Ala Leu Leu Asp Asn Cys Phe Arg Val Met Glu Leu Leu Tyr Cys
                165                 170                 175

Ser Cys Cys Lys Gln Ser Ser Val Leu Asn Trp Gln Asp Cys Glu Val
            180                 185                 190

Pro Ser Pro Gln Ser Cys Ser Pro Glu Pro Ser Leu Gln Tyr Ala Ala
        195                 200                 205

Thr Gln Leu Tyr Pro Pro Pro Trp Ser Pro Ser Ser Pro Pro His
    210                 215                 220

Ser Thr Gly Ser Val Arg Pro Val Arg Ala Gln Gly Glu Gly Leu Leu
225                 230                 235                 240

Pro Tyr Pro Ala Phe Leu Tyr Lys Val Val Ile Glu Gly Lys Pro Ile
                245                 250                 255

Pro Asn Pro Leu Leu Gly Leu Asp Ser Thr Arg Thr Gly His His His
                260                 265                 270

His His His His His Gly Gly Gln
        275                 280

<210> SEQ ID NO 238
<211> LENGTH: 280
<212> TYPE: PRT
<213> ORGANISM: Homo sapiens

<400> SEQUENCE: 238

Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
                20                  25                  30

Glu Glu Cys Thr Val Thr Gly Phe Leu Arg Asp Lys Leu Gln Tyr Arg
            35                  40                  45

Ser Arg Leu Gln Tyr Met Lys His Tyr Phe Pro Ile Asn Tyr Lys Ile
    50                  55                  60

Ser Val Pro Tyr Glu Gly Val Phe Arg Ile Ala Asn Val Thr Arg Leu
65                  70                  75                  80

Arg Ala Gln Val Ser Glu Arg Glu Leu Arg Tyr Leu Trp Val Leu Val
                85                  90                  95

Ser Leu Ser Ala Thr Glu Ser Val Gln Asp Val Leu Leu Glu Gly His
                100                 105                 110

Pro Ser Trp Lys Tyr Leu Gln Glu Val Gln Thr Leu Leu Leu Asn Val
        115                 120                 125

Gln Gln Gly Leu Thr Asp Val Glu Val Ser Pro Lys Val Glu Ser Val
130                 135                 140

Leu Ser Leu Leu Asn Ala Pro Gly Pro Asn Leu Lys Leu Val Arg Pro
145                 150                 155                 160

Lys Ala Leu Leu Asp Asn Cys Phe Arg Val Met Glu Leu Leu Tyr Cys
                165                 170                 175

Ser Cys Cys Lys Gln Ser Ser Val Leu Asn Trp Gln Asp Cys Glu Val
            180                 185                 190

Pro Ser Pro Gln Ser Cys Ser Pro Glu Pro Ser Leu Gln Tyr Ala Ala
        195                 200                 205
```

```
Thr Gln Leu Tyr Pro Pro Pro Trp Ser Pro Ser Ser Pro Pro His
        210                 215                 220
Ser Thr Gly Ser Val Arg Pro Val Arg Ala Gln Gly Glu Gly Leu Leu
225                 230                 235                 240
Pro Tyr Pro Ala Phe Leu Tyr Lys Val Val Ile Glu Gly Lys Pro Ile
                245                 250                 255
Pro Asn Pro Leu Leu Gly Leu Asp Ser Thr Arg Thr Gly His His His
            260                 265                 270
His His His His His Gly Gly Gln
        275                 280

<210> SEQ ID NO 239
<211> LENGTH: 280
<212> TYPE: PRT
<213> ORGANISM: Homo sapiens

<400> SEQUENCE: 239

Met Pro Arg Gly Phe Thr Trp Leu Arg Tyr Leu Gly Ile Phe Leu Gly
1               5                   10                  15
Val Ala Leu Gly Asn Glu Pro Leu Glu Met Trp Pro Leu Thr Gln Asn
                20                  25                  30
Glu Glu Cys Thr Val Thr Gly Phe Leu Arg Asp Lys Leu Gln Tyr Arg
            35                  40                  45
Ser Arg Leu Gln Tyr Met Lys His Tyr Phe Pro Ile Asn Tyr Lys Ile
        50                  55                  60
Ser Val Pro Tyr Glu Gly Val Phe Arg Ile Ala Asn Val Thr Arg Leu
65                  70                  75                  80
Arg Ala Gln Val Ser Glu Arg Glu Leu Arg Tyr Leu Trp Val Leu Val
                85                  90                  95
Ser Leu Ser Ala Thr Glu Ser Val Gln Asp Val Leu Leu Glu Gly His
            100                 105                 110
Pro Ser Trp Lys Tyr Leu Gln Glu Val Gln Thr Leu Leu Leu Asn Val
        115                 120                 125
Gln Gln Gly Leu Thr Asp Val Glu Val Ser Pro Lys Val Glu Ser Val
130                 135                 140
Leu Ser Leu Leu Asn Ala Pro Gly Pro Asn Leu Lys Leu Val Arg Pro
145                 150                 155                 160
Lys Ala Leu Leu Asp Asn Cys Phe Arg Val Met Glu Leu Leu Tyr Cys
                165                 170                 175
Ser Cys Cys Lys Gln Ser Ser Val Leu Asn Trp Gln Asp Cys Glu Val
            180                 185                 190
Pro Ser Pro Gln Ser Cys Ser Pro Glu Pro Ser Leu Gln Tyr Ala Ala
        195                 200                 205
Thr Gln Leu Tyr Pro Pro Pro Trp Ser Pro Ser Ser Pro Pro His
        210                 215                 220
Ser Thr Gly Ser Val Arg Pro Val Arg Ala Gln Gly Glu Gly Leu Leu
225                 230                 235                 240
Pro Tyr Pro Ala Phe Leu Tyr Lys Val Val Ile Glu Gly Lys Pro Ile
                245                 250                 255
Pro Asn Pro Leu Leu Gly Leu Asp Ser Thr Arg Thr Gly His His His
            260                 265                 270
His His His His His Gly Gly Gln
        275                 280

<210> SEQ ID NO 240
<211> LENGTH: 246
```

```
<212> TYPE: PRT
<213> ORGANISM: Homo sapiens

<400> SEQUENCE: 240

Met Lys Thr Cys Trp Lys Ile Pro Val Phe Phe Val Cys Ser Phe
1               5                   10                  15

Leu Glu Pro Trp Ala Ser Ala Glu Phe Asn Glu Pro Leu Glu Met Trp
            20                  25                  30

Pro Leu Thr Gln Asn Glu Glu Cys Thr Val Thr Gly Phe Leu Arg Asp
            35                  40                  45

Lys Leu Gln Tyr Arg Ser Arg Leu Gln Tyr Met Lys His Tyr Phe Pro
50                  55                  60

Ile Asn Tyr Lys Ile Ser Val Pro Tyr Glu Gly Val Phe Arg Ile Ala
65                  70                  75                  80

Asn Val Thr Arg Leu Arg Ala Gln Val Ser Glu Arg Glu Leu Arg Tyr
                85                  90                  95

Leu Trp Val Leu Val Ser Leu Ser Ala Thr Glu Ser Val Gln Asp Val
            100                 105                 110

Leu Leu Glu Gly His Pro Ser Trp Lys Tyr Leu Gln Glu Val Gln Thr
        115                 120                 125

Leu Leu Leu Asn Val Gln Gln Gly Leu Thr Asp Val Glu Val Ser Pro
130                 135                 140

Lys Val Glu Ser Val Leu Ser Leu Leu Asn Ala Pro Gly Pro Asn Leu
145                 150                 155                 160

Lys Leu Val Arg Pro Lys Ala Leu Leu Asp Asn Cys Phe Arg Val Met
                165                 170                 175

Glu Leu Leu Tyr Cys Ser Cys Cys Lys Gln Ser Ser Val Leu Asn Trp
            180                 185                 190

Gln Asp Cys Glu Val Pro Ser Pro Gln Ser Cys Ser Pro Glu Pro Ser
        195                 200                 205

Leu Gln Tyr Ala Ala Thr Gln Leu Tyr Pro Pro Pro Trp Ser Pro
        210                 215                 220

Ser Ser Pro Pro His Ser Thr Gly Ser Val Arg Pro Val Arg Ala Gln
225                 230                 235                 240

Gly Glu Gly Leu Leu Pro
            245

<210> SEQ ID NO 241
<211> LENGTH: 288
<212> TYPE: PRT
<213> ORGANISM: Homo sapiens

<400> SEQUENCE: 241

Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
        35                  40                  45

Ser Arg Leu Gln Tyr Met Lys His Tyr Phe Pro Ile Asn Tyr Lys Ile
50                  55                  60

Ser Val Pro Tyr Glu Gly Val Phe Arg Ile Ala Asn Val Thr Arg Leu
65                  70                  75                  80

Arg Ala Gln Val Ser Glu Arg Glu Leu Arg Tyr Leu Trp Val Leu Val
                85                  90                  95

Ser Leu Ser Ala Thr Glu Ser Val Gln Asp Val Leu Leu Glu Gly His
```

```
            100                 105                 110
Pro Ser Trp Lys Tyr Leu Gln Glu Val Gln Thr Leu Leu Leu Asn Val
        115                 120                 125

Gln Gln Gly Leu Thr Asp Val Glu Val Ser Pro Lys Val Glu Ser Val
130                 135                 140

Leu Ser Leu Leu Asn Ala Pro Gly Pro Asn Leu Lys Leu Val Arg Pro
145                 150                 155                 160

Lys Ala Leu Leu Asp Asn Cys Phe Arg Val Met Glu Leu Leu Tyr Cys
                165                 170                 175

Ser Cys Cys Lys Gln Ser Ser Val Leu Asn Trp Gln Asp Cys Glu Val
            180                 185                 190

Pro Ser Pro Gln Ser Cys Ser Pro Glu Pro Ser Leu Gln Tyr Ala Ala
        195                 200                 205

Thr Gln Leu Tyr Pro Pro Pro Trp Ser Pro Ser Ser Pro His
210                 215                 220

Ser Thr Gly Ser Val Arg Pro Val Arg Ala Gln Gly Glu Gly Leu Leu
225                 230                 235                 240

Pro Gly Ser Glu Asn Leu Tyr Phe Gln Gly Phe Glu Gly Lys Pro Ile
                245                 250                 255

Pro Asn Pro Leu Leu Gly Leu Asp Ser Thr Arg Trp Ser His Pro Gln
            260                 265                 270

Phe Glu Lys Thr Gly His His His His His His Gly Gly Gln
        275                 280                 285

<210> SEQ ID NO 242
<211> LENGTH: 293
<212> TYPE: PRT
<213> ORGANISM: Homo sapiens

<400> SEQUENCE: 242

Met Lys Thr Cys Trp Lys Ile Pro Val Phe Phe Phe Val Cys Ser Phe
1               5                   10                  15

Leu Glu Pro Trp Ala Ser Ala Glu Phe Asn Glu Pro Leu Glu Met Trp
            20                  25                  30

Pro Leu Thr Gln Asn Glu Glu Cys Thr Val Thr Gly Phe Leu Arg Asp
        35                  40                  45

Lys Leu Gln Tyr Arg Ser Arg Leu Gln Tyr Met Lys His Tyr Phe Pro
    50                  55                  60

Ile Asn Tyr Lys Ile Ser Val Pro Tyr Glu Gly Val Phe Arg Ile Ala
65                  70                  75                  80

Asn Val Thr Arg Leu Arg Ala Gln Val Ser Glu Arg Glu Leu Arg Tyr
                85                  90                  95

Leu Trp Val Leu Val Ser Leu Ser Ala Thr Glu Ser Val Gln Asp Val
            100                 105                 110

Leu Leu Glu Gly His Pro Ser Trp Lys Tyr Leu Gln Glu Val Gln Thr
        115                 120                 125

Leu Leu Leu Asn Val Gln Gln Gly Leu Thr Asp Val Glu Val Ser Pro
    130                 135                 140

Lys Val Glu Ser Val Leu Ser Leu Leu Asn Ala Pro Gly Pro Asn Leu
145                 150                 155                 160

Lys Leu Val Arg Pro Lys Ala Leu Leu Asp Asn Cys Phe Arg Val Met
                165                 170                 175

Glu Leu Leu Tyr Cys Ser Cys Cys Lys Gln Ser Ser Val Leu Asn Trp
            180                 185                 190

Gln Asp Cys Glu Val Pro Ser Pro Gln Ser Cys Ser Pro Glu Pro Ser
```

```
                195                 200                 205
Leu Gln Tyr Ala Ala Thr Gln Leu Tyr Pro Pro Pro Trp Ser Pro
    210                 215                 220

Ser Ser Pro Pro His Ser Thr Gly Ser Val Arg Pro Val Arg Ala Gln
225                 230                 235                 240

Gly Glu Gly Leu Leu Pro Gly Ser Glu Asn Leu Tyr Phe Gln Gly Phe
                245                 250                 255

Glu Gly Lys Pro Ile Pro Asn Pro Leu Leu Gly Leu Asp Ser Thr Arg
            260                 265                 270

Trp Ser His Pro Gln Phe Glu Lys Thr Gly His His His His His
        275                 280                 285

His His Gly Gly Gln
        290

<210> SEQ ID NO 243
<211> LENGTH: 288
<212> TYPE: PRT
<213> ORGANISM: Homo sapiens

<400> SEQUENCE: 243

Met Lys Thr Cys Trp Lys Ile Pro Val Phe Phe Phe Val Cys Ser Phe
1               5                   10                  15

Leu Glu Pro Trp Ala Ser Ala Glu Gly His His His His His His
                20                  25                  30

His Gly Gly Gln Trp Ser His Pro Gln Phe Glu Lys Gly Lys Pro Ile
            35                  40                  45

Pro Asn Pro Leu Leu Gly Leu Asp Ser Thr Glu Asn Leu Tyr Phe Gln
50                  55                  60

Gly Glu Phe Asn Glu Pro Leu Glu Met Trp Pro Leu Thr Gln Asn Glu
65                  70                  75                  80

Glu Cys Thr Val Thr Gly Phe Leu Arg Asp Lys Leu Gln Tyr Arg Ser
                85                  90                  95

Arg Leu Gln Tyr Met Lys His Tyr Phe Pro Ile Asn Tyr Lys Ile Ser
                100                 105                 110

Val Pro Tyr Glu Gly Val Phe Arg Ile Ala Asn Val Thr Arg Leu Arg
            115                 120                 125

Ala Gln Val Ser Glu Arg Glu Leu Arg Tyr Leu Trp Val Leu Val Ser
        130                 135                 140

Leu Ser Ala Thr Glu Ser Val Gln Asp Val Leu Leu Glu Gly His Pro
145                 150                 155                 160

Ser Trp Lys Tyr Leu Gln Glu Val Gln Thr Leu Leu Leu Asn Val Gln
                165                 170                 175

Gln Gly Leu Thr Asp Val Glu Val Ser Pro Lys Val Glu Ser Val Leu
            180                 185                 190

Ser Leu Leu Asn Ala Pro Gly Pro Asn Leu Lys Leu Val Arg Pro Lys
        195                 200                 205

Ala Leu Leu Asp Asn Cys Phe Arg Val Met Glu Leu Leu Tyr Cys Ser
    210                 215                 220

Cys Cys Lys Gln Ser Ser Val Leu Asn Trp Gln Asp Cys Glu Val Pro
225                 230                 235                 240

Ser Pro Gln Ser Cys Ser Pro Glu Pro Ser Leu Gln Tyr Ala Ala Thr
                245                 250                 255

Gln Leu Tyr Pro Pro Pro Trp Ser Pro Ser Ser Pro Pro His Ser
            260                 265                 270

Thr Gly Ser Val Arg Pro Val Arg Ala Gln Gly Glu Gly Leu Leu Pro
```

<210> SEQ ID NO 244
<211> LENGTH: 241
<212> TYPE: PRT
<213> ORGANISM: Homo sapiens

<400> SEQUENCE: 244

Met Lys Thr Cys Trp Lys Ile Pro Val Phe Phe Val Cys Ser Phe
1               5                   10                  15

Leu Glu Pro Trp Ala Ser Ala Glu Phe Met Trp Pro Leu Thr Gln Asn
                20                  25                  30

Glu Glu Cys Thr Val Thr Gly Phe Leu Arg Asp Lys Leu Gln Tyr Arg
            35                  40                  45

Ser Arg Leu Gln Tyr Met Lys His Tyr Phe Pro Ile Asn Tyr Lys Ile
50                  55                  60

Ser Val Pro Tyr Glu Gly Val Phe Arg Ile Ala Asn Val Thr Arg Leu
65                  70                  75                  80

Arg Ala Gln Val Ser Glu Arg Glu Leu Arg Tyr Leu Trp Val Leu Val
                85                  90                  95

Ser Leu Ser Ala Thr Glu Ser Val Gln Asp Val Leu Leu Glu Gly His
            100                 105                 110

Pro Ser Trp Lys Tyr Leu Gln Glu Val Gln Thr Leu Leu Leu Asn Val
        115                 120                 125

Gln Gln Gly Leu Thr Asp Val Glu Val Ser Pro Lys Val Glu Ser Val
130                 135                 140

Leu Ser Leu Leu Asn Ala Pro Gly Pro Asn Leu Lys Leu Val Arg Pro
145                 150                 155                 160

Lys Ala Leu Leu Asp Asn Cys Phe Arg Val Met Glu Leu Leu Tyr Cys
                165                 170                 175

Ser Cys Cys Lys Gln Ser Ser Val Leu Asn Trp Gln Asp Cys Glu Val
            180                 185                 190

Pro Ser Pro Gln Ser Cys Ser Pro Glu Pro Ser Leu Gln Tyr Ala Ala
        195                 200                 205

Thr Gln Leu Tyr Pro Pro Pro Trp Ser Pro Ser Ser Pro Pro His
    210                 215                 220

Ser Thr Gly Ser Val Arg Pro Val Arg Ala Gln Gly Glu Gly Leu Leu
225                 230                 235                 240

Pro

<210> SEQ ID NO 245
<211> LENGTH: 236
<212> TYPE: PRT
<213> ORGANISM: Homo sapiens

<400> SEQUENCE: 245

Met Lys Thr Cys Trp Lys Ile Pro Val Phe Phe Val Cys Ser Phe
1               5                   10                  15

Leu Glu Pro Trp Ala Ser Ala Glu Phe Gln Asn Glu Glu Cys Thr Val
                20                  25                  30

Thr Gly Phe Leu Arg Asp Lys Leu Gln Tyr Arg Ser Arg Leu Gln Tyr
            35                  40                  45

Met Lys His Tyr Phe Pro Ile Asn Tyr Lys Ile Ser Val Pro Tyr Glu
50                  55                  60

Gly Val Phe Arg Ile Ala Asn Val Thr Arg Leu Arg Ala Gln Val Ser
65                  70                  75                  80

```
Glu Arg Glu Leu Arg Tyr Leu Trp Val Leu Val Ser Leu Ser Ala Thr
                85                  90                  95

Glu Ser Val Gln Asp Val Leu Leu Glu Gly His Pro Ser Trp Lys Tyr
            100                 105                 110

Leu Gln Glu Val Gln Thr Leu Leu Leu Asn Val Gln Gln Gly Leu Thr
        115                 120                 125

Asp Val Glu Val Ser Pro Lys Val Glu Ser Val Leu Ser Leu Leu Asn
    130                 135                 140

Ala Pro Gly Pro Asn Leu Lys Leu Val Arg Pro Lys Ala Leu Leu Asp
145                 150                 155                 160

Asn Cys Phe Arg Val Met Glu Leu Leu Tyr Cys Ser Cys Cys Lys Gln
                165                 170                 175

Ser Ser Val Leu Asn Trp Gln Asp Cys Glu Val Pro Ser Pro Gln Ser
            180                 185                 190

Cys Ser Pro Glu Pro Ser Leu Gln Tyr Ala Ala Thr Gln Leu Tyr Pro
        195                 200                 205

Pro Pro Pro Trp Ser Pro Ser Ser Pro Pro His Ser Thr Gly Ser Val
    210                 215                 220

Arg Pro Val Arg Ala Gln Gly Glu Gly Leu Leu Pro
225                 230                 235

<210> SEQ ID NO 246
<211> LENGTH: 218
<212> TYPE: PRT
<213> ORGANISM: Homo sapiens

<400> SEQUENCE: 246

Met Lys Thr Cys Trp Lys Ile Pro Val Phe Phe Phe Val Cys Ser Phe
1               5                   10                  15

Leu Glu Pro Trp Ala Ser Ala Glu Phe Asn Glu Pro Leu Glu Met Trp
            20                  25                  30

Pro Leu Thr Gln Asn Glu Glu Cys Thr Val Thr Gly Phe Leu Arg Asp
        35                  40                  45

Lys Leu Gln Tyr Arg Ser Arg Leu Gln Tyr Met Lys His Tyr Phe Pro
    50                  55                  60

Ile Asn Tyr Lys Ile Ser Val Pro Tyr Glu Gly Val Phe Arg Ile Ala
65                  70                  75                  80

Asn Val Thr Arg Leu Arg Ala Gln Val Ser Glu Arg Glu Leu Arg Tyr
                85                  90                  95

Leu Trp Val Leu Val Ser Leu Ser Ala Thr Glu Ser Val Gln Asp Val
            100                 105                 110

Leu Leu Glu Gly His Pro Ser Trp Lys Tyr Leu Gln Glu Val Gln Thr
        115                 120                 125

Leu Leu Leu Asn Val Gln Gln Gly Leu Thr Asp Val Glu Val Ser Pro
    130                 135                 140

Lys Val Glu Ser Val Leu Ser Leu Leu Asn Ala Pro Gly Pro Asn Leu
145                 150                 155                 160

Lys Leu Val Arg Pro Lys Ala Leu Leu Asp Asn Cys Phe Arg Val Met
                165                 170                 175

Glu Leu Leu Tyr Cys Ser Cys Cys Lys Gln Ser Ser Val Leu Asn Trp
            180                 185                 190

Gln Asp Cys Glu Val Pro Ser Pro Gln Ser Cys Ser Pro Glu Pro Ser
        195                 200                 205

Leu Gln Tyr Ala Ala Thr Gln Leu Tyr Pro
    210                 215
```

<210> SEQ ID NO 247
<211> LENGTH: 236
<212> TYPE: PRT
<213> ORGANISM: Homo sapiens

<400> SEQUENCE: 247

```
Met Lys Thr Cys Trp Lys Ile Pro Val Phe Phe Val Cys Ser Phe
1               5                   10                  15

Leu Glu Pro Trp Ala Ser Ala Glu Phe Asn Glu Pro Leu Glu Met Trp
            20                  25                  30

Pro Leu Thr Gln Asn Glu Glu Cys Thr Val Thr Gly Phe Leu Arg Asp
                35                  40                  45

Lys Leu Gln Tyr Arg Ser Arg Leu Gln Tyr Met Lys His Tyr Phe Pro
        50                  55                  60

Ile Asn Tyr Lys Ile Ser Val Pro Tyr Glu Gly Val Phe Arg Ile Ala
65                  70                  75                  80

Asn Val Thr Arg Leu Arg Ala Gln Val Ser Arg Glu Leu Arg Tyr
                85                  90                  95

Leu Trp Val Leu Val Ser Leu Ser Ala Thr Glu Ser Val Gln Asp Val
            100                 105                 110

Leu Leu Glu Gly His Pro Ser Trp Lys Tyr Leu Gln Glu Val Gln Thr
        115                 120                 125

Leu Leu Leu Asn Val Gln Gln Gly Leu Thr Asp Val Glu Val Ser Pro
    130                 135                 140

Lys Val Glu Ser Val Leu Ser Leu Leu Asn Ala Pro Gly Pro Asn Leu
145                 150                 155                 160

Lys Leu Val Arg Pro Lys Ala Leu Leu Asp Asn Cys Phe Arg Val Met
                165                 170                 175

Glu Leu Leu Tyr Cys Ser Cys Cys Lys Gln Ser Ser Val Leu Asn Trp
            180                 185                 190

Gln Asp Cys Glu Val Pro Ser Pro Gln Ser Cys Ser Pro Glu Pro Ser
        195                 200                 205

Leu Gln Tyr Ala Ala Thr Gln Leu Tyr Pro Pro Pro Trp Ser Pro
    210                 215                 220

Ser Ser Pro Pro His Ser Thr Gly Ser Val Arg Pro
225                 230                 235
```

<210> SEQ ID NO 248
<211> LENGTH: 246
<212> TYPE: PRT
<213> ORGANISM: Homo sapiens

<400> SEQUENCE: 248

```
Met Lys Thr Cys Trp Lys Ile Pro Val Phe Phe Val Cys Ser Phe
1               5                   10                  15

Leu Glu Pro Trp Ala Ser Ala Glu Phe Asn Glu Pro Leu Glu Asn Glu
            20                  25                  30

Pro Leu Glu Met Trp Pro Leu Thr Gln Asn Glu Glu Cys Thr Val Thr
        35                  40                  45

Gly Phe Leu Arg Asp Lys Leu Gln Tyr Arg Ser Arg Leu Gln Tyr Met
    50                  55                  60

Lys His Tyr Phe Pro Ile Asn Tyr Lys Ile Ser Val Pro Tyr Glu Gly
65                  70                  75                  80

Val Phe Arg Ile Ala Asn Val Thr Arg Leu Arg Ala Gln Val Ser Glu
                85                  90                  95

Arg Glu Leu Arg Tyr Leu Trp Val Leu Val Ser Leu Ser Ala Thr Glu
```

```
            100                 105                 110
Ser Val Gln Asp Val Leu Leu Glu Gly His Pro Ser Trp Lys Tyr Leu
        115                 120                 125
Gln Glu Val Gln Thr Leu Leu Leu Asn Val Gln Gln Gly Leu Thr Asp
        130                 135                 140
Val Glu Val Ser Pro Lys Val Glu Ser Val Leu Ser Leu Leu Asn Ala
145                 150                 155                 160
Pro Gly Pro Asn Leu Lys Leu Val Arg Pro Lys Ala Leu Leu Asp Asn
                165                 170                 175
Cys Phe Arg Val Met Glu Leu Leu Tyr Cys Ser Cys Cys Lys Gln Ser
                180                 185                 190
Ser Val Leu Asn Trp Gln Asp Cys Glu Val Pro Ser Pro Gln Ser Cys
            195                 200                 205
Ser Pro Glu Pro Ser Leu Gln Tyr Ala Ala Thr Gln Leu Tyr Pro Pro
        210                 215                 220
Pro Pro Trp Ser Pro Ser Ser Pro Pro His Ser Thr Gly Ser Val Arg
225                 230                 235                 240
Pro Val Arg Ala Gln Gly
                245

<210> SEQ ID NO 249
<211> LENGTH: 231
<212> TYPE: PRT
<213> ORGANISM: Homo sapiens

<400> SEQUENCE: 249

Met Lys Thr Cys Trp Lys Ile Pro Val Phe Phe Val Cys Ser Phe
1               5                   10                  15
Leu Glu Pro Trp Ala Ser Ala Glu Phe Met Trp Pro Leu Thr Gln Asn
                20                  25                  30
Glu Glu Cys Thr Val Thr Gly Phe Leu Arg Asp Lys Leu Gln Tyr Arg
            35                  40                  45
Ser Arg Leu Gln Tyr Met Lys His Tyr Phe Pro Ile Asn Tyr Lys Ile
        50                  55                  60
Ser Val Pro Tyr Glu Gly Val Phe Arg Ile Ala Asn Val Thr Arg Leu
65                  70                  75                  80
Arg Ala Gln Val Ser Glu Arg Glu Leu Arg Tyr Leu Trp Val Leu Val
                85                  90                  95
Ser Leu Ser Ala Thr Glu Ser Val Gln Asp Val Leu Leu Glu Gly His
                100                 105                 110
Pro Ser Trp Lys Tyr Leu Gln Glu Val Gln Thr Leu Leu Leu Asn Val
            115                 120                 125
Gln Gln Gly Leu Thr Asp Val Glu Val Ser Pro Lys Val Glu Ser Val
        130                 135                 140
Leu Ser Leu Leu Asn Ala Pro Gly Pro Asn Leu Lys Leu Val Arg Pro
145                 150                 155                 160
Lys Ala Leu Leu Asp Asn Cys Phe Arg Val Met Glu Leu Leu Tyr Cys
                165                 170                 175
Ser Cys Cys Lys Gln Ser Ser Val Leu Asn Trp Gln Asp Cys Glu Val
                180                 185                 190
Pro Ser Pro Gln Ser Cys Ser Pro Glu Pro Ser Leu Gln Tyr Ala Ala
            195                 200                 205
Thr Gln Leu Tyr Pro Pro Pro Trp Ser Pro Ser Ser Pro Pro His
        210                 215                 220
Ser Thr Gly Ser Val Arg Pro
```

<210> SEQ ID NO 250
<211> LENGTH: 219
<212> TYPE: PRT
<213> ORGANISM: Mus musculus

<400> SEQUENCE: 250

Met Pro Trp Gly Leu Ala Trp Leu Tyr Cys Leu Gly Ile Leu Leu Asp
1               5                   10                  15

Val Ala Leu Gly Asn Glu Asn Leu Glu Ile Trp Thr Leu Thr Gln Asp
                20                  25                  30

Lys Glu Cys Asp Leu Thr Gly Tyr Leu Arg Gly Lys Leu Gln Tyr Lys
            35                  40                  45

Asn Arg Leu Gln Tyr Met Lys His Tyr Phe Pro Ile Asn Tyr Arg Ile
        50                  55                  60

Ala Val Pro Tyr Glu Gly Val Leu Arg Val Ala Asn Ile Thr Arg Leu
65                  70                  75                  80

Gln Lys Ala His Val Ser Glu Arg Glu Leu Arg Tyr Leu Trp Val Leu
                85                  90                  95

Val Ser Leu Asn Ala Thr Glu Ser Val Met Asp Val Leu Leu Glu Gly
                100                 105                 110

His Pro Ser Trp Lys Tyr Leu Gln Glu Val Gln Thr Leu Leu Glu Asn
            115                 120                 125

Val Gln Arg Ser Leu Met Ala Val Gly Val His Leu Pro Gly His Val
        130                 135                 140

Leu Val Thr Leu Leu Ser Gln Leu Pro Gly Leu Pro Ser Pro Trp Ala
145                 150                 155                 160

Arg Ser Phe Asp Thr Ser Trp Glu Leu Leu Met Met Lys Gly Cys Gly
                165                 170                 175

Asp Trp Pro Ser Arg Gly Ser Cys Val Ile Ser Ser Glu Tyr Ser Arg
            180                 185                 190

Pro Lys Pro Glu Ala Gly Ala Ala Gln Ser Leu Ala Gly Gln Leu Leu
        195                 200                 205

Pro Gly His Gly Thr Ala Val Leu Phe Leu Leu
    210                 215

<210> SEQ ID NO 251
<211> LENGTH: 266
<212> TYPE: PRT
<213> ORGANISM: Mus musculus

<400> SEQUENCE: 251

Met Pro Trp Gly Leu Ala Trp Leu Tyr Cys Leu Gly Ile Leu Leu Asp
1               5                   10                  15

Val Ala Leu Gly Asn Glu Asn Leu Glu Ile Trp Thr Leu Thr Gln Asp
                20                  25                  30

Lys Glu Cys Asp Leu Thr Gly Tyr Leu Arg Gly Lys Leu Gln Tyr Lys
            35                  40                  45

Asn Arg Leu Gln Tyr Met Lys His Tyr Phe Pro Ile Asn Tyr Arg Ile
        50                  55                  60

Ala Val Pro Tyr Glu Gly Val Leu Arg Val Ala Asn Ile Thr Arg Leu
65                  70                  75                  80

Gln Lys Ala His Val Ser Glu Arg Glu Leu Arg Tyr Leu Trp Val Leu
                85                  90                  95

Val Ser Leu Asn Ala Thr Glu Ser Val Met Asp Val Leu Leu Glu Gly
                100                 105                 110

His Pro Ser Trp Lys Tyr Leu Gln Glu Val Gln Thr Leu Leu Glu Asn
            115                 120                 125

Val Gln Arg Ser Leu Met Ala Val Gly Val His Leu Pro Gly His Val
130                 135                 140

Leu Val Thr Leu Leu Ser Gln Leu Pro Gly Leu Pro Ser Pro Trp Ala
145                 150                 155                 160

Arg Ser Phe Asp Thr Ser Trp Glu Leu Met Met Lys Gly Cys Gly
                165                 170                 175

Asp Trp Pro Ser Arg Gly Ser Cys Val Ile Ser Ser Glu Tyr Ser Arg
            180                 185                 190

Pro Lys Pro Glu Ala Gly Ala Ala Gln Ser Leu Ala Gly Gln Leu Leu
        195                 200                 205

Pro Gly His Gly Thr Ala Val Leu Phe Leu Leu Gly Ser Glu Asn Leu
    210                 215                 220

Tyr Phe Gln Gly Phe Glu Gly Lys Pro Ile Pro Asn Pro Leu Leu Gly
225                 230                 235                 240

Leu Asp Ser Thr Arg Trp Ser His Pro Gln Phe Glu Lys Thr Gly His
                245                 250                 255

His His His His His His Gly Gly Gln
            260                 265

<210> SEQ ID NO 252
<211> LENGTH: 235
<212> TYPE: PRT
<213> ORGANISM: Mus musculus

<400> SEQUENCE: 252

Met Pro Trp Gly Leu Ala Trp Leu Tyr Cys Leu Gly Ile Leu Leu Asp
1               5                   10                  15

Val Ala Leu Gly Asn Glu Asn Leu Glu Ile Trp Thr Leu Thr Gln Asp
            20                  25                  30

Lys Glu Cys Asp Leu Thr Gly Tyr Leu Arg Gly Lys Leu Gln Tyr Lys
        35                  40                  45

Asn Arg Leu Gln Tyr Met Lys His Tyr Phe Pro Ile Asn Tyr Arg Ile
    50                  55                  60

Ala Val Pro Tyr Glu Gly Val Leu Arg Val Ala Asn Ile Thr Arg Leu
65                  70                  75                  80

Gln Lys Ala His Val Ser Glu Arg Glu Leu Arg Tyr Leu Trp Val Leu
                85                  90                  95

Val Ser Leu Asn Ala Thr Glu Ser Val Met Asp Val Leu Leu Glu Gly
            100                 105                 110

His Pro Ser Trp Lys Tyr Leu Gln Glu Val Gln Thr Leu Leu Glu Asn
            115                 120                 125

Val Gln Arg Ser Leu Met Asp Val Glu Ile Gly Pro His Val Glu Ala
130                 135                 140

Val Leu Ser Leu Leu Ser Thr Pro Gly Leu Ser Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Pro Ile Leu Lys Trp Gln Asp Cys Glu
            180                 185                 190

Leu Pro Arg Leu His Pro His Ser Pro Gly Ser Leu Met Gln Cys Thr
        195                 200                 205

Ala Thr Asn Val Tyr Pro Leu Ser Arg Gln Thr Pro Thr Ser Leu Pro
    210                 215                 220

```
Gly Ser Pro Ser Ser His Gly Ser Leu Pro
225                 230             235

<210> SEQ ID NO 253
<211> LENGTH: 282
<212> TYPE: PRT
<213> ORGANISM: Mus musculus

<400> SEQUENCE: 253

Met Pro Trp Gly Leu Ala Trp Leu Tyr Cys Leu Gly Ile Leu Leu Asp
1               5                   10                  15

Val Ala Leu Gly Asn Glu Asn Leu Glu Ile Trp Thr Leu Thr Gln Asp
            20                  25                  30

Lys Glu Cys Asp Leu Thr Gly Tyr Leu Arg Gly Lys Leu Gln Tyr Lys
        35                  40                  45

Asn Arg Leu Gln Tyr Met Lys His Tyr Phe Pro Ile Asn Tyr Arg Ile
    50                  55                  60

Ala Val Pro Tyr Glu Gly Val Leu Arg Val Ala Asn Ile Thr Arg Leu
65                  70                  75                  80

Gln Lys Ala His Val Ser Glu Arg Glu Leu Arg Tyr Leu Trp Val Leu
                85                  90                  95

Val Ser Leu Asn Ala Thr Glu Ser Val Met Asp Val Leu Leu Glu Gly
            100                 105                 110

His Pro Ser Trp Lys Tyr Leu Gln Glu Val Gln Thr Leu Leu Glu Asn
        115                 120                 125

Val Gln Arg Ser Leu Met Asp Val Glu Ile Gly Pro His Val Glu Ala
    130                 135                 140

Val Leu Ser Leu Leu Ser Thr Pro Gly Leu Ser Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Pro Ile Leu Lys Trp Gln Asp Cys Glu
            180                 185                 190

Leu Pro Arg Leu His Pro His Ser Pro Gly Ser Leu Met Gln Cys Thr
        195                 200                 205

Ala Thr Asn Val Tyr Pro Leu Ser Arg Gln Thr Pro Thr Ser Leu Pro
    210                 215                 220

Gly Ser Pro Ser Ser His Gly Ser Leu Pro Gly Ser Glu Asn Leu
225                 230             235                 240

Tyr Phe Gln Gly Phe Glu Gly Lys Pro Ile Pro Asn Pro Leu Leu Gly
                245                 250                 255

Leu Asp Ser Thr Arg Trp Ser His Pro Gln Phe Glu Lys Thr Gly His
            260                 265                 270

His His His His His His Gly Gly Gln
        275                 280

<210> SEQ ID NO 254
<211> LENGTH: 222
<212> TYPE: PRT
<213> ORGANISM: Homo sapiens

<400> SEQUENCE: 254

Asn Glu Pro Leu Glu Met Trp Pro Leu Thr Gln Asn Glu Glu Cys Thr
1               5                   10                  15

Val Thr Gly Phe Leu Arg Asp Lys Leu Gln Tyr Arg Ser Arg Leu Gln
            20                  25                  30
```

```
Tyr Met Lys His Tyr Phe Pro Ile Asn Tyr Lys Ile Ser Val Pro Tyr
         35                  40                  45

Glu Gly Val Phe Arg Ile Ala Asn Val Thr Arg Leu Gln Arg Ala Gln
 50                  55                  60

Val Ser Glu Arg Glu Leu Arg Tyr Leu Trp Val Leu Val Ser Leu Ser
 65                  70                  75                  80

Ala Thr Glu Ser Val Gln Asp Val Leu Leu Glu Gly His Pro Ser Trp
                 85                  90                  95

Lys Tyr Leu Gln Glu Val Gln Thr Leu Leu Leu Asn Val Gln Gln Gly
                100                 105                 110

Leu Thr Asp Val Glu Val Ser Pro Lys Val Glu Ser Val Leu Ser Leu
            115                 120                 125

Leu Asn Ala Pro Gly Pro Asn Leu Lys Leu Val Arg Pro Lys Ala Leu
130                 135                 140

Leu Asp Asn Cys Phe Arg Val Met Glu Leu Leu Tyr Cys Ser Cys Cys
145                 150                 155                 160

Lys Gln Ser Ser Val Leu Asn Trp Gln Asp Cys Glu Val Pro Ser Pro
                165                 170                 175

Gln Ser Cys Ser Pro Glu Pro Ser Leu Gln Tyr Ala Ala Thr Gln Leu
            180                 185                 190

Tyr Pro Pro Pro Pro Trp Ser Pro Ser Ser Pro Pro His Ser Thr Gly
        195                 200                 205

Ser Val Arg Pro Val Arg Ala Gln Gly Glu Gly Leu Leu Pro
210                 215                 220

<210> SEQ ID NO 255
<211> LENGTH: 242
<212> TYPE: PRT
<213> ORGANISM: Homo sapiens

<400> SEQUENCE: 255

Met Pro Arg Gly Phe Thr Trp Leu Arg Tyr Leu Gly Ile Phe Leu Gly
 1                5                  10                  15

Val Ala Leu Gly Asn Glu Pro Leu Glu Met Trp Pro Leu Thr Gln Asn
                 20                  25                  30

Glu Glu Cys Thr Val Thr Gly Phe Leu Arg Asp Lys Leu Gln Tyr Arg
             35                  40                  45

Ser Arg Leu Gln Tyr Met Lys His Tyr Phe Pro Ile Asn Tyr Lys Ile
 50                  55                  60

Ser Val Pro Tyr Glu Gly Val Phe Arg Ile Ala Asn Val Thr Arg Leu
 65                  70                  75                  80

Gln Arg Ala Gln Val Ser Glu Arg Glu Leu Arg Tyr Leu Trp Val Leu
                 85                  90                  95

Val Ser Leu Ser Ala Thr Glu Ser Val Gln Asp Val Leu Leu Glu Gly
            100                 105                 110

His Pro Ser Trp Lys Tyr Leu Gln Glu Val Gln Thr Leu Leu Leu Asn
        115                 120                 125

Val Gln Gln Gly Leu Thr Asp Val Glu Val Ser Pro Lys Val Glu Ser
130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
            180                 185                 190
```

```
Val Pro Ser Pro Gln Ser Cys Ser Pro Glu Pro Ser Leu Gln Tyr Ala
        195                 200                 205

Ala Thr Gln Leu Tyr Pro Pro Pro Trp Ser Pro Ser Ser Pro Pro
    210                 215                 220

His Ser Thr Gly Ser Val Arg Pro Val Arg Ala Gln Gly Glu Gly Leu
225                 230                 235                 240

Leu Pro

<210> SEQ ID NO 256
<211> LENGTH: 222
<212> TYPE: PRT
<213> ORGANISM: Homo sapiens

<400> SEQUENCE: 256

Asn Glu Pro Leu Glu Met Trp Pro Leu Thr Gln Asn Glu Glu Cys Thr
1               5                   10                  15

Val Thr Gly Phe Leu Arg Asp Lys Leu Gln Tyr Arg Ser Arg Leu Gln
            20                  25                  30

Tyr Met Lys His Tyr Phe Pro Ile Asn Tyr Lys Ile Ser Val Pro Tyr
        35                  40                  45

Glu Gly Val Phe Arg Ile Ala Asn Val Thr Arg Leu Gln Arg Ala Gln
    50                  55                  60

Val Ser Glu Arg Glu Leu Arg Tyr Leu Trp Val Leu Val Ser Leu Ser
65                  70                  75                  80

Ala Thr Glu Ser Val Gln Asp Val Leu Leu Glu Gly His Pro Ser Trp
                85                  90                  95

Lys Tyr Leu Gln Glu Val Glu Thr Leu Leu Leu Asn Val Gln Gln Gly
            100                 105                 110

Leu Thr Asp Val Glu Val Ser Pro Lys Val Glu Ser Val Leu Ser Leu
        115                 120                 125

Leu Asn Ala Pro Gly Pro Asn Leu Lys Leu Val Arg Pro Lys Ala Leu
    130                 135                 140

Leu Asp Asn Cys Phe Arg Val Met Glu Leu Leu Tyr Cys Ser Cys Cys
145                 150                 155                 160

Lys Gln Ser Ser Val Leu Asn Trp Gln Asp Cys Glu Val Pro Ser Pro
                165                 170                 175

Gln Ser Cys Ser Pro Glu Pro Ser Leu Gln Tyr Ala Thr Gln Leu
            180                 185                 190

Tyr Pro Pro Pro Trp Ser Pro Ser Ser Pro Pro His Ser Thr Gly
        195                 200                 205

Ser Val Arg Pro Val Arg Ala Gln Gly Glu Gly Leu Leu Pro
    210                 215                 220

<210> SEQ ID NO 257
<211> LENGTH: 1777
<212> TYPE: DNA
<213> ORGANISM: Homo sapiens

<400> SEQUENCE: 257
gcctggactg tgggttgggg gcagcctcag cctctccaac ctggcaccca ctgcccgtgg     60
cccttaggca cctgcttggg gtcctggagc cccttaaggc caccagcaaa tcctaggaga    120
ccgagtcttg gcacgtgaac agagccgat ttcacactga gcagctgcag tcggagaaat    180
cagagaaagc gtcacccagc cccagattcc gaggggcctg ccagggactc tctcctcctg    240
ctccttggaa aggaagaccc cgaaagaccc ccaagccacc ggctcagacc tgcttctggg    300
ctgccatggg acttgcggcc accgcccccc ggctgtcctc cacgctgccg ggcagataag    360
```

```
ggcagctgct gcccttgggg cacctgctca ctcccgcagc ccagccactc ctccagggcc    420
agcccttccc tgactgagtg accacctctg ctgccccgag gccatgtagg ccgtgcttag    480
gcctctgtgg acacactgct ggggacggcg cctgagctct caggggacg aggaacacca    540 cgatgccccg gggcttcacc tggctgcgct atcttgggat cttccttggc gtggccttgg    600
ggaatgagcc tttggagatg tggcccttga cgcagaatga ggagtgcact gtcacgggtt    660
ttctgcggga caagctgcag tacaggagcc gacttcagta catgaaacac tacttcccca    720
tcaactacaa gatcagtgtg ccttacgagg gggtgttcag aatcgccaac gtcaccaggc    780
tgcagagggc ccaggtgagc gagcgggagc tgcggtatct gtgggtcttg gtgagcctca    840
gtgccactga gtcggtgcag gacgtgctgc tcgagggcca cccatcctgg aagtacctgc    900
aggaggtgga gacgctgctg ctgaatgtcc agcagggcct cacggatgtg gaggtcagcc    960
ccaaggtgga atccgtgttg tccctcttga atgcccagg gccaaacctg aagctggtgc   1020
ggcccaaagc cctgctggac aactgcttcc gggtcatgga gctgctgtac tgctcctgct   1080
gtaaacaaag ctccgtccta aactggcagg actgtgaggt gccaagtcct cagtcttgca   1140
gcccagagcc ctcattgcag tatgcggcca cccagctgta ccctccgccc ccgtggtccc   1200
ccagctcccc gcctcactcc acgggctcgg tgaggccggt cagggcacag ggcgagggcc   1260
tcttgccctg agcaccctgg atggtgactg cggataggg cagccagacc agctcccaca   1320
ggagttcaac tgggtctgag acttcaaggg gtggtggtgg gagccccct gggagagga    1380 cccctgggaa gggtgttttt cctttgaggg ggattctgtg ccacagcagg gctcagcttc   1440
ctgccttcca tagctgtcat ggcctcacct ggagcggagg ggacctgggg acctgaaggt   1500
ggatggggac acagctcctg gcttctcctg gtgctgccct cactgtcccc ccgcctaaag   1560
ggggtactga gcctcctgtg gcccgcagca gtgagggcac agctgtgggt tgcaggggag   1620
acagccagca cggcgtggcc attctatgac ccccccagcct ggcagactgg ggagctgggg   1680
gcagagggcg gtgccaagtg ccacatcttg ccatagtgga tgctcttcca gtttctttt    1740 tctattaaac accccacttc ctttgaaaaa aaaaaaa                            1777
```

<210> SEQ ID NO 258
<211> LENGTH: 741
<212> TYPE: DNA
<213> ORGANISM: Artificial Sequence
<220> FEATURE:
<223> OTHER INFORMATION: Description of Artificial Sequence: Synthetic construct

<400> SEQUENCE: 258

```
atgaagacct gctggaaaat tccagttttc ttctttgtgt gcagtttcct ggaaccctgg     60
gcatctgcag aattcaatga gcctttggag atgtggccct tgacgcagaa tgaggagtcc    120
actgtcacgg gttttctgcg ggacaagctg cagtacagga gccgacttca gtacatgaaa    180
cactacttcc ccatcaacta caagatcagt gtgccttacg agggggtgtt cagaatcgcc    240
aacgtcacca ggctgagggc ccaggtgagc gagcgggagc tgcggtatct gtgggtcttg    300
gtgagcctca gtgccactga gtcggtgcag gacgtgctgc tcgagggcca cccatcctgg    360
aagtacctgc aggaggtgca gacgctgctg ctgaatgtcc agcagggcct cacggatgtg    420
gaggtcagcc ccaaggtgga atccgtgttg tccctcttga atgcccagg gccaaacctg    480 aagctggtgc ggcccaaagc cctgctggac aactgcttcc gggtcatgga gctgctgtac    540
tgctcctgct gtaaacaaag ctccgtccta aactggcagg actgtgaggt gccaagtcct    600
```

| cagtcttgca gcccagagcc ctcattgcag tatgcggcca cccagctgta ccctccgccc | 660 |
| ccgtggtccc ccagctcccc gcctcactcc acgggctcgg tgaggccggt cagggcacag | 720 |
| ggcgagggcc tcttgccctg a | 741 |

<210> SEQ ID NO 259
<211> LENGTH: 741
<212> TYPE: DNA
<213> ORGANISM: Artificial Sequence
<220> FEATURE:
<223> OTHER INFORMATION: Description of Artificial Sequence: Synthetic construct

<400> SEQUENCE: 259

| atgaagacct gctggaaaat tccagttttc ttctttgtgt gcagtttcct ggaaccctgg | 60 |
| gcatctgcag aattcaatga gcctttggag atgtggccct tgacgcagaa tgaggagtgc | 120 |
| actgtcacgg gttttctgcg ggacaagctg cagtacagga gccgacttca gtacatgaaa | 180 |
| cactacttcc ccatcaacta caagatcagt gtgccttacg aggggggtgtt cagaatcgcc | 240 |
| aacgtcacca ggctgagggc ccaggtgagc gagcgggagc tgcggtatct gtgggtcttg | 300 |
| gtgagcctca gtgccactga gtcggtgcag gacgtgctgc tcgagggcca ccatcctgg | 360 |
| aagtacctgc aggaggtgca gacgctgctg ctgaatgtcc agcagggcct cacggatgtg | 420 |
| gaggtcagcc ccaaggtgga atccgtgttg tccctcttga atgccccagg ccaaacctg | 480 |
| aagctggtgc ggcccaaagc cctgctggac aactgcttcc gggtcatgga gctgctgtac | 540 |
| tgctcctgct ctaaacaaag ctccgtccta aactggcagg actgtgaggt gccaagtcct | 600 |
| cagtcttgca gcccagagcc ctcattgcag tatgcggcca cccagctgta ccctccgccc | 660 |
| ccgtggtccc ccagctcccc gcctcactcc acgggctcgg tgaggccggt cagggcacag | 720 |
| ggcgagggcc tcttgccctg a | 741 |

<210> SEQ ID NO 260
<211> LENGTH: 741
<212> TYPE: DNA
<213> ORGANISM: Artificial Sequence
<220> FEATURE:
<223> OTHER INFORMATION: Description of Artificial Sequence: Synthetic construct

<400> SEQUENCE: 260

| atgaagacct gctggaaaat tccagttttc ttctttgtgt gcagtttcct ggaaccctgg | 60 |
| gcatctgcag aattcaatga gcctttggag atgtggccct tgacgcagaa tgaggagtgc | 120 |
| actgtcacgg gttttctgcg ggacaagctg cagtacagga gccgacttca gtacatgaaa | 180 |
| cactacttcc ccatcaacta caagatcagt gtgccttacg aggggggtgtt cagaatcgcc | 240 |
| aacgtcacca ggctgagggc ccaggtgagc gagcgggagc tgcggtatct gtgggtcttg | 300 |
| gtgagcctca gtgccactga gtcggtgcag gacgtgctgc tcgagggcca ccatcctgg | 360 |
| aagtacctgc aggaggtgca gacgctgctg ctgaatgtcc agcagggcct cacggatgtg | 420 |
| gaggtcagcc ccaaggtgga atccgtgttg tccctcttga atgccccagg ccaaacctg | 480 |
| aagctggtgc ggcccaaagc cctgctggac aactgcttcc gggtcatgga gctgctgtac | 540 |
| tcctcctgct gtaaacaaag ctccgtccta aactggcagg actgtgaggt gccaagtcct | 600 |
| cagtcttgca gcccagagcc ctcattgcag tatgcggcca cccagctgta ccctccgccc | 660 |
| ccgtggtccc ccagctcccc gcctcactcc acgggctcgg tgaggccggt cagggcacag | 720 |
| ggcgagggcc tcttgccctg a | 741 |

<210> SEQ ID NO 261
<211> LENGTH: 741
<212> TYPE: DNA
<213> ORGANISM: Artificial Sequence
<220> FEATURE:
<223> OTHER INFORMATION: Description of Artificial Sequence: Synthetic construct

<400> SEQUENCE: 261

```
atgaagacct gctggaaaat tccagttttc ttctttgtgt gcagtttcct ggaaccctgg      60
gcatctgcag aattcaatga gcctttggag atgtggccct tgacgcagaa tgaggagtgc     120
actgtcacgg gttttctgcg ggacaagctg cagtacagga gccgacttca gtacatgaaa     180
cactacttcc ccatcaacta caagatcagt gtgccttacg aggggtgtt cagaatcgcc      240
aacgtcacca ggctgagggc ccaggtgagc gagcgggagc tgcggtatct gtgggtcttg     300
gtgagcctca gtgccactga gtcggtgcag gacgtgctgc tcgagggcca cccatcctgg     360
aagtacctgc aggaggtgca gacgctgctg ctgaatgtcc agcagggcct cacggatgtg     420
gaggtcagcc ccaaggtgga atccgtgttg tccctcttga atgccccagg gccaaacctg     480
aagctggtgc ggcccaaagc cctgctggac aactgcttcc gggtcatgga gctgctgtac     540
tgctcctgct gtaaacaaag ctccgtccta aactggcagg actctgaggt gccaagtcct     600
cagtcttgca gcccagagcc ctcattgcag tatgcggcca cccagctgta ccctccgccc     660
ccgtggtccc ccagctcccc gcctcactcc acgggctcgg tgaggccggt cagggcacag     720
ggcgagggcc tcttgccctg a                                                741
```

<210> SEQ ID NO 262
<211> LENGTH: 741
<212> TYPE: DNA
<213> ORGANISM: Artificial Sequence
<220> FEATURE:
<223> OTHER INFORMATION: Description of Artificial Sequence: Synthetic construct

<400> SEQUENCE: 262

```
atgaagacct gctggaaaat tccagttttc ttctttgtgt gcagtttcct ggaaccctgg      60
gcatctgcag aattcaatga gcctttggag atgtggccct tgacgcagaa tgaggagtgc     120
actgtcacgg gttttctgcg ggacaagctg cagtacagga gccgacttca gtacatgaaa     180
cactacttcc ccatcaacta caagatcagt gtgccttacg aggggtgtt cagaatcgcc      240
aacgtcacca ggctgagggc ccaggtgagc gagcgggagc tgcggtatct gtgggtcttg     300
gtgagcctca gtgccactga gtcggtgcag gacgtgctgc tcgagggcca cccatcctgg     360
aagtacctgc aggaggtgca gacgctgctg ctgaatgtcc agcagggcct cacggatgtg     420
gaggtcagcc ccaaggtgga atccgtgttg tccctcttga atgccccagg gccaaacctg     480
aagctggtgc ggcccaaagc cctgctggac aactccttcc gggtcatgga gctgctgtac     540
tgctcctgct gtaaacaaag ctccgtccta aactggcagg actgtgaggt gccaagtcct     600
cagtcttgca gcccagagcc ctcattgcag tatgcggcca cccagctgta ccctccgccc     660
ccgtggtccc ccagctcccc gcctcactcc acgggctcgg tgaggccggt cagggcacag     720
ggcgagggcc tcttgccctg a                                                741
```

<210> SEQ ID NO 263
<211> LENGTH: 741
<212> TYPE: DNA
<213> ORGANISM: Artificial Sequence
<220> FEATURE:

<223> OTHER INFORMATION: Description of Artificial Sequence: Synthetic
      construct

<400> SEQUENCE: 263

```
atgaagacct gctggaaaat tccagttttc ttctttgtgt gcagtttcct ggaaccctgg      60
gcatctgcag aattcaatga gcctttggag atgtggccct tgacgcagaa tgaggagtgc     120
actgtcacgg ttttctgcg ggacaagctg cagtacagga ccgacttca gtacatgaaa      180
cactacttcc ccatcaacta caagatcagt gtgccttacg aggggtgtt cagaatcgcc     240
aacgtcacca ggctgagggc ccaggtgagc gagcgggagc tgcggtatct gtgggtcttg     300
gtgagcctca gtgccactga gtcggtgcag gacgtgctgc tcgagggcca cccatcctgg     360
aagtacctgc aggaggtgca gacgctgctg ctgaatgtcc agcagggcct cacggatgtg     420
gaggtcagcc ccaaggtgga atccgtgttg tccctcttga atgccccagg gccaaacctg     480
aagctggtgc ggcccaaagc cctgctggac aactgcttcc gggtcatgga gctgctgtac     540
tgctcctcct gtaaacaaag ctccgtccta aactggcagg actgtgaggt gccaagtcct     600
cagtcttgca gcccagagcc ctcattgcag tatgcggcca cccagctgta ccctccgccc     660
ccgtggtccc ccagctcccc gcctcactcc acgggctcgg tgaggccggt cagggcacag     720
ggcgagggcc tcttgccctg a                                                741
```

<210> SEQ ID NO 264
<211> LENGTH: 741
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 264

```
atgaagacct gctggaaaat tccagttttc ttctttgtgt gcagtttcct ggaaccctgg      60
gcatctgcag aattcaatga gcctttggag atgtggccct tgacgcagaa tgaggagtgc     120
actgtcacgg ttttctgcg ggacaagctg cagtacagga ccgacttca gtacatgaaa      180
cactacttcc ccatcaacta caagatcagt gtgccttacg aggggtgtt cagaatcgcc     240
aacgtcacca ggctgagggc ccaggtgagc gagcgggagc tgcggtatct gtgggtcttg     300
gtgagcctca gtgccactga gtcggtgcag gacgtgctgc tcgagggcca cccatcctgg     360
aagtacctgc aggaggtgca gacgctgctg ctgaatgtcc agcagggcct cacggatgtg     420
gaggtcagcc ccaaggtgga atccgtgttg tccctcttga atgccccagg gccaaacctg     480
aagctggtgc ggcccaaagc cctgctggac aactgcttcc gggtcatgga gctgctgtac     540
tgctcctgct gtaaacaaag ctccgtccta aactggcagg actgtgaggt gccaagtcct     600
cagtcttcca gcccagagcc ctcattgcag tatgcggcca cccagctgta ccctccgccc     660
ccgtggtccc ccagctcccc gcctcactcc acgggctcgg tgaggccggt cagggcacag     720
ggcgagggcc tcttgccctg a                                                741
```

<210> SEQ ID NO 265
<211> LENGTH: 246
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 265

Met Lys Thr Cys Trp Lys Ile Pro Val Phe Phe Phe Val Cys Ser Phe

```
                1               5                  10                 15
Leu Glu Pro Trp Ala Ser Ala Glu Phe Asn Glu Pro Leu Glu Met Trp
                20                 25                 30

Pro Leu Thr Gln Asn Glu Glu Ser Thr Val Thr Gly Phe Leu Arg Asp
            35                 40                 45

Lys Leu Gln Tyr Arg Ser Arg Leu Gln Tyr Met Lys His Tyr Phe Pro
        50                 55                 60

Ile Asn Tyr Lys Ile Ser Val Pro Tyr Glu Gly Val Phe Arg Ile Ala
65                  70                 75                 80

Asn Val Thr Arg Leu Arg Ala Gln Val Ser Glu Arg Glu Leu Arg Tyr
                85                 90                 95

Leu Trp Val Leu Val Ser Leu Ser Ala Thr Glu Ser Val Gln Asp Val
                100                105                110

Leu Leu Glu Gly His Pro Ser Trp Lys Tyr Leu Gln Glu Val Gln Thr
            115                120                125

Leu Leu Leu Asn Val Gln Gln Gly Leu Thr Asp Val Glu Val Ser Pro
        130                135                140

Lys Val Glu Ser Val Leu Ser Leu Leu Asn Ala Pro Gly Pro Asn Leu
145                 150                155                160

Lys Leu Val Arg Pro Lys Ala Leu Leu Asp Asn Cys Phe Arg Val Met
                165                170                175

Glu Leu Leu Tyr Cys Ser Cys Cys Lys Gln Ser Ser Val Leu Asn Trp
                180                185                190

Gln Asp Cys Glu Val Pro Ser Pro Gln Ser Cys Ser Pro Glu Pro Ser
            195                200                205

Leu Gln Tyr Ala Ala Thr Gln Leu Tyr Pro Pro Pro Trp Ser Pro
        210                215                220

Ser Ser Pro Pro His Ser Thr Gly Ser Val Arg Pro Val Arg Ala Gln
225                 230                235                240

Gly Glu Gly Leu Leu Pro
                245

<210> SEQ ID NO 266
<211> LENGTH: 246
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 266

Met Lys Thr Cys Trp Lys Ile Pro Val Phe Phe Val Cys Ser Phe
1               5                  10                 15

Leu Glu Pro Trp Ala Ser Ala Glu Phe Asn Glu Pro Leu Glu Met Trp
                20                 25                 30

Pro Leu Thr Gln Asn Glu Glu Cys Thr Val Thr Gly Phe Leu Arg Asp
            35                 40                 45

Lys Leu Gln Tyr Arg Ser Arg Leu Gln Tyr Met Lys His Tyr Phe Pro
        50                 55                 60

Ile Asn Tyr Lys Ile Ser Val Pro Tyr Glu Gly Val Phe Arg Ile Ala
65                  70                 75                 80

Asn Val Thr Arg Leu Arg Ala Gln Val Ser Glu Arg Glu Leu Arg Tyr
                85                 90                 95

Leu Trp Val Leu Val Ser Leu Ser Ala Thr Glu Ser Val Gln Asp Val
                100                105                110

Leu Leu Glu Gly His Pro Ser Trp Lys Tyr Leu Gln Glu Val Gln Thr
```

```
                115                 120                 125
Leu Leu Leu Asn Val Gln Gln Gly Leu Thr Asp Val Glu Val Ser Pro
        130                 135                 140

Lys Val Glu Ser Val Leu Ser Leu Leu Asn Ala Pro Gly Pro Asn Leu
145                 150                 155                 160

Lys Leu Val Arg Pro Lys Ala Leu Leu Asp Asn Cys Phe Arg Val Met
                165                 170                 175

Glu Leu Leu Tyr Cys Ser Cys Ser Lys Gln Ser Ser Val Leu Asn Trp
            180                 185                 190

Gln Asp Cys Glu Val Pro Ser Pro Gln Ser Cys Ser Pro Glu Pro Ser
        195                 200                 205

Leu Gln Tyr Ala Ala Thr Gln Leu Tyr Pro Pro Pro Trp Ser Pro
    210                 215                 220

Ser Ser Pro Pro His Ser Thr Gly Ser Val Arg Pro Val Arg Ala Gln
225                 230                 235                 240

Gly Glu Gly Leu Leu Pro
                245

<210> SEQ ID NO 267
<211> LENGTH: 246
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 267

Met Lys Thr Cys Trp Lys Ile Pro Val Phe Phe Val Cys Ser Phe
1               5                   10                  15

Leu Glu Pro Trp Ala Ser Ala Glu Phe Asn Glu Pro Leu Glu Met Trp
                20                  25                  30

Pro Leu Thr Gln Asn Glu Glu Cys Thr Val Thr Gly Phe Leu Arg Asp
            35                  40                  45

Lys Leu Gln Tyr Arg Ser Arg Leu Gln Tyr Met Lys His Tyr Phe Pro
    50                  55                  60

Ile Asn Tyr Lys Ile Ser Val Pro Tyr Glu Gly Val Phe Arg Ile Ala
65                  70                  75                  80

Asn Val Thr Arg Leu Arg Ala Gln Val Ser Glu Arg Glu Leu Arg Tyr
                85                  90                  95

Leu Trp Val Leu Val Ser Leu Ser Ala Thr Glu Ser Val Gln Asp Val
            100                 105                 110

Leu Leu Glu Gly His Pro Ser Trp Lys Tyr Leu Gln Glu Val Gln Thr
        115                 120                 125

Leu Leu Leu Asn Val Gln Gln Gly Leu Thr Asp Val Glu Val Ser Pro
    130                 135                 140

Lys Val Glu Ser Val Leu Ser Leu Leu Asn Ala Pro Gly Pro Asn Leu
145                 150                 155                 160

Lys Leu Val Arg Pro Lys Ala Leu Leu Asp Asn Cys Phe Arg Val Met
                165                 170                 175

Glu Leu Leu Tyr Ser Ser Cys Cys Lys Gln Ser Ser Val Leu Asn Trp
            180                 185                 190

Gln Asp Cys Glu Val Pro Ser Pro Gln Ser Cys Ser Pro Glu Pro Ser
        195                 200                 205

Leu Gln Tyr Ala Ala Thr Gln Leu Tyr Pro Pro Pro Trp Ser Pro
    210                 215                 220

Ser Ser Pro Pro His Ser Thr Gly Ser Val Arg Pro Val Arg Ala Gln
```

Gly Glu Gly Leu Leu Pro
            245

<210> SEQ ID NO 268
<211> LENGTH: 246
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 268

Met Lys Thr Cys Trp Lys Ile Pro Val Phe Phe Val Cys Ser Phe
1               5                   10                  15

Leu Glu Pro Trp Ala Ser Ala Glu Phe Asn Glu Pro Leu Glu Met Trp
                20                  25                  30

Pro Leu Thr Gln Asn Glu Glu Cys Thr Val Thr Gly Phe Leu Arg Asp
            35                  40                  45

Lys Leu Gln Tyr Arg Ser Arg Leu Gln Tyr Met Lys His Tyr Phe Pro
        50                  55                  60

Ile Asn Tyr Lys Ile Ser Val Pro Tyr Glu Gly Val Phe Arg Ile Ala
65                  70                  75                  80

Asn Val Thr Arg Leu Arg Ala Gln Val Ser Glu Arg Glu Leu Arg Tyr
                85                  90                  95

Leu Trp Val Leu Val Ser Leu Ser Ala Thr Glu Ser Val Gln Asp Val
            100                 105                 110

Leu Leu Glu Gly His Pro Ser Trp Lys Tyr Leu Gln Glu Val Gln Thr
        115                 120                 125

Leu Leu Leu Asn Val Gln Gln Gly Leu Thr Asp Val Gly Val Ser Pro
    130                 135                 140

Lys Val Glu Ser Val Leu Ser Leu Leu Asn Ala Pro Gly Pro Asn Leu
145                 150                 155                 160

Lys Leu Val Arg Pro Lys Ala Leu Leu Asp Asn Cys Phe Arg Val Met
                165                 170                 175

Glu Leu Leu Tyr Cys Ser Cys Cys Lys Gln Ser Ser Val Leu Asn Trp
            180                 185                 190

Gln Asp Ser Glu Val Pro Ser Pro Gln Ser Cys Ser Pro Glu Pro Ser
        195                 200                 205

Leu Gln Tyr Ala Ala Thr Gln Leu Tyr Pro Pro Pro Trp Ser Pro
    210                 215                 220

Ser Ser Pro Pro His Ser Thr Gly Ser Val Arg Pro Val Arg Ala Gln
225                 230                 235                 240

Gly Glu Gly Leu Leu Pro
            245

<210> SEQ ID NO 269
<211> LENGTH: 246
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 269

Met Lys Thr Cys Trp Lys Ile Pro Val Phe Phe Val Cys Ser Phe
1               5                   10                  15

Leu Glu Pro Trp Ala Ser Ala Glu Phe Asn Glu Pro Leu Glu Met Trp
                20                  25                  30

```
Pro Leu Thr Gln Asn Glu Glu Cys Thr Val Thr Gly Phe Leu Arg Asp
            35                  40                  45

Lys Leu Gln Tyr Arg Ser Arg Leu Gln Tyr Met Lys His Tyr Phe Pro
 50                  55                  60

Ile Asn Tyr Lys Ile Ser Val Pro Tyr Glu Gly Val Phe Arg Ile Ala
 65                  70                  75                  80

Asn Val Thr Arg Leu Arg Ala Gln Val Ser Glu Arg Glu Leu Arg Tyr
                 85                  90                  95

Leu Trp Val Leu Val Ser Leu Ser Ala Thr Glu Ser Val Gln Asp Val
                100                 105                 110

Leu Leu Glu Gly His Pro Ser Trp Lys Tyr Leu Gln Glu Val Gln Thr
            115                 120                 125

Leu Leu Leu Asn Val Gln Gln Gly Leu Thr Asp Val Glu Val Ser Pro
            130                 135                 140

Lys Val Glu Ser Val Leu Ser Leu Leu Asn Ala Pro Gly Pro Asn Leu
145                 150                 155                 160

Lys Leu Val Arg Pro Lys Ala Leu Leu Asp Asn Ser Phe Arg Val Met
                165                 170                 175

Glu Leu Leu Tyr Cys Ser Cys Cys Lys Gln Ser Ser Val Leu Asn Trp
                180                 185                 190

Gln Asp Cys Glu Val Pro Ser Pro Gln Ser Cys Ser Pro Glu Pro Ser
            195                 200                 205

Leu Gln Tyr Ala Ala Thr Gln Leu Tyr Pro Pro Pro Trp Ser Pro Ser
            210                 215                 220

Ser Pro Pro His Ser Thr Gly Ser Val Arg Pro Val Arg Ala Gln Gly
225                 230                 235                 240

Gly Glu Gly Leu Leu Pro
                245

<210> SEQ ID NO 270
<211> LENGTH: 246
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 270

Met Lys Thr Cys Trp Lys Ile Pro Val Phe Phe Val Cys Ser Phe
 1               5                  10                  15

Leu Glu Pro Trp Ala Ser Ala Glu Phe Asn Glu Pro Leu Glu Met Trp
                 20                  25                  30

Pro Leu Thr Gln Asn Glu Glu Cys Thr Val Thr Gly Phe Leu Arg Asp
            35                  40                  45

Lys Leu Gln Tyr Arg Ser Arg Leu Gln Tyr Met Lys His Tyr Phe Pro
 50                  55                  60

Ile Asn Tyr Lys Ile Ser Val Pro Tyr Glu Gly Val Phe Arg Ile Ala
 65                  70                  75                  80

Asn Val Thr Arg Leu Arg Ala Gln Val Ser Glu Arg Glu Leu Arg Tyr
                 85                  90                  95

Leu Trp Val Leu Val Ser Leu Ser Ala Thr Glu Ser Val Gln Asp Val
                100                 105                 110

Leu Leu Glu Gly His Pro Ser Trp Lys Tyr Leu Gln Glu Val Gln Thr
            115                 120                 125

Leu Leu Leu Asn Val Gln Gln Gly Leu Thr Asp Val Glu Val Ser Pro
            130                 135                 140
```

```
Lys Val Glu Ser Val Leu Ser Leu Leu Asn Ala Pro Gly Pro Asn Leu
145                 150                 155                 160

Lys Leu Val Arg Pro Lys Ala Leu Leu Asp Asn Cys Phe Arg Val Met
                165                 170                 175

Glu Leu Leu Tyr Cys Ser Ser Cys Lys Gln Ser Ser Val Leu Asn Trp
            180                 185                 190

Gln Asp Cys Glu Val Pro Ser Pro Gln Ser Cys Ser Pro Glu Pro Ser
        195                 200                 205

Leu Gln Tyr Ala Ala Thr Gln Leu Tyr Pro Pro Pro Trp Ser Pro
    210                 215                 220

Ser Ser Pro Pro His Ser Thr Gly Ser Val Arg Pro Val Arg Ala Gln
225                 230                 235                 240

Gly Glu Gly Leu Leu Pro
            245

<210> SEQ ID NO 271
<211> LENGTH: 246
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 271

Met Lys Thr Cys Trp Lys Ile Pro Val Phe Phe Val Cys Ser Phe
1               5                   10                  15

Leu Glu Pro Trp Ala Ser Ala Glu Phe Asn Gly Pro Leu Glu Met Trp
                20                  25                  30

Pro Leu Thr Gln Asn Glu Glu Cys Thr Val Thr Gly Phe Leu Arg Asp
            35                  40                  45

Lys Leu Gln Tyr Arg Ser Arg Leu Gln Tyr Met Lys His Tyr Phe Pro
        50                  55                  60

Ile Asn Tyr Lys Ile Ser Val Pro Tyr Glu Gly Val Phe Arg Ile Ala
65                  70                  75                  80

Asn Val Thr Arg Leu Arg Ala Gln Val Ser Glu Arg Glu Leu Arg Tyr
                85                  90                  95

Leu Trp Val Leu Val Ser Leu Ser Ala Thr Glu Ser Val Gln Asp Val
            100                 105                 110

Leu Leu Glu Gly His Pro Ser Trp Lys Tyr Leu Gln Glu Val Gln Thr
        115                 120                 125

Leu Leu Leu Asn Val Gln Gln Gly Leu Thr Asp Val Glu Val Ser Pro
    130                 135                 140

Lys Val Glu Ser Val Leu Ser Leu Leu Asn Ala Pro Gly Pro Asn Leu
145                 150                 155                 160

Lys Leu Val Arg Pro Lys Ala Leu Leu Asp Asn Cys Phe Arg Val Met
                165                 170                 175

Glu Leu Leu Tyr Cys Ser Cys Cys Lys Gln Ser Ser Val Leu Asn Trp
            180                 185                 190

Gln Asp Cys Glu Val Pro Ser Pro Gln Ser Ser Pro Glu Pro Ser
        195                 200                 205

Leu Gln Tyr Ala Ala Thr Gln Leu Tyr Pro Pro Pro Trp Ser Pro
    210                 215                 220

Ser Ser Pro Pro His Ser Thr Gly Ser Val Arg Pro Val Arg Ala Gln
225                 230                 235                 240

Gly Glu Gly Leu Leu Pro
            245
```

<210> SEQ ID NO 272
<211> LENGTH: 7207
<212> TYPE: DNA
<213> ORGANISM: Artificial Sequence
<220> FEATURE:
<223> OTHER INFORMATION: Description of Artificial Sequence: Synthetic pTT5-G sequence

<400> SEQUENCE: 272

```
gtacatttat attggctcat gtccaatatg accgccatgt tgacattgat tattgactag      60
ttattaatag taatcaatta cggggtcatt agttcatagc ccatatatgg agttccgcgt     120
tacataactt acggtaaatg gcccgcctgg ctgaccgccc aacgacccce gcccattgac     180
gtcaataatg acgtatgttc ccatagtaac gccaataggg actttccatt gacgtcaatg     240
ggtggagtat ttacggtaaa ctgcccactt ggcagtacat caagtgtatc atatgccaag     300
tccgccccct attgacgtca atgacggtaa atggcccgcc tggcattatg cccagtacat     360
gaccttacgg gactttccta cttggcagta catctacgta ttagtcatcg ctattaccat     420
ggtgatgcgg ttttggcagt acaccaatgg gcgtggatag cggtttgact cacggggatt     480
tccaagtctc cacccccattg acgtcaatgg gagtttgttt tggcaccaaa atcaacggga     540
ctttccaaaa tgtcgtaata accccgcccc gttgacgcaa atgggcggta ggcgtgtacg     600
gtgggaggtc tatataagca gagctcgttt agtgaaccgt cagatcctca ctctcttccg     660
catcgctgtc tgcagggcc agctgttggg ctcgcggttg aggacaaaact cttcgcggtc     720
tttccagtac tcttggatcg gaaacccgtc ggcctccgaa cggtactccg ccaccgaggg     780
acctgagcca gtccgcatcg accggatcgg aaaacctctc gagaaaggcg tctaaccagt     840
cacagtcgca aggtaggctg agcaccgtgg cgggcggcag cgggtggcgg tcggggttgt     900
ttctggcgga ggtgctgctg atgatgtaat taaagtaggc ggtcttgagc cggcggatgg     960
tcgaggtgag gtgtggcagg cttgagatcc agctgttggg gtgagtactc cctctcaaaa    1020
gcgggcatga cttctgcgct aagattgtca gtttccaaaa acgaggagga tttgatattc    1080
acctggcccg atcggccat acacttgagt gacaatgaca tccactttgc ctttctctcc    1140
acaggtgtcc actcccaggt ccaagtttaa acagcggccg cgccgccacc atgaagacct    1200
gctgaaaat tccagttttc ttctttgtgt gcagtttcct ggaaccctgg gcatctgcag    1260
aattcgatat catcacaagt ttgtacaaaa aagctgaacg agaaacgtaa aatgatataa    1320
atatcaatat attaaattag attttgcata aaaaacagac tacataatac tgtaaaacac    1380
aacatatcca gtcatattgg cggccgcatt aggcacccca ggctttacac tttatgcttc    1440
cggctcgtat aatgtgtgga ttttgagtta ggatccgtcg agattttcag gagctaagga    1500
agctaaaatg gagaaaaaaa tcactggata taccaccgtt gatatatccc aatggcatcg    1560
taaagaacat tttgaggcat ttcagtcagt tgctcaatgt acctataacc agaccgttca    1620
gctggatatt acggcctttt taaagaccgt aaagaaaaat aagcacaagt tttatccggc    1680
ctttattcac attcttgccc gcctgatgaa tgctcatccg gaattccgta tggcaatgaa    1740
agacggtgag ctggtgatat gggatagtgt tcacccttgt tacaccgttt tccatgagca    1800
aactgaaacg ttttcatcgc tctggagtga ataccacgac gatttccggc agtttctaca    1860
catatattcg caagatgtgg cgtgttacgg tgaaaacctg gcctatttcc ctaaagggtt    1920
tattgagaat atgttttcg tctcagccaa tccctgggtg agtttcacca gttttgattt    1980
aaacgtggcc aatatggaca acttcttcgc cccgttttc accatgggca aatattatac    2040
```

```
gcaaggcgac aaggtgctga tgccgctggc gattcaggtt catcatgccg tttgtgatgg    2100
cttccatgtc ggcagaatgc ttaatgaatt acaacagtac tgcgatgagt ggcagggcgg    2160
ggcgtaaacg cgtggatccg gcttactaaa agccagataa cagtatgcgt atttgcgcgc    2220 tgattttttgc ggtataagaa tatatactga tatgtatacc cgaagtatgt caaaaagagg    2280
tatgctatga agcagcgtat tacagtgaca gttgacagcg acagctatca gttgctcaag    2340
gcatatatga tgtcaatatc tccggtctgg taagcacaac catgcagaat gaagcccgtc    2400
gtctgcgtgc cgaacgctgg aaagcggaaa atcaggaagg gatggctgag gtcgcccggt    2460
ttattgaaat gaacggctct tttgctgacg agaacagggg ctggtgaaat gcagtttaag    2520
gtttacacct ataaaagaga gagccgttat cgtctgtttg tggatgtaca gagtgatatt    2580
attgacacgc ccgggcgacg gatggtgatc cccctggcca gtgcacgtct gctgtcagat    2640
aaagtctccc gtgaacttta cccggtggtg catatcgggg atgaaagctg gcgcatgatg    2700
accaccgata tggccagtgt gccggtctcc gttatcgggg aagaagtggc tgatctcagc    2760
caccgcgaaa atgacatcaa aaacgccatt aacctgatgt tctggggaat ataaatgtca    2820
ggctccctta tacacagcca gtctgcaggt cgaccatagt gactggatat gttgtgtttt    2880
acagcattat gtagtctgtt ttttatgcaa aatctaattt aatatattga tatttatatc    2940
attttacgtt tctcgttcag cttttcttgta caaagtggtg atcggatccg aaaacctgta    3000
ttttcagggc ttcgaaggta agcctatccc taaccctctc ctcggtctcg attctacgcg    3060
ttggagccac ccgcagttcg agaaaaccgg tcatcatcac catcaccatc accatggagg    3120
acagtgaaga tccccccgacc tcgacctctg gctaataaag gaaatttatt ttcattgcaa    3180
tagtgtgttg gaattttttg tgtctctcac tcggaaggac atatgggagg gcaaatcatt    3240
tggtcgagat ccctcggaga tctctagcta gagccccgcc gccggacgaa ctaaacctga    3300
ctacggcatc tctgcccctt cttcgcgggg cagtgcatgt aatcccttca gttggttggt    3360
acaacttgcc aactgaaccc taaacgggta gcatatgctt cccgggtagt agtatatact    3420
atccagacta accctaattc aatagcatat gttacccaac gggaagcata tgctatcgaa    3480 ttaggggttag taaaagggtc ctaaggaaca gcgatgtagg tgggcgggcc aagataggg   3540 cgcgattgct gcgatctgga ggacaaatta cacacacttg cgcctgagcg ccaagcacag    3600
ggttgttggt cctcatattc acgaggtcgc tgagagcacg tgggctaatg ttgccatgg    3660 gtagcatata ctacccaaat atctggatag catatgctat cctaatctat atctgggtag    3720
cataggctat cctaatctat atctgggtag catatgctat cctaatctat atctgggtag    3780
tatatgctat cctaatttat atctgggtag cataggctat cctaatctat atctgggtag    3840
catatgctat cctaatctat atctgggtag tatatgctat cctaatctgt atccgggtag    3900
catatgctat cctaatagag attagggtag tatatgctat cctaatttat atctgggtag    3960
catatactac ccaaatatct ggatagcata tgctatccta atctatatct gggtagcata    4020
tgctatccta atctatatct gggtagcata ggctatccta atctatatct gggtagcata    4080
tgctatccta atctatatct gggtagtata tgctatccta atttatatct gggtagcata    4140
ggctatccta atctatatct gggtagcata tgctatccta atctatatct gggtagtata    4200
tgctatccta atctgtatcc gggtagcata tgctatcctc acgatgataa gctgtcaaac    4260
atgagaatta attcttgaag acgaaagggc ctcgtgatac gcctattttt ataggttaat    4320
gtcatgataa taatggtttc ttagacgtca ggtggcactt ttcggggaaa tgtgcgcgga    4380 accccctattt gtttattttt ctaaatacat tcaaatatgt atccgctcat gagacaataa    4440
```

```
ccctgataaa tgcttcaata atccggaatt gccagctggg gcgccctctg gtaaggttgg    4500
gaagccctgc aaagtaaact ggatggcttt cttgccgcca aggatctgat ggcgcagggg    4560
atcaagatct gatcaagaga caggatgagg atcgtttcgc atgattgaac aagatggatt    4620
gcacgcaggt tctccggccg cttgggtgga gaggctattc ggctatgact gggcacaaca    4680
gacaatcggc tgctctgatg ccgccgtgtt ccggctgtca gcgcaggggc gcccggttct    4740
ttttgtcaag accgacctgt ccggtgccct gaatgaactg caggacgagg cagcgcggct    4800
atcgtggctg gccacgacgg gcgttccttg cgcagctgtg ctcgacgttg tcactgaagc    4860
gggaagggac tggctgctat tgggcgaagt gccggggcag gatctcctgt catcccacct    4920
tgctcctgcc gagaaagtat ccatcatggc tgatgcaatg cggcggctgc atacgcttga    4980
tccggctacc tgcccattcg accaccaagc gaaacatcgc atcgagcgag cacgtactcg    5040
gatggaagcc ggtcttgtcg atcaggatga tctggacgaa gagcatcagg ggctcgcgcc    5100
agccgaactg ttcgccaggc tcaaggcgcg catgcccgac ggcgaggatc tcgtcgtgac    5160
ccatggcgat gcctgcttgc cgaatatcat ggtggaaaat ggccgctttt ctggattcat    5220
cgactgtggc cggctgggtg tggcggaccg ctatcaggac atagcgttgg ctacccgtga    5280
tattgctgaa gagcttggcg gcgaatgggc tgaccgcttc ctcgtgcttt acggtatcgc    5340
cgctcccgat tcgcagcgca tcgccttcta tcgccttctt gacgagttct tctgaattga    5400
aaaaggaaga gtatgagtat tcaacatttc cgtgtcgccc ttattccctt ttttgcggca    5460
ttttgccttc ctgttttgc tcacccagaa acgctggtga agtaaaaga tgctgaagat    5520
cagttgggtg cacgagtggg ttacatcgaa ctggatctca acagcggtaa gatccttgag    5580
agttttcgcc ccgaagaacg ttttccaatg atgagcactt taaagttct gctatgtggc    5640
gcggtattat cccgtgttga cgccgggcaa gagcaactcg gtcgccgcat acactattct    5700
cagaatgact tggttgagta ctcaccagtc acagaaaagc atcttacgga tggcatgaca    5760
gtaagagaat tatgcagtgc tgccataaca tgagtgataa cactgcggcc aacttacttc    5820
tgacaacgat cggaggaccg aaggagctaa ccgcttttt gcacaacatg ggggatcatg    5880
taactcgcct tgatcgttgg gaaccggagc tgaatgaagc cataccaaac gacgagcgtg    5940
acaccacgat gcctgcagca atggcaacaa cgttgcgcaa actattaact ggcgaactac    6000
ttactctagc ttcccggcaa caattaatag actggatgga ggcggataaa gttgcaggac    6060
cacttctgcg ctcggccctt ccggctggct ggtttattgc tgataaatct ggagccggtg    6120
agcgtgggtc tcgcggtatc attgcagcac tggggccaga tggtaagccc tcccgtatcg    6180
tagttatcta cacgacgggg agtcaggcaa ctatggatga acgaaataga cagatcgctg    6240
agataggtgc ctcactgatt aagcattggt aactgtcaga ccaagtttac tcatatatac    6300
tttagattga tttaaaactt cattttaat ttaaaggat ctaggtgaag atcctttttg    6360
ataatctcat gaccaaaatc ccttaacgtg agttttcgtt ccactgagcg tcagaccccg    6420
tagaaaagat caaaggatct cttgagatc ctttttttct gcgcgtaatc tgctgcttgc    6480
aaacaaaaaa accaccgcta ccagcggtgg tttgtttgcc ggatcaagag ctaccaactc    6540
tttttccgaa ggtaactggc ttcagcagag cgcagatacc aaatactgtc cttctagtgt    6600
agccgtagtt aggccaccac ttcaagaact ctgtagcacc gcctacatac ctcgctctgc    6660
taatcctgtt accagtggct gctgccagtg gcgataagtc gtgtcttacc gggttggact    6720
caagacgata gttaccggat aaggcgcagc ggtcgggctg aacggggggt tcgtgcacac    6780
agcccagctt ggagcgaacg acctacaccg aactgagata cctacagcgt gagcattgag    6840
```

```
aaagcgccac gcttcccgaa gggagaaagg cggacaggta tccggtaagc ggcagggtcg    6900
gaacaggaga gcgcacgagg gagcttccag ggggaaacgc ctggtatctt tatagtcctg    6960
tcgggtttcg ccacctctga cttgagcgtc gattttgtg atgctcgtca gggggcgga     7020 gcctatggaa aaacgccagc aacgcggcct ttttacggtt cctggccttt tgctggcctt    7080
ttgctcacat gttctttcct gcgttatccc ctgattctgt ggataaccgt attaccgcct    7140
ttgagtgagc tgataccgct cgccgcagcc gaacgaccga gcgcagcgag tcagtgagcg    7200
aggaagc                                                              7207

<210> SEQ ID NO 273
<211> LENGTH: 7288
<212> TYPE: DNA
<213> ORGANISM: Artificial Sequence
<220> FEATURE:
<223> OTHER INFORMATION: Description of Artificial Sequence: Synthetic
      pTT5-H sequence

<400> SEQUENCE: 273
gtacatttat attggctcat gtccaatatg accgccatgt tgacattgat tattgactag      60
ttattaatag taatcaatta cggggtcatt agttcatagc ccatatatgg agttccgcgt     120
tacataactt acggtaaatg gcccgcctgg ctgaccgccc aacgaccccc gcccattgac     180
gtcaataatg acgtatgttc ccatagtaac gccaataggg actttccatt gacgtcaatg     240
ggtggagtat ttacggtaaa ctgcccactt ggcagtacat caagtgtatc atatgccaag     300
tccgccccct attgacgtca atgacggtaa atggcccgcc tggcattatg cccagtacat     360
gaccttacgg gactttccta cttggcagta catctacgta ttagtcatcg ctattaccat     420
ggtgatgcgg ttttggcagt acaccaatgg gcgtggatag cggtttgact cacggggatt     480
tccaagtctc cacccattg acgtcaatgg gagtttgttt tggcaccaaa atcaacggga     540
ctttccaaaa tgtcgtaata accccgcccc gttgacgcaa atgggcggta ggcgtgtacg     600
gtgggaggtc tatataagca gagctcgttt agtgaaccgt cagatcctca ctctcttccg     660
catcgctgtc tgcgagggcc agctgttggg ctcgcggttg aggacaaaact cttcgcggtc     720 tttccagtac tcttggatcg gaaacccgtc ggcctccgaa cggtactccg ccaccgaggg     780
acctgagcca gtccgcatcg accggatcgg aaaacctctc gagaaaggcg tctaaccagt     840
cacagtcgca aggtaggctg agcaccgtgg cgggcggcag cgggtggcgg tcggggttgt     900
ttctggcgga ggtgctgctg atgatgtaat taaagtaggc ggtcttgagc cggcggatgg     960
tcgaggtgag gtgtggcagg cttgagatcc agctgttggg gtgagtactc cctctcaaaa    1020
gcgggcatga cttctgcgct aagattgtca gtttccaaaa acgaggagga tttgatattc    1080
acctggcccg atctggccat acacttgagt gacaatgaca tccactttgc ctttctctcc    1140
acaggtgtcc actcccaggt ccaagtttaa acagcggccg cgccgccacc atgaagacct    1200
gctggaaaat tccagttttc ttctttgtgt gcagtttcct ggaaccctgg gcatctgcag    1260
aaggtcatca tcaccatcac catcaccatg gaggacagtg gagccaccccg cagttcgaga    1320 aaggtaagcc tatccctaac cctctcctcg gtctcgattc tacggaaaac ctgtatttc    1380 agggcgaatt cgatatcatc acaagtttgt acaaaaaagc tgaacgagaa acgtaaaatg    1440
atataaatat caatatatta aattagattt tgcataaaaa acagactaca taatactgta    1500
aaacacaaca tatccagtca tattggcggc gcattaggc accccaggct ttacacttta    1560
tgcttccggc tcgtataatg tgtggatttt gagttaggat ccgtcgagat ttcaggagc    1620 taaggaagct aaaatggaga aaaaaatcac tggatatacc accgttgata tatcccaatg    1680
```

```
gcatcgtaaa gaacattttg aggcatttca gtcagttgct caatgtacct ataaccagac    1740
cgttcagctg gatattacgg cctttttaaa gaccgtaaag aaaaataagc acaagtttta    1800
tccggccttt attcacattc ttgcccgcct gatgaatgct catccggaat tccgtatggc    1860
aatgaaagac ggtgagctgg tgatatggga tagtgttcac ccttgttaca ccgttttcca    1920
tgagcaaact gaaacgtttt catcgctctg gagtgaatac cacgacgatt ccggcagtt     1980 tctacacata tattcgcaag atgtggcgtg ttacggtgaa aacctggcct atttccctaa    2040
agggtttatt gagaatatgt ttttcgtctc agccaatccc tgggtgagtt tcaccagttt    2100
tgatttaaac gtggccaata tggacaactt cttcgccccc gttttcacca tgggcaaata    2160
ttatacgcaa ggcgacaagg tgctgatgcc gctggcgatt caggttcatc atgccgtttg    2220
tgatggcttc catgtcggca gaatgcttaa tgaattacaa cagtactgcg atgagtggca    2280
gggcggggcg taaacgcgtg gatccggctt actaaaagcc agataacagt atgcgtattt    2340
gcgcgctgat ttttgcggta taagaatata tactgatatg tatacccgaa gtatgtcaaa    2400
aagaggtatg ctatgaagca gcgtattaca gtgacagttg acagcgacag ctatcagttg    2460
ctcaaggcat atatgatgtc aatatctccg gtctggtaag cacaaccatg cagaatgaag    2520
cccgtcgtct gcgtgccgaa cgctggaaag cggaaaatca ggaagggatg gctgaggtcg    2580
cccggtttat tgaaatgaac ggctcttttg ctgacgagaa caggggctgg tgaaatgcag    2640
tttaaggttt acacctataa aagagagagc cgttatcgtc tgtttgtgga tgtacagagt    2700
gatattattg cacgcccgg gcgacggatg gtgatccccc tggccagtgc acgtctgctg     2760
tcagataaag tctcccgtga actttacccg gtggtgcata tcgggatga agctggcgc      2820 atgatgacca ccgatatggc cagtgtgccg gtctccgtta tcggggaaga agtggctgat    2880
ctcagccacc gcgaaaatga catcaaaaac gccattaacc tgatgttctg gggaatataa    2940
atgtcaggct cccttataca cagccagtct gcaggtcgac catagtgact ggatatgttg    3000
tgttttacag cattatgtag tctgttttt atgcaaaatc taatttaata tattgatatt     3060
tatatcattt tacgttctc gttcagcttt cttgtacaaa gtggtgatcg gatccttcga     3120
aggtaagcct atccctaacc ctctcctcgg tctcgattct acgcgtaccg gtcatcatca    3180
ccatcaccat caccatggag gacagtgaag atccccgac ctcgacctct ggctaataaa     3240
ggaaatttat tttcattgca atagtgtgtt ggaatttttt gtgtctctca ctcggaagga    3300
catatgggag gcaaatcat ttggtcgaga tccctcggag atctctagct agagccccgc     3360
cgccggacga actaaacctg actacggcat ctctgcccct tcttcgcggg gcagtgcatg    3420
taatcccttc agttggttgg tacaacttgc caactgaacc ctaaacgggt agcatatgct    3480
tcccgggtag tagtatatac tatccagact aaccctaatt caatagcata tgttacccaa    3540
cgggaagcat atgctatcga attagggtta gtaaaagggt cctaaggaac agcgatgtag    3600
gtgggcgggc caagataggg gcgcgattgc tgcgatctgg aggacaaatt acacacactt    3660
gcgcctgagc gccaagcaca gggttgttgg tcctcatatt cacgaggtcg ctgagagcac    3720
ggtgggctaa tgttgccatg ggtagcatat actacccaaa tatctggata gcatatgcta    3780
tcctaatcta tatctgggta gcataggcta tcctaatcta tatctgggta gcatatgcta    3840
tcctaatcta tatctgggta gtatatgcta tcctaattta tatctgggta gcataggcta    3900
tcctaatcta tatctgggta gcatatgcta tcctaatcta tatctgggta gtatatgcta    3960
tcctaatctg tatccgggta gcatatgcta tcctaataga gattagggta gtatatgcta    4020
tcctaattta tatctgggta gcatatacta cccaaatatc tggatagcat atgctatcct    4080
```

```
aatctatatc tgggtagcat atgctatcct aatctatatc tgggtagcat aggctatcct    4140
aatctatatc tgggtagcat atgctatcct aatctatatc tgggtagtat atgctatcct    4200
aatttatatc tgggtagcat aggtatccta atctatatct gggtagcata tgctatccta    4260
atctatatct gggtagtata tgctatccta atctgtatcc gggtagcata tgctatcctc    4320
acgatgataa gctgtcaaac atgagaatta attcttgaag acgaaagggc tcgtgatac     4380 gcctattttt ataggttaat gtcatgataa taatggtttc ttagacgtca ggtggcactt    4440
ttcggggaaa tgtgcgcgga acccctattt gtttattttt ctaaatacat tcaaatatgt    4500
atccgctcat gagacaataa ccctgataaa tgcttcaata atccggaatt gccagctggg    4560
gcgccctctg gtaaggttgg aagccctgc aaagtaaact ggatggcttt cttgccgcca     4620
aggatctgat ggcgcagggg atcaagatct gatcaagaga caggatgagg atcgtttcgc    4680
atgattgaac aagatggatt gcacgcaggt tctccggccg cttggtgga gaggctattc      4740 ggctatgact gggcacaaca gacaatcggc tgctctgatg ccgccgtgtt ccggctgtca    4800
gcgcaggggc gcccggttct ttttgtcaag accgacctgt ccggtgccct gaatgaactg    4860
caggacgagg cagcgcggct atcgtggctg gccacgacgg gcgttccttg cgcagctgtg    4920
ctcgacgttg tcactgaagc gggaagggac tggctgctat gggcgaagt gccggggcag     4980 gatctcctgt catcccacct tgctcctgcc gagaaagtat ccatcatggc tgatgcaatg    5040
cggcggctgc atacgcttga tccggctacc tgcccattcg accaccaagc gaaacatcgc    5100
atcgagcgag cacgtactcg gatggaagcc ggtcttgtcg atcaggatga tctggacgaa    5160
gagcatcagg ggctcgcgcc agccgaactg ttcgccaggc tcaaggcgcg catgcccgac    5220
ggcgaggatc tcgtcgtgac ccatggcgat gcctgcttgc cgaatatcat ggtggaaaat    5280
ggccgctttt ctggattcat cgactgtggc cggctgggtg tggcggaccg ctatcaggac    5340
atagcgttgg ctacccgtga tattgctgaa gagcttggcg gcgaatgggc tgaccgcttc    5400
ctcgtgcttt acggtatcgc cgctcccgat tcgcagcgca tcgccttcta tcgccttctt    5460
gacgagttct tctgaattga aaaggaaga gtatgagtat tcaacatttc cgtgtcgccc     5520
ttattccctt ttttgcggca ttttgccttc ctgttttgc tcacccagaa acgctggtga     5580
aagtaaaaga tgctgaagat cagttgggtg cacgagtggg ttacatcgaa ctggatctca    5640
acagcggtaa gatccttgag agttttcgcc ccgaagaacg ttttccaatg atgagcactt    5700
ttaaagttct gctatgtggc gcggtattat cccgtgttga cgccgggcaa gagcaactcg    5760
gtcgccgcat acactattct cagaatgact tggttgagta ctcaccagtc acagaaaagc    5820
atcttacgga tggcatgaca gtaagagaat tatgcagtgc tgccataacc atgagtgata    5880
acactgcggc caacttactt ctgacaacga tcggaggacc gaaggagcta accgcttttt    5940
tgcacaacat gggggatcat gtaactcgcc ttgatcgttg ggaaccggag ctgaatgaag    6000
ccataccaaa cgacgagcgt gacaccacga tgcctgcagc aatggcaaca acgttgcgca    6060
aactattaac tggcgaacta cttactctag cttcccggca acaattaata gactggatgg    6120
aggcggataa agttgcagga ccacttctgc gctcggccct tccggctggc tggtttattg    6180
ctgataaatc tggagccggt gagcgtgggt ctcgcggtat cattgcagca ctggggccag    6240
atggtaagcc ctcccgtatc gtagttatct acacgacggg gagtcaggca actatggatg    6300
aacgaaatag acagatcgct gagataggtg cctcactgat taagcattgg taactgtcag    6360
accaagttta ctcatatata ctttagattg atttaaaact tcattttaa tttaaaagga    6420 tctaggtgaa gatcctttt gataatctca tgaccaaaat cccttaacgt gagttttcgt     6480
```

```
tccactgagc gtcagacccc gtagaaaaga tcaaaggatc ttcttgagat ccttttttc    6540 tgcgcgtaat ctgctgcttg caaacaaaaa aaccaccgct accagcggtg gtttgtttgc    6600
cggatcaaga gctaccaact cttttttcga aggtaactgg cttcagcaga gcgcagatac    6660
caaatactgt ccttctagtg tagccgtagt taggccacca cttcaagaac tctgtagcac    6720
cgcctacata cctcgctctg ctaatcctgt taccagtggc tgctgccagt ggcgataagt    6780
cgtgtcttac cgggttggac tcaagacgat agttaccgga taaggcgcag cggtcgggct    6840 gaacggggggg ttcgtgcaca cagcccagct tggagcgaac gacctacacc gaactgagat    6900
acctacagcg tgagcattga aaagcgcca cgcttcccga agggagaaag gcggacaggt    6960
atccggtaag cggcagggtc ggaacaggag agcgcacgag ggagcttcca ggggggaaacg    7020 cctggtatct ttatagtcct gtcgggtttc gccacctctg acttgagcgt cgatttttgt    7080
gatgctcgtc aggggggcgg agcctatgga aaaacgccag caacgcggcc ttttttacggt    7140 tcctggcctt ttgctggcct tttgctcaca tgttctttcc tgcgttatcc cctgattctg    7200
tggataaccg tattaccgcc tttgagtgag ctgataccgc tcgccgcagc cgaacgaccg    7260
agcgcagcga gtcagtgagc gaggaagc                                      7288
```

<210> SEQ ID NO 274
<211> LENGTH: 7129
<212> TYPE: DNA
<213> ORGANISM: Artificial Sequence
<220> FEATURE:
<223> OTHER INFORMATION: Description of Artificial Sequence: Synthetic pTT5-I sequence

<400> SEQUENCE: 274

```
gtacatttat attggctcat gtccaatatg accgccatgt tgacattgat tattgactag      60
ttattaatag taatcaatta cggggtcatt agttcatagc ccatatatgg agttccgcgt     120
tacataactt acggtaaatg gcccgcctgg ctgaccgccc aacgaccccc gcccattgac     180
gtcaataatg acgtatgttc ccatagtaac gccaataggg actttccatt gacgtcaatg     240
ggtggagtat ttacggtaaa ctgcccactt ggcagtacat caagtgtatc atatgccaag     300 tccgcccct attgacgtca atgacggtaa atggcccgcc tggcattatg cccagtacat     360
gaccttacgg gactttccta cttggcagta catctacgta ttagtcatcg ctattaccat     420
ggtgatgcgg ttttggcagt acaccaatgg gcgtggatag cggtttgact cacggggatt     480
tccaagtctc cacccattg acgtcaatgg gagtttgttt ggcaccaaa atcaacggga      540 ctttccaaaa tgtcgtaata accccgcccc gttgacgcaa atgggcggta ggcgtgtacg     600
gtgggaggtc tatataagca gagctcgttt agtgaaccgt cagatcctca ctctcttccg     660
catcgctgtc tgcgagggcc agctgttggg ctcgcggttg aggacaaaact cttcgcggtc    720 tttccagtac tcttggatcg gaaacccgtc ggcctccgaa cggtactccg ccaccgaggg    780
acctgagcca gtccgcatcg accggatcgg aaaacctctc gagaaaggcg tctaaccagt    840
cacagtcgca aggtaggctg agcaccgtgg cgggcggcag cgggtggcgg tcggggttgt    900
ttctggcgga ggtgctgctg atgatgtaat aaagtaggc ggtcttgagc cggcggatgg    960
tcgaggtgag gtgtggcagg cttgagatcc agctgttggg gtgagtactc cctctcaaaa   1020
gcgggcatga cttctgcgct aagattgtca gtttccaaaa acgaggagga tttgatattc   1080
acctggcccg atctggccat acacttgagt gacaatgaca tccactttgc ctttctctcc   1140
acaggtgtcc actcccaggt ccaagtttaa acagcggccg gaattcgata tcatcacaag   1200
```

```
tttgtacaaa aaagctgaac gagaaacgta aaatgatata aatatcaata tattaaatta   1260
gattttgcat aaaaaacaga ctacataata ctgtaaaaca caacatatcc agtcatattg   1320
gcggccgcat taggcacccc aggctttaca ctttatgctt ccggctcgta taatgtgtgg   1380
attttgagtt aggatccgtc gagattttca ggagctaagg aagctaaaat ggagaaaaaa   1440
atcactggat ataccaccgt tgatatatcc caatggcatc gtaaagaaca ttttgaggca   1500
tttcagtcag ttgctcaatg tacctataac cagaccgttc agctggatat tacgccattt   1560
ttaaagaccg taaagaaaaa taagcacaag ttttatccgg cctttattca cattcttgcc   1620
cgcctgatga atgctcatcc ggaattccgt atggcaatga agacggtga gctggtgata   1680
tgggatagtg ttcacccttg ttacaccgtt ttccatgagc aaactgaaac gttttcatcg   1740
ctctggagtg aataccacga cgatttccgg cagtttctac acatatattc gcaagatgtg   1800
gcgtgttacg gtgaaaacct ggcctatttc cctaaagggt ttattgagaa tatgtttttc   1860
gtctcagcca atccctgggt gagtttcacc agttttgatt taaacgtggc caatatggac   1920
aacttcttcg cccccgtttt caccatgggc aaatattata cgcaaggcga caaggtgctg   1980
atgccgctgg cgattcaggt tcatcatgcc gtttgtgatg gcttccatgt cggcagaatg   2040
cttaatgaat tacaacagta ctgcgatgag tggcagggcg gggcgtaaac gcgtggatcc   2100
ggcttactaa aagccagata acagtatgcg tatttgcgcg ctgatttttg cggtataaga   2160
atatatactg atatgtatac ccgaagtatg tcaaaaagag gtatgctatg aagcagcgta   2220
ttacagtgac agttgacagc gacagctatc agttgctcaa ggcatatatg atgtcaatat   2280
ctccggtctg gtaagcacaa ccatgcagaa tgaagcccgt cgtctgcgtg ccgaacgctg   2340
gaaagcggaa aatcaggaag ggatggctga ggtcgcccgg tttattgaaa tgaacggctc   2400
ttttgctgac gagaacaggg gctggtgaaa tgcagtttaa ggtttacacc tataaaagag   2460
agagccgtta tcgtctgttt gtggatgtac agagtgatat tattgacacg cccgggcgac   2520
ggatggtgat cccctggcc agtgcacgtc tgctgtcaga taaagtctcc cgtgaacttt   2580
acccggtggt gcatatcggg gatgaaagct ggcgcatgat gaccaccgat atggccagtg   2640
tgccggtctc cgttatcggg gaagaagtgg ctgatctcag ccaccgcgaa aatgacatca   2700
aaaacgccat taacctgatg ttctggggaa tataaatgtc aggctcccctt atacacagcc   2760
agtctgcagg tcgaccatag tgactggata tgttgtgttt tacagcatta tgtagtctgt   2820
tttttatgca aaatctaatt taatatattg atatttatat cattttacgt ttctcgttca   2880
gctttcttgt acaaagtggt gatcggatcc gaaacctgt attttcaggg cttcgaaggt   2940
aagcctatcc ctaaccctct cctcggtctc gattctacgc gttggagcca cccgcagttc   3000
gagaaaaccg gtcatcatca ccatcaccat caccatggag acagtgaag atccccccgac   3060
ctcgacctct ggctaataaa ggaaatttat tttcattgca atagtgtgtt ggaatttttt   3120
gtgtctctca ctcggaagga catatgggag ggcaaatcat ttggtcgaga tccctcggag   3180
atctctagct agagccccgc cgccggacga actaaacctg actacggcat ctctgcccct   3240
tcttcgcggg gcagtgcatg taatcccttc agttggttgg tacaacttgc caactgaacc   3300
ctaaacgggt agcatatgct tcccgggtag tagtatatac tatccagact aaccctaatt   3360
caatagcata tgttacccaa cgggaagcat atgctatcga attagggtta gtaaagggt   3420
cctaaggaac agcgatgtag gtgggcgggc caagataggg gcgcgattgc tgcgatctgg   3480
aggacaaatt acacacactt gcgcctgagc gccaagcaca gggttgttgg tcctcatatt   3540
cacgaggtcg ctgagagcac ggtgggctaa tgttgccatg ggtagcatat actacccaaa   3600
```

```
tatctggata gcatatgcta tcctaatcta tatctgggta gcataggcta tcctaatcta    3660
tatctgggta gcatatgcta tcctaatcta tatctgggta gtatatgcta tcctaattta    3720
tatctgggta gcataggcta tcctaatcta tatctgggta gcatatgcta tcctaatcta    3780
tatctgggta gtatatgcta tcctaatctg tatccgggta gcatatgcta tcctaataga    3840
gattagggta gtatatgcta tcctaattta tatctgggta gcatatacta cccaaatatc    3900
tggatagcat atgctatcct aatctatatc tgggtagcat atgctatcct aatctatatc    3960
tgggtagcat aggctatcct aatctatatc tgggtagcat atgctatcct aatctatatc    4020
tgggtagtat atgctatcct aatttatatc tgggtagcat aggctatcct aatctatatc    4080
tgggtagcat atgctatcct aatctatatc tgggtagtat atgctatcct aatctgtatc    4140
cgggtagcat atgctatcct cacgatgata agctgtcaaa catgagaatt aattcttgaa    4200
gacgaaaggg cctcgtgata cgcctatttt tataggttaa tgtcatgata ataatggttt    4260
cttagacgtc aggtggcact tttcggggaa atgtgcgcgg aaccoctatt tgtttatttt    4320 tctaaataca ttcaaatatg tatccgctca tgagacaata accctgataa atgcttcaat    4380
aatccggaat tgccagctgg ggcgccctct ggtaaggttg ggaagccctg caaagtaaac    4440
tggatggctt tcttgccgcc aaggatctga tggcgcaggg atcaagatc tgatcaagag    4500 acaggatgag gatcgtttcg catgattgaa caagatggat tgcacgcagg ttctccggcc    4560
gcttgggtgg agaggctatt cggctatgac tgggcacaac agacaatcgg ctgctctgat    4620
gccgccgtgt tccggctgtc agcgcagggg cgcccggttc tttttgtcaa gaccgacctg    4680
tccggtgccc tgaatgaact gcaggacgag gcagcgcggc tatcgtggct ggccacgacg    4740
ggcgttcctt gcgcagctgt gctcgacgtt gtcactgaag cgggaaggga ctggctgcta    4800
ttgggcgaag tgccggggca ggatctcctg tcatcccacc ttgctcctgc cgagaaagta    4860
tccatcatgg ctgatgcaat gcggcggctg catacgcttg atccggctac ctgcccattc    4920
gaccaccaag cgaaacatcg catcgagcga gcacgtactc ggatggaagc cggtcttgtc    4980
gatcaggatg atctggacga agagcatcag gggctcgcgc cagccgaact gttcgccagg    5040
ctcaaggcgc gcatgcccga cggcgaggat ctcgtcgtga cccatggcga tgcctgcttg    5100
ccgaatatca tggtggaaaa tggccgcttt tctggattca tcgactgtgg ccggctgggt    5160
gtggcggacc gctatcagga catagcgttg gctacccgtg atattgctga agagcttggc    5220
ggcgaatggg ctgaccgctt cctcgtgctt tacggtatcg ccgctcccga ttcgcagcgc    5280
atcgccttct atcgccttct tgacgagttc ttctgaattg aaaaaggaag agtatgagta    5340
ttcaacattt ccgtgtcgcc cttattccct tttttgcggc attttgcctt cctgtttttg    5400
ctcacccaga aacgctggtg aaagtaaaag atgctgaaga tcagttgggt gcacgagtgg    5460
gttacatcga actggatctc aacagcggta agatccttga gttttcgc cccgaagaac    5520 gttttccaat gatgagcact tttaaagttc tgctatgtgg cgcggtatta tccgtgttg    5580 acgccgggca agagcaactc ggtcgccgca tacactattc tcagaatgac ttggttgagt    5640
actcaccagt cacagaaaag catcttacgg atggcatgac agtaagagaa ttatgcagtg    5700
ctgccataac catgagtgat aacactgcgg ccaacttact tctgacaacg atcggaggac    5760
cgaaggagct aaccgctttt ttgcacaaca tgggggatca tgtaactcgc cttgatcgtt    5820
gggaaccgga gctgaatgaa gccataccaa acgacgagcg tgacaccacg atgcctgcag    5880
caatggcaac aacgttgcgc aaactattaa ctggcgaact acttactcta gcttcccggc    5940
aacaattaat agactggatg gaggcggata aagttgcagg accacttctg cgctcggccc    6000
```

| | |
|---|---|
| ttccggctgg ctggtttatt gctgataaat ctggagccgg tgagcgtggg tctcgcggta | 6060 |
| tcattgcagc actggggcca gatggtaagc cctcccgtat cgtagttatc tacacgacgg | 6120 |
| ggagtcaggc aactatggat gaacgaaata gacagatcgc tgagataggt gcctcactga | 6180 |
| ttaagcattg gtaactgtca gaccaagttt actcatatat actttagatt gatttaaaac | 6240 |
| ttcatttta atttaaaagg atctaggtga agatcctttt tgataatctc atgaccaaaa | 6300 |
| tcccttaacg tgagttttcg ttccactgag cgtcagaccc cgtagaaaag atcaaaggat | 6360 |
| cttcttgaga tcctttttt ctgcgcgtaa tctgctgctt gcaaacaaaa aaaccaccgc | 6420 |
| taccagcggt ggtttgtttg ccggatcaag agctaccaac tctttttccg aaggtaactg | 6480 |
| gcttcagcag agcgcagata ccaaatactg tccttctagt gtagccgtag ttaggccacc | 6540 |
| acttcaagaa ctctgtagca ccgcctacat acctcgctct gctaatcctg ttaccagtgg | 6600 |
| ctgctgccag tggcgataag tcgtgtctta ccgggttgga ctcaagacga tagttaccgg | 6660 |
| ataaggcgca gcggtcgggc tgaacggggg gttcgtgcac acagcccagc ttggagcgaa | 6720 |
| cgacctacac cgaactgaga tacctacagc gtgagcattg agaaagcgcc acgcttcccg | 6780 |
| aagggagaaa ggcggacagg tatccggtaa gcggcagggt cggaacagga gagcgcacga | 6840 |
| gggagcttcc agggggaaac gcctggtatc tttatagtcc tgtcgggttt cgccacctct | 6900 |
| gacttgagcg tcgatttttg tgatgctcgt caggggggcg gagcctatgg aaaaacgcca | 6960 |
| gcaacgcggc ctttttacgg ttcctggcct tttgctggcc ttttgctcac atgttctttc | 7020 |
| ctgcgttatc ccctgattct gtggataacc gtattaccgc ctttgagtga gctgataccg | 7080 |
| ctcgccgcag ccgaacgacc gagcgcagcg agtcagtgag cgaggaagc | 7129 |

<210> SEQ ID NO 275
<211> LENGTH: 5472
<212> TYPE: DNA
<213> ORGANISM: Artificial Sequence
<220> FEATURE:
<223> OTHER INFORMATION: Description of Artificial Sequence: Synthetic pCI-neo sequence

<400> SEQUENCE: 275

| | |
|---|---|
| tcaatattgg ccattagcca tattattcat tggttatata gcataaatca atattggcta | 60 |
| ttggccattg catacgttgt atctatatca taatatgtac atttatattg gctcatgtcc | 120 |
| aatatgaccg ccatgttggc attgattatt gactagttat taatagtaat caattacggg | 180 |
| gtcattagtt catagcccat atatggagtt ccgcgttaca taacttacgg taaatggccc | 240 |
| gcctggctga ccgcccaacg acccccgccc attgacgtca ataatgacgt atgttcccat | 300 |
| agtaacgcca atagggactt tccattgacg tcaatgggtg gagtatttac ggtaaactgc | 360 |
| ccacttggca gtacatcaag tgtatcatat gccaagtccg ccccctattg acgtcaatga | 420 |
| cggtaaatgg cccgcctggc attatgccca gtacatgacc ttacgggact ttcctacttg | 480 |
| gcagtacatc tacgtattag tcatcgctat taccatggtg atgcggtttt ggcagtacac | 540 |
| caatgggcgt ggatagcggt ttgactcacg gggatttcca agtctccacc ccattgacgt | 600 |
| caatgggagt ttgttttggc accaaaatca acgggacttt ccaaaatgtc gtaacaactg | 660 |
| cgatcgcccg ccccgttgac gcaaatgggc ggtaggcgtg tacggtggga ggtctatata | 720 |
| agcagagctc gtttagtgaa ccgtcagatc actagaagct ttattgcggt agtttatcac | 780 |
| agttaaattg ctaacgcagt cagtgcttct gacacaacag tctcgaactt aagctgcagt | 840 |
| gactctctta aggtagcctt gcagaagttg gtcgtgaggc actgggcagg taagtatcaa | 900 |
| ggttacaaga caggtttaag gagaccaata gaaactgggc ttgtcgagac agagaagact | 960 |

```
cttgcgtttc tgataggcac ctattggtct tactgacatc cactttgcct ttctctccac    1020
aggtgtccac tcccagttca attacagctc ttaaggctag agtacttaat acgactcact    1080
ataggctagc ctcgagaatt cacgcgtggt acctctagag tcgacccggg cggccgcttc    1140
cctttagtga gggttaatgc ttcgagcaga catgataaga tacattgatg agtttggaca    1200
aaccacaact agaatgcagt gaaaaaaatg ctttatttgt gaaatttgtg atgctattgc    1260
tttatttgta accattataa gctgcaataa acaagttaac aacaacaatt gcattcattt    1320
tatgtttcag gttcaggggg agatgtggga ggttttttaa agcaagtaaa acctctacaa    1380
atgtggtaaa atccgataag gatcgatccg ggctggcgta atagcgaaga ggcccgcacc    1440
gatcgccctt cccaacagtt gcgcagcctg aatggcgaat ggacgcgccc tgtagcggcg    1500
cattaagcgc ggcgggtgtg gtggttacgc gcagcgtgac cgctacactt gccagcgccc    1560
tagcgcccgc tcctttcgct ttcttccctt cctttctcgc cacgttcgcc ggctttcccc    1620
gtcaagctct aaatcggggg ctcccttag ggttccgatt tagtgcttta cggcacctcg    1680
accccaaaaa acttgattag ggtgatggtt cacgtagtgg gccatcgccc tgatagacgg    1740
tttttcgccc tttgacgttg gagtccacgt tctttaatag tggactcttg ttccaaactg    1800
gaacaacact caaccctatc tcggtctatt cttttgattt ataagggatt ttgccgattt    1860
cggcctattg gttaaaaaat gagctgattt aacaaaaatt taacgcgaat tttaacaaaa    1920
tattaacgct tacaatttcc tgatgcggta ttttctcctt acgcatctgt gcggtatttc    1980
acaccgcata cgcggatctg cgcagcacca tggcctgaaa taacctctga aagaggaact    2040
tggttaggta ccttctgagg cggaaagaac cagctgtgga atgtgtgtca gttagggtgt    2100
ggaaagtccc caggctcccc agcaggcaga agtatgcaaa gcatgcatct caattagtca    2160
gcaaccaggt gtggaaagtc cccaggctcc ccagcaggca gaagtatgca aagcatgcat    2220
ctcaattagt cagcaaccat agtcccgccc ctaactccgc ccatcccgcc cctaactccg    2280
cccagttccg cccattctcc gccccatggc tgactaattt ttttttattta tgcagaggcc    2340 gaggccgcct cggcctctga gctattccag aagtagtgag gaggcttttt tggaggccta    2400
ggcttttgca aaaagcttga ttcttctgac acaacagtct cgaacttaag gctagagcca    2460
ccatgattga acaagatgga ttgcacgcag gttctccggc cgcttgggtg gagaggctat    2520
tcggctatga ctgggcacaa cagacaatcg gctgctctga tgccgccgtg ttccggctgt    2580
cagcgcaggg gcgcccggtt ctttttgtca agaccgacct gtccggtgcc ctgaatgaac    2640
tgcaggacga ggcagcgcgg ctatcgtggc tggccacgac gggcgttcct tgcgcagctg    2700
tgctcgacgt tgtcactgaa gcgggaaggg actggctgct attgggcgaa gtgccggggc    2760
aggatctcct gtcatctcac cttgctcctg ccgagaaagt atccatcatg gctgatgcaa    2820
tgcggcggct gcatacgctt gatccggcta cctgcccatt cgaccaccaa gcgaaacatc    2880
gcatcgagcg agcacgtact cggatggaag ccggtcttgt cgatcaggat gatctggacg    2940
aagagcatca ggggctcgcg ccagccgaac tgttcgccag gctcaaggcg cgcatgcccg    3000
acggcgagga tctcgtcgtg acccatggcg atgcctgctt gccgaatatc atggtggaaa    3060
atggccgctt ttctggattc atcgactgtg gccggctggg tgtggcggac cgctatcagg    3120
acatagcgtt ggctacccgt gatattgctg aagagcttgg cggcgaatgg gctgaccgct    3180
tcctcgtgct ttacggtatc gccgctcccg attcgcagcg catcgccttc tatcgccttc    3240
ttgacgagtt cttctgagcg ggactctggg gttcgaaatg accgaccaag cgacgcccaa    3300
cctgccatca cgatggccgc aataaaatat ctttattttc attacatctg tgtgttggtt    3360
```

```
ttttgtgtga atcgatagcg ataaggatcc gcgtatggtg cactctcagt acaatctgct   3420
ctgatgccgc atagttaagc cagccccgac accgccaac accgctgac gcgccctgac    3480 gggcttgtct gctcccggca tccgcttaca gacaagctgt gaccgtctcc gggagctgca   3540
tgtgtcagag gttttcaccg tcatcaccga aacgcgcgag acgaaagggc ctcgtgatac   3600
gcctattttt ataggttaat gtcatgataa taatggtttc ttagacgtca ggtggcactt   3660
ttcggggaaa tgtgcgcgga acccctattt gtttatttt ctaaatacat tcaaatatgt    3720
atccgctcat gagacaataa ccctgataaa tgcttcaata atattgaaaa aggaagagta   3780
tgagtattca acatttccgt gtcgccctta ttccctttt tgcggcattt tgccttcctg    3840 ttttgctca cccagaaacg ctggtgaaag taaaagatgc tgaagatcag ttgggtgcac    3900
gagtgggtta catcgaactg gatctcaaca gcggtaagat ccttgagagt tttcgccccg   3960
aagaacgttt tccaatgatg agcactttta agttctgct atgtggcgcg gtattatccc    4020
gtattgacgc cgggcaagag caactcggtc gccgcataca ctattctcag aatgacttgg   4080
ttgagtactc accagtcaca gaaaagcatc ttacggatgg catgacagta agagaattat   4140
gcagtgctgc cataaccatg agtgataaca ctgcggccaa cttacttctg acaacgatcg   4200
gaggaccgaa ggagctaacc gcttttttgc acaacatggg ggatcatgta actcgccttg   4260
atcgttggga accggagctg aatgaagcca taccaaacga cgagcgtgac accacgatgc   4320
ctgtagcaat ggcaacaacg ttgcgcaaac tattaactgg cgaactactt actctagctt   4380
cccggcaaca attaatagac tggatggagg cggataaagt tgcaggacca cttctgcgct   4440
cggcccttcc ggctggctgg tttattgctg ataaatctgg agccggtgag cgtgggtctc   4500
gcggtatcat tgcagcactg gggccagatg gtaagccctc ccgtatcgta gttatctaca   4560
cgacggggag tcaggcaact atggatgaac gaaatagaca gatcgctgag ataggtgcct   4620
cactgattaa gcattggtaa ctgtcagacc aagtttactc atatatactt tagattgatt   4680
taaaacttca ttttttaattt aaaaggatct aggtgaagat cctttttgat aatctcatga   4740
ccaaaatccc ttaacgtgag ttttcgttcc actgagcgtc agacccccgta gaaaagatca   4800 aaggatcttc ttgagatcct ttttttctgc gcgtaatctg ctgcttgcaa acaaaaaaac   4860
caccgctacc agcggtggtt tgtttgccgg atcaagagct accaactctt tttccgaagg   4920
taactggctt cagcagagcg cagataccaa atactgttct tctagtgtag ccgtagttag   4980
gccaccactt caagaactct gtagcaccgc ctacatacct cgctctgcta atcctgttac   5040
cagtggctgc tgccagtggc gataagtcgt gtcttaccgg gttggactca agacgatagt   5100
taccggataa ggcgcagcgg tcgggctgaa cggggggttc gtgcacacag cccagcttgg   5160
agcgaacgac ctacaccgaa ctgagatacc tacagcgtga gctatgagaa agcgccacgc   5220
ttcccgaagg gagaaaggcg gacaggtatc cggtaagcgg cagggtcgga acaggagagc   5280
gcacgaggga gcttccaggg ggaaacgcct ggtatcttta tagtcctgtc gggtttcgcc   5340
acctctgact tgagcgtcga ttttgtgat gctcgtcagg gggcggagc ctatggaaaa    5400 acgccagcaa cgcggccttt ttacggttcc tggccttttg ctggccttt gctcacatgg    5460 ctcgacagat ct                                                      5472
```

<210> SEQ ID NO 276
<211> LENGTH: 5428
<212> TYPE: DNA
<213> ORGANISM: Artificial Sequence
<220> FEATURE:
<223> OTHER INFORMATION: Description of Artificial Sequence: Synthetic pCDNA3.1 sequence

<400> SEQUENCE: 276

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattctgc    960
agatatccag cacagtggcg gccgctcgag tctagagggc ccgtttaaac ccgctgatca   1020
gcctcgactg tgccttctag ttgccagcca tctgttgttt gcccctcccc cgtgccttcc   1080
ttgaccctgg aaggtgccac tcccactgtc ctttcctaat aaaatgagga aattgcatcg   1140
cattgtctga gtaggtgtca ttctattctg gggggtgggg tggggcagga cagcaagggg   1200
gaggattggg aagacaatag caggcatgct ggggatgcgg tgggctctat ggcttctgag   1260
gcggaaagaa ccagctgggg ctctaggggg tatccccacg cgccctgtag cggcgcatta   1320
agcgcggcgg gtgtggtggt tacgcgcagc gtgaccgcta cacttgccag cgccctagcg   1380
cccgctcctt tcgctttctt cccttccttt ctcgccacgt tcgccggctt tccccgtcaa   1440
gctctaaatc gggggctccc tttagggttc cgatttagtg ctttacgca cctcgacccc   1500
aaaaaacttg attagggtga tggttcacgt agtgggccat cgccctgata cggttttt    1560
cgccctttga cgttggagtc acgttctttt aatagtggac tcttgttcca aactggaaca   1620
acactcaacc ctatctcggt ctattctttt gatttataag ggattttgcc gatttcggcc   1680
tattggttaa aaaatgagct gatttaacaa aaatttaacg cgaattaatt ctgtggaatg   1740
tgtgtcagtt agggtgtgga agtccccag gctccccagc aggcagaagt atgcaaagca   1800
tgcatctcaa ttagtcagca accaggtgtg gaaagtcccc aggctcccca gcaggcagaa   1860
gtatgcaaag catgcatctc aattagtcag caaccatagt cccgccccta actccgccca   1920
tcccgcccct aactccgccc agttccgccc attctccgcc ccatggctga ctaattttt    1980
ttatttatgc agaggccgag gccgcctctg cctctgagct attccagaag tagtgaggag   2040
gcttttttgg aggcctaggc ttttgcaaaa agctcccggg agcttgtata tccattttcg   2100
gatctgatca agagacagga tgaggatcgt ttcgcatgat tgaacaagat ggattgcacg   2160
caggttctcc ggccgcttgg gtggagaggc tattcggcta tgactgggca caacagacaa   2220
tcggctgctc tgatgccgcc gtgttccggc tgtcagcgca ggggcgcccg gttctttttg   2280
```

```
tcaagaccga cctgtccggt gccctgaatg aactgcagga cgaggcagcg cggctatcgt    2340
ggctggccac gacgggcgtt ccttgcgcag ctgtgctcga cgttgtcact gaagcgggaa    2400
gggactggct gctattgggc gaagtgccgg ggcaggatct cctgtcatct caccttgctc    2460
ctgccgagaa agtatccatc atggctgatg caatgcggcg gctgcatacg cttgatccgg    2520
ctacctgccc attcgaccac caagcgaaac atcgcatcga gcgagcacgt actcggatgg    2580
aagccggtct tgtcgatcag gatgatctgg acgaagagca tcaggggctc gcgccagccg    2640
aactgttcgc caggctcaag gcgcgcatgc ccgacggcga ggatctcgtc gtgacccatg    2700
gcgatgcctg cttgccgaat atcatggtgg aaaatggccg cttttctgga ttcatcgact    2760
gtggccggct gggtgtggcg gaccgctatc aggacatagc gttggctacc cgtgatattg    2820
ctgaagagct tggcggcgaa tgggctgacc gcttcctcgt gctttacggt atcgccgctc    2880
ccgattcgca gcgcatcgcc ttctatcgcc ttcttgacga gttcttctga gcgggactct    2940
ggggttcgaa atgaccgacc aagcgacgcc caacctgcca tcacgagatt tcgattccac    3000
cgccgccttc tatgaaaggt tgggcttcgg aatcgttttc cgggacgccg gctggatgat    3060
cctccagcgc ggggatctca tgctggagtt cttcgcccac cccaacttgt ttattgcagc    3120
ttataatggt tacaaataaa gcaatagcat cacaaatttc acaaataaag catttttttc    3180
actgcattct agttgtggtt tgtccaaact catcaatgta tcttatcatg tctgtatacc    3240
gtcgacctct agctagagct tggcgtaatc atggtcatag ctgtttcctg tgtgaaattg    3300
ttatccgctc acaattccac acaacatacg agccggaagc ataaagtgta aagcctgggg    3360
tgcctaatga gtgagctaac tcacattaat tgcgttgcgc tcactgcccg ctttccagtc    3420
gggaaacctg tcgtgccagc tgcattaatg aatcggccaa cgcgcgggga gaggcggttt    3480
gcgtattggg cgctcttccg cttcctcgct cactgactcg ctgcgctcgg tcgttcggct    3540
gcggcgagcg gtatcagctc actcaaaggc ggtaatacgg ttatccacag aatcagggga    3600
taacgcagga aagaacatgt gagcaaaagg ccagcaaaag gccaggaacc gtaaaaaggc    3660
cgcgttgctg cgttttttcc ataggctccg cccccctgac gagcatcaca aaaatcgacg    3720
ctcaagtcag aggtggcgaa acccgacagg actataaaga taccaggcgt ttccccctgg    3780
aagctccctc gtgcgctctc ctgttccgac cctgccgctt accggatacc tgtccgcctt    3840
tctcccttcg ggaagcgtgg cgctttctca tagctcacgc tgtaggtatc tcagttcggt    3900
gtaggtcgtt cgctccaagc tgggctgtgt gcacgaaccc cccgttcagc ccgaccgctg    3960
cgccttatcc ggtaactatc gtcttgagtc caacccggta agacacgact tatcgccact    4020
ggcagcagcc actggtaaca ggattagcag agcgaggtat gtaggcggtg ctacagagtt    4080
cttgaagtgg tggcctaact acggctacac tagaagaaca gtatttggta tctgcgctct    4140
gctgaagcca gttaccttcg gaaaaagagt tggtagctct tgatccggca aacaaaccac    4200
cgctggtagc ggtttttttg tttgcaagca gcagattacg cgcagaaaaa aaggatctca    4260
agaagatcct ttgatctttt ctacggggtc tgacgctcag tggaacgaaa actcacgtta    4320
agggattttg gtcatgagat tatcaaaaag gatcttcacc tagatccttt taaattaaaa    4380
atgaagtttt aaatcaatct aaagtatata tgagtaaact tggtctgaca gttaccaatg    4440
cttaatcagt gaggcaccta tctcagcgat ctgtctattt cgttcatcca tagttgcctg    4500
actccccgtc gtgtagataa ctacgatacg ggagggctta ccatctggcc ccagtgctgc    4560
aatgataccg cgagacccac gctcaccggc tccagattta tcagcaataa accagccagc    4620
cggaagggcc gagcgcagaa gtggtcctgc aactttatcc gcctccatcc agtctattaa    4680
```

```
ttgttgccgg gaagctagag taagtagttc gccagttaat agtttgcgca acgttgttgc    4740
cattgctaca ggcatcgtgg tgtcacgctc gtcgtttggt atggcttcat tcagctccgg    4800
ttcccaacga tcaaggcgag ttacatgatc ccccatgttg tgcaaaaaag cggttagctc    4860
cttcggtcct ccgatcgttg tcagaagtaa gttggccgca gtgttatcac tcatggttat    4920
ggcagcactg cataattctc ttactgtcat gccatccgta agatgctttt ctgtgactgg    4980
tgagtactca accaagtcat tctgagaata gtgtatgcgg cgaccgagtt gctcttgccc    5040
ggcgtcaata cgggataata ccgcgccaca tagcagaact ttaaaagtgc tcatcattgg    5100
aaaacgttct cggggcgaaa actctcaag gatcttaccg ctgttgagat ccagttcgat    5160
gtaacccact cgtgcaccca actgatcttc agcatctttt actttcacca gcgtttctgg    5220
gtgagcaaaa acaggaaggc aaaatgccgc aaaaaaggga ataagggcga cacggaaatg    5280
ttgaatactc atactcttcc tttttcaata ttattgaagc atttatcagg gttattgtct    5340
catgagcgga tacatatttg aatgtattta gaaaaataaa caaataggg ttccgcgcac    5400 atttccccga aaagtgccac ctgacgtc                                       5428

<210> SEQ ID NO 277
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis Tag

<400> SEQUENCE: 277

His His His His His His
1               5

<210> SEQ ID NO 278
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis Tag

<400> SEQUENCE: 278

His His His His His His His His
1               5

<210> SEQ ID NO 279
<211> LENGTH: 11
<212> TYPE: PRT
<213> ORGANISM: Homo sapiens

<400> SEQUENCE: 279

Asn Val Thr Arg Leu Gln Arg Ala Gln Val Ser
1               5                   10

<210> SEQ ID NO 280
<211> LENGTH: 10
<212> TYPE: PRT
<213> ORGANISM: Homo sapiens

<400> SEQUENCE: 280

Asn Val Thr Arg Leu Arg Ala Gln Val Ser
1               5                   10

<210> SEQ ID NO 281
<211> LENGTH: 18
<212> TYPE: DNA
```

-continued

```
<213> ORGANISM: Homo sapiens

<400> SEQUENCE: 281
aacgtcacca ggctggtg                                                 18

<210> SEQ ID NO 282
<211> LENGTH: 21
<212> TYPE: DNA
<213> ORGANISM: Homo sapiens

<400> SEQUENCE: 282
cagcagaggg cccaggtgag c                                             21

<210> SEQ ID NO 283
<211> LENGTH: 7
<212> TYPE: PRT
<213> ORGANISM: Tobacco Etch Virus

<400> SEQUENCE: 283

Glu Asn Leu Tyr Phe Gln Gly
1               5

<210> SEQ ID NO 284
<211> LENGTH: 18
<212> TYPE: DNA
<213> ORGANISM: Artificial Sequence
<220> FEATURE:
<223> OTHER INFORMATION: Description of Artificial Sequence: Synthetic
      pTT5-I sequence

<400> SEQUENCE: 284
gaattcgccg ccaccatg                                                 18
```

COMPOSITIONS AND METHODS OF USE FOR MGD-CSF IN DISEASE TREATMENT

PRIORITY CLAIM

This application is a continuation of application Ser. No. 11/632,319, filed Jul. 24, 2007 now abandoned, which is a national stage application of PCT International Application No. PCT/US2005/025941, filed Jul. 21, 2005, which claims priority to provisional applications 60/590,565, filed Jul. 22, 2004; 60/647,604, filed Jan. 27, 2005; 60/664,932, filed Mar. 24, 2005; and provisional application 60/699,019 entitled "Novel MGD-CSF Polypeptides, Polynucleotides, and Methods of Use Thereof," filed Jul. 14, 2005. This application also relates to applications PCT/US03/34811, filed Oct. 31, 2003; PCT/US04/11270, filed Apr. 30, 2004; 60/590,565 filed Jul. 22, 2004; 60/642,604, filed Jan. 11, 2005; 60/647,013, filed Jan. 27, 2005; and 60/654,229, filed Feb. 18, 2005. These applications are all incorporated by reference in their entireties.

TECHNICAL FIELD

The present invention relates to a novel secreted molecule identified herein as "monocyte, granulocyte, and dendritic cell colony stimulating factor" (MGD-CSF). It relates to the polypeptide and polynucleotide sequences of MGD-CSF, fusion molecules containing MGD-CSF, vectors, host cells, compositions, and kits comprising MGD-CSF, and methods of using MGD-CSF and related molecules to diagnose, prevent, determine the prognosis for, and treat diseases, including immune-related diseases, infectious diseases, and cancer. MGD-CSF is a splice variant of MCG34647, a gene with a previously unknown function.

BACKGROUND ART

Cells of the innate immune system, such as monocytes, macrophages, natural killer (NK) cells, and polymorphonuclear neutrophils (PMN), are the first-line defenders against cancer and infectious disease by nature of their phagocytic, cytolytic, and antimicrobial properties. Monocytes and macrophages are believed to play an important role in inflammatory diseases through their activation and secretion of inflammatory mediators. For example, granulocyte macrophage-colony stimulating factor (GM-CSF) is known to promote proliferation and differentiation of granulocytes, monocytes, and macrophages. Granulocyte-colony stimulating factor (G-CSF) is known to promote the differentiation and growth of granulocytes and neutrophils (Ogawa, *Blood* 81:3844-2853 (1993)). At present, both G-CSF and GM-CSF are being used as protein therapeutics to promote the recovery of blood cells after chemotherapy, radiation, and bone marrow transplants.

NK cells are known to play a role in host responses to cancer. In both syngeneic and xenogenic transplant models, tumor Cells grow more efficiently in NK-/- mice, and survival rates for the mice in these models are significantly less than those for mice possessing NK cells. In addition, potentiating an NK response with soluble protein factors, such as IL-2 or IL-15, has been shown to increase the efficiency by which NK cells kill tumor cells in the presence of anti-tumor antibodies both in vitro and in vivo (Carson et al., *J. Exp. Med.* 180:1395-1403 (1994)).

Additionally, NK cells are also known to play a role in host response to infectious disease. For example, mice lacking NK cells are known to have increased susceptibility to viruses and intracellular pathogens. Similarly, humans with naturally occurring NK cell deficiencies are also known to be highly susceptible to infections. In vitro, NK mediated killing of cells infected with virus or other intracellular pathogens is known to be potentiated by cytokines such as interferon-α, interferon-β, interleukin-12, and interleukin-18 (Wu et al., *Adv. Cancer Res.* 90:127 (2003)); Biron et al., *Rev. Immunol.* 17:189 (1999); Naume et al., *Scand. J. Immunol.* 40:128 (1994)).

It is also known that activated NK cells can be correlated with failure rates for women undergoing in vitro fertilization (IVF) procedures, and may be further linked to spontaneous pregnancy loss (Dosiou et al., *Endocr. Rev.* 26:44 (2005)). Additionally, elevated levels of activated NK cells may be found in a number of patients with immune endometriosis, one known underlying cause of infertility in women (Dosiou et al., *Endocr. Rev.* 26:44 (2005)).

Antigen-processing dendritic cells are capable of sensitizing T cells to both new and recall antigens. Dendritic cells express high levels of major histocompatibility complex class I and II antigens, which play a role in cancer immunotherapy, along with other immunomodulatory proteins, adhesins, and cytokines. Dendritic cell cancer vaccines have been reported to be produced by extracting a patient's dendritic cells and using immune cell stimulants to reproduce large amounts of dendritic cells in vitro or ex vivo. The dendritic cells can then be exposed to antigens from the patient's cancer cells. The combination of dendritic cells and antigens is injected into the patient, and the dendritic cells program the patient's T cells. Dendritic cells break down the antigens on the cancer cell surfaces, then display them to killer T cells. (Song et al., *Yonsei Med. J.* 45 Suppl.:48-52 (2004)).

Cancer patients recovering from autologous hematopoietic cell transplantation exhibit decreased levels of circulating dendritic cells. Dendritic cells develop from hematopoietic progenitors and promoting their development may help regain normal dendritic cell levels. The ability to generate dendritic cells by inducing proliferation of isolated human dendritic cells and inducing proliferation and differentiation of hematopoietic stem cells facilitates efficacy tests of dendritic cell vaccination and facilitates effective vaccination practice. There is a need in the art for factors that stimulate dendritic cell proliferation and/or hematopoietic stem cell proliferation and/or differentiation to dendritic cells. There is also a need in the art for factors that promote the generation of dendritic cells from hematopoietic cells to increase circulating dendritic cells in preparation for hematopoietic cell transplantation.

Osteoclasts share a common progenitor with dendritic cells, macrophages, and microglia (Servet-Delprat et al., *BMC Immunol.* 3:15 (2002)). These multinucleated, adherent, bone-resorbing cells differentiate in the bone marrow and function in the vicinity of the bone to regulate bone remodeling and calcium homeostasis. Osteoclast differentiation and function has been reported to be regulated by secreted factors, including M-CSF and osteoprotegerin (RANK ligand) (Miyamoto et al., *Keio. J. Med.* 52:1-7 (2003)). Factors which play a role in the regulation of osteoclast differentiation and function may be therapeutic in treating osteoporosis and other bone diseases.

Microglial cells function as immune effectors of the central nervous system, where they also produce neurotrophic factors and regulate glutamate uptake. These mononuclear phagocytes are distributed throughout the central nervous system parenchyma in both the white and grey matter. Microglia have been reported to be present in increased numbers in patients with Alzheimer's disease, wherein they display marked increases in nitric oxide production and inflammatory cytokines, including IL-1 and MIP1 alpha (Vincent et al. *Neurobiol. Aging* 23:349-362 (2002)). Factors that regulate microglial differentiation and function may be therapeutic in treating Alzheimer's disease and other neural diseases, including demyelinating diseases such as multiple sclerosis, acute disseminated encephalomyelopathy, progressive multifocal leukoencephalopathy, stroke, and Parkinson's disease.

Gene MGC34647 encodes the hypothetical protein NP_689669 (Strausberg et al., *Proc. Natl. Acad. Sci.* 99:16,899 (2002)). The functions of this gene and its encoded polypeptides are previously unknown. The sequences of MGC34647 and NP_689669 correspond to SEQ ID. NOS.: 49 and 103, respectively, of WO 2002/048337. They correspond to the amino acid sequence of a secreted protein of unknown function and its coding sequence, respectively.

INDUSTRIAL APPLICABILITY

Current therapies for immune diseases, cancer, infectious diseases, and immune-mediated recurrent pregnancy loss are inadequate, insufficient, and often toxic. Novel therapeutic compounds and therapies that increase the efficacy of the innate immune response to these conditions can provide more efficient therapy and may have a better therapeutic index than current therapies.

BRIEF DESCRIPTION OF THE FIGURES AND TABLES

Brief Description of the Figures

FIG. 1 shows the amino acid sequence alignment of exon 4 of MGD-CSF (MGD-CSF_exon4); SEQ ID NO:8), MGC34647 (NP_689669); SEQ ID NO:10) and MGD-CSF SEQ ID NO:7), as further described in Example 1. Amino acid identity is designated by (*).

FIG. 2 also shows the nucleic acid sequences of the multiple cloning site flanking sequences for the pTT5-G (Residues 1182-1265 and 2984-3127 of SEQ ID NO:272), pTT5-H, (Residues 1182-1391 and 1597-1602 of SEQ ID NO:273, and pTT5-I (SEQ ID NO:284 and residues 2905-3048 of SEQ ID NO:274 vectors.

FIG. 4A shows the expression of intracellular (cells) and secreted (supernatant) CLN00732663, a MGD-CSF vector with a C-terminal His tag, in 293-6E cells. FIG. 4B shows the expression of intracellular (cells) and secreted (supernatant) CLN00816424, a MGD-CSF vector with a C-terminal His tag and a collagen leader sequence, in 293-6E cells. Both FIGS. 4A and 4B show Positope™ (Invitrogen, Carlsbad, Calif.) (right panels) as a positive control for expression. Molecular weights are indicated on the left panels.

FIG. 5A shows the degree of cell proliferation of cells transfected with CLN00542945 (black bars), CLN00732663 (light grey bars), CLN00821867 (diagonal stripe bars), and CLN00816424 (cross-hatched bars), and compared to a control gene encoding secreted alkaline phosphatase (SEAP) (dark grey bars). Both the cells transfected with CLN00816424 and the control SEAP cells increased in number from 3 through 6 days post-transfection, as further described in Example 4. FIG. 5B shows the percentage of viable cells transfected with CLN00542945 (black bars), CLN00732663 (light grey bars), CLN00821867 (diagonal stripe bars), and CLN00816424 (cross-hatched bars), and compared to a control gene encoding secreted alkaline phosphatase (SEAP) (dark grey bars). The cells transfected with CLN00816424 and the control SEAP remained viable but the cells transfected with MGD-CSF, CLN00732663, and CLN00821867 demonstrated increased toxicity, which was dependent on culture conditions, but was not gene-specific, and was evidenced by their decreased viability over time in culture.

FIG. 6A shows the expression of MGD-CSF in cultures of suspension 293-T cells grown in FreeStyle medium with 3% FBS and in HyQ-CHO medium with 1% FBS, as further described in Example 5. FIG. 6B shows the expression of MGD-CSF in suspension cultures with low serum (panel 1), in the absence of serum (panel 2), and in adherent culture (panel 3), as compared to purified MGD-CSF standard produced from a bacterial host (panel 4).

FIG. 8B shows the electrophoretic migration pattern of muteins of MGD-CSF under reducing and non-reducing SDS-PAGE conditions, as described in greater detail in Example 8. The left panel shows an SDS-PAGE gel run under conditions that reduce disulfide bonds and the middle panel shows an SDS-PAGE gel run under conditions that do not reduce disulfide bonds. Wild type MGD-CSF expressed with its natural signal peptide (wt natSP), wild type MGD-CSF expressed with the collagen signal peptide (wt coISP), and the cysteine to serine muteins C35S, C167S, C176S, C178S, C179S, C190S, and C198S mutants are shown in both panels. Purified MGD-CSF is shown as a standard for quantitation and comparison in the right panel. C179S and C190S were expressed at lower yields than wild type MGD-CSF, and C35S was not expressed at a detectable level.

FIG. 12 shows the ability of MGD-CSF to induce myelocytic cell proliferation, as further described in Example 9C.

FIG. 18 shows the effect of MGD-CSF on human bone marrow colony formation, as described in greater detail in Example 11. FIG. 18A shows the dose-dependent stimulatory effect of MGD-CSF on the formation of CFU-G (left panel) and CFU-M (right panel) in comparison to the effects of G-CSF and GM-CSF.

(bottom right panel) in comparison to the effects of G-CSF and GM-CSF in the presence of the cytokines IL-3 and stem cell factor (SCF).

Figure 19:
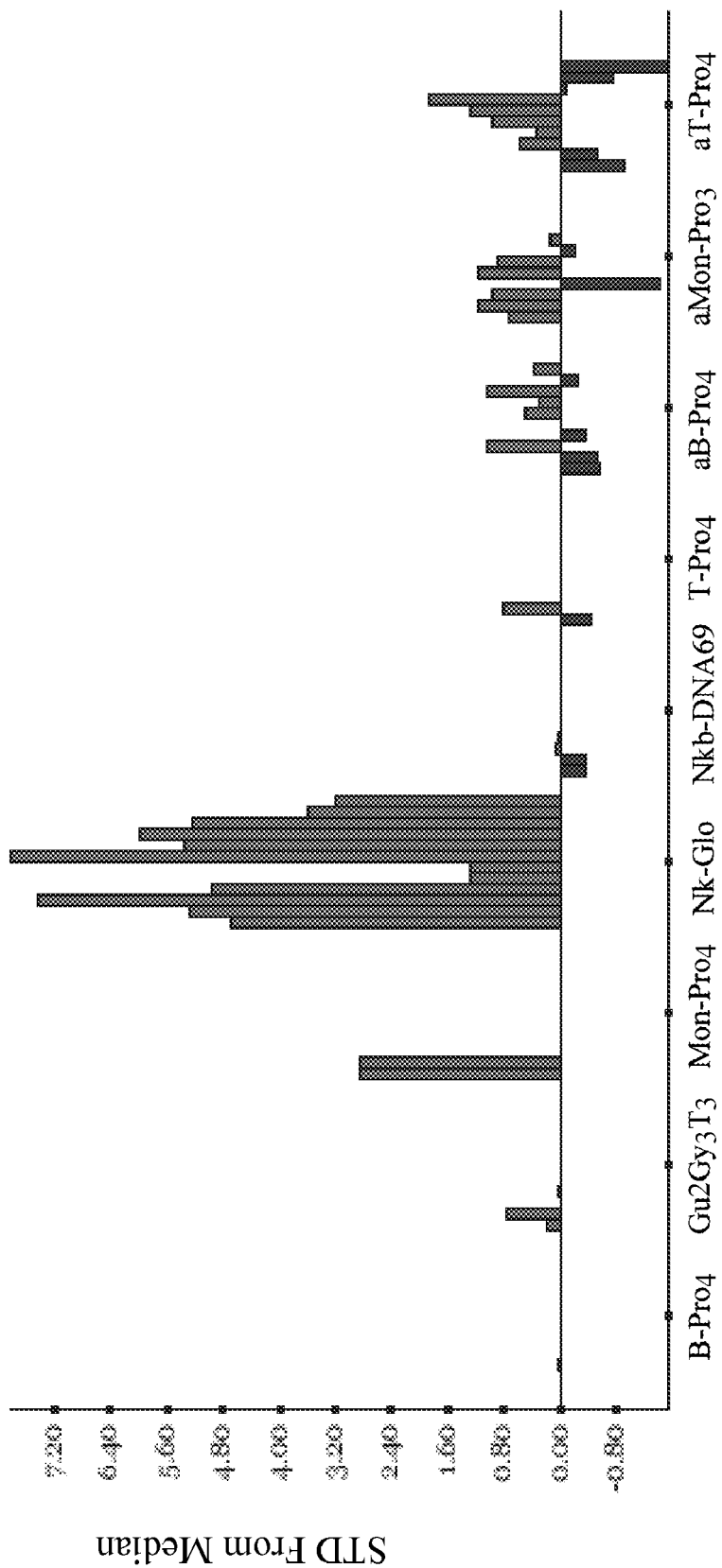

FIG. 19 shows a profile of the effect of MGD-CSF in assays for various biological activities, as described in greater detail in Example 12. MGD-CSF stimulated the proliferation of activated monocytes (MonPro4) and the proliferation of peripheral NK cells (NKGlo).

Figure 20:
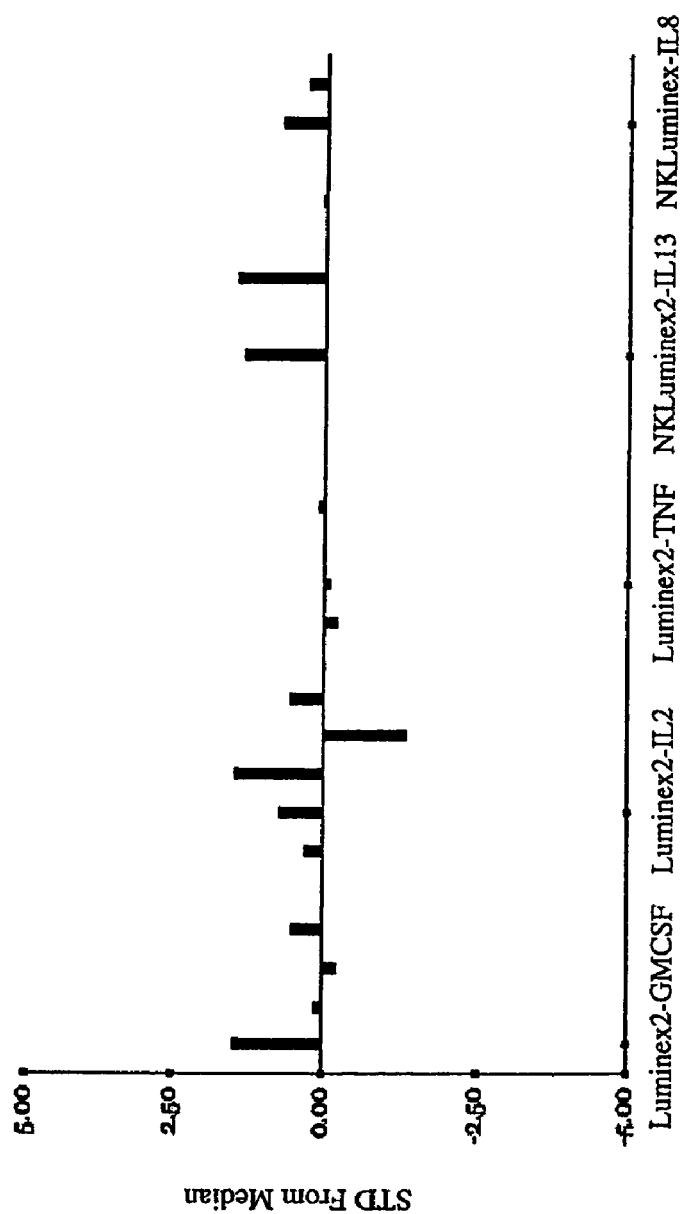

FIG. 20 shows a profile of the effect of MGD-CSF in various assays of cytokine secretion, as described in greater detail in Example 13. MGD-CSF stimulated the secretion of GM-CSF (Luminex2-GMCSF), IL-2 (Luminex2-IL2), and IL-13 (Luminex2-IL13).

Figure 21:
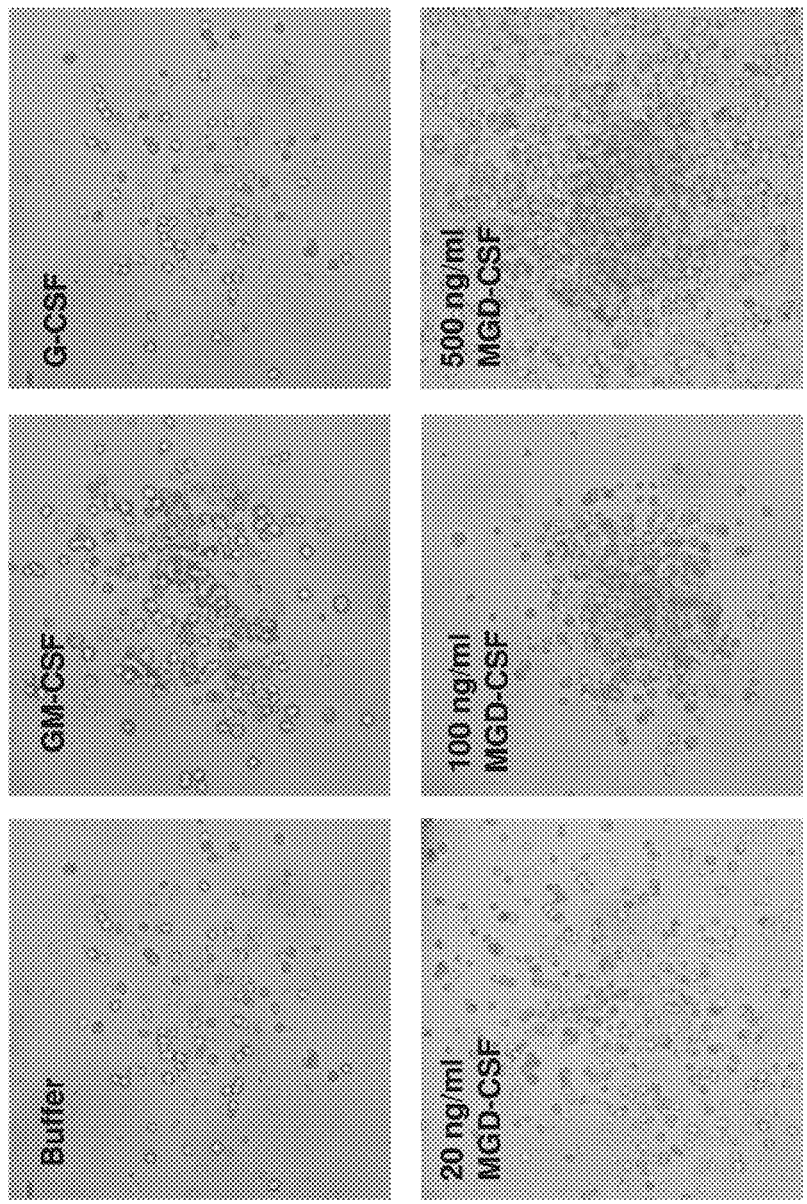

FIG. 21 shows the effect of MGD-CSF on CFU-M formation, as described in greater detail in Example 14. Examples of CFU-M formation induced by buffer, GM-CSF, and G-CSF are shown in the top three panels. The dose-dependent effect of CFU-M formation induced by 20 ng/ml, 100 ng/ml, and 500 ng/ml, MGD-CSF is shown in the bottom three panels.

Figure 22:
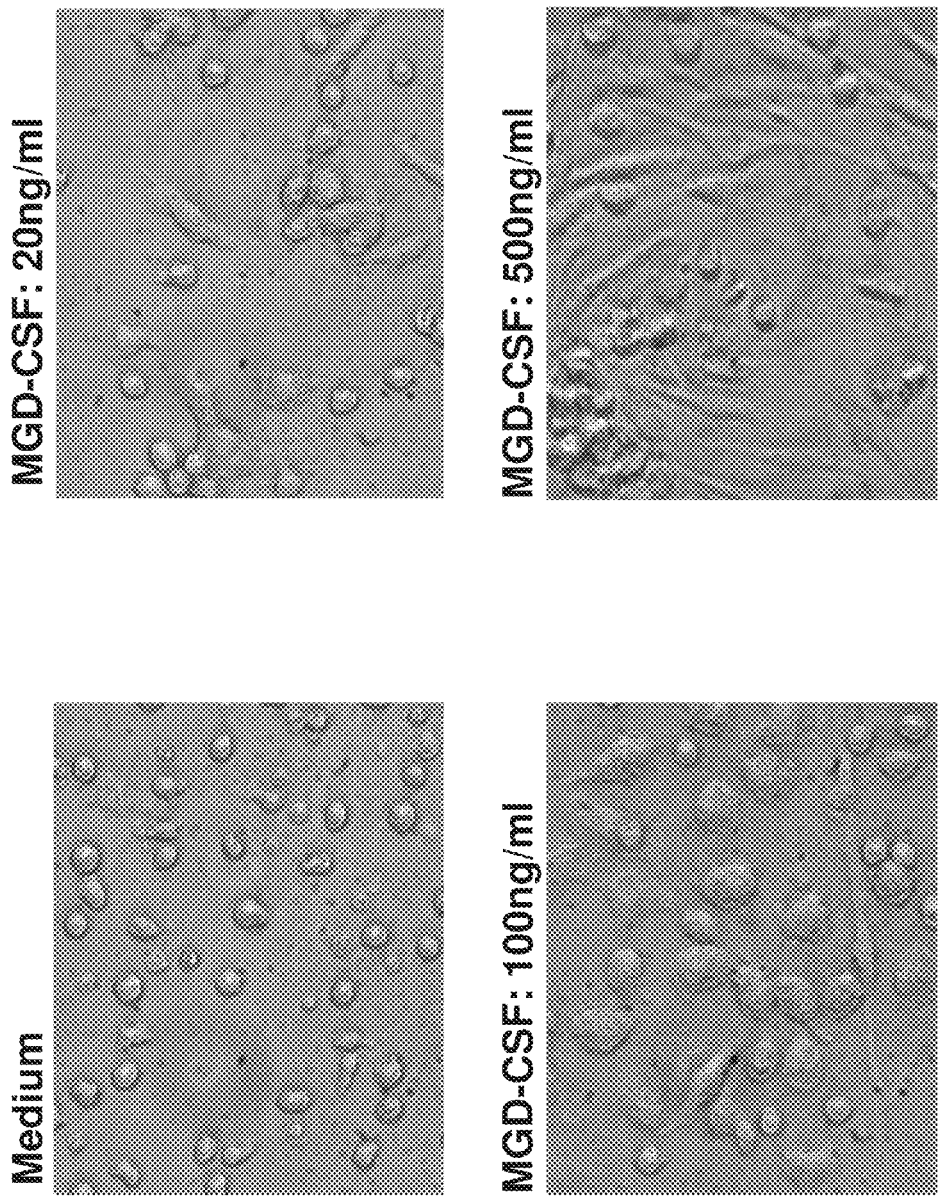

FIG. 22 shows the effect of MGD-CSF on dendritic cell formation, as described in greater detail in Example 15. Examples of dendritic cell formation induced by medium, 20 ng/ml MGD-CSF, 100 ng/ml MGD-CSF, and 500 ng/ml MGD-CSF are shown. MGD-CSF induced the formation of elongated differentiated dendritic cells from spherical undifferentiated hematopoeitic stem cells.

BRIEF DESCRIPTION OF THE TABLES

Table 1 provides information regarding SEQ. ID. NOS.:1-271, which are listed in the Sequence Listing. Column 1 shows an internal designation identification number (FP ID). Column 2 shows the nucleotide sequence identification number for the open reading frame of the nucleic acid sequence (SEQ. ID. NO.:(N1)). Column 3 shows the amino acid sequence identification number for the polypeptide sequence (SEQ. ID. NO.:(P1)). Column 4 shows the nucleotide sequence identification number for the entire nucleic acid sequence, including coding and noncoding regions (SEQ. ID. NO.:(N0)). Column 5 shows the corresponding nomenclature or the NCBI accession number (Source ID). Column 6 shows the type of sequence, for example, the function or vector composition (Type).

Table 2 annotates MGD-CSF with respect to NP_689669, the publicly disclosed sequence with the greatest degree of similarity. Row 1 shows an internal designation identification number (FP ID). Row 2 shows the clone identification number (Clone ID). Row 3 shows the predicted length of the polypeptide in number of amino acid residues (Pred Prot Len). Row 4 shows the public accession identification number of a top human hit found in the NCBI public database (Top Human Hit Accession No). Row 5 shows the annotation of the top human hit set forth in row 4 (Top Human Hit Annotation). Row 6 shows the length of the top human hit in number of amino acid residues (Top Human Hit Len). Row 7 shows the length of the match in number of amino acid residues between the query sequence designated by the FP ID and the top human hit (Match Len). Row 8 shows the percent identity between the FP ID and the top human hit over the length of the FP ID amino acid sequence expressed as a percentage (Top Human Hit % ID over Query Len). Row 9 shows the percent identity between the FP ID and the top human hit over the length of the top human hit (% ID over Hum Hit Len).

Table 3 shows the protein coordinates of MGD-CSF and NCBI NP_689669. Row 1 shows an internal designation ID number of the polypeptide (FP ID). Row 2 shows the clone identification number or NCBI accession number of the polypeptide (Clone ID). Row 3 shows an internal cluster identification number of the polypeptide (Cluster). Row 4 shows that NP-689669 is secreted (Classification). Row 5 shows the predicted protein length in number of amino acid residues (Pred Prot Len). Row 6 shows an internal parameter predicting the likelihood that the FP ID is secreted with "1" being a high likelihood the polypeptide is secreted and "0" being a low likelihood of secretion (Treevote). Row 7 shows the location of the signal peptide coordinates (Signal Peptide Coords). Row 8 shows the protein coordinates of the mature polypeptide with the first amino acid residue at the N-terminus of the full-length polypeptide being amino acid number 1 (Mature Protein Coords).

Table 4 provides annotation for the secretory leader sequences shown in Table 1. Column 1 shows an internal designation ID number of the polypeptide (FP ID). Column 2 shows the reference identification number (Source ID). Column 3 shows the NCBI annotation of the sequences.

Table 5 provides annotation for the MGD-CSF constructs shown Table 1. Column 1 shows the clone identification number (Clone ID). Column 2 shows the NCBI annotation (Annotation). Column 3 lists the vector (Vector Description). Column 4 lists the tag, if any (Tag).

Table 6 shows the effect of MGD-CSF constructs on myelocytic cell proliferation in vitro as further described in Example 9C. Column 1 shows the clone identification number (Clone ID). Column 2 shows the amino acid sequence of the clone. Column 3 provides a semiquantitative description of the potency of the activity of each clone to stimulate monocyte proliferation (Potency). Column 4 provides a semiquantitative description of the degree of expression of each construct (Expression).

Table 7 shows the effect of MGD-CSF constructs on myelocytic cell proliferation in vivo. Table 7A shows the results of injecting a group of six mice, three with a control vector and three with human MGD-CSF constructs on myelocytic cell proliferation. Table 7B shows the results of injecting a group of twelve mice, six with a control vector and six with mouse MGD-CSF. In both Tables 7A and 7B, column 1 lists the identification number of the animal (Animal ID), column 2 describes the vector as a control or MGD-CSF (Description), and column 3 indicates the number of monocytes in the peripheral blood (Monocytes/ul).

Table 8 shows the expression of the MGD-CSF gene as determined by interrogating a GeneLogic database using Affymetrix U133 chip probes. Column 1 lists diseases in which MGC34647 was overexpressed (Disease). Column 2 lists specific pathologies associated with the diseases of column 1 (Pathology). Column 3 lists the number of disease specimens that tested positive for the presence of MGC34647 (MGC34647 Positive). Column 4 lists the number of specimens examined (Total Gene Logic). Column 5 lists the percent of specimens examined which were positive (% Total). Columns 6 and 7 indicate that three acute promyelocytic leukemia samples (13% of the total examined) were derived from the bone marrow.

SUMMARY

MGD-CSF promotes the proliferation, survival, and/or differentiation of monocytes, granulocytes, dendritic cells, and NK cells. Therefore, MGD-CSF finds use as a protein therapeutic for treating cancers through its ability to stimulate the proliferation and/or activation of immune cells such as NK cells, monocytes, macrophages, granulocytes, and dendritic cells to fight tumor cells. MGD-CSF may be used alone or in combination with therapeutic monoclonal antibodies (for example, Rittman) to treat cancer, since MGD-CSF may promote antibody dependent cell cytotoxicity mediated by NK cells, monocytes, or granulocytes. MGD-CSF can also be used as an antagonistic therapeutic protein to effect hematopoietic regeneration adjunctive to chemotherapy and bone marrow transplantation. It can further be used to expand the number of dendritic cells in vivo or ex vivo. In addition, MGD-CSF may be useful as an anti-infectious agent in the treatment of infectious diseases, such as those caused by bacteria or viruses (for example, hepatitis C virus (HCV) or human immunodeficiency virus (HIV)).

MGD-CSF promotes the proliferation and/or the differentiation of immune cells, and thus finds use in treating immune diseases. It may play a role in the pathogenesis and treatment of autoimmune diseases. MGD-CSF antagonists may be developed as therapeutics for treating immune diseases. Antagonists may include monoclonal antibodies against MGD-CSF; MGD-CSF receptor(s), including soluble receptors; non-functional mutants; antisense DNA; and RNAi.

The invention provides an isolated nucleic acid molecule comprising a first polynucleotide that comprises a first nucleotide sequence chosen from SEQ. ID. NOS.:1, 2, 3, and 5; a first polynucleotide encoding a first polypeptide comprising a first amino acid sequence chosen from SEQ. ID. NOS.:7, 8, 9, and 11; a polynucleotide comprising a nucleotide sequence that is complementary to the first nucleotide sequence; and a biologically active fragment of any of these. In an embodiment, the biologically active polypeptide fragment comprises at least six contiguous amino acid residues chosen from SEQ. ID. NOS.: 7, 8, 9, and 11, and wherein at least two of the contiguous six amino acid residues are leucine and arginine residues at amino acid residue positions 80 and 81, respectively. This isolated nucleic acid molecule may be chosen from a cDNA molecule, a genomic DNA molecule, a cRNA molecule, a siRNA molecule, an RNAi molecule, an mRNA molecule, an antisense molecule, and a ribozyme. In an embodiment, this nucleic acid molecule further comprises its complement.

In an embodiment, the first nucleotide sequence is SEQ. ID. NO.:3. This embodiment may further comprise a second polynucleotide. This second polynucleotide may comprise a second nucleotide sequence encoding a homologous or heterologous secretory leader. The secretory leader may be chosen from SEQ. ID. NOS.:14-211.

The invention also provides a nucleic acid molecule at least about 70%, at least about 80%, or at least about 90% identical to the isolated nucleic acid molecule described above. The invention provides an isolated nucleic acid molecule that specifically hybridizes under stringent conditions to the sequence set forth in SEQ. ID. NOS.:1, 2, or 3, or to the complement of the sequence set forth in SEQ. ID. NOS.:1, 2, 3, and 5, wherein the nucleic acid molecule encodes a polypeptide that can stimulate the proliferation and differentiation of granulocytes, monocytes, and dendritic cells.

The invention further provides an isolated polypeptide comprising a first amino acid sequence chosen from SEQ. D. NOS.:7, 8, 9, and 11; a sequence encoded by SEQ. ID. NOS.: 1, 2, 3, and 5; and a biologically active fragment of any of these. This isolated polypeptide may be present in a cell culture, for example, a bacterial cell culture, a mammalian cell culture, an insect cell culture, or a yeast cell culture; or in a cell culture medium. This isolated polypeptide may also be present in a plant or a non-human animal.

In an embodiment, the biologically active fragment comprises at least six contiguous amino acid residues chosen from SEQ. ID. NOS.:7, 8, 9, and 11, wherein at least two of the contiguous six amino acid residues are leucine and arginine at amino acid residue 80 and 81 of SEQ. ID. NO.:5.

The invention yet further provides an isolated polypeptide at least about 70%, at least about 80%, or at least about 90% homologous to an isolated polypeptide comprising a first amino acid sequence chosen from SEQ. ID. NOS.:7, 8, 9, and 11; a sequence encoded by SEQ. ID. NOS.:1, 2, 3, and 5; and a biologically active fragment of any of these.

The invention provides an isolated polypeptide comprising a first amino acid sequence chosen from SEQ. ID. NOS.:7, 8, 9, and 11; a sequence encoded by SEQ. ID. NOS.:1, 2, 3, and 5; and a biologically active fragment of any of these, further comprising a second amino acid sequence, wherein the second amino acid sequence is a homologous secretory leader or a heterologous secretory leader, and wherein the first and second amino acid sequences are operably linked. The heterologous leader sequence may be chosen from SEQ. ID. NOS.: 14-211.

The invention also provides a vector comprising the nucleic acid molecule described above and a promoter that regulates its expression. This vector may be a viral or a plasmid vector. The promoter may be naturally contiguous to the nucleic acid molecule or may not be naturally contiguous to the nucleic acid molecule. It may be an inducible promoter, a conditionally-active promoter, a constitutive promoter, and/or a tissue-specific promoter.

Additionally, the invention provides a recombinant host cell comprising a cell and one or more isolated nucleic acid, polypeptide, or vector described above. The host cell may be prokaryotic or eukaryotic, for example, a human, non-human mammalian, insect, fish, plant, or fungal cell. In an embodiment, the mammalian cell is of the CHO cell line or the 293 cell line, for example, a 293T cell or a 293E cell.

The invention further provides a non-human animal injected with an isolated nucleic acid or polypeptide of the invention. This animal may, for example, be a rodent, a non-human primate, a rabbit, a dog, or a pig.

The invention yet further provides a nucleic acid composition comprising an isolated nucleic acid molecule of the invention and a carrier. The invention provides a polypeptide composition comprising an isolated polypeptide of the invention and a carrier. The invention provides a vector composition comprising a vector of the invention and a carrier. The invention provides a host cell composition comprising a host cell of the invention and a carrier. In an embodiment, the carrier is a pharmaceutically acceptable carrier.

In another aspect, the invention provides a method of producing a recombinant host cell comprising providing a vector that comprises an isolated nucleic acid molecule of the invention and allowing a cell to come into contact with the vector to form a recombinant host cell transfected with the nucleic acid molecule.

The invention provides a method of producing a polypeptide comprising providing an isolated nucleic acid molecule of the invention and expressing the nucleic acid molecule in an expression system to produce the polypeptide. In an embodiment, the expression system is a cellular expression system, for example, a prokaryotic or a eukaryotic expression system. This expression system may comprise a host cell transfected with an isolated nucleic acid molecule of the invention, forming a recombinant host cell, and further comprising culturing the recombinant host cell to produce the polypeptide. In an embodiment, the expression system is a cell-free expression system chosen from a wheat germ lysate, a rabbit reticulocyte, a ribosomal display, and an E. coli lysate.

The invention also provides a polypeptide produced by such a method. For example, it provides a polypeptide produced by a eukaryotic expression system, as described above, wherein the host cell is chosen from a mammalian cell, an insect cell, a plant cell, a yeast cell, and a bacterial cell.

In yet another aspect, the invention provides a diagnostic kit comprising a composition that comprises an isolated nucleic acid molecule of the invention, a reporter for detecting the nucleic acid molecule or its complement, and a vehicle. It provides a diagnostic kit comprising an antibody that specifically binds to an isolated polypeptide of the invention and a carrier. It also provides a diagnostic kit comprising an isolated polypeptide of the invention and a carrier.

In a further aspect, the invention provides a method of determining the presence of an antibody specific to an isolated polypeptide of the invention in a patient sample comprising providing a composition comprising an isolated polypeptide of the invention, allowing the polypeptide to interact with the sample; and determining whether interaction has occurred between the polypeptide and antibody in the sample, if present.

In yet a further aspect, the invention provides an isolated antibody that specifically binds to and/or interferes with the activity of an antigen that comprises at least six contiguous amino acid residues chosen from SEQ. ID. NOS.:7-12. For example, these contiguous amino acid residues may comprise the consecutive amino acid residues leu-arg at amino acid positions 80 and 81 of SEQ. ID. NO.:7 or the consecutive amino acid residues leu-gln-arg of SEQ. ID. NO.:12. This antibody may be chosen from a polyclonal antibody, a monoclonal antibody, a single chain antibody, and active fragments of any of these, for example, an antigen binding fragment, an Fc fragment, a cdr fragment, a $V_H$ fragment, a $V_C$ fragment, and a framework fragment.

The invention also provides an isolated polypeptide as described above, further comprising at least one fusion partner. By way of example, the fusion partner may be chosen from a polymer, a polypeptide, a succinyl group, fetuin A, fetuin B, a leucine zipper domain, a tetranectin trimerization domain, a mannose binding protein, and an Fc region. The polymer may be a polyethylene glycol moiety, which may, for example, attach through an amino group of an amino acid of the polypeptide. This polyethylene glycol moiety may be a branched or linear chain polymer.

The invention further provides a method of screening for an agent that modulates activity of an isolated polypeptide of the invention comprising providing a test system in which an isolated polypeptide of the invention affects biological activity; and screening multiple agents for an effect on the activity of an isolated polypeptide of the invention on the test system. The modulator may, for example, be a small molecule drug. The modulator may also, for example, be an antibody.

The invention further provides a method of stimulating immune cells comprising providing a composition comprising a substantially pure polypeptide chosen from any of SEQ. ID. NOS.:7-12, and active fragments thereof; and contacting one or more immune cells with the polypeptide. The polypeptide may be encoded by a nucleic acid molecule comprising a nucleotide sequence chosen from SEQ. ID. NOS.:1-6. Suitable immune cells include granulocytes; monocytes; lymphocytes, such as NK cells; macrophages; peripheral blood mononuclear cells; and dendritic cells.

The invention yet further provides a method of increasing a population of immune cells comprising providing a composition comprising a substantially pure polypeptide chosen from SEQ. ID. NOS.:7-12 and active fragments of any of these; and contacting one or more immune cells or immune cell precursors with the polypeptide. The polypeptide may be encoded by a nucleic acid molecule comprising a nucleotide sequence chosen from SEQ. M. NOS.:1-6. Suitable immune cell populations include populations of monocytes; lymphocytes, for example, NK cells; macrophages; and peripheral blood mononuclear cells.

The invention additionally provides a method of stimulating an immune response in a subject comprising providing a composition comprising a substantially pure polynucleotide encoding a polypeptide chosen from SEQ. ID. NOS.:7-12 and active fragments of any of these; and administering the composition to the subject. The polypeptide may be encoded by a nucleic acid molecule comprising a nucleotide sequence chosen from SEQ. ID. NOS.:1-6. The polypeptide may be administered locally or systemically. It may be administered intravenously, by enema, intraperitoneally, subcutaneously, topically, or transdermally.

The invention provides a method of increasing immune cells in a subject undergoing cancer therapy comprising providing a composition comprising a substantially pure polypeptide chosen from any of SEQ. ID. NOS.:7-12 and active fragments of any of these; and administering the composition to the subject. The polypeptide may be encoded by a nucleic acid molecule comprising a nucleotide sequence chosen from SEQ. ID. NOS.:1-6. Suitable immune cell populations include populations of monocytes; lymphocytes, for example, NK cells; macrophages; and peripheral blood mononuclear cells. The cancer therapy is may comprise chemotherapy and/or radiation therapy. The polypeptide may be administered after a bone marrow transplant.

The invention also provides a method of treating or preventing cancer in a subject comprising providing a composition comprising a substantially pure polypeptide chosen from SEQ. ID. NOS.:7-12 and active fragments of any of these; and administering the composition to the subject.

The invention further provides a method for inhibiting tumor growth in a subject comprising providing a composition comprising a substantially pure polypeptide chosen from SEQ. ID. NOS.:7-12 and active fragments of any of these; and administering the composition to the subject. The tumor may comprise human tumor cells, for example, solid tumor cells or leukemic tumor cells.

The invention yet further provides a method of treating or preventing an infection in a subject comprising providing a composition comprising a substantially pure polypeptide chosen from SEQ. ID. NOS.:7-12 and active fragments of any of these; and administering the composition to the subject. The polypeptide may be encoded by a nucleic acid molecule comprising a nucleotide sequence chosen from SEQ. ID. NOS.:1-6. This method can, for example, treat or prevent a bacterial infection, a mycoplasma infection, a fungal infection, a viral infection, an intracellular pathogen, and/or an intracellular parasite. The method may be practiced by administering the composition to the subject locally or systemically.

Additionally, the invention provides a method for modulating an immune response in a subject, comprising providing a modulator of a polypeptide chosen from SEQ. ID. NOS.:7-12 and active fragments of any of these; and administering the modulator to the subject. The modulator may, for example, be an antibody, a soluble receptor, and/or a polypeptide. Suitable antibody modulators include monoclonal antibodies, polyclonal antibodies, cdr fragments, $V_H$ fragments, $V_C$ fragments, framework fragments, single chain antibodies, and active fragments of an antibody. The modulator may also, for example, be an aptamer, an RNAi, an antisense molecule, and/or a ribozyme. The method can, for example, modulate the immune response by suppressing inflammation and/or autoimmune disease. The method can also, for example, modulate the immune response by treating or preventing rheumatoid arthritis, osteoarthritis, psoriasis, inflammatory bowel disease, multiple sclerosis, myocardial infarction, stroke, and/or fulminant liver failure.

The invention provides a method of modulating an immune response to pregnancy comprising providing a modulator of a polypeptide chosen from SEQ. ID. NOS.:7-12 and active fragments of any of these; and administering the modulator to the subject. The method can, for example, by reduce recurrent pregnancy loss, modulating the immune response.

The invention provides a method of enhancing immune response to a vaccine in a subject comprising providing a polypeptide composition comprising a substantially purified polypeptide chosen from SEQ. ID. NOS.:7-12 and active fragments of any of these; providing a vaccine composition; and administering the polypeptide composition and the vaccine composition to the subject. The polypeptide composition may be administered to the subject prior to, substantially contemporaneously with, or after administering the vaccine composition.

The invention also provides a method of treating or preventing an inflammatory disease in a subject comprising providing a modulator of a polypeptide chosen from SEQ. ID. NOS.:7-12 and active fragments of any of these; and administering the modulator to the subject. The modulator may, for example, be an aptamer, an RNAi, an antisense molecule, and/or a ribozyme. The modulator may also, for example, be an antibody, a soluble receptor, and/or a polypeptide. Suitable antibody modulators include monoclonal antibodies, polyclonal antibodies, cdr fragments, $V_H$ fragments, $V_C$ fragments, framework fragments, single chain antibodies, and active fragments of an antibody.

The invention further provides a method of treating or preventing an autoimmune disease in a subject comprising providing a modulator of a polypeptide chosen from SEQ. ID. NOS.:7-12 and active fragments of any of these; and administering the modulator to the subject. The modulator may, for example, be an aptamer, an RNAi, an antisense molecule, and/or a ribozyme. The modulator may also, for example, be an antibody, a soluble receptor, and/or a polypeptide. Suitable antibody modulators include monoclonal antibodies, polyclonal antibodies, cdr fragments, $V_H$ fragments, $V_C$ fragments, framework fragments, single chain antibodies, and active fragments of an antibody.

The invention yet further provides a method of increasing the number of NK cells in a subject comprising providing a polypeptide chosen from SEQ. ID. NOS.:7-12 and active fragments of any of these; and administering the polypeptide to the subject.

The invention provides a method of modulating an NK cell population in a subject comprising providing a modulator of a polypeptide chosen from SEQ. ID. NOS.:7-12 and active fragments of any of these; and administering the modulator to the subject. The modulator may, for example, be an aptamer, an RNAi, an antisense molecule, and/or a ribozyme. The modulator may also, for example, be an antibody, a soluble receptor, and/or a polypeptide. Suitable antibody modulators include monoclonal antibodies, polyclonal antibodies, cdr fragments, $V_H$ fragments, $V_C$ fragments, framework fragments, single chain antibodies, and active fragments of an antibody. In an embodiment, the NK cell population stimulates an immune response. In an embodiment, the NK cell population suppresses pregnancy loss. In an embodiment, the NK cell population stimulates an anti-cancer response.

The invention also provides a method of increasing a population of hematopoietic stem cells comprising providing a composition comprising a substantially pure polypeptide chosen from SEQ. ID. NOS.:7-12 and active fragments of any of these; and contacting the population of hematopoietic stem cells with the polypeptide.

The invention further provides a method of providing cytoprotection to a population of cells comprising providing a composition comprising a substantially pure polypeptide chosen from SEQ. ID. NOS.:7-12 and active fragments of any of these; and contacting the population of cells with the polypeptide.

The methods for modulating or enhancing immune responses, treating or preventing disease, increasing the number of NK cells, modulating an NK cell population, increasing a population of hematopoietic stem cells, and providing cytoprotection may be practiced, for example, by administering the compositions described above locally or systemically. They may also be practiced by providing the polypeptide compositions described above, wherein the polypeptide is encoded by a nucleic acid molecule comprising a nucleotide sequence chosen from SEQ. ID. NOS.:1-6 and active fragments of any of these. They may further be practiced by providing the polypeptide compositions described above, wherein the polypeptide further comprises at least one fusion partner. By way of example, the fusion partner may be chosen from a polymer, a polypeptide, a succinyl group, fetuin A, fetuin B, a leucine zipper domain, a tetranectin trimerization domain, a mannose binding protein, and an Fc region. The polymer may be a polyethylene glycol moiety, which may, for example, attach through an amino group of an amino acid of the polypeptide. This polyethylene glycol moiety may be a branched or linear chain polymer.

DESCRIPTION OF EMBODIMENTS

Definitions

The terms used herein have their ordinary meanings, as set forth below, and can be further understood in the context of the specification.

"Monocyte, granulocyte, and dendritic cell colony stimulating factor" (MGD-CSF) is a novel, isolated, secreted molecule having the nucleic acid and amino acid sequences shown as SEQ. ID. NOS.:1, and 7, respectively. Provisional applications 60/590,565 and 60/564,932 referred to MGD-CSF as FPT025. The term "molecules of the invention" is used herein to include any of SEQ ID NOS.:1-13, any of SEQ ID NOS.:1-13 with a secretory leader of any of SEQ. ID NOS.:14-211, and any of the constructs of SEQ. ID NOS.: 212-271.

The terms "nucleic acid molecule," "nucleotide," "polynucleotide," and "nucleic acid" are used interchangeably herein to refer to polymeric forms of nucleotides of any length. They can include both double- and single-stranded sequences and include, but are not limited to, cDNA from viral, prokaryotic, and eukaryotic sources; mRNA; genomic DNA sequences from viral (e.g. DNA viruses and retroviruses) or prokaryotic sources; RNAi; cRNA; antisense molecules; ribozymes; and synthetic DNA sequences. The term also captures sequences that include any of the known base analogs of DNA and RNA.

"Recombinant," as used herein to describe a nucleic acid molecule, means a polynucleotide of genomic, cDNA, viral, semisynthetic, and/or synthetic origin which, by virtue of its origin or manipulation, is not associated with all or a portion of the polynucleotide with which it is associated in nature.

The term "recombinant" as used with respect to a protein or polypeptide, means a polypeptide produced by expression of a recombinant polynucleotide. The term "recombinant" as used with respect to a host cell means a host cell into which a recombinant polynucleotide has been introduced.

A "complementary" nucleotide sequence acid molecule is a one that is comprised of its base pair complements. Deoxyribonucleotides with the base adenine are complementary to those with the base thymidine, and deoxyribonucleotides with the base thymidine are complementary to those with the base adenine. Deoxyribonucleotides with the base cytosine are complementary to those with the base guanine, and deoxyribonucleotides with the base guanine are complementary to those with the base cytosine. Ribonucleotides with the base adenine are complementary to those with the base uracil, and deoxyribonucleotides with the base uracil are complementary to those with the base adenine. Ribonucleotides with the base cytosine are complementary to those with the base guanine, and deoxyribonucleotides with the base guanine are complementary to those with the base cytosine.

A "promoter," as used herein, is a DNA regulatory region capable of binding RNA polymerase in a mammalian cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence may be a transcription initiation site, as well as protein binding domains (consensus sequences) responsible for the binding of RNA polymerase. Eukaryotic promoters will often, but not always, contain "TATA" boxes and "CAT" boxes. Promoters include those that are naturally contiguous to a nucleic acid molecule and those that are not naturally contiguous to a nucleic acid molecule. Additionally, the term "promoter" includes inducible promoters, conditionally active promoters such as a cre-lox promoter, constitutive promoters, and tissue specific promoters.

"Operably linked" refers to an arrangement of elements wherein the components so described are configured so as to perform their desired function. Thus, a secretory leader sequence operably linked to a polypeptide sequence is capable of effecting the secretion of the polypeptide from the cell.

"Transfected" means possessing introduced DNA or RNA, with or without the use of any accompanying facilitating agents such as lipofectamine. Methods for transfection that are known in the art include calcium phosphate transfection, DEAE dextran transfection, protoplast fusion, electroporation, and lipofection.

"Expression of a nucleic acid molecule" refers to the conversion of the information contained in the nucleic acid molecule into a gene product. The gene product can be the direct transcriptional product of a gene (e.g., mRNA, tRNA, rRNA, antisense RNA, ribozyme, structural RNA, or any other type of RNA) or a peptide or polypeptide produced by translation of an mRNA. Gene products also include RNAs which are modified by processes such as capping, polyadenylation, methylation, and editing; and proteins modified by, for example, methylation, acetylation, phosphorylation, ubiquitination, ADP-ribosylation, myristilation, and glycosylation.

A "vector" is an agent, typically a virus or a plasmid, which can be used to transfer genetic material to a cell or organism.

A "host cell" is an individual cell or a cell culture which can be or has been a recipient of any recombinant vector(s) or isolated polynucleotide(s). Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention may be called a "recombinant host cell."

A "stem cell" is an undifferentiated pluripotent or multipotent cell with the ability to self-renew, to remain undifferentiated, and to become differentiated. Stem cells can divide without limit, at least for the lifetime of the animal in which they naturally reside. Stem cells are not terminally differentiated, meaning they are not at the end of a differentiation pathway. When a stem cell divides, each daughter cell can either remain a stem cell or it can embark on a course that leads to terminal differentiation. A stem cell can be an embryonic stem cell, a juvenile stem cell, or an adult stem cell. A "hematopoeitic stem cell" is involved in the process of hematopoeisis, which is the process of forming mature blood cells from precursor cells.

The terms "polypeptide" and "protein" are used interchangeably to refer to a polymer of amino acid residues, and are not limited to a minimum length. Thus, peptides, oligopeptides, dimers, multimers, and the like, are included within the definition. Both full-length proteins and fragments thereof are encompassed by the definition. The terms also include post-expression modifications of the polypeptide, for example, glycosylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "leader sequence" comprises a sequence of amino acid residues, beginning at amino acid residue 1, which is located at the amino terminus of the polypeptide, and extending to a cleavage site, which, upon proteolytic cleavage, results in formation of a mature protein. Leader sequences are generally hydrophobic and have some positively charged residues. Leader sequences can be natural or synthetic, heterologous, or homologous with the protein to which they are attached. A "secretory leader" is a leader sequence that directs a protein to be secreted from the cell.

A "fusion partner" is a polypeptide fused in-frame at the N-terminus and/or C-terminus of a therapeutic or prophylactic polypeptide, or internally to a therapeutic or prophylactic polypeptide.

The term "receptor" refers to a polypeptide that binds to a specific ligand. The ligand is usually an extracellular molecule which, upon binding to the receptor, usually initiates a cellular response, such as initiation of a signal transduction pathway. A "soluble receptor" is a receptor that lacks a membrane anchor domain, such as a transmembrane domain. A "soluble receptor" may include naturally occurring splice variants of a wild-type transmembrane protein receptor in which the transmembrane domain is spliced out. A "soluble receptor" may include the extracellular domain or any fragment of the extracellular domain of a transmembrane protein receptor. Soluble receptors can modulate a target protein. They can, for example, compete with wild-type receptors for ligand binding and participate in ligand/receptor interactions, thus modulating the activity of or the number of the receptors and/or the cellular activity downstream from the receptors. This modulation may trigger intracellular responses, for example, signal transduction events which activate cells, signal transduction events which inhibit cells, or events that modulate cellular growth, proliferation, differentiation, and/ or death, or induce the production of other factors that, in turn, mediate such activities.

An "isolated," "purified," "substantially isolated," or "substantially pure" molecule (such as a polypeptide or polynucleotide) is one that has been manipulated to exist in a higher concentration than in nature. For example, a subject antibody is isolated, purified, substantially isolated, or substantially purified when at least 10%, or 20%, or 40%, or 50%, or 70%, or 90% of non-subject-antibody materials with which it is associated in nature have been removed. As used herein, an "isolated," "purified," "substantially isolated," or "substantially purified" molecule includes recombinant molecules.

A "biologically active" entity, or an entity having "biological activity," is one having structural, regulatory, or biochemical functions of a naturally occurring molecule or any function related to or associated with a metabolic or physiological process. Biologically active polynucleotide fragments are those exhibiting activity similar, but not necessarily identical, to an activity of a polynucleotide of the present invention. The biological activity can include an improved desired activity, or a decreased undesirable activity. For example, an entity demonstrates biological activity when it participates in a molecular interaction with another molecule, such as hybridization, when it has therapeutic value in alleviating a disease condition, when it has prophylactic value in inducing an immune response, when it has diagnostic and/or prognostic value in determining the presence of a molecule, such as a biologically active fragment of a polynucleotide that can, for example, be detected as unique for the polynucleotide molecule, or that can be used as a primer in a polymerase chain reaction. A biologically active polypeptide or fragment thereof includes one that can participate in a biological reaction, including, but not limited to, one that can serve as an epitope or immunogen to stimulate an immune response, such as production of antibodies; or that can participate in modulating the immune response.

The terms "antibody" and "immunoglobulin" are used interchangeably to refer to a protein, for example, one generated by the immune system, synthetically, or recombinantly, that is capable of recognizing and binding to a specific antigen. Antibodies are commonly known in the art. Antibodies may recognize polypeptide or polynucleotide antigens. The term includes active fragments, including for example, an antigen binding fragment of an immunoglobulin, a variable and/or constant region of a heavy chain, a variable and/or constant region of a light chain, a complementarity determining region (cdr), and a framework region. The terms include polyclonal and monoclonal antibody preparations, as well as preparations including hybrid antibodies, altered antibodies, chimeric antibodies, hybrid antibody molecules, F(ab)$_2$ and F(ab) fragments; Fv molecules (for example, noncovalent heterodimers), dimeric and trimeric antibody fragment constructs; minibodies, humanized antibody molecules, and any functional fragments obtained from such molecules, wherein such fragments retain specific binding.

A "vaccine" is a preparation that produces or artificially increases immunity to a particular disease. It may, for example, be comprised of killed microorganisms, living attenuated organisms, or living virulent organisms that is administered to produce or artificially increase immunity to a particular disease. It includes a preparation containing weakened or dead microbes of the kind that cause a particular disease, administered to stimulate the immune system to produce antibodies against that disease. The term includes nucleic acid and polypeptide vaccines.

The term "binds specifically," in the context of antibody binding, refers to high avidity and/or high affinity binding of an antibody to a specific epitope. Hence, an antibody that binds specifically to one epitope (a "first epitope") and not to another (a "second epitope") is a "specific antibody." An antibody specific to a first epitope may cross react with and bind to a second epitope if the two epitopes share homology or other similarity. The term "binds specifically," in the context of a polynucleotide, refers to hybridization under stringent conditions. Conditions that increase stringency of both DNA/DNA and DNA/RNA hybridization reactions are widely known and published in the art (*Curr. Prot. Molec. Biol.*, John Wiley & Sons (2001)).

The terms "subject," "individual," "host," and "patient" are used interchangeably herein to refer to a living animal, including a human and a non-human animal. The subject may, for example, be an organism possessing immune cells capable of responding to antigenic stimulation, and stimulatory and inhibitory signal transduction through cell surface receptor binding. The subject may be a mammal, such as a human or non-human mammal, for example, dogs, cats, pigs, cows, sheep, goats, horses, rats, and mice. The term "subject" does not preclude individuals that are entirely normal with respect to a disease, or normal in all respects.

A "patient sample" is any biological specimen derived from a patient. The term includes, but is not limited to, biological fluids such as blood, serum, plasma, urine, cerebrospinal fluid, tears, saliva, lymph, dialysis fluid, lavage fluid, semen, and other liquid samples, as well as cell and tissues of biological origin. The term also includes cells or cells derived therefrom and the progeny thereof, including cells in culture, cell supernatants, and cell lysates. It further includes organ or tissue culture-derived fluids, tissue biopsy samples, tumor biopsy samples, stool samples, and fluids extracted from physiological tissues, as well as cells dissociated from solid tissues, tissue sections, and cell lysates. This definition encompasses samples that have been manipulated in any way after their procurement, such as by treatment with reagents, solubilization, or enrichment for certain components, such as polynucleotides or polypeptides. Also included in the term are derivatives and fractions of patient samples. A patient sample may be used in a diagnostic, prognostic, or other monitoring assay.

A "disease" is a pathological condition, for example, one that can be identified by symptoms or other identifying factors as diverging from a healthy or a normal state. The term "disease" includes disorders, syndromes, conditions, and injuries. Diseases include, but are not limited to, proliferative, inflammatory, immune, metabolic, infectious, and ischemic diseases.

The term "modulate" refers to the production, either directly or indirectly, of an increase or a decrease, a stimulation, inhibition, interference, or blockage in a measured activity when compared to a suitable control. A "modulator" of a polypeptide or polynucleotide or an "agent" are terms used interchangeably herein to refer to a substance that affects, for example, increases, decreases, stimulates, inhibits, interferes with, or blocks a measured activity of the polypeptide or polynucleotide, when compared to a suitable control.

"Preventing," as used herein, includes providing prophylaxis with respect to the occurrence or recurrence of a disease in a subject that may be predisposed to the disease but has not yet been diagnosed with the disease. Treatment and prophylaxis can be administered to an organism, including a human, or to a cell in vivo, in vitro, or ex vivo, and the cell subsequently administered the subject.

"Treatment," as used herein, covers any administration or application of remedies for disease in a mammal, including a human, and includes inhibiting the disease. It includes arresting disease development and relieving the disease, such as by causing regression or restoring or repairing a lost, missing, or defective function, or stimulating an inefficient process.

A "carrier" refers to a solid, semisolid or liquid filler, diluent, encapsulating material, formulation auxiliary, or excipient of any conventional type. A "pharmaceutically acceptable carrier" refers to a non-toxic "carrier." A pharmaceutically acceptable carrier is non-toxic to recipients at the dosages and concentrations employed and is compatible with other ingredients of the formulation. Pharmaceutically acceptable carriers can be, for example, vehicles, adjuvants, or diluents.

MGD-CSF and Related Nucleic Acids and Polypeptides

The invention provides a novel isolated secreted molecule, identified herein as "monocyte, granulocyte, and dendritic cell colony stimulating factor" (MGD-CSF). The invention provides methods of using MGD-CSF, as well as related factors, which include variants and mutants of MGD-CSF. MGD-CSF is related to NP_689669, Molecular Genomics Clone MGC34647, and Incyte SEQ. ID. NOS.:232, 255 and 257 (WO 2002/048337), as further described below.

MGD-CSF is 241 amino acids in length and comprises a signal peptide or secretory leader sequence. MGD-CSF is a subclone derived from the mother clone CLN00506579, in clone family CLN00212388. MGD-CSF belongs to Five Prime's cluster 190647. This cluster of secreted proteins includes all expressed sequences representing a single gene. Its status as a secreted molecule is confirmed by its Treevote of 0.92. The Treevote is the result of an algorithm constructed on the basis of a number of physical and chemical attributes that predicts whether a predicted amino acid sequence is secreted; a Treevote greater than 0.50 is indicative of a secreted molecule.

As shown in FIG. 1, MGD-CSF is related to a hypothetical protein predicted to be encoded by the mRNA sequence of NP_689669, as designated by the National Center for Biotechnology Information (NCBI) (Strausberg et al., *Proc. Natl. Acad. Sci.* 99:16,899 (2002)). This hypothetical human protein is predicted to comprise 242 amino acids. The coding sequence for NP 689669 has been described by the National Institutes of Health's Mammalian Gene Collection (MGC) as MCG34647. The nucleic acid sequences of MGC34647 correspond to SEQ ID. NOS.:49 and 103, respectively, as designated in WO 2002/048337, wherein SEQ. ID. NO.:49 was described as secreted protein of unknown function, encoded by SEQ. ID. NO.:103. The functions of MGC34647 and NP 689669 were heretofore undisclosed. MGD-CSF is a novel splice variant of MGC34647. The junction between exon 3 and exon 4 is differentially spliced such that amino acid L80 is followed by R81.

Gene MGC34647 is predicted to encode a protein with an open reading frame of 242 amino acids, with a nucleic acid coding sequence 729 nucleotides in length. The proprotein is predicted to weigh 27,479 daltons and have an isoelectric point of 7.72. Following cleavage of a signal peptide, which comprises amino acids 1-20, the mature protein is predicted to weigh 25,229 daltons and have an isoelectric point of 6.74. This mature protein is predicted to be 222 amino acids long, encoded by a nucleic acid molecule of 669 nucleotides.

MGC34647 has six exons. It maps to the genome on chromosome 16q22.1 from the start position of 70456649 to the stop position of 70470765.

MGC34647 expression has been observed in spleen, parotid gland, joint meniscus, bile duct, seminal vesicle, medulla oblongata, pituitary gland, salivary gland, and the Sequence Listing, as further described below. Based on these localizations, MGC34647 is predicted to have several specific therapeutic uses. It may be the target of an antagonistic antibody for autoimmune diseases, for example, multiple sclerosis, rheumatoid arthritis, and systemic lupus erythematosus (SLE). It may, for example, be used as a protein therapeutic agonist for hematopoietic cell regeneration during chemotherapy and bone marrow transplant, as an antagonistic protein therapeutic to enhance cell-mediated immunity for treating infectious diseases, or as a protein therapeutic antagonist for cytoprotection.

Nucleic Acids

The present invention provides nucleic acid molecules comprising a polynucleotide sequence corresponding to the novel MGD-CSF sequences as set forth in the Tables and Sequence Listing, for example, SEQ. ID. NOS.:1, 2, 3, and 5. The invention provides uses for these nucleic acid molecules, and for related nucleic acid molecules, such as those shown in SEQ. ID. NOS.:4 and 13. These uses are described herein.

The invention provides a DNA molecule that contains a promoter of a liver-expressed gene operably linked to a gene encoding MGD-CSF or NP_688669, and that can be expressed in vivo to produce a protein that is functionally active. DNA molecules as described have a variety of uses, for example as tools in basic research to study the in vivo function of an artificially introduced MGD-CSF or NP_688669, the interaction of more than one artificially introduced MGD-CSF or NP_688669, the in vivo dynamics of artificially introduced MGD-CSF or NP_688669 fusion proteins, or to identify the in vivo targets of an artificially introduced MGD-CSF or NP_688669 protein, and as therapeutic treatments, as further described below.

Non-limiting embodiments of nucleic acid molecules include genes or gene fragments, exons, introns, mRNA, tRNA, rRNA, siRNA, ribozymes, antisense cDNA, recombinant polynucleotides, branched polynucleotides, plasmids, vectors, isolated DNA of any sequence, isolated RNA of any sequence, nucleic acid probes, and primers. Nucleic acid molecules include splice variants of an mRNA. Nucleic acids can be naturally occurring, for example DNA or RNA, or can be synthetic analogs, as known in the art. Such analogs demonstrate stability under assay conditions, thus they are suitable as probes. A nucleic acid molecule can also comprise modified nucleic acid molecules, such as methylated nucleic acid molecules and nucleic acid molecule analogs. Analogs of purines and pyrimidines are known in the art.

Nucleic acids of the invention are useful as hybridization probes for differential identification of the tissue(s) or cell type(s) present in a biological sample. Fragments of the full length MGD-CSF variant may be used as hybridization probes for cDNA libraries to isolate the full length gene and to isolate other genes which have a high sequence similarity or a similar biological activity. Probes of this type can have at least 30 bases and may comprise, for example, 50 or more bases. The probe may also be used in a screening procedure to identify a cDNA clone corresponding to a full length transcript and a genomic clone or clones that contain complete MGD-CSF genes, including regulatory and promoter regions, exons, and introns. An example of such a screen would include isolating the coding regions of MGD-CSF genes by using a known nucleic acid sequence to synthesize an oligonucleotide probe. Labeled oligonucleotides having a sequence complementary to a gene of the present invention can be used to screen a human cDNA, a genomic DNA, or a mRNA library to identify complementary library components.

The present invention further relates to polynucleotides which hybridize to the hereinabove-described sequences if there is at least 91%, at least 92%, or at least 95% identity between the sequences. The present invention relates to polynucleotides which hybridize under stringent conditions to the hereinabove-described polynucleotides. Stringent conditions generally include condition under which hybridization will occur only if there is at least 95%, or at least 97% identity between the sequences. For example, overnight incubation at 42° C. in a solution containing 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C., constitute stringent conditions.

The polynucleotides which hybridize to the polynucleotides shown in the Tables and Sequence Listing can encode polypeptides which retain substantially the same biological function or activity as the mature polypeptide. Alternatively, a polynucleotide may have at least 20 bases, at least 30 bases, or at least 50 bases which hybridize to a polynucleotide of the present invention and which has an identity thereto, and which may or may not retain the same biological function or activity as the mature polypeptide. Thus, the present invention is directed to polynucleotides having at least a 70% identity, at least an 80% identity, at least a 90% identity, or at least a 95% identity to a polynucleotide which encodes the polypeptides set forth in the Sequence Listing, as well as fragments thereof, which fragments have at least 30 bases or at least 50 bases, and to polypeptides encoded by such polynucleotides.

Using the information provided herein, such as the nucleotide sequences set forth in the Tables and Sequence Listing, nucleic acid molecules of the present invention encoding a MGD-CSF polypeptide may be obtained using standard cloning and screening procedures, such as those for cloning cDNAs using mRNA as starting material.

Variant and Mutant Polynucleotides

The present invention further relates to variants of the nucleic acid molecules of the present invention, which encode portions, analogs, or derivatives of the MGD-CSF molecules. Variants may occur naturally, such as a natural allelic variant, such as one of several alternate forms of a gene occupying a given locus on a chromosome of an organism, as described in, for example, *Genes II*, Lewin, B., ed., John Wiley & Sons, New York (1985). Non-naturally occurring variants may be produced using mutagenesis techniques known in the art.

Such variants include those produced by nucleotide substitutions, deletions, or additions. The substitutions, deletions, or additions may involve one or more nucleotides. The variants may be altered in coding regions, non-coding regions, or both. Alterations in the coding regions may produce conservative or non-conservative amino acid substitutions, deletions or additions. These may take the form of silent substitutions, additions, or deletions which do not alter the properties or activities of the described MGD-CSF proteins, or portions thereof.

In an embodiment, the invention provides nucleic acid molecules encoding mature proteins, including those with cleaved signal peptide or leader sequences, for example, as shown in the Sequence Listing. Other embodiments include an isolated nucleic acid molecule comprising a polynucleotide having a nucleotide sequence at least 70% identical, at least 80% identical, at least 90% identical, or at least 95% identical to a polynucleotide from the Sequence Listing, a polypeptide encoded by a polynucleotide shown in the Sequence Listing, a polypeptide shown in the Sequence Listing, or a biologically active fragment of any of these.

A polynucleotide having a nucleotide sequence at least, for example, 95% identical to a reference nucleotide sequence encoding a MGD-CSF polypeptide is one in which the nucleotide sequence is identical to the reference sequence except that it may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 70%, 80%, 90%, or 95% identical to, for instance, the nucleotide sequences set forth in the Sequence Listing can be determined conventionally using known computer programs such as the Bestfit program (Wisconsin Sequence Analysis Package, Version 8 for Unix, Genetics Computer Group, Madison, Wis.). Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 70%, 80%, 90%, or 95% identical to the nucleic acid sequences set forth in the Sequence Listing irrespective of whether they encode a polypeptide having MGD-CSF activity. Even where a particular nucleic acid molecule does not encode a polypeptide having MGD-CSF activity, one of skill in the art would know how to use the nucleic acid molecule, for instance, as a hybridization probe or a polymerase chain reaction (PCR) primer. Uses of the nucleic acid molecules of the present invention that do not encode a polypeptide having MGD-CSF activity include, inter alia, isolating the MGD-CSF gene or allelic variants thereof in a cDNA library; and in situ hybridization (for example, fluorescent in situ hybridization (FISH)) to metaphase chromosomal spreads to provide the precise chromosomal location of the MGD-CSF genes, as described in Verna et al., *Human Chromosomes: A Manual of Basic Techniques*, Pergamon Press, New York (1988); and Northern blot analysis for detecting MGD-CSF mRNA expression in specific tissues.

The present application is also directed to nucleic acid molecules having sequences at least 70%, 80%, 90%, or 95% identical to a nucleic acid sequence of the Sequence Listing which, encode a polypeptide having MGD-CSF polypeptide activity, that is, a polypeptide exhibiting activity either identical to or similar, to an activity of the MGD-CSF polypeptides of the invention, as measured in a particular biological assay. For example, the MGD-CSF polypeptides of the present invention may stimulate immune cell proliferation, inhibit tumor growth, and/or kill tumor cells.

Due to the degeneracy of the genetic code, one of ordinary skill in the art will immediately recognize that a large number of the nucleic acid molecules having a sequence at least 70%, 80%, 90%, or 95% identical to the nucleic acid sequence of the nucleic acid sequences set forth in the Sequence Listing will encode a polypeptide having MGD-CSF polypeptide activity. In fact, since multiple degenerate variants of these nucleotide sequences encode the same polypeptide, this will be clear to the skilled artisan even without performing the above described comparison assay. It will be further recognized in the art that a reasonable number of nucleic acid molecules that are not degenerate variants will also encode a polypeptide having MGD-CSF polypeptide activity, the skilled artisan is fully aware of amino acid substitutions that are either less likely or not likely to significantly affect protein function (for example, replacing one aliphatic amino acid with a second aliphatic amino acid), as further described below.

Vectors and Host Cells

The present invention also relates to vectors which include the isolated nucleic acid molecules of the present invention, host cells which are genetically engineered with the recombinant vectors, and the production of MGD-CSF polypeptides or fragments thereof by recombinant techniques. It provides recombinant vectors that contain, for example, nucleic acid constructs that encode secretory leader sequences (see, for example, the Sequence Listing; the secretory leader may be a collagen secretory leader), and a selected heterologous polypeptide of interest, and host cells that are genetically engineered with the recombinant vectors. The vector may be, for example, a phage, plasmid, or viral vector. Retroviral vectors may be replication competent or replication defective. In the latter case, viral propagation generally will occur only in complementing host cells. Vectors of the invention may contain Kozak sequences (Lodish et al., *Molecular Cell Biology*, 4$^{th}$ ed., 1999). Vectors of the invention may also contain the ATG start codon of the sequence of interest.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert can be operatively linked to an appropriate promoter, such as the phage lambda PL promoter; the *E. coli* lac, trp, phoA, and tac promoters; the SV40 early and late promoters; and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs can include a translation initiating codon at the beginning and a termination codon (UAA, UGA, or UAG) appropriately positioned at the end of the polypeptide to be translated.

The invention provides the expression of genes of interest in animals, including humans, under the control of a promoter that functions, inter alfa, in the liver. The hydrodynamics-based procedure of tail vein injection (Zhang et al., *Hum. Gene Ther.* 10:1735 (1999)) has been demonstrated to transfect cells with a gene of interest. The invention also provides for the manipulation of the level of gene expression by controlling the amount and frequency of intravascular DNA administration. The invention further provides promoters that function to express genes in the liver.

One large family of proteins expressed in the liver is the cytochrome P450 protein family. These proteins are a group of heme-thiolate monooxygenases that perform a variety of oxidation reactions, often as part of the body's mechanism to dispose of harmful substances by making them more water-soluble. Much of the body's total mass of cytochrome P450 proteins is found in the liver, specifically, in the microsomes of hepatocytes. There are over a thousand different cytochrome P450 proteins. However, only 49 genes and 15 pseudogenes have been sequenced in humans. In humans, cytochrome P450 3A4 has been identified as the most important cytochrome P450 protein in oxidative metabolism. It is the most prevalent cytochrome P450 protein in the body, and is an inducible protein.

Operably linking the promoter sequence of genes expressed in the liver, for example the promoter sequence of any of the cytochrome P450 proteins to a gene of interest can lead to expression of that gene in the liver and any other site where the promoter is active. The invention encompasses promoters that function to express genes, including, but not limited to, cytochrome P450 gene, such as cytochrome P450 3A4; c-jun; jun-b; c-fos; c-myc; serum amyloid A; apolipoprotein B editing catalytic subunit; liver regeneration factors; such as LRF-1 signal transducers, and activators of transcription such as STAT-3; serum alkaline phosphatase (SAP); insulin-like growth factor-binding proteins such as IGFBP-1; cyclin D1; active protein-1; CCAAT enhancer core binding protein; beta ornithine decarbonylase; phosphatase of regenerating liver-1; early growth response gene-1; hepatocyte growth factors; hemopexin; insulin-like growth factors (IGF) such as IGF2; hepatocyte nuclear family 1; hepatocyte nuclear family 4; hepatocyte Arg-Ser-rich domain-containing proteins; glucose 6-phosphatase; and acute phase proteins, such as serum amyloid A and serum amyloid P (SAA/SAP).

As shown in Table 7 and Example 9, operably linking the promoter sequence of cytochrome P450 3A4 to MGD-CSF and injecting resulting the construct into the tail vein of a mouse induces in the expression of MGD-CSF and a concomitant increase in monocyte production by the mouse. Thus, the invention provides therapeutic molecules of the invention, delivered in vivo. This method can be used to deliver naked DNA, in the presence or absence of a pharmaceutically acceptable carrier, or vector DNA with a sequence of interest. Methods of evaluating the function of the molecules of the invention delivered in vivo are known in the art, and some are described herein.

As indicated, the expression vectors may include at least one selectable marker. Such markers include dihydrofolate reductase, G418 or neomycin resistance for eukaryotic cell culture and tetracycline, kanamycin, or ampicillin resistance genes for culturing in *E. coli* and other bacteria. Representative examples of appropriate hosts include, but are not limited to, bacterial cells, such as *E. coli, Streptomyces*, and *Salmonella typhimurium* cells; fungal cells, such as yeast cells; insect cells such as *Drosophila* S2 and *Spodoptera* Sf9 cells; animal cells such as CHO, COS, 293 and Bowes melanoma cells; and plant cells. Appropriate culture mediums and conditions for the above-described host cells are known in the art.

The selectable markers are genes that confer a phenotype on a cell expressing the marker, so that the cell can be identified under appropriate conditions. Generally, a selectable marker allows the selection of transformed cells based on their ability to thrive in the presence or absence of a chemical or other agent that inhibits an essential cell function. Suitable markers, therefore, include genes coding for proteins which confer drug resistance or sensitivity thereto, impart color to, or change the antigenic characteristics of those cells transfected with a molecule encoding the selectable marker, when the cells are grown in an appropriate selective medium. For example, selectable markers include cytotoxic markers and drug resistance markers, whereby cells are selected by their ability to grow on media containing one or more of the cytotoxins or drugs; auxotrophic markers by which cells are selected for their ability to grow on defined media with or without particular nutrients or supplements, such as thymidine and hypoxanthine; metabolic markers for which cells are selected, for example, their ability to grow on defined media containing the appropriate sugar as the sole carbon source, and markers which confer the ability of cells to form colored colonies on chromogenic substrates or cause cells to fluoresce.

Among vectors suitable for use in bacteria include pQE70, pQE60, and pQE-9, available from Qiagen, Mississauga, Ontario, Canada; pBS vectors, Phagescript vectors, Bluescript vectors, pNH8A, pNH6a, pNH18A, pNH46A, available from Stratagene (La Jolla, Calif.); and ptrc99a, pKK223-3, pKK233-3, pDR540, pRIT5 available from Pharmacia (Peapack, N.J.). Among suitable eukaryotic vectors are pWLNEO, pSV2CAT, pOG44, pXT1, and pSG available from Stratagene; and pSVK3, pBPV, pMSG and pSVL, available from Pharmacia. Other suitable vectors will be apparent to the skilled artisan.

Figure 2:
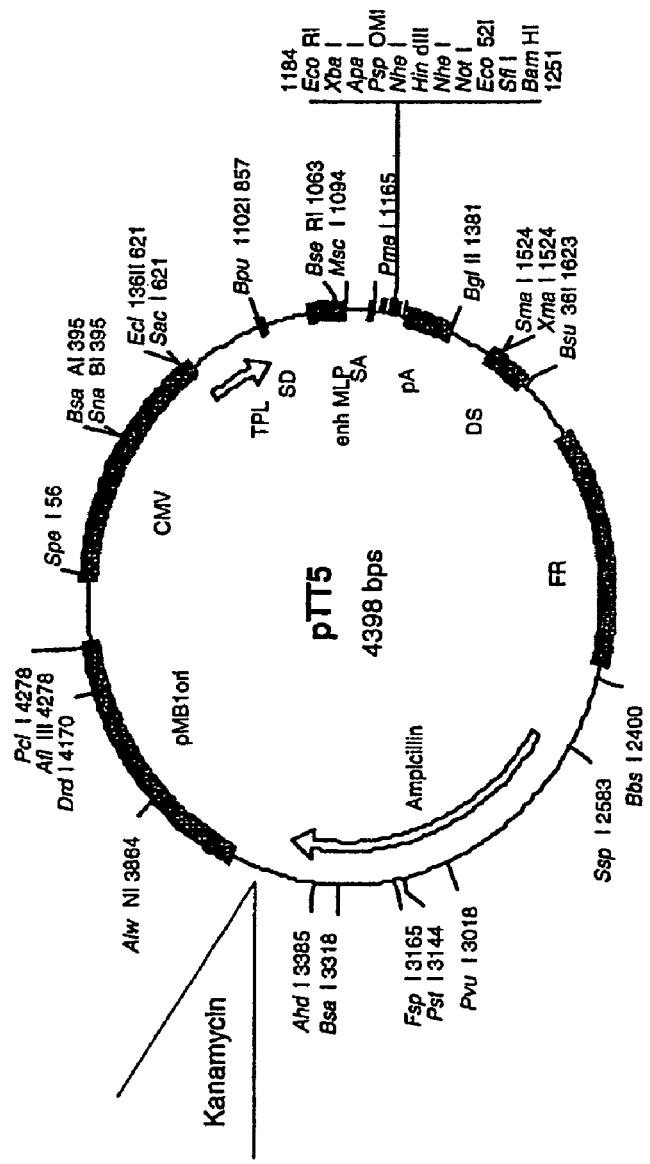
FIG. 2 shows a diagram of the pTT5 backbone vector used to generate pTT5-Gateway, which was used to transiently transfect mammalian cells, as further described in Example 2.
Figure 3:
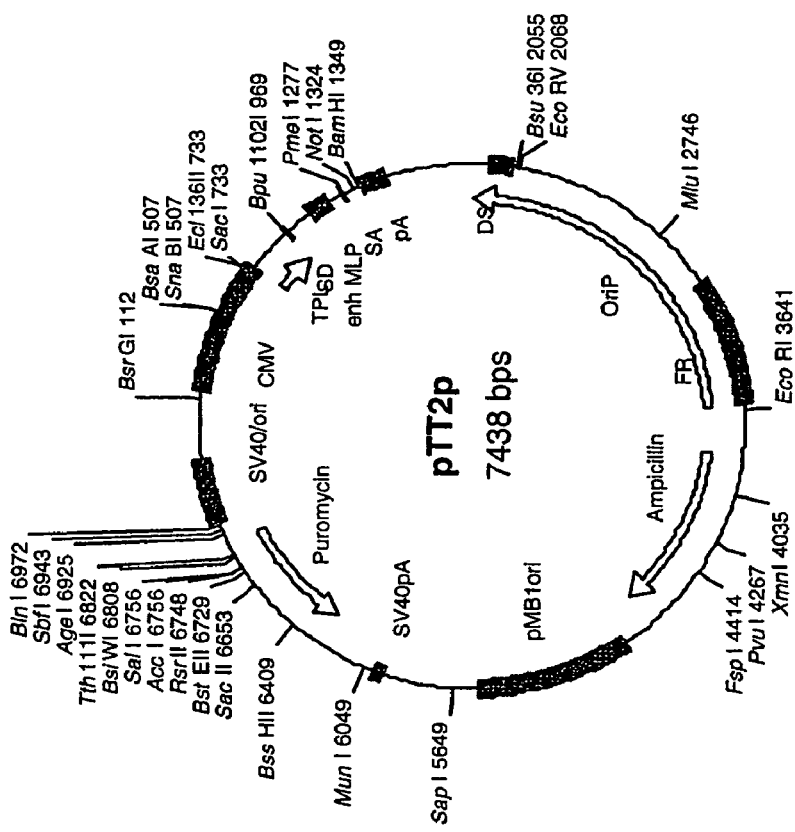
FIG. 3 shows a diagram of the pTT2 backbone vector used to stably transfect mammalian cells, as further described in Example 2.

Other suitable vectors include those employing a pTT vector backbone (FIG. 2, FIG. 3, and Durocher et al. *Nucl. Acids Res.* 30 (2002)). Briefly, the pTT vector backbone may be prepared by obtaining pIRESpuro/EGFP (pEGFP) and pSEAP basic vector(s), for example from Clontech (Palo Alto, Calif.), and pcDNA3.1, pcDNA3.1/Myc-(His)$_6$ (6×His tag disclosed as SEQ ID NO.:277) and pCEP4 vectors can be obtained from, for example, Invitrogen. As used herein, the pTT5 backbone vector can generate pTT5-Gateway and be used to transiently express proteins in mammalian cells. The pTT5 vector can be derivatized to pTT5-A, pTT5-B, pTT5-D, pTT5-E, p'175-H, and pTT5-I, for example. As used herein, the pTT2 vector can generate constructs for stable expression in mammalian cell lines.

The expression vector pTT5 allows for extrachromosomal replication of the cDNA driven by a cytomegalovirus (CMV) promoter. The plasmid vector pcDNA-pDEST40 is a Gateway-adapted vector which can utilize a CMV promoter for high-level expression. SuperGlo GFP variant (sgGFP) can be obtained from Q-Biogene (Carlsbad, Calif.). Preparing a pCEP5 vector can be accomplished by removing the CMV promoter and polyadenylation signal of pCEP4 by sequential digestion and self-ligation using SalI and XbaI enzymes resulting in plasmid pCEP4Δ. A GblII fragment from pAd-CMV5 (Massie et al., J. Virol., 72: 2289-2296 (1998)), encoding the CMV5-poly(A) expression cassette ligated in BglII-linearized pCEP4Δ, resulting in pCEP5 vector.

The pTT vector can be prepared by deleting the hygromycin (BsmI and SalI excision followed by fill-in and ligation) and EBNA1 (ClaI and NsiI excision followed by fill-in and ligation) expression cassettes. The ColEI origin (FspI-SalI fragment, including the 3' end of β-lactamase ORF) can be replaced with a FspI-SalI fragment from pcDNA3.1 containing the pMB1 origin (and the same 3' end of β-lactamase ORF). A Myc-(His)$_6$ (6×His tag disclosed as SEQ ID NO.: 277) C-terminal fusion tag can be added to SEAP (HindIII-HpaI fragment from pSEAP-basic) following in-frame ligation in pcDNA3.1/Myc-His digested with HindIII and EcoRV. Plasmids can subsequently be amplified in *E. coli* (DH5a) grown in LB medium and purified using MAXI prep columns (Qiagen, Mississauga, Ontario, Canada). To quantify, plasmids can be subsequently diluted in 50 mM Tris-HCl pH 7.4 and absorbencies can be measured at 260 nm and 280 nm. Plasmid preparations with $A_{260}/A_{280}$ ratios between about 1.75 and about 2.00 are suitable.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Sambrook, J., et al. (2001) *Molecular Cloning, A Laboratory Manual.* 3$^{rd}$ ed. Cold Spring Harbor Laboratory Press.

The polypeptides may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide.

Polypeptides

The invention further provides isolated MGD-CSF polypeptides containing the amino acid sequences encoded by the nucleotide sequences set forth in the Tables and Sequence Listing for example, SEQ. ID. NOS.:7, 8, 9, and 11, which correspond to the full-length polypeptide, exon 4, the mature polypeptide, and the fragment TRLRAQ (SEQ ID NO.:11) (present at the junction between exon 3 and exon 4 of MGD-CSF), respectively. The invention provides novel uses for these novel polypeptides and for related polypeptides, such as those shown in SEQ. ID. NOS.:10 and 12.

The invention provides secreted proteins, which are capable of being directed to the ER, secretory vesicles, or the extracellular space as a result of a secretory leader, signal peptide, or leader sequence, as well as proteins released into the extracellular space without necessarily containing a signal sequence. If a secreted protein is released into the extracellular space, it may undergo extracellular processing to a mature polypeptide. Release into the extracellular space can occur by many mechanisms, including exocytosis and proteolytic cleavage.

Figure 8A:
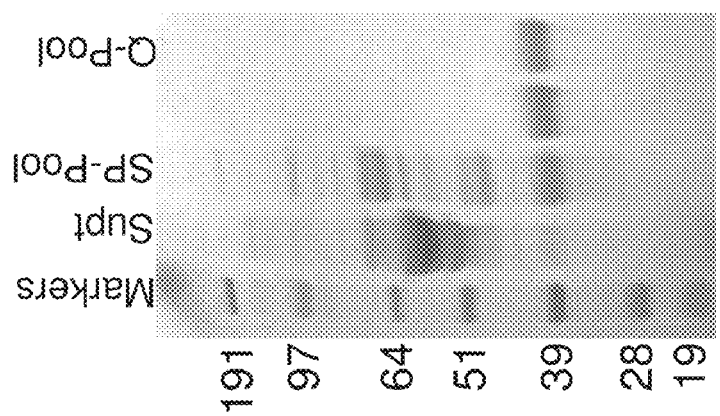
FIG. 8A shows the isolation of MGD-CSF from 293-T cells, as further described in Example 7. Cell culture supernatant (Supt) was fractionated on an SP-Sepharose® FF column (SP-Pool), a Heparin Sepharose® HP column (Hep-Pool), and a Q-Sepharose® column (Q-Pool). MGD-CSF is glycosylated and has an apparent molecular weight of 39 kDa by SDS-polyacrylamide gel electrophoresis. Molecular weight markers are shown in the left lane.

As shown in FIG. 8A, the MGD-CSF polypeptides can be recovered and isolated from recombinant cell cultures by well-known methods. Such methods include ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. High performance liquid chromatography (HPLC) can be employed for purification. Polypeptides of the present invention include products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

Typically, a heterologous polypeptide, whether modified or unmodified, may be expressed as described above, or as a fusion protein, and may include not only secretion signals, but also a secretory leader sequence. A secretory leader sequence of the invention directs certain proteins to the endoplasmic reticulum (ER). The ER separates the membrane-bound proteins from other proteins. Once localized to the ER, proteins can be further directed to the Golgi apparatus for distribution to vesicles, including secretory vesicles; the plasma membrane; lysosomes; and other organelles.

Proteins targeted to the ER by a secretory leader sequence can be released into the extracellular space as a secreted protein. For example, vesicles containing secreted proteins can fuse with the cell membrane and release their contents into the extracellular space via exocytosis. Exocytosis can occur constitutively or upon receipt of a triggering signal. In the latter case, the proteins may be stored in secretory vesicles (or secretory granules) until exocytosis is triggered. Similarly, proteins residing on the cell membrane can also be secreted into the extracellular space by proteolytic cleavage of a linker holding the protein to the membrane.

Additionally, peptide moieties and/or purification tags may be added to the polypeptide to facilitate purification. Such regions may be removed prior to final preparation of the polypeptide. The addition of peptide moieties to polypeptides to engender secretion or excretion, to improve stability, and to facilitate purification, among other reasons, are familiar and routine techniques in the art. Suitable purification tags include, for example, V5, HISX6 (SEQ ID NO.:277), HISX8 (SEQ ID NO.:278), avidin, and biotin.

The invention provides a fusion protein comprising a heterologous region from an immunoglobulin that is useful to stabilize and purify proteins. The addition of peptide moieties to polypeptides to engender secretion or excretion, to improve stability and to facilitate purification, among others, are familiar and routine techniques in the art. For example, EP 0 464 533 (Canadian counterpart 2045869) discloses fusion proteins containing various portions of constant region of immunoglobulin molecules together with another human protein or part thereof. In many cases, the Fc part of a fusion protein is advantageous for use in therapy and diagnosis and thus results, for example, in improved pharmacokinetic properties (EP 0 232 262). On the other hand, for some uses it would be desirable to be able to delete the Fc part after the fusion protein has been expressed, detected, and purified in the advantageous manner described. This is the case when the Fc portion proves to be a hindrance to use in therapy and/or diagnosis, for example, when the fusion protein is to be used as an antigen for immunizations. In drug discovery, for example, human proteins, such as hIL-5, have been fused with Fc portions for the purpose of high-throughput screening assays to identify antagonists of hIL-5. See, Bennett et al., *J. Molec. Recog.*, 8:52-58 (1995) and Johanson et al, *J. Biol. Chem.*, 270:9459-9471 (1995).

The polypeptides of the present invention can be provided in an isolated form, and can be substantially purified, as described above. A recombinantly produced version of the herein described MGD-CSF polypeptides can also be substantially isolated, for example, according to the one-step method described in Smith and Johnson, *Gene*, 67:31-40 (1988). Polypeptides of the invention can further be isolated from natural or recombinant sources using anti-MGD-CSF antibodies of the invention produced using methods well known in the art.

The polypeptides herein may be purified or isolated in the presence of ions or agents that aid in the refolding of the molecules or aid in dimerizing or trimerizing the molecules as conventional in the art. For example, cofactors may be added to promote physiologic folding or multimerization.

Further polypeptides of the present invention include polypeptides which have at least 70%, 80%, 90%, or 95% identity to those described above. The polypeptides of the invention also contain those which are at least 70%, 80%, 90%, or 95% identical to a polypeptide encoded by a nucleic acid sequence of the Sequence Listing.

The % identity of two polypeptides can be measured by a similarity score determined by comparing the amino acid sequences of the two polypeptides using the Bestfit program with the default settings for determining similarity. Bestfit uses the local homology algorithm of Smith and Waterman, *Advances in Applied Mathematics* 2:482-489 (1981) to find the best segment of similarity between two sequences.

A polypeptide having an amino acid sequence at least, for example, 95% identical to a reference amino acid sequence of a MGD-CSF polypeptide is one in which the amino acid sequence of the polypeptide is identical to the reference sequence except that the polypeptide sequence may include up to five amino acid alterations per each 100 amino acids of the reference polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids, up to 5% of the total amino acid residues in the reference sequence, may be inserted into the reference sequence. These alterations of the reference sequence may occur at the amino or carboxy terminal positions of the reference amino acid sequence or anywhere between those terminal positions, interspersed either individually among residues in the reference sequence, or in one or more contiguous groups within the reference sequence.

As a practical matter, whether any particular polypeptide is at least 70%, 80%, 90%, or 95% identical to, for instance, an amino acid sequence or to a polypeptide sequence encoded by a nucleic acid sequence set forth in the Sequence Listing can be determined conventionally using known computer programs, such the Bestfit program. When using Bestfit or other sequence alignment program to determine whether a particular sequence is, for instance, 95% identical to a reference sequence according to the present invention, the parameters are set, of course, that the percentage of identity is calculated over the full length of the reference amino acid sequence and that gaps in homology of up to 5% of the total number of amino acid residues in the reference sequence are allowed.

Variant and Mutant Polypeptides

Protein engineering may be employed to improve or alter the characteristics of MGD-CSF polypeptides of the invention. Recombinant DNA technology known to those skilled in the art can be used to create novel mutant proteins or "muteins" including single or multiple amino acid substitutions, deletions, additions, or fusion proteins. Such modified polypeptides can show desirable properties, such as enhanced activity or increased stability. In addition, they may be purified in higher yields and show better solubility than the corresponding natural polypeptide, at least under certain purification and storage conditions.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., *J. Biol. Chem.*, 268:2984-2988 (1993), reported modified KGF proteins that had heparin binding activity even if 3, 8, or 27 amino-terminal amino acid residues were missing.

However, even if deletion of one or more amino acids from the N-terminus of a protein results in modification or loss of one or more biological functions of the protein, other biological activities may still be retained. Thus, the ability of the shortened protein to induce and/or bind to antibodies which recognize the complete or mature from of the protein generally will be retained when less than the majority of the residues of the complete or mature protein are removed from the N-terminus. Whether a particular polypeptide lacking N-terminal residues of a complete protein retains such immunologic activities can be determined by routine methods described herein and otherwise known in the art. Accordingly, the present invention further provides polypeptides having one or more residues deleted from the amino terminus of the amino acid sequences of the MGD-CSF molecules as shown in the Sequence Listing.

Similarly, many examples of biologically functional C-terminal deletion muteins are known. For instance, interferon gamma increases in activity as much as ten fold when 8-10 amino acid residues are deleted from the carboxy terminus of the protein, see, for example, Dobeli et al., *J. Biotechnology*, 7:199-216 (1988).

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature protein are removed from the C-terminus. Whether a particular polypeptide lacking C-terminal residues of a complete protein retains such immunologic activities can be determined by routine methods described herein and otherwise known in the art.

Cysteine to Serine Muteins

The MGD-CSF sequence includes seven cysteine residues, located at amino acid positions 35, 167, 176, 178, 179, 190, and 198. In an embodiment, the invention provides mutant MGC34647 molecules with serine mutated to cysteine. These mutants are shown in Table 1 and in the Sequence Listing, designated SEQ. ID. NOS.:258-271. The collagen signal peptide described by SEQ. ID. NO.:14 was used to improve the secretion of the expressed polypeptide. As set forth in Table 1 and FIG. 8B and explained in more detail in Example 18, the cysteines at positions 35, 167, 176, 178, 179, 190, and 198 were each substituted for serine. These constructs may be cloned into any suitable vector, as known in the art, for example, the pTT5-G vector.

Analyzing these muteins provides an understanding of the disulfide bond pattern of MGD-CSF and may identify a protein with improved properties, for example, improved expression and secretion from mammalian cells, decreased aggregation of the purified protein, and the potential to produce active recombinant MGD-CSF, when expressed in *E. coli*.

Other Mutants

In addition to terminal deletion forms of the protein discussed above, it also will be recognized by one of ordinary skill in the art that some amino acid sequences of the MGD-CSF polypeptides can be varied without significant effect of the structure or function of the protein. If such differences in sequence are contemplated, it should be remembered that there will be critical areas on the protein which determine activity.

Thus, the invention further includes variations of the MGD-CSF polypeptides which show substantial MGD-CSF polypeptide activity or which include regions of the MGD-CSF proteins such as the protein portions discussed below. Such mutants include deletions, insertions, inversions, repeats, and type substitutions, selected according to general rules known in the art, so as have little effect on activity. For example, guidance concerning how to make phenotypically silent amino acid substitutions is provided in Bowie et al., *Science*, 247:1306-1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections, or screens, to identify sequences that maintain functionality.

These studies report that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, et al., supra, and the references cited therein. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, and replacements between the aromatic residues Phe and Tyr.

Thus, a fragment, derivative, or analog of a polypeptide of the Sequence Listing or polypeptide encoded by a nucleic acid sequence of the Sequence Listing may be (i) one in which one or more of the amino acid residues are substituted with a conserved or non-conserved amino acid residue; such a substituted amino acid residue may or may not be one encoded by the genetic code; (ii) one in which one or more of the amino acid residues includes a substituent group; (iii) one in which the mature polypeptide is fused with another compound, such as a compound to increase the half-life of the polypeptide (for example, polyethylene glycol); or (iv) one in which the additional amino acids are fused to the above form of the polypeptide, such as an IgG Fc fusion region peptide, a leader or secretory sequence, a sequence employed to purify the above form of the polypeptide, or a proprotein sequence. Such fragments, derivatives, and analogs are deemed to be within the scope of those skilled in the art from the teachings herein.

Thus, the MGD-CSF polypeptides of the present invention may include one or more amino acid substitutions, deletions, or additions, either from natural mutations or human manipulation. As indicated, these changes may be of a minor nature, such as conservative amino acid substitutions, that do not significantly affect the folding or activity of the protein. Conservative amino acid substitutions include the aromatic substitutions Phe, Trp, and Tyr; the hydrophobic substitutions Leu, Iso, and Val; the polar substitutions Glu and Asp; the basic substitutions Arg, Lys, and His; the acidic substitutions Asp and Glu; and the small amino acid substations Ala, Ser, Thr, Met, and Gly.

Amino acids essential for the functions of MGD-CSF polypeptides can be identified by methods known in the art, such as site-directed mutagenesis or alanine-scanning mutagenesis, see, for example, Cunningham and Wells, *Science*, 244:1081-1085 (1989). The latter procedure introduces single alanine mutations. The resulting mutant molecules are then tested for biological activity such as receptor binding, or in vitro or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because, for example, aggregates can be immunogenic, Pinckard et al., *Clin. Exp. Immunol.*, 2:331-340 (1967); Robbins et al., *Diabetes*, 36:838-845 (1987); Cleland et al., *Crit. Rev. Therapeutic Drug Carrier Systems*, 10:307-377 (1993).

Replacing amino acids can also change the selectivity of the binding of a ligand to cell surface receptors. For example, Ostade et al., *Nature*, 361:266-268 (1993) describes mutations resulting in selective binding of TNF-α to only one of the two known types of TNF receptors. Sites that are critical for ligand-receptor binding can also be determined by structural analysis such as crystallization, nuclear magnetic resonance, or photoaffinity labeling, for example, Smith et al., *J. Mol. Biol.*, 224:899-904 (1992) and de Vos et al., *Science*, 255:306-312 (1992).

Epitope-Bearing Portions

As described in detail below, the polypeptides of the present invention can be used to raise polyclonal and monoclonal antibodies, which are useful in assays for detecting MGD-CSF protein expression, also as described below, or as agonists and/or antagonists capable of enhancing or inhibiting MGD-CSF protein function. These polypeptides can also be used in a yeast two-hybrid system to capture MGD-CSF protein binding proteins, which are also candidate agonists and antagonists, according to the present invention. The yeast two hybrid system is described in Fields and Song, *Nature*, 340:245-246 (1989).

In another aspect, the invention provides a polypeptide comprising one or more epitope-bearing portion of a polypeptide of the invention. The invention provides polyclonal antibodies specific to MGD-CSF and provides that MGD-CSF has, at minimum, two antigenic epitopes. The epitope of this polypeptide portion is an immunogenic or antigenic epitope of a polypeptide of the invention. Immunogenic epitopes are those parts of a protein that elicit an antibody response when the whole protein is provided as the immunogen. On the other hand, a region of a protein molecule to which an antibody can bind is an antigenic epitope. The number of immunogenic epitopes of a protein generally is less than the number of antigenic epitopes. See, for instance, Geysen et al., *Proc. Natl. Acad. Sci.*, 81:3998-4002 (1983).

As to the selection of polypeptides bearing an antigenic epitope (that is, those which contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe et al., *Science*, 219:660-666 (1983). Peptides capable of eliciting protein-reactive sera are frequently represented in the primary sequence of a protein, can be characterized by a set of simple chemical rules, and are confined neither to immunodominant regions of intact proteins (that is, to immunogenic epitopes) nor to the amino or carboxyl terminals. Antigenic epitope-bearing peptides and polypeptides of the invention are therefore useful for raising antibodies, including monoclonal antibodies, that bind specifically to a polypeptide of the invention. See, for instance, Wilson et al., *Cell*, 37:767-778 (1984). The epitope-bearing peptides and polypeptides of the invention may be produced by any conventional means. See, for example, Houghten, *Proc. Natl. Acad. Sci.* 82:5131-5135 (1985), and U.S. Pat. No. 4,631,211 (1986).

Epitope-bearing peptides and polypeptides of the invention can be used to induce antibodies according to methods well known in the art. See, for instance, Bittle, et al, *J. Gen. Virol.*, 66:2347-2354 (1985). Immunogenic epitope-bearing peptides of the invention, those parts of a protein that elicit an antibody response when the whole protein is the immunogen, are identified according to methods known in the art. See, for instance, U.S. Pat. No. 5,194,392 (1990), which describes a general method of detecting or determining the sequence of monomers (amino acids or other compounds) which is a topological equivalent of the epitope (mimotope) which is complementary to a particular antigen binding site (paratope) of an antibody of interest. More generally, U.S. Pat. No. 4,433,092 (1989) describes a method of detecting or determining a sequence of monomers which is a topographical equivalent of a ligand which is complementary to the ligand binding site of a particular receptor of interest. Similarly, U.S. Pat. No. 5,480,971 (1996) discloses linear C1-C7-alkyl peralkylated oligopeptides, and sets and libraries of such peptides, as well as methods for using such oligopeptide sets and libraries for determining the sequence of a peralkylated oligopeptide that, for example, binds to an acceptor molecule of interest. Thus, non-peptide analogs of the epitope-bearing peptides of the invention also can be made routinely by these methods.

Fusion Molecules

As one of skill in the art will appreciate, MGD-CSF polypeptides of the present invention, and the epitope-bearing fragments thereof described above, can be combined with heterologous polypeptides, resulting in chimeric polypeptides. These fusion proteins facilitate purification and show an increased half-life in vivo. This has been reported, for example, in chimeric proteins consisting of the first two domains of the human CD4-polypeptide and various domains of the constant regions of the heavy or light chains of mammalian immunoglobulins, for example, EP 0 394 827; Traunecker et al., *Nature*, 331:84-86 (1988). Fusion proteins that have a disulfide-linked dimeric structure due to the IgG portion can also be more efficient in binding and neutralizing other molecules than the monomeric MGD-CSF protein or protein fragment alone, for example, as described by Fountoulakis et al., *J. Biochem.*, 270:3958-3964 (1995). Suitable chemical moieties for derivatization of a heterologous polypeptide include, for example, polymers, such as water soluble polymers, the constant domain of immunoglobulins, all or part of human serum albumin; fetuin A; fetuin B; a leucine zipper domain; a tetranectin trimerization domain; mannose binding protein (also known as mannose binding lectin), for example, mannose binding protein 1; and an Fc region, as described herein and further described in U.S. Pat. No. 6,686,179, and U.S. Application Nos. 60/589,788 and 60/654,229. Methods of making fusion proteins are well-known to the skilled artisan.

For example, the short plasma half-life of unmodified interferon alpha makes frequent dosing necessary over an extended period of time, in order to treat viral and proliferative disorders. Interferon alpha fused with HSA has a longer half life and requires less frequent dosing than unmodified interferon alpha; the half-life was 18-fold longer and the clearance rate was approximately 140 times slower (Osborn et al., *J. Pharmacol. Exp. Ther.* 303:540-548, 2002). Interferon beta fused with HSA also has favorable pharmacokinetic properties; its half life was reported to be 36-40 hours, compared to 8 hours for unmodified interferon beta (Sung et al., *J. Interferon Cytokine Res.* 23:25-36, 2003). A HSA-interleukin-2 fusion protein has been reported to have both a longer half-life and favorable biodistribution compared to unmodified interleukin-2. This fusion protein was observed to target tissues where lymphocytes reside to a greater extent than unmodified interleukin 2, suggesting that it exerts greater efficacy (Yao et al., *Cancer Immunol. Immunother.* 53:404-410, 2004).

The Fc receptor of human immunoglobulin G subclass 1 has also been used as a fusion partner for a therapeutic molecule. It has been recombinantly linked to two soluble p75 tumor necrosis factor (TNF) receptor molecules. This fusion protein has been reported to have a longer circulating half-life than monomeric soluble receptors, and to inhibit TNFα-induced proinflammatory activity in the joints of patients with rheumatoid arthritis (Goldenberg, *Clin. Ther.* 21:75-87, 1999). This fusion protein has been used clinically to treat rheumatoid arthritis, juvenile rheumatoid arthritis, psoriatic arthritis, and ankylosing spondylitis (Nanda and Bathon, *Expert Opin. Pharmacother.* 5:1175-1186, 2004).

Polymers, for example, water soluble polymers, are useful in the present invention as the polypeptide to which each polymer is attached will not precipitate in an aqueous environment, such as typically found in a physiological environment. Polymers employed in the invention will be pharmaceutically acceptable for the preparation of a therapeutic product or composition. One skilled in the art will be able to select the desired polymer based on such considerations as whether the polymer/protein conjugate will be used therapeutically and, if so, the desired dosage, circulation time, and resistance to proteolysis.

Suitable, clinically acceptable, water soluble polymers include, but are not limited to, polyethylene glycol (PEG), polyethylene glycol propionaldehyde, copolymers of ethylene glycol/propylene glycol, monomethoxy-polyethylene glycol, carboxymethyl cellulose, dextran, polyvinyl alcohol (PVA), polyvinyl pyrrolidone, poly-1,3-dioxolane, poly-1,3, 6-trioxane, ethylene/maleic anhydride copolymer, poly (β-amino acids) (either homopolymers or random copolymers), poly(n-vinyl pyrrolidone) polyethylene glycol, polypropylene glycol homopolymers (PPG) and other polyakylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll, or dextran and mixtures thereof.

As used herein, polyethylene glycol (PEG) is meant to encompass any of the forms that have been used to derivatize other proteins, such as mono-(C1-C10) alkoxy- or aryloxy-polyethylene glycol. Polyethylene glycol propionaldehyde may have advantages in manufacturing due to its stability in water.

Specifically, a modified heterologous polypeptide of the invention may be prepared by attaching polyaminoacids or branch point amino acids to the polypeptide. For example, the polyaminoacid may be a carrier protein that serves to increase the circulation half life of the polypeptide (in addition to the advantages achieved via a fusion molecule). For the therapeutic purpose of the present invention, such polyaminoacids should ideally be those that have or do not create neutralizing antigenic response, or other adverse responses. Such polyaminoacids may be chosen from serum album (such as human serum albumin), an additional antibody or portion thereof, for example the Fc region, fetuin A, fetuin B, leucine zipper nuclear factor erythroid derivative-2 (NFE2), neuroretinal leucine zipper, tetranectin, or other polyaminoacids, for example, lysines. As described herein, the location of attachment of the polyaminoacid may be at the N-terminus, or C-terminus, or other places in between, and also may be connected by a chemical linker moiety to the selected molecule.

Polymers used herein, for example water soluble polymers, may be of any molecular weight and may be branched or unbranched. The polymers each typically have an average molecular weight of between about 2 kDa to about 100 kDa (the term "about" indicating that in preparations of a polymer, some molecules will weigh more, some less, than the stated molecular weight). The average molecular weight of each polymer may be between about 5 kDa and about 50 kDa, or between about 12 kDa and about 25 kDa. Generally, the higher the molecular weight or the more branches, the higher the polymer:protein ratio. Other sizes may also be used, depending on the desired therapeutic profile; for example, the duration of sustained release; the effects, if any, on biological activity; the ease in handling; the degree or lack of antigenicity; and other known effects of a polymer on a modified molecule of the invention.

Polymers employed in the present invention are typically attached to a heterologous polypeptide with consideration of effects on functional or antigenic domains of the polypeptide. In general, chemical derivatization may be performed under any suitable condition used to react a protein with an activated polymer molecule. Activating groups which can be used to link the polymer to the active moieties include sulfone, maleimide, sulfhydryl, thiol, triflate, tresylate, azidirine, oxirane, and 5-pyridyl.

Polymers of the invention are typically attached to a heterologous polypeptide at the alpha (α) or epsilon (ε) amino groups of amino acids or a reactive thiol group, but it is also contemplated that a polymer group could be attached to any reactive group of the protein that is sufficiently reactive to become attached to a polymer group under suitable reaction conditions. Thus, a polymer may be covalently bound to a heterologous polypeptide via a reactive group, such as a free amino or carboxyl group. The amino acid residues having a free amino group may include lysine residues and the N-terminal amino acid residue. Those having a free carboxyl group may include aspartic acid residues, glutamic acid residues, and the C-terminal amino acid residue. Those having a reactive thiol group include cysteine residues.

Methods for preparing fusion molecules conjugated with polymers, such as water soluble polymers, will each generally involve (a) reacting a heterologous polypeptide with a polymer under conditions whereby the polypeptide becomes attached to one or more polymers and (b) obtaining the reaction product. Reaction conditions for each conjugation may be selected from any of those known in the art or those subsequently developed, but should be selected to avoid or limit exposure to reaction conditions such as temperatures, solvents, and pH levels that would inactivate the protein to be modified. In general, the optimal reaction conditions for the reactions will be determined case-by-case based on known parameters and the desired result. For example, the larger the ratio of polymer:polypeptide conjugate, the greater the percentage of conjugated product. The optimum ratio (in terms of efficiency of reaction in that there is no excess unreacted polypeptide or polymer) may be determined by factors such as the desired degree of derivatization (e.g., mono-, di-tri-etc.), the molecular weight of the polymer selected, whether the polymer is branched or unbranched and the reaction conditions used. The ratio of polymer (for example, PEG) to a polypeptide will generally range from 1:1 to 100:1. One or more purified conjugates may be prepared from each mixture by standard purification techniques, including among others, dialysis, salting-out, ultrafiltration, ion-exchange chromatography, gel filtration chromatography, and electrophoresis.

One may specifically desire an N-terminal chemically modified protein. One may select a polymer by molecular weight, branching, etc., the proportion of polymers to protein (polypeptide or peptide) molecules in the reaction mix, the type of reaction to be performed, and the method of obtaining the selected N-terminal chemically modified protein. The method of obtaining the N-terminal chemically modified protein preparation (separating this moiety from other monoderivatized moieties if necessary) may be by purification of the N-terminal chemically modified protein material from a population of chemically modified protein molecules.

Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively attach a polymer to the N-terminus of the protein by performing the reaction at a pH which allows one to take advantage of the pKa differences between the $\epsilon$-amino group of the lysine residues and that of the $\alpha$-amino group of the N-terminal residue of the protein. By such selective derivatization, attachment of a polymer to a protein is controlled: the conjugation with the polymer takes place predominantly at the N-terminus of the protein and no significant modification of other reactive groups, such as the lysine side chain amino groups, occurs. Using reductive alkylation, the polymer may be of the type described above and should have a single reactive aldehyde for coupling to the protein. Polyethylene glycol propionaldehyde, containing a single reactive aldehyde, may also be used.

In one embodiment, the present invention contemplates the chemically derivatized polypeptide to include mono- or poly- (e.g., 2-4) PEG moieties. Pegylation may be carried out by any of the pegylation reactions known in the art. Methods for preparing a pegylated protein product will generally include (a) reacting a polypeptide with polyethylene glycol (such as a reactive ester or aldehyde derivative of PEG) under conditions whereby the protein becomes attached to one or more PEG groups; and (b) obtaining the reaction product(s). In general, the optimal reaction conditions for the reactions will be determined case by case based on known parameters and the desired result.

There are a number of PEG attachment methods available to those skilled in the art. See, for example, EP 0 401 384; Malik et al., *Exp. Hematol.*, 20:1028-1035 (1992); Francis, *Focus on Growth Factors*, 3(2):4-10 (1992); EP 0 154 316; EP 0 401 384; WO 92/16221; WO 95/34326; and the other publications cited herein that relate to pegylation.

The step of pegylation as described herein may be carried out via an acylation reaction or an alkylation reaction with a reactive polyethylene glycol molecule. Thus, protein products according to the present invention include pegylated proteins wherein the PEG group(s) is (are) attached via acyl or alkyl groups. Such products may be mono-pegylated or poly-pegylated (for example, those containing 2-6 or 2-5 PEG groups). The PEG groups are generally attached to the protein at the $\alpha$- or $\epsilon$-amino groups of amino acids, but it is also contemplated that the PEG groups could be attached to any amino group attached to the protein that is sufficiently reactive to become attached to a PEG group under suitable reaction conditions.

Pegylation by acylation generally involves reacting an active ester derivative of polyethylene glycol (PEG) with a polypeptide of the invention. For acylation reactions, the polymer(s) selected typically have a single reactive ester group. Any known or subsequently discovered reactive PEG molecule may be used to carry out the pegylation reaction. An example of a suitable activated PEG ester is PEG esterified to N-hydroxysuccinimide (NHS). As used herein, acylation is contemplated to include, without limitation, the following types of linkages between the therapeutic protein and a polymer such as PEG: amide, carbamate, urethane, and the like, see for example, Chamow, *Bioconjugate Chem.*, 5:133-140 (1994). Reaction conditions may be selected from any of those known in the pegylation art or those subsequently developed, but should avoid conditions such as temperature, solvent, and pH that would inactivate the polypeptide to be modified.

Pegylation by acylation will generally result in a polypegylated protein. The connecting linkage may be an amide. The resulting product may be substantially only (e.g., >95%) mono, di- or tri-pegylated. However, some species with higher degrees of pegylation may be formed in amounts depending on the specific reaction conditions used. If desired, more purified pegylated species may be separated from the mixture (particularly unreacted species) by standard purification techniques, including among others, dialysis, salting-out, ultrafiltration, ion-exchange chromatography, gel filtration chromatography and electrophoresis.

Pegylation by alkylation generally involves reacting a terminal aldehyde derivative of PEG with a polypeptide in the presence of a reducing agent. For the reductive alkylation reaction, the polymer(s) selected should have a single reactive aldehyde group. An exemplary reactive PEG aldehyde is polyethylene glycol propionaldehyde, which is water stable, or mono C1-C10 alkoxy or aryloxy derivatives thereof, see for example, U.S. Pat. No. 5,252,714.

Additionally, heterologous polypeptides of the present invention and the epitope-bearing fragments thereof described herein can be combined with parts of the constant domain of immunoglobulins (IgG), resulting in chimeric polypeptides. These particular fusion molecules facilitate purification and show an increased half-life in vivo. This has been shown, for example, in chimeric proteins consisting of the first two domains of the human CD4-polypeptide and various domains of the constant regions of the heavy or light chains of mammalian immunoglobulins, such as EP 0 394 827; Traunecker et al., *Nature*, 331:84-86 (1988). Fusion molecules that have a disulfide-linked dimeric structure due to the IgG part can also be more efficient in binding and neutralizing other molecules than, for example, a monomeric polypeptide or polypeptide fragment alone; see, for example, Fountoulakis et al., *J. Biochem.*, 270:3958-3964 (1995).

In another described embodiment, a human serum albumin fusion molecule may also be prepared as described herein and as further described in U.S. Pat. No. 6,686,179.

Moreover, the polypeptides of the present invention can be fused to marker sequences, such as a peptide that facilitates purification of the fused polypeptide. The marker amino acid sequence may be a hexa-histidine peptide such as the tag provided in a pQE vector (Qiagen, Mississauga, Ontario, Canada), among others, many of which are commercially available. As described in Gentz et al., *Proc. Natl. Acad. Sci.* 86:821-824 (1989), for instance, hexa-histidine provides for convenient purification of the fusion protein. Another peptide tag useful for purification, the hemagglutinin HA tag, corresponds to an epitope derived from the influenza hemagglutinin protein. (Wilson et al., *Cell* 37:767 (1984)). Any of these above fusions can be engineered using the polynucleotides or the polypeptides of the present invention.

Secretory Leader Sequences

As demonstrated herein, and in U.S. 60/647,013, in order for some secreted proteins to express and secrete in larger quantities, a secretory leader sequence from another, different, secreted protein is desirable. Employing heterologous secretory leader sequences is advantageous in that a resulting mature amino acid sequence of the secreted polypeptide is not altered as the secretory leader sequence is removed in the ER during the secretion process. Moreover, the addition of a heterologous secretory leader is required to express and secrete some proteins.

Thus, to identify potential robust secretory leader sequence(s) that could universally be used to secrete proteins and to express MGD-CSF, Applicants have cloned and expressed a number of different secreted proteins and measured their expression and secretion levels in the supernatant of cells of the human embryonic kidney cell line 293, which are transformed by adenovirus 5 (Graham et al., *J. Gen. Virol.* 36:59 (1977)). Several high expressers and high level secretory proteins were observed.

In one embodiment, secretory leader sequences belonging to the secreted protein collagen type IX alpha I chain, long form was selected to further examine its ability to promote expression and secretion when used as a heterologous secretory leader sequence. As described herein, the amino acid sequence of the secreted protein collagen type IX alpha I chain, long form is predicted to be MKTCWKIPVFFFVCSFLEPWASA (SEQ ID NO.:14). As further described herein, vectors were constructed containing this particular secretory leader, several proteins were cloned removing the secretory leader from the full length encoding sequence, and by cloning them into vectors containing SEQ ID NO.:14, resulting in secreted proteins with a heterologous secretory leader sequence. High expression and secretion of several other selected proteins were also observed.

Identified secretory leader sequences, described herein include, for example, interleukin-9 precursor, T cell growth factor P40, P40 cytokine, triacylglycerol lipase, pancreatic precursor, somatoliberin precursor, vasopressin-neurophysin 2-copeptin precursor, beta-enoendorphin-dynorphin precursor, complement C2 precursor, small inducible cytokine A14 precursor, elastase 2A precursor, plasma serine protease inhibitor precursor, granulocyte-macrophage colony-stimulating factor precursor, interleukin-2 precursor, interleukin-3 precursor, alpha-fetoprotein precursor, alpha-2-HS-glycoprotein precursor, serum albumin precursor, inter-alpha-trypsin inhibitor light chain, serum amyloid P-component precursor, apolipoprotein A-II precursor, apolipoprotein D precursor, colipase precursor, carboxypeptidase A1 precursor, alpha-s1 casein precursor, beta casein precursor, cystatin SA precursor, follitropin beta chain precursor, glucagon precursor, complement factor H precursor, histidine-rich glycoprotein precursor, interleukin-5 precursor, alpha-lactalbumin precursor, Von Ebner's gland protein precursor, matrix Gla-protein precursor, alpha-1-acid glycoprotein 2 precursor, phospholipase A2 precursor, dendritic cell chemokine 1, statherin precursor, transthyretin precursor, apolipoprotein A-1 precursor, apolipoprotein C-III precursor, apolipoprotein E precursor, complement component C8 gamma chain precursor, serotransferrin precursor, beta-2-microglobulin precursor, neutrophils defensins 1 precursor, triacylglycerol lipase gastric precursor, haptoglobin precursor, neutrophils defensins 3 precursor, neuroblastoma suppressor of tumorigenicity 1 precursor, small inducible cytokine A13 precursor, CD5 antigen-like precursor, phospholipids transfer protein precursor, dickkopf related protein-4 precursor, elastase 2B precursor, alpha-1-acid glycoprotein 1 precursor, beta-2-glycoprotein 1 precursor, neutrophil gelatinase-associated lipocalin precursor, C-reactive protein precursor, interferon gamma precursor, kappa casein precursor, plasma retinol-binding protein precursor, interleukin-13 precursor, and any of the secreted proteins set forth in the Tables or Sequence Listing.

The secretory leader sequences, vectors, and methods described herein, are useful in the expression of a wide variety of polypeptides, including, for example, secreted polypeptides, extracellular proteins, transmembrane proteins, and receptors, such as soluble receptors. Examples of such polypeptides include, but are not limited to cytokines and growth factors, such as interleukins 1-18, interferons, lymphokines, hormones, Regulated on Activation, Normal T Expressed and Secreted (RANTES), lymphotoxin-13, Fas ligand, flt-3 ligand, ligand for receptor activator of NF-kappa B (RANKL), soluble receptors, TNF-related apoptosis-inducing ligand (TRAIL), CD40 ligand, Ox40 ligand, 4-1BB ligand (and other members of the TNF family), thymic stroma-derived lymphopoietin, stimulatory factors, for example, granulocyte colony stimulating factor (G-CSF) and granulocyte-macrophage colony stimulating factor (GM-CSF), inhibitory factors, mast cell growth factor, stem cell growth factor, epidermal growth factor, growth hormone, tumor necrosis factor (TNF), leukemia inhibitory factor (LIF), oncostatin-M, hematopoietic factors such as erythropoietin and thrombopoietin, and splice variants of any of these.

Descriptions of some proteins that can be expressed according to the invention may be found in, for example, *Human Cytokines: Handbook for Basic and Clinical Research, Vol. II* (Aggarwal and Gutterman, eds. Blackwell Sciences, Cambridge Mass., 1998); *Growth Factors: A Practical Approach* (McKay and Leigh, eds., Oxford University Press Inc., New York, 1993) and *The Cytokine Handbook* (A. W. Thompson, ed.; Academic Press, San Diego Calif.; 1991).

Receptors for any of the aforementioned proteins may also be expressed using secretory leader sequences, vectors and methods described herein, including, for example, both forms of tumor necrosis factor receptor (referred to as p55 and p75), interleukin-1 receptors (type 1 and 2), interleukin-4 receptor, interleukin-15 receptor, interleukin-17 receptor, interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL, and receptors that comprise death domains, such as Fas or apoptosis-inducing receptor (AIR).

Other proteins that can be expressed using the secretory leader sequences, vectors and methods described herein include, for example, cluster of differentiation antigens (referred to as CD proteins), for example, those disclosed in *Leukocyte Typing VI* (*Proceedings of the VIth International Workshop and Conference*; Kishimoto, Kikutani et al., eds.; Kobe, Japan, 1996), or CD molecules disclosed in subsequent workshops. Examples of such molecules include CD27, CD30, CD39, CD40; and ligands thereto (CD27 ligand, CD30 ligand and CD40 ligand). Several of these are members of the TNF receptor family, which also includes 41BB and OX40; the ligands are often members of the TNF family (as are 4-1BB ligand and OX40 ligand); accordingly, members of the TNF and TNFR families can also be expressed using the present invention.

Proteins that are enzymatically active may also be expressed employing the herein described secretory leader sequences, vectors and methods and include, for example, metalloproteinase-disintegrin family members, various kinases (including streptokinase and tissue plasminogen activator as well as death associated kinase containing ankyrin repeats, and IKR 1 and 2), TNF-alpha converting enzyme, and numerous other enzymes. Ligands for enzymatically active proteins can also be expressed by applying the instant invention.

The secretory leader sequences, vectors, and methods described herein are also useful for the expression of other types of recombinant proteins, including, for example, immunoglobulin molecules or portions thereof, and chimeric antibodies (antibodies having a human constant region couples to a murine antigen binding region) or fragments thereof. Numerous techniques are known by which DNA encoding immunoglobulin molecules can be manipulated to yield DNAs capable of encoding recombinant proteins such as single chain antibodies, antibodies with enhanced affinity, or other antibody-based polypeptides (see, for example, Larrick et al., *Biotechnology* 7:934-938, 1989; Reichmann et al., *Nature* 332:323-327, 1988; Roberts et al., *Nature* 328:731-734, 1987; Verhoeyen et al., *Science* 239:1534-1536, 1988; and Chaudhary et al., *Nature* 339:394-397, 1989).

Co-Translational and Post-Translational Modifications

The invention encompasses polypeptides which are differentially modified during or after translation, for example by glycosylation, acetylation, phosphorylation, amidation, derivatization by known protecting/blocking groups, proteolytic cleavage, or linkage to an antibody molecule or other cellular ligand. Any of numerous chemical modifications may be carried out by known techniques, including, but not limited to, specific chemical cleavage by cyanogen bromide, trypsin, chymotrypsin, papain, V8 protease; $NABH_4$; acetylation; formylation; oxidation; reduction; and/or metabolic synthesis in the presence of tunicamycin.

Additional post-translational modifications encompassed by the invention include, for example, for example, N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic, or affinity label to allow for detection and isolation of the protein.

Also provided by the invention are chemically modified derivatives of the polypeptides of the invention which may provide additional advantages such as increased solubility, stability, and circulating time of the polypeptide, or decreased immunogenicity (see U.S. Pat. No. 4,179,337). The chemical moieties for derivitization may be chosen from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three, or more attached chemical moieties.

A polymer may be of any molecular weight, and may be branched or unbranched. For polyethylene glycol, a suitable molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, such as EP 0 401 384 (coupling PEG to G-CSF); see also Malik et al., *Exp. Hematol.* 20:1028-1035 (1992) (reporting pegylation of GM-CSF using tresyl chloride). For example, polyethylene glycol may be covalently bound through amino acid residues via a reactive group, such as a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Suitable for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

Chromosome Assays

In certain embodiments relating to chromosomal mapping, a cDNA herein disclosed is used to clone the genomic nucleic acid of MGD-CSF. This can be accomplished using a variety of well known techniques and libraries, which generally are commercially available. The genomic DNA then is used for in situ chromosome mapping using techniques well known for this purpose. Therefore, the nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase Chromosomal spread can be used to provide a precise chromosomal location in one step. This technique can be used with a cDNA as short as approximately 50-60 bases. For a review of this technique, see Verma et al., *Human Chromosomes: A Manual of Basic Techniques*, Pergamon Press, New York (1988).

Once a sequence has been mapped to a precise chromosomal location, the physical position of the sequence on the chromosome can be correlated with genetic map data. (Such data are found, for example, in V. McKusick, *Mendelian Inheritance in Man*, available on line through Johns Hopkins University Welch Medical Library). The relationship between genes and diseases that have been mapped to the same chromosomal region are then identified through linkage analysis (coinheritance of physically adjacent genes).

Next, differences can be determined in the cDNA or genomic sequences of affected and unaffected individuals. If a mutation is observed in some or all of the affected individuals but not in any normal individuals, then the mutation is likely to be the causative agent of the disease. With current resolution of physical mapping and genetic mapping techniques, a cDNA precisely localized to a chromosomal region associated with the disease could be one of between 50 and 500 potential causative genes (assuming 1 megabase mapping resolution and one gene per 20 kb).

The gene encoding MGD-CSF is located at chromosome 16q22.1. Linkage analysis studies suggest that a gene on 16q22 is involved in the causation of familial myelogenous leukemia (Horwitz et al., *Am. J. Hum. Genetics* 61:873-881 (1997)). In this study of a family with 11 relevant meioses transmitting autosomal dominant acute myeloid leukemia and myelodysplasia, linkages to the well-known leukemia translocation breakpoint regions 21q22.1-q22.2 and 9p22-p21 were excluded. Horwitz et al., linked these diseases, using the microsatellite marker D16S522, with a maximum 2-point lod score of 2.82 at recombination fraction theta=0.0, thus providing evidence for linkage to 16q22. Haplotype analysis showed a 23.5-cM region of 16q22 that was inherited in common by all affected family members and extended from D16S451 to D16S289. Nonparametric linkage analysis gave a P-value of 0.00098 for the conditional probability of linkage. Mutational analysis excluded expansion of the AT-rich minisatellite repeat FRA16B fragile site and the CAG trinucleotide repeat in the E2F-4 transcription factor, which is present in many growth-responsive and growth-promoting genes. The 'repeat expansion detection' method, capable of detecting dynamic mutation associated with anticipation, more generally excluded large CAG repeat expansion as a cause of leukemia in this family. MGD-CSF is located at chromosome 16q22.1. Thus, it may potentially play a role in acute myeloid leukemia and myelodysplasia and may be used to treat these diseases.

Therapeutic Compositions and Formulations

The polypeptides, agonists, and antagonists of the present invention may be employed in combination with a suitable pharmaceutical carrier to comprise a pharmaceutical composition for parenteral administration. Such compositions comprise a therapeutically effective amount of the polypeptide, agonist, or antagonist and a pharmaceutically acceptable carrier or excipient. Such a carrier includes, but is not limited to, saline, buffered saline, dextrose, water, glycerol, ethanol, and combinations thereof. The formulation should suit the mode of administration.

The MGD-CSF polypeptide compositions will be formulated and dosed in a fashion consistent with good medical practice, taking into account the clinical condition of the individual subject, the site of delivery of the MGD-CSF polypeptide composition, the method of administration, the scheduling of administration, and other factors known to practitioners. The effective amount of MGD-CSF polypeptide for purposes herein is thus determined by such considerations.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides, agonists and antagonists of the present invention may be employed in conjunction with other therapeutic compounds.

The pharmaceutical compositions may be administered in a convenient manner such as by the oral, topical, intravenous, intraperitoneal, intramuscular, subcutaneous, intranasal, or intradermal routes. The pharmaceutical compositions are administered in an amount which is effective for treating and/or prophylaxis of the specific indication. In general, they are administered in an amount of at least about 10 micrograms/kg body weight and in most cases they will be administered in an amount not in excess of about 8 milligrams/kg body weight per day.

The polypeptides of the invention, and agonist and antagonist compounds which are polypeptides, may also be employed in accordance with the present invention by expression of such polypeptides in vivo, i.e., gene therapy. Thus, for example, cells may be engineered with a polynucleotide (DNA or RNA) encoding for the polypeptide ex vivo; the engineered cells are then provided to a patient. Such methods are well-known in the art. For example, cells may be engineered by procedures known in the art by use of a retroviral particle containing RNA encoding for the polypeptide of the present invention.

Similarly, cells may be engineered in vivo for expressing the polypeptide in vivo, for example, by procedures known in the art. As known in the art, a cell producing a retroviral particle containing RNA encoding the polypeptide of the present invention may be administered to a patient for the purpose of engineering cells in vivo and expressing the polypeptide in vivo. These and other methods for administering a polypeptide of the present invention by similar methods should be apparent to those skilled in the art from the teachings of the present invention. For example, the expression vehicle for engineering cells may be other than a retroviral particle, for example, an adenovirus, which may be used to engineer cells in vivo after combination with a suitable delivery vehicle.

Retroviruses from which the retroviral plasmid vectors hereinabove mentioned may be derived include, but are not limited to, Moloney murine leukemia virus, spleen necrosis virus, Rous sarcoma virus, Harvey sarcoma virus, avian leukosis virus, gibbon ape leukemia virus, human immunodeficiency virus, adenovirus (HIV), myeloproliferative sarcoma virus, and mammary tumor virus.

The nucleic acid sequence encoding the polypeptide of the present invention is under the control of a suitable promoter. Vectors of the invention include one or more promoters. Suitable promoters which may be employed include, but are not limited to, the retroviral long terminal repeat (LTR); the SV40 promoter; and the human cytomegalovirus (CMV) promoter described in Miller, et al., *Biotechniques*, Vol. 7, No. 9, 980-990 (1989), or any other homologous or heterologous promoter, for example, cellular promoters such as eukaryotic cellular promoters including, but not limited to, the histone, pol III, and β-actin promoters. Other viral promoters which may be employed include, but are not limited to, adenovirus promoters, for example, the adenoviral major late promoter; thymidine kinase (TK) promoters; and B19 parvovirus promoters.

Suitable promoters include, but are not limited to, the respiratory syncytial virus (RSV) promoter; inducible promoters, such as the MMT promoter, the metallothionein promoter; heat shock promoters; the albumin promoter; the ApoA1 promoter; human globin promoters; viral thymidine kinase promoters, such as the herpes simplex thymidine kinase promoter; retroviral LTRs (including the modified retroviral LTRs hereinabove described); the beta-actin promoter; and human growth hormone promoters. The promoter also may be the native promoter which controls the gene encoding the polypeptide. The selection of a suitable promoter will be apparent to those skilled in the art from the teachings contained herein.

A retroviral plasmid vector can be employed to transduce packaging cell lines to form producer cell lines. Examples of packaging cells which may be transfected include, but are not limited to, the PE501, PA317, PA12, T19-14X, VT-19-17-H2, CRE, CRIP, GP+E-86, GP+envAm12, and DAN cell lines as described in Miller, *Human Gene Therapy*, 1:5-14 (1990). The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

In some embodiments, MGD-CSF compositions are provided in formulation with pharmaceutically acceptable excipients, a wide variety of which are known in the art (Gennaro, *Remington: The Science and Practice of Pharmacy with Facts and Comparisons: Drugfacts Plus*, 20th ed. (2003); Ansel et al., *Pharmaceutical Dosage Forms and Drug Delivery Systems*, 7th ed., Lippencott Williams and Wilkins (2004); Kibbe et al., *Handbook of Pharmaceutical Excipients*, 3rd ed., Pharmaceutical Press (2000)). Pharmaceutically acceptable excipients, such as vehicles, adjuvants, carriers or diluents, are available to the public. Moreover, pharmaceutically acceptable auxiliary substances, such as pH adjusting and buffering agents, tonicity adjusting agents, stabilizers, wetting agents and the like, are available to the public.

In pharmaceutical dosage forms, the compositions of the invention can be administered in the form of their pharmaceutically acceptable salts, or they can also be used alone or in appropriate association, as well as in combination, with other pharmaceutically active compounds. The subject compositions are formulated in accordance to the mode of potential administration. Administration of the agents can be achieved in various ways, including oral, buccal, nasal, rectal, parenteral, intraperitoneal, intradermal, transdermal, subcutaneous, intravenous, intra-arterial, intracardiac, intraventricular, intracranial, intratracheal, and intrathecal administration, etc., or otherwise by implantation or inhalation. Thus, the subject compositions can be formulated into preparations in solid, semi-solid, liquid or gaseous forms, such as tablets, capsules, powders, granules, ointments, solutions, suppositories, enemas, injections, inhalants and aerosols. The following methods and excipients are merely exemplary and are in no way limiting.

Compositions for oral administration can form solutions, suspensions, tablets, pills, granules, capsules, sustained release formulations, oral rinses, or powders. For oral preparations, the agents, polynucleotides, and polypeptides can be used alone or in combination with appropriate additives, for example, with conventional additives, such as lactose, mannitol, corn starch, or potato starch; with binders, such as crystalline cellulose, cellulose derivatives, acacia, corn starch, or gelatins; with disintegrators, such as corn starch, potato starch, or sodium carboxymethylcellulose; with lubricants, such as talc or magnesium stearate; and if desired, with diluents, buffering agents, moistening agents, preservatives, and flavoring agents.

Suitable excipient vehicles are, for example, water, saline, dextrose, glycerol, ethanol, or the like, and combinations thereof. In addition, if desired, the vehicle can contain minor amounts of auxiliary substances such as wetting or emulsifying agents or pH buffering agents. Actual methods of preparing such dosage forms are known, or will be apparent, to those skilled in the art (Gennaro, supra). The composition or formulation to be administered will contain a quantity of the agent adequate to achieve the desired state in the subject being treated.

The agents, polynucleotides, and polypeptides can be formulated into preparations for injection by dissolving, suspending, or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Other formulations for oral or parenteral delivery can also be used, as conventional in the art.

The antibodies, agents, polynucleotides, and polypeptides can be utilized in aerosol formulation to be administered via inhalation. The compounds of the present invention can be formulated into pressurized acceptable propellants such as dichlorodifluoromethane, propane, nitrogen, and the like. Further, the agent, polynucleotides, or polypeptide composition may be converted to powder form for administration intranasally or by inhalation, as conventional in the art.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

A polynucleotide, polypeptide, or other modulator, can also be introduced into tissues or host cells by other routes, such as viral infection, microinjection, or vesicle fusion. For example, expression vectors can be used to introduce nucleic acid compositions into a cell as described above. Further, jet injection can be used for intramuscular administration (Furth et al., *Anal. Biochem.* 205:365-368 (1992)). The DNA can be coated onto gold microparticles, and delivered intradermally by a particle bombardment device, or "gene gun" as described in the literature (Tang et al., *Nature* 356:152-154 (1992)), where gold microprojectiles are coated with the DNA, then bombarded into skin cells.

Unit dosage forms for oral or rectal administration such as syrups, elixirs, and suspensions can be provided wherein each dosage unit, for example, teaspoonful, tablespoonful, tablet, or suppository, contains a predetermined amount of the composition containing one or more agents. Similarly, unit dosage forms for injection or intravenous administration can comprise the agent(s) in a composition as a solution in sterile water, normal saline, or another pharmaceutically acceptable carrier.

Identification of Agonists and Antagonists

The invention provides modulators, including polypeptides, polynucleotides, and other agents that increase or decrease the activity of their target. Modulators of the invention may act as an agonist or antagonist, and may interfere with the binding or activity of polypeptides or polynucleotides. Such modulators, or agents, include, for example, polypeptide variants, whether agonist or antagonist; antibodies, whether agonist or antagonist; soluble receptors, usually antagonists; small molecule drugs, whether agonist or antagonist; RNAi, usually an antagonist; antisense molecules, usually an antagonist; and ribozymes, usually an antagonist. In some embodiments, an agent is a subject polypeptide, where the subject polypeptide itself is administered to an individual. In some embodiments, an agent is an antibody specific for a subject "target" polypeptide. In some embodiments, an agent is a chemical compound, such as a small molecule, that may be useful as an orally available drug. Such modulation includes the recruitment of other molecules that directly effect the modulation. For example, an antibody that modulates the activity of a subject polypeptide that is a receptor on a cell surface may bind to the receptor and fix complement, activating the complement cascade and resulting in lysis of the cell. An agent which modulates a biological activity of a subject polypeptide or polynucleotide increases or decreases the activity or binding at least about 10%, at least about 15%, at least about 20%, at least about 25%, at least about 50%, at least about 80%, or at least about 2-fold, at least about 5-fold, or at least about 10-fold or more when compared to a suitable control.

The invention also provides a method of screening compounds to identify those which modulate the biological activity of a polypeptide of the present invention. Examples of the biological activities of the polypeptides of the invention are described in greater detail herein, for example in the Examples and the Figures.

The invention further provides a method wherein a mammalian cell or membrane preparation expressing a receptor for a polypeptide of the present invention, as described above, is incubated with a labeled polypeptide of the present invention in the presence of the compound. The ability of the compound to enhance or block this interaction is then measured. Alternatively, the response of a known second messenger system following interaction of a compound to be screened and a MGD-CSF receptor is measured and the ability of the compound to bind to the receptor and elicit a second messenger response is measured to determine if the compound is a potential agonist or antagonist. Such second messenger systems include, but are not limited to, those mediated by cAMP, guanylate cyclase, ion channels, and phosphoinositide hydrolysis.

Examples of antagonistic compounds include antibodies, or in some cases, oligonucleotides, which bind to a receptor of a polypeptide of the present invention but elicit no second messenger response, or which bind to the MGD-CSF polypeptide itself. Alternatively, a potential antagonist may be a mutant form of the polypeptide which binds to the receptors but elicits no second messenger response, thus effectively blocking the action of the polypeptide.

Another compound antagonistic to MGD-CSF genes and gene products is an antisense construct prepared using antisense technology. Antisense technology can be used to control gene expression through triple-helix formation or antisense DNA or RNA; both methods are based on the binding of a polynucleotide to DNA or RNA. For example, a 5' coding portion of the polynucleotide sequence, which encodes mature polypeptides of the present invention, can be used to design an antisense RNA oligonucleotide of from about 10 to about 40 base pairs in length. A DNA oligonucleotide is designed to be complementary to a region of the gene involved in transcription, for example, a triple helix; see Lee et al., *Nucl. Acids Res.*, 6:3073 (1979); Cooney et al., *Science,* 241:456 (1988); and Dervan et al., *Science,* 251:1360 (1991); thereby preventing transcription and the production of the polypeptides of the present invention. The antisense RNA oligonucleotide hybridizes to the mRNA in vivo and blocks translation of the mRNA molecule into the polypeptide, as described by Okano, *J. Neurochem.,* 56:560 (1991); *Oligodeoxynucleotides as Antisense Inhibitors of Gene Expression,* CRC Press, Boca Raton, Fla. (1988). The oligonucleotides described above can also be delivered to cells such that the antisense RNA or DNA is expressed in vivo to inhibit polypeptide production.

Potential antagonist compounds also include small molecules which bind to and occupy the binding site of the receptors, thereby making the receptor inaccessible to its polypeptide such that normal biological activity is prevented. Examples of small molecules include, but are not limited to, small peptides or peptide-like molecules. Antagonist compounds may be employed to inhibit the effects of the polypeptides of the invention, described in further detail in the Examples and Figures. The antagonists may be employed to diagnose, determine a prognosis for, prevent, and treat immune-related diseases, as described in further detail below.

The present invention also provides methods for identifying agents, such as antibodies, which enhance or block the actions of MGD-CSF molecules on cells. For example, these agents may enhance or block interaction of MGD-CSF-binding molecules, such as receptors. Agents of interest include both agonists and antagonists. The invention provides agonists which increase the natural biological functions of MGD-CSF or which function in a manner similar to MGD-CSF. The invention also provides antagonists, which decrease or eliminate the functions of MGD-CSF.

One method of identifying MGD-CSF agonists and antagonists involves biochemical assays following subcellular fractionation. For example, a cellular compartment, such as a membrane or cytosolic preparation may be prepared from a cell that expresses a molecule that binds MGD-CSF molecules, such as a molecule of a signaling or regulatory pathway modulated by MGD-CSF molecules. Subcellular fractionation methods are known in the art of cell biology, and can be tailored to produce crude fractions with discrete and defined components, for example, organelles or organellar membranes. The preparation is incubated with labeled MGD-CSF molecules in the absence or the presence of a candidate molecule which may be an MGD-CSF agonist or antagonist. The ability of the candidate molecule to interact with the binding molecule or an MGD-CSF molecules is reflected in decreased binding of the labeled ligand. Molecules which bind gratuitously, that is, without inducing the effects of MGD-CSF molecules, are most likely antagonists. Molecules that bind well and elicit effects that are the same as or closely related to MGD-CSF molecules may potentially prove to be agonists.

The effects of potential agonists and antagonists may by measured, for instance, by determining an activity of one or more components of a second messenger system following interaction of the candidate molecule with a cell or appropriate cell preparation, and comparing the effect with that of MGD-CSF molecules, or with that of molecules that elicit the same effects as MGD-CSF. Second messenger systems which may be useful in this regard include, but are not limited to, cAMP, cGMP, ion channels, and phosphoinositide hydrolysis second messenger systems.

Another example of an assay for the identification of MGD-CSF antagonists is a competitive assay that combines a mixture of MGD-CSF molecules and a potential antagonist, with membrane-bound MGD-CSF receptor molecules. Under appropriate conditions for a competitive inhibition assay, this assay can also be performed with recombinant MGD-CSF receptor molecules. MGD-CSF molecules can be labeled, such as by radioactivity, such that the number of MGD-CSF molecules bound to a receptor molecule can be determined accurately to assess the effectiveness of the potential antagonist.

Potential antagonists include small organic molecules, polypeptides, and antibodies that bind to a polypeptide of the invention, and thereby inhibit or extinguish its activity. Potential antagonists also may be small organic molecules, polypeptides such as closely related proteins or antibodies that bind the same sites on a binding molecule, such as a receptor molecule, without inducing MGD-CSF-induced activities, thereby preventing the action of MGD-CSF molecules by excluding MGD-CSF molecules from binding. Antagonists of the invention include fragments of the MGD-CSF molecules having the nucleic acid and amino acid sequences shown in the Sequence Listing.

Other potential antagonists include antisense molecules. Antisense technology can be used to control gene expression through, for example, antisense DNA or RNA, or through triple-helix formation. Antisense techniques are discussed, for example, in Okano, *J. Neurochem.*, 56:560 (1991); *Oligodeoxynucleotides as Antisense Inhibitors of Gene Expression*, CRC Press, Boca Raton, Fla. (1988). Triple helix formation is discussed in, for instance, Lee et al., *Nucleic Acids Research,* 6:3073 (1979); Cooney et al., *Science,* 241:456 (1988); and Dervan et al., *Science,* 251:1360 (1991). The methods are based on the binding of a polynucleotide to a complementary DNA or RNA. For example, the 5' coding portion of a polynucleotide that encodes the mature polypeptide of the present invention may be used to design an antisense RNA oligonucleotide of from about 10 to about 40 base pairs in length. A DNA oligonucleotide is designed to be complementary to a region of the gene involved in transcription, thereby preventing transcription and the subsequent production of MGD-CSF molecules. The antisense RNA oligonucleotide hybridizes to the mRNA in vivo and blocks translation of the mRNA molecule into a MGD-CSF polypeptide. The oligonucleotides described above can also be delivered to cells such that the antisense RNA or DNA may be expressed in vivo to inhibit production of MGD-CSF molecules.

Diagnosis

This invention is also related to the use of the genes and gene products of the present invention as part of a diagnostic assay for detecting diseases or susceptibility to diseases related to the presence of mutations in the nucleic acid sequences encoding the polypeptide of the present invention. Individuals carrying mutations in a gene of the present invention may be detected at the DNA level by a variety of techniques. Nucleic acids for diagnosis may be obtained from a patient's cells, such as, for example, from blood, urine, saliva, tissue biopsy, and autopsy material. The genomic DNA may be used directly for detection or may be amplified enzymatically by using PCR, for example, as described by Saiki et al., *Nature,* 324: 163-166 (1986), prior to analysis. RNA or cDNA may also be used for the same purpose. As an example, PCR primers complementary to the nucleic acid encoding a polypeptide of the present invention can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Genetic testing based on DNA sequence differences may be achieved by detecting alterations in electrophoretic mobility of DNA fragments in gels run with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures, for example, as described by Myers et al., *Science,* 230:1242 (1985).

Sequence changes at specific locations may also be revealed by nuclease protection assays, such as RNase and S1 protection or the chemical cleavage method as shown in Cotton et al., *Proc. Natl. Acad. Sci.,* 85:4397-4401 (1985). Thus, the detection of a specific DNA sequence may be achieved by methods such as hybridization, RNase protection, chemical cleavage, direct DNA sequencing or the use of restriction enzymes, for example, Restriction Fragment Length Polymorphisms (RFLP) and Southern blotting of genomic DNA. In addition to more conventional gel-electrophoresis and DNA sequencing, mutations can also be detected by in situ analysis.

The present invention also relates to a diagnostic assay for detecting altered levels of MGD-CSF proteins in various tissues. An over-expression of these proteins compared to normal control tissue samples may detect the presence of abnormal cellular proliferation, for example, a tumor. Assays used to detect protein levels in a host-derived sample are well-known to those of skill in the art and include radioimmunoassays, competitive-binding assays, Western Blot analysis, ELISA assays, "sandwich" assays, and other assays for the expression levels of the genes encoding the MGD-CSF proteins known in the art. Expression can be assayed by qualitatively or quantitatively measuring or estimating the level of MGD-CSF protein, or the level of mRNA encoding MGD-CSF protein, in a biological sample. Assays may be performed directly, for example, by determining or estimating absolute protein level or mRNA level, or relatively, by comparing the MGD-CSF protein or mRNA to a second biological sample. In performing these assays, the MGD-CSF protein or mRNA level in the first biological sample is measured or estimated and compared to a standard MGD-CSF protein level or mRNA level; suitable standards include second biological samples obtained from an individual not having the disorder of interest. Standards may be obtained by averaging levels of MGD-CSF in a population of individuals not having a disorder related to MGD-CSF expression. As will be appreciated in the art, once a standard MGD-CSF protein level or mRNA level is known, it can be used repeatedly as a standard for comparison.

An ELISA assay, for example, as described by Coligan, et al., *Current Protocols in Immunology*, 1(2), Chap. 6, (1991), utilizes an antibody prepared with specificity to a polypeptide antigen of the present invention. In addition, a reporter antibody is prepared against the monoclonal antibody. To the reporter antibody is attached a detectable reagent such as a radioactive tag, a fluorescent tag, or an enzymatic tag, e.g., a horseradish peroxidase. A sample is removed from a host and incubated on a solid support, e.g. a polystyrene dish, that binds the proteins in the sample. Any free protein binding sites on the dish are then covered by incubating with a non-specific protein, e.g., bovine serum albumin. Next, the specific antibody, e.g., a monoclonal antibody, is incubated in the dish, during which time the antibody attaches to any polypeptides of the present invention attached to the polystyrene dish. All unbound monoclonal antibody is washed out with buffer. The reporter antibody, for example, one linked to horseradish peroxidase is placed in the dish, resulting in the binding of the reporter antibody to any antibody bound to the protein of interest; unattached reporter antibody is then removed. Substrate, e.g., peroxidase, is then added to the dish, and the amount of signal produced color, e.g., developed in a given time period provides a measurement of the amount of a polypeptide of the present invention present in a given volume of patient sample when compared against a standard.

A competition assay may be employed wherein antibodies specific to a polypeptide of the present invention are attached to a solid support, and labeled MGD-CSF, along with a sample derived from the host, are passed over the solid support. The label can be detected and quantified, for example, by liquid scintillation chromatography, and the measurement can be correlated to the quantity of the polypeptide of interest present in the sample. A "sandwich" assay, similar to an ELISA assay, may be employed, wherein a polypeptide of the present invention is passed over a solid support and binds to antibody modules attached to the solid support. A second antibody is then bound to the polypeptide of interest. A third antibody, which is labeled and specific to the second antibody is then passed over the solid support and binds to the second antibody. The amount of antibody binding can be quantified; it correlates with the amount of the polypeptide of interest. See,e.g., U.S. Pat. No. 4,376,110.

Biological samples of the invention can include any biological sample obtained from a subject, body fluid, cell line, tissue culture, or other source which contains MGD-CSF protein or mRNA. As indicated, biological samples include body fluids (such as sera, plasma, urine, synovial fluid, and spinal fluid) which contain free MGD-CSF protein, ovarian or renal system tissue, and other tissue sources found to express complete or mature MGD-CSF polypeptide or an MGD-CSF receptor. Methods for obtaining tissue biopsies and body fluids from mammals are well known in the art. Where the biological sample is to include mRNA, a tissue biopsy may provide the source.

Total cellular RNA can be isolated from a biological sample using any suitable technique such as the single-step guanidinium-thiocyanate-phenol-chloroform method described in Chomczynski and Sacchi, *Anal. Biochem.*, 162: 156-159 (1987). Levels of mRNA encoding the MGD-CSF protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Total cellular RNA can be isolated from a biological sample using any suitable technique such as the single-step guanidinium-thiocyanate-phenol-chloroform method described in Chomczynski and Sacchi, *Anal. Biochem.*, 162: 156-159 (1987). Levels of mRNA encoding the MGD-CSF protein are then assayed using any appropriate method. These include Northern blot analysis, S1 nuclease mapping, PCR, reverse transcription in combination with PCR (RT-PCR), and reverse transcription in combination with the ligase chain reaction (RT-LCR).

Assaying MGD-CSF protein levels in a biological sample can be performed using antibody-based techniques. For example, MGD-CSF protein expression in tissues can be studied with classical immunohistological methods, for example, Jalkanen, M., et al., *J. Cell. Biol.*, 101:976-985 (1985); Jalkanen, M., et al., *J. Cell. Biol.*, 105:3087-3096 (1987). Other antibody-based methods useful for detecting MGD-CSF protein gene expression include immunoassays, such as the enzyme linked immunosorbent assay (ELISA) and the radioimmunoassay (RIA). Suitable antibody assay labels are known in the art and include enzyme labels, such as glucose oxidase, radioisotopes, and fluorescent labels, such as fluorescein and rhodamine, and biotin.

In addition to assaying MGD-CSF protein levels in a biological sample obtained from an individual, MGD-CSF protein can also be detected in vivo by imaging. Antibody labels or markers for in vivo imaging of MGD-CSF protein include those detectable by X-radiography, NMR, or ESR. For X-radiography, suitable labels include radioisotopes such as barium or cesium, which emit detectable radiation but are not overtly harmful to a subject. Suitable markers for NMR and ESR include those with a detectable characteristic spin, such as deuterium, which may be incorporated into the antibody by labeling of nutrients for the relevant hybridoma.

A MGD-CSF protein-specific antibody or antibody fragment which has been labeled with an appropriate detectable imaging moiety, such as a radioisotope, a radio-opaque substance, or a material detectable by nuclear magnetic resonance, is introduced, for example, parenterally, subcutaneously or intraperitoneally, into the subject to be examined for an immune system disorder. It will be understood in the art that the size of the subject and the imaging system used will determine the quantity of imaging moiety needed to produce diagnostic images. The labeled antibody or antibody fragment will then accumulate at the location of cells which contain MGD-CSF protein. In vivo tumor imaging is described in Burchiel et al., ed., Chapter 13, *Tumor Imaging: The Radiochemical Detection of Cancer*, Masson Publishing, Inc. (1982).

Therapeutic Uses of MGD-CSF Molecules, Agonists, and Antagonists

Molecules of the invention and fragments and variants thereof may be used in diagnosing, prognosing, preventing, treating, and developing treatments for any disorder mediated, either directly or indirectly, by defective or insufficient amounts of MGD-CSF. MGD-CSF polypeptides, agonists, or antagonists may be administered to a patient afflicted with such a disorder. A gene therapy approach may be applied to treat such disorders. Disclosure herein of sequences of the invention permits the detection of defective MGD-CSF related genes, and the replacement thereof with normal or corrective genes. Defective genes may be detected in in vitro diagnostic assays, and by comparison of the sequences of the invention with that of a gene derived from a patient suspected of harboring a defect.

Molecules of the invention, such as recombinant MGD-CSF may have multiple effects on the proliferation of different cell types and may have multiple effects on the proliferation and differentiation of the same cell type under different conditions. Under conditions wherein MGD-CSF inhibits proliferation and/or differentiation, recombinant MGD-CSF or related molecules may be used to treat diseases characterized by abnormal proliferation and/or differentiation. Under conditions wherein MGD-CSF promotes proliferation and/or differentiation, agents inhibitory to MGD-CSF or related molecules may be used to treat diseases characterized by abnormal proliferation and/or differentiation. Suitable inhibitors are described herein, and may include inhibitory antibodies, small molecule inhibitors, antisense oligonucleotides, siRNA, and soluble receptors.

Disease Applications

The molecules of the invention are useful for treating cancer, immune diseases, such as an autoimmune disease or an inflammatory disease, ischemic diseases, infectious diseases, bone diseases, and neural diseases. The molecules of the invention are useful for inhibiting the multiplication of a tumor cell or cancer cell, and for treating cancer. The molecules of the invention can be used accordingly in a variety of settings for the treatment of animal cancers. Other particular types of cancers that can be treated with molecules of the invention include, but are not limited to, those disclosed below.

MGD-CSF may play a role in the retention, proliferation, and survival of hematopoietic cells in the bone marrow. Therefore, it may be useful in the treatment of hemaptopoietic cell (for example, neutrophil) deficiency in cancer patients receiving chemotherapy or radiotherapy.

The molecules of the invention may be employed to treat lymphoproliferative disease which results in lymphadenopathy. The molecules of the invention may mediate apoptosis by stimulating clonal deletion of T cells and may therefore be employed to treat autoimmune disease to stimulate peripheral tolerance and cytotoxic T cell mediated apoptosis. The molecules of the invention may also be employed as a research tool in elucidating the biology of allergies and of autoimmune disorders including systemic lupus erythematosus (SLE), Graves' disease, immunoproliferative disease lymphadenopathy (IPL), angioimmunoproliferative lymphadenopathy (AIL), immunoblastive lymphadenopathy (IBL), rheumatoid arthritis, diabetes, and multiple sclerosis, and to treat graft versus host disease.

The molecules of the invention are useful for killing or inhibiting the replication of a cell that produces an autoimmune disease or an inflammatory disease or for treating an autoimmune disease or an inflammatory disease. They can be used accordingly in a variety of settings for the treatment of an autoimmune disease or an inflammatory disease in an animal.

The molecules of the invention may also be used to treat, prevent, diagnose and/or determine a prognosis for diseases which include, but are not limited to, autoimmune disorders, immunodeficiency disorders, and graft versus host disease, and recurrent pregnancy loss. Additionally, molecules of the invention may be employed as agents to boost immunoresponsiveness among individuals having a temporary immune deficiency. Conditions resulting in a temporary immune deficiency that may be ameliorated or treated by administering the molecules of the invention include, but are not limited to, recovery from infectious diseases, such as viral infections (for example, influenza, infectious mononucleosis, or measles), conditions associated with malnutrition, recovery from or conditions associated with stress, recovery from blood transfusion, and recovery from surgery.

Molecules of the invention may be used to diagnose, determine a prognosis for, treat, or prevent one or more of the following diseases, disorders, or conditions associated therewith: primary immuodeficiencies, immune-mediated thrombocytopenia, Kawasaki syndrome, bone marrow transplant (for example, recent bone marrow transplant in adults or children), chronic B cell lymphocytic leukemia, HIV infection (for example, adult or pediatric HIV infection), chronic inflammatory demyelinating polyneuropathy, and post-transfusion purpura.

Additionally, molecules of the invention may be used to diagnose, determine a prognosis for, treat or prevent one or more of the following diseases, disorders, or conditions associated therewith: Guillain-Barre syndrome, anemia (for example, anemia associated with parvovirus B19, patients with stable multiple myeloma who are at high risk for infection (for example, recurrent infection), autoimmune hemolytic anemia (for example, warm-type autoimmune hemolytic anemia), thrombocytopenia (for example, neonatal thrombocytopenia), and immune-mediated neutropenia), transplantation (for example, cytomegalovirus (CMV)-negative recipients of CMV-positive organs), hypogammaglobulinemia (for example, hypogammaglobulinemic neonates with risk factor for infection or morbidity), epilepsy (for example, intractable epilepsy), systemic vasculitic syndromes, myasthenia gravis (for example, decompensation in myasthenia gravis), dermatomyositis, and polymyositis.

Further autoimmune disorders and conditions associated with these disorders that may be treated, prevented, diagnosed, and/or have their prognosis determined by molecules of the invention include, but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (for example, IgA nephropathy), multiple sclerosis, neuritis, uveitis ophthalmia, polyendocrinopathies, purpura (for example, Henloch-Scoenlein purpura), Reiter's disease, stiff-man syndrome, autoimmune pulmonary inflammation, Guillain-Barre Syndrome, insulin dependent diabetes mellitis, and autoimmune inflammatory eye disease.

Additional autoimmune disorders that may be treated, prevented, diagnosed, and/or have their prognosis determined by molecules of the invention include but are not limited to autoimmune thyroiditis; hypothyroidism, including Hashimoto's thyroiditis and thyroiditis characterized, for example, by cell-mediated and humoral thyroid cytotoxicity; SLE (which is often characterized, for example, by circulating and locally generated immune complexes); Goodpasture's syndrome (which is often characterized, for example, by anti-basement membrane antibodies); pemphigus (which is often characterized, for example, by epidermal acantholytic antibodies); receptor autoimmunities such as, for example, Graves' disease (which is often characterized, for example, by antibodies to a thyroid stimulating hormone receptor; myasthenia gravis, which is often characterized, for example, by acetylcholine receptor antibodies); insulin resistance (which is often characterized, for example, by insulin receptor antibodies); autoimmune hemolytic anemia (which is often characterized, for example, by phagocytosis of antibody-sensitized red blood cells); and autoimmune thrombocytopenic purpura (which is often characterized, for example, by phagocytosis of antibody-sensitized platelets).

Further autoimmune disorders which may be treated, prevented, diagnosed, and/or have their prognosis determined by molecules of the invention include but are not limited to rheumatoid arthritis (which is often characterized, for example, by immune complexes in joints); scleroderma with anti-collagen antibodies (which is often characterized, for example, by nucleolar and other nuclear antibodies); mixed connective tissue disease, (which is often characterized, for example, by antibodies to extractable nuclear antigens, for example, ribonucleoprotein); polymyositis/dermatomyositis (which is often characterized, for example, by nonhistone anti-nuclear antibodies); pernicious anemia (which is often characterized, for example, by antiparietal cell, antimicrosome, and anti-intrinsic factor antibodies); idiopathic Addison's disease (which is often characterized, for example, by humoral and cell-mediated adrenal cytotoxicity); infertility (which is often characterized, for example, by antispermatozoal antibodies); glomerulonephritis (which is often characterized, for example, by glomerular basement membrane antibodies or immune complexes); by primary glomerulonephritis, by IgA nephropathy; bullous pemphigoid (which is often characterized, for example, by IgG and complement in the basement membrane); Sjögren's syndrome (which is often characterized, for example, by multiple tissue antibodies and/or the specific nonhistone antinuclear antibody (SS-B)); diabetes mellitus (which is often characterized, for example, by cell-mediated and humoral islet cell antibodies); and adrenergic drug resistance, including adrenergic drug resistance with asthma or cystic fibrosis (which is often characterized, for example, by beta-adrenergic receptor antibodies).

Yet further autoimmune disorders which may be treated, prevented, have their prognosis determined by, and/or diagnosed with antagonists thereof, include, but are not limited to the following disorders: chronic active hepatitis (which is often characterized, for example by smooth muscle antibodies); primary biliary cirrhosis (which is often characterized, for example, by anti-mitchondrial antibodies); other endocrine gland failure (which is characterized, for example, by specific tissue antibodies in some cases); vitiligo (which is often characterized, for example, by anti-melanocyte antibodies); vasculitis (which is often characterized, for example, by immunoglobulin and complement in vessel walls and/or low serum complement); post-myocardial infarction conditions (which are often characterized, for example, by anti-myocardial antibodies); cardiotomy syndrome (which is often characterized, for example, by anti-myocardial antibodies); urticaria (which is often characterized, for example, by IgG and IgM antibodies to IgE); atopic dermatitis (which is often characterized, for example, by IgG and IgM antibodies to IgE); asthma (which is often characterized, for example, by IgG and IgM antibodies to IgE); inflammatory myopathies; and other inflammatory, granulomatous, degenerative, and atrophic disorders.

In an embodiment, the molecules of the invention, for example, anti-MGD-CSF antibodies, are used to treat or prevent SLE and/or associated diseases, disorders, or conditions. Lupus-associated diseases, disorders, and conditions which may be treated or prevented with molecules of the invention include, but are not limited to, hematologic disorders, for example, hemolytic anemia, leukopenia, lymphopenia, and thrombocytopenia; immunologic disorders, for example, anti-DNA antibodies, and anti-Sm antibodies, rashes, photosensitivity, oral ulcers, arthritis, fever, fatigue, weight loss, serositis, for example, pleuritus (pleurisy); renal disorders, for example, nephritis; neurological disorders, for example, seizures, peripheral neuropathy and CNS related disorders; gastroinstestinal disorders; Raynaud's phenomenon; and pericarditis.

The molecules of the invention may also be employed to inhibit neoplasia, such as tumor cell growth. The MGD-CSF polypeptides may be responsible for tumor destruction through apoptosis and cytotoxicity to certain cells. Diseases associated with increased cell survival, or the inhibition of apoptosis, that may be treated, prevented, diagnosed, and/or have their prognosis determined by the molecules of the invention include, but are not limited to, cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjögren's syndrome, Graves' disease, Hashimoto's thyroiditis, autoimmune diabetes, biliary cirrhosis, Behcet's disease, Crohn's disease, polymyositis, systemic lupus erythematosus and immune-related glomerulonephritis, autoimmune gastritis, autoimmune thrombocytopenic purpura, and rheumatoid arthritis) and viral infections (such as herpes viruses, pox viruses and adenoviruses), inflammation, graft vs. host disease (acute and/or chronic), acute graft rejection, and chronic graft rejection. In an embodiment, of the invention are used to inhibit growth, progression, and/or metastasis of cancers, in particular those listed above or in the paragraph that follows.

Additional diseases or conditions associated with increased cell survival, that may be treated, prevented, diagnosed, and/or have their prognosis determined by the of the invention include, but are not limited to, progression, and/or metastases of malignancies and related disorders such as leukemia (including acute leukemias (for example, acute lymphocytic leukemia, acute myelocytic leukemia, including myeloblastic, promyelocytic, myelomonocytic, monocytic, and erythroleukemia)) and chronic leukemias (for example, chronic myelocytic (granulocytic) leukemia and chronic lymphocytic leukemia), myelodysplastic syndrome polycythemia vera, lymphomas (for example, Hodgkin's disease and non-Hodgkin's disease), multiple myeloma, Waldenstrom's macroglobulinemia, heavy chain diseases, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis, that may be treated, prevented, diagnosed, and/or have their prognosis determined by molecules of the invention include, but are not limited to, AIDS (such as HIV-induced nephropathy and HIV encephalitis), neurodegenerative disorders (such as Alzheimer's disease, Parkinson's disease, amyotrophic lateral sclerosis, retinitis pigmentosa, cerebellar degeneration and brain tumor or prior associated disease), autoimmune disorders such as multiple sclerosis, Sjögren's syndrome, Graves' disease, Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, and rheumatoid arthritis, myelodysplastic syndromes (such as aplastic anemia), graft vs. host disease (acute and/or chronic), ischemic injury (such as that caused by myocardial infarction, stroke and reperfusion injury), liver injury or disease (for example, hepatitis related liver injury, cirrhosis, ischemia/reperfusion injury, cholestosis (bile duct injury) and liver cancer), toxin-induced liver disease (such as that caused by alcohol), septic shock, ulcerative colitis, cachexia, and anorexia.

Another embodiment of the present invention is directed to the use of MGD-CSF polynucleotides, polypeptides, or antagonists to reduce MGD-CSF or NP_689669 mediated death of T cells in HIV-infected patients. The role of T cell apoptosis in the development of AIDS has been the subject of a number of studies (see, for example, Meyaard et al., *Science*, 257:217-219 (1992); Groux et al., *J. Exp. Med.*, 175:331 (1992); and Oyaizu et al., in *Cell Activation and Apoptosis in HIV Infection*, Andrieu and Lu, eds., Plenum Press, New York, pp. 101-114 (1995)).

It is likely that T cell apoptosis occurs through multiple mechanisms. Fas-mediated apoptosis has been implicated in the loss of T cells in HIV individuals (Katsikis et al., *J. Exp. Med.* 181:2029-2036 (1995). Activated human T cells are induced to undergo programmed cell death (apoptosis) upon triggering through the CD3/T cell receptor complex, a process termed activated-induced cell death (AICD). AICD of CD4 T cells isolated from HIV-infected asymptomatic individuals has been reported (Groux et al., supra). Thus, AICD may play a role in the depletion of CD4+ T cells and the progression to AIDS in HIV-infected individuals. Accordingly, the invention provides a method of inhibiting MGD-CSF-mediated T cell death in HIV patients, comprising administering molecules of the invention to the patients. In an embodiment, the patient is asymptomatic when treatment with MGD-CSF polynucleotides, polypeptides, or antagonists commences. If desired, prior to treatment, peripheral blood T cells may be extracted from an HIV patient, and tested for susceptibility to MGD-CSF-mediated cell death by procedures known in the art. In one embodiment, a patient's blood or plasma is contacted with molecules of the invention, for example, anti-MGD-CSF or NP_689669 antibodies, ex vivo. The antibodies or other antagonists may be bound to a suitable chromatography matrix by procedures known in the art. The patient's blood or plasma flows through a chromatography column containing the antagonist bound to the matrix, before being returned to the patient. The immobilized antagonist binds MGD-CSF or NP_689699, thus removing it from the patient's blood.

In additional embodiments, a molecule of the invention is administered in combination with other inhibitors of T cell apoptosis. For example, as discussed above, Fas-mediated apoptosis also has been implicated in loss of T cells in HIV positive individuals (Katsikis et al., *J. Exp. Med.*, 181:2029-2036 (1995)). Thus, a patient susceptible to both Fas ligand mediated and MGD-CSF-mediated T cell death may be treated with both an agent that blocks MGD-CSF or NP_689699 interactions with their receptors and an agent that blocks Fas-ligand/Fas interactions. Suitable agents for blocking binding of Fas-ligand to Fas include, but are not limited to, soluble Fas polypeptides; multimeric forms of soluble Fas polypeptides (for example, dimers of sFas/Fc); anti-Fas antibodies that bind Fas without transducing the biological signal that results in apoptosis; anti-Fas-ligand antibodies that block binding of Fas-ligand to Fas; and muteins of Fas-ligand that bind Fas but do not transduce the biological signal that results in apoptosis. Monoclonal antibodies may be employed according to this method. Examples of suitable agents for blocking Fas-ligand/Fas interactions, including blocking anti-Fas monoclonal antibodies, are described in WO 95/10540.

In another example, agents which block binding of MGD-CSF or NP_689669 to a receptor are administered with the molecules of the invention. Such agents include, but are not limited to, soluble MGD-CSF receptor polypeptides, multimeric forms of soluble receptor polypeptides, and MGD-CSF receptor antibodies that bind the MGD-CSF or NP_689669 receptor without transducing the biological signal that results in apoptosis, antibodies that block binding of MGD-CSF or NP_689669 to one or more receptors, and muteins that bind to receptors but do not transduce a biological signal that results in apoptosis.

Molecules of the invention may also be employed to regulate hematopoeisis, including erythropoiesis. Hematopoeisis is a multi-step cell proliferation and differentiation process which begins with a pool of multipotent stem cells. These cells can proliferate and differentiate into hematopoietic progenitors in reply to different stimuli. The molecules of the invention may be used to either stimulate or inhibit development of hematopoietic cells, for example, erythropoietic precursor cells.

In an embodiment, the molecules of the invention are used to treat or prevent bone diseases. Molecules of the invention promote the differentiation of hematopoeitic stem cells into osteoclastic precursor cells. Accordingly, molecules of the invention can be used to treat bone diseases such as those characterized by defects in osteoclast differentiation and function, for example, osteoporosis. MGD-CSF and related molecules may be used as therapeutics, for example, protein therapeutics or in gene therapy, to treat these diseases.

In an embodiment, the molecules of the invention are used to treat or prevent neural diseases. Molecules of the invention promote the differentiation of hematopoeitic stem cells into microglial precursor cells. Accordingly, molecules of the invention can be used to treat neural diseases such as those characterized by defects in microglial differentiation and function, for example, Alzheimer's disease, multiple sclerosis, acute disseminated encephalomyelopathy, progressive multifocal leukoencephalopathy, stroke, and Parkinson's disease. MGD-CSF and related molecules may be used as therapeutics, for example, protein therapeutics or in gene therapy, to treat these diseases.

In an embodiment, the molecules of the invention are used to treat or prevent cardiovascular disorders, including peripheral artery disease, such as limb ischemia. Cardiovascular disorders include cardiovascular abnormalities, such as arterio-arterial fistula, arteriovenous fistula, cerebral arteriovenous malformations, congenital heart defects, pulmonary atresia, and scimitar syndrome. Congenital heart defects include aortic coarctation, cor triatriatum, coronaryvessel anomalies, crisscross heart, dextrocardia, patent ductus arteriosus, Ebstein's anomaly, Eisenmenger complex, hypoplastic left heart syndrome, levocardia, trilogy of Fallot, tetralogy of Fallot, transposition of great vessels, double outlet right ventricle, tricuspid atresia, persistent truncus arteriosus, and heart septal defects, such as aortopulmonary septal defect, endocardial cushion defects, Lutembacher's Syndrome, and ventricular heart septal defects.

Cardiovascular disorders which can be treated with molecules of the invention also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, scimitar syndrome, cardiovascular syphilis, and cardiovascular tuberculosis.

Arrhythmias that can be treated with molecules of the invention include sinus arrhythmia, atrial fibrillation, atrial flutter, bradycardia, extrasystole, Adams-Stokes syndrome, bundle-branch block, sinoatrial block, long QT syndrome, parasystole, Lown-Ganong-Levine syndrome, Mahaim-type pre-excitation syndrome, Wolff-Parkinson-White syndrome, sick sinus syndrome, tachycardias, and ventricular fibrillation. Tachycardias that can be treated with molecules of the invention include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia. Heart valve diseases include aortic valve insufficiency, aortic valve stenosis, heart murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial disease that can be treated with molecules of the invention diseases also include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns syndrome, myocardial reperfusion injury, and myocarditis. Myocardial ischemias that can be treated with molecules of the invention include coronary diseases, such as angina pectoris, coronary aneurysm, coronary arteriosclerosis, coronary thrombosis, coronary vasospasm, myocardial infarction, and myocardial stunning.

Cardiovascular diseases that can be treated with molecules of the invention also include vascular diseases such as aneurysms, angiodysplasia, angiomatosis, bacillary angiomatosis, Hippel-Lindau disease, Klippel-Trenaunay-Weber syndrome, Sturge-Weber syndrome, angioneurotic edema, aortic diseases, Takayasu's arteritis, aortitis, Leriche's syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic venoocclusive disease, hypertension, hypotension, ischemia, peripheral vascular diseases, phlebitis, pulmonary venoocclusive disease, Raynaud's disease, CREST syndrome, retinal vein occlusion, scimitar syndrome, superior vena cava syndrome, telangiectasia, ataxia telangiectasia, hereditary hemorrhagic telangiectasia, varicocele, varicose veins, varicose ulcer, vasculitis, and venous insufficiency. Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases that can be treated with molecules of the invention include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders that can be treated with molecules of the invention include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subarachnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms that can be treated with molecules of the invention include air embolisms, amniotic fluid embolisms, cholesterol embolisms, blue toe syndrome, fat embolisms, pulmonary embolisms, and thromboembolisms. Thromboses include coronary thrombosis, hepatic vein thrombosis, retinal vein occlusion, carotid artery thrombosis, sinus thrombosis, Wallenberg's syndrome, and thrombophlebitis.

Ischemias that can be treated with molecules of the invention include cerebral ischemia, ischemic colitis, compartment syndromes, anterior compartment syndrome, myocardial ischemia, reperfusion injuries, and peripheral limb ischemia. Vasculitis that can be treated with molecules of the invention includes aortitis, arteritis, Behcet's syndrome, Churg-Strauss syndrome, mucocutaneous lymph node syndrome, thromboangiitis obliterans, hypersensitivity vasculitis, Schoenlein-Henoch purpura, allergic cutaneous vasculitis, and Wegener's granulomatosis.

The present further provides for treatment of diseases associated with neovascularization by administration of the molecules of the invention. Malignant and metastatic conditions which can be treated with the molecules of the invention include, but are not limited to those malignancies, solid tumors, and cancers described herein and otherwise known in the art (for a review of such disorders, see Fishman et al., *Medicine*, 4th ed., J.B. Lippincott Co., Philadelphia (1997)).

Additionally, ocular disorders associated with neovascularization which can be treated with molecules of the invention include, but are not limited to, neovascular glaucoma, diabetic retinopathy, retinoblastoma, retrolental fibroplasia, uveitis, retinopathy of prematurity, macular degeneration, corneal graft neovascularization, as well as other eye inflammatory diseases, ocular tumors, and diseases associated with choroidal or iris neovascularization. See, for example, reviews by Waltman et al., *Am. J. Ophthal.,* 85:704-710 (1978) and Gartner et al., *Surv. Ophthal.,* 22:291-312 (1978).

Additionally, disorders which can be treated with molecules of the invention include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Molecules of the invention antagonists thereof, are useful in the diagnosis and treatment or prevention of a wide range of diseases and/or conditions, including, but not limited to, cancer (for example, immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, and small cell carcinoma of the lung, stomach cancer, etc.). They are also useful in the diagnosis and treatment or prevention of lymphoproliferative disorders (for example, lymphadenopathy), microbial disorders (for example, viral, bacterial, etc.), infections, for example, HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (for example, HAV, HBV, HCV, etc.), *Helicobacter pylori* infection, invasive Staphylococci, etc.), and parasitic infection. They are further useful in the diagnosis and treatment or prevention of nephritis, bone disease (for example, osteoporosis), atherosclerosis, pain, cardiovascular disorders (for example, neovascularization, hypovascularization), and reduced circulation (for example, ischemic diseases, such as myocardial infarction, stroke, etc., AIDS, allergy, inflammation, neurodegenerative disease (for example, Alzheimer's disease, Parkinson's disease, amyotrophic lateral sclerosis, pigmentary retinitis, cerebellar degeneration, etc., graft rejection (acute and chronic), graft vs. host disease, diseases resulting from osteomyelodysplasia (for example, aplastic anemia, etc.), joint tissue destruction in rheumatism, liver disease (for example, acute and chronic hepatitis, liver injury, biliary disease, and cirrhosis), autoimmune disease (for example, multiple sclerosis, rheumatoid arthritis, SLE, immune complex glomerulonephritis, autoimmune diabetes, autoimmune thrombocytopenic purpura, Graves' disease, Hashimoto's thyroiditis, etc.), cardiomyopathy (for example, dilated cardiomyopathy), diabetes, diabetic complications (for example, diabetic nephropathy, diabetic neuropathy, diabetic retinopathy), influenza, asthma, psoriasis, glomerulonephritis, septic shock, and ulcerative colitis.

Molecules of the invention are useful in promoting angiogenesis and wound healing (for example, wounds, burns, and bone fractures). They are also useful as an adjuvant to enhance immune responsiveness to specific antigen and/or anti-viral immune responses.

More generally, the molecules of the invention are useful in modulating the immune response. For example, they may be useful in preparing for or recovering from surgery, trauma, radiation therapy; chemotherapy, and transplantation, or may be used to boost the immune response and/or the recovery process in elderly and immunocompromised individuals.

They are useful as immunosuppressive agents, for example, in the treatment or prevention of autoimmune disorders. In specific embodiments, molecules of the invention are used to treat or prevent chronic inflammatory, allergic, or autoimmune conditions, such as those described herein or otherwise known in the art.

The uses of the molecules of the invention include, but are not limited to, the treatment or prevention of adult respiratory distress syndrome, anaphylaxis, allergic asthma, allergen rhinitis, drug allergies (for example, to penicillin or cephalosporins), primary central nervous system lymphoma (PCNSL), glioblastoma, chronic lymphocytic leukemia (CLL), lymphadenopathy, rheumatoid arthritis, osteoarthritis, acute lymphoblastic leukemia (ALL), Hodgkin's disease and non-Hodgkin's lymphoma, opthalmopathy, uveoretinitis, the autoimmune phase of Type 1 diabetes, myasthenia gravis, autoimmune hepatological disorder, autoimmune inflammatory bowel disease, and Crohn's disease. The combination of MGD-CSF protein with an immunotherapeutic agent such as IL-2 or IL-12 may result in synergistic or additive effects useful in treating established cancers.

Additionally, the molecules of the invention may be employed not only as therapeutic molecules as described herein, but additionally as research tools in elucidating the biology of tumor-related diseases, such as cancer. Thus, molecules of the invention are useful for inhibiting the multiplication of a tumor cell or cancer cell, or for treating cancer in an animal. The molecules of the invention can be used accordingly in a variety of settings for the treatment of animal cancers such as sarcomas, adenomas, adenocarcinomas, carcinomas, papillomas, lymphomas, and the like. Other particular types of cancers that can be treated with molecules of the invention include, but are not limited to prostate, breast (including, for example, intraductal and inflammatory), colon, colorectal, bladder, ovarian, cervical, papillary carcinoma, papillary adenocarcinomas, cystadenocarcinoma, embryonal carcinoma, uterine cancer, and testicular cancer.

Antibodies and Vaccines

Antibodies

Antibodies specific to MGD-CSF or NP_689669 are suitable for use in the present invention and can be raised against the intact MGD-CSF protein or an antigenic polypeptide fragment thereof. The protein or fragment may be presented with or without a carrier protein, such as an albumin, to an animal, such as a rabbit or mouse). In general, polypeptide fragments are sufficiently immunogenic to produce a satisfactory immune response without a carrier if they are at least about 25 amino acids in length.

Antibodies of the invention include polyclonal and monoclonal antibody preparations, as well as preparations including hybrid antibodies, altered antibodies, chimeric antibodies and, humanized antibodies, as well as hybrid (chimeric) antibody molecules (see, for example, Winter et al., *Nature* 349: 293-299 (1991)); and U.S. Pat. No. 4,816,567); F(ab')$_2$ and F(ab) fragments; Fv molecules (noncovalent heterodimers, see, for example, Inbar et al., *Proc. Natl. Acad. Sci.* 69:2659-2662 (1972)); and Ehrlich et al. (1980) Biochem 19:4091-4096); single chain Fv molecules (sFv) (see, e.g., Huston et al., *Proc. Natl. Acad. Sci.* 85:5879-5883 (1980)); dimeric and trimeric antibody fragment constructs; minibodies (see, e.g., Pack et al., *Biochem.* 31:1579-1584 (1992); Cumber et al., *J. Immunology* 149B:120-126 (1992)); humanized antibody molecules (see, e.g., Riechmann et al., *Nature* 332:323-327 (1988); Verhoeyan et al., *Science* 239:1534-1536 (1988)); heteroconjugate and bispecific antibodies (see, e.g., U.S. Pat. No. 6,010,902 and U.S. Patent Appln. 2002/0155604); and any functional fragments obtained from such molecules, wherein such fragments retain specific binding.

Methods of making monoclonal and polyclonal antibodies are known in the art. Monoclonal antibodies are generally antibodies having a homogeneous antibody population. The term is not limited regarding the species or source of the antibody, nor is it intended to be limited by the manner in which it is made. The term encompasses whole immunoglobulins. Polyclonal antibodies are generated by immunizing a suitable animal, such as a mouse, rat, rabbit, sheep or goat, with an antigen of interest, such as a stem cell transformed with a gene encoding an antigen. In order to enhance immunogenicity, the antigen can be linked to a carrier prior to immunization. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Furthermore, the antigen may be conjugated to a bacterial toxoid, such as a toxoid from diphtheria, tetanus, cholera, etc., in order to enhance the immunogenicity thereof.

In addition, techniques developed for the production of chimeric antibodies (Morrison et al., *Proc. Natl. Acad. Sci.*, 81:851-855 (1984); Neuberger et al., *Nature*, 312:604-608 (1984); Takeda et al., *Nature*, 314:452-454 (1985)) by splicing genes from a mouse antibody molecule of appropriate antigen specificity together with genes from a human antibody molecule of appropriate biological activity can be used. Chimeric antibodies, which are antibodies in which different portions are derived from different animal species, such as those having a variable region derived from a murine monoclonal antibody and a human immunoglobulin constant region, for example, humanized antibodies, and insertion/deletions relating to cdr and framework regions, are suitable for use in the invention.

The invention also includes humanized antibodies, i.e., those with mostly human immunoglobulin sequences. Humanized antibodies of the invention generally refer to non-human immunoglobulins that have been modified to incorporate portions of human sequences. A humanized antibody may include a human antibody that contains entirely human immunoglobulin sequences.

The antibodies of the invention may be prepared by any of a variety of methods. For example, cells expressing an MGD-CSF or NP-689669 protein or an antigenic fragment thereof can be administered to an animal in order to induce the production of sera containing polyclonal antibodies. A preparation of MGD-CSF or NP_689669 protein can be prepared and purified to render it substantially free of natural contaminants, and the preparation introduced into an animal in order to produce polyclonal antisera with specific binding activity.

Antibodies of the invention specifically bind to their respective antigen(s); they may display high avidity and/or high affinity to a specific polypeptide, or more accurately, to an epitope of an antigen. Antibodies of the invention may bind to one epitope, or to more than one epitope. They may display different affinities and/or avidities to different epitopes on one or more molecules. When an antibody binds more strongly to one epitope than to another, adjusting the binding conditions can, in some instances, result in antibody binding almost exclusively to the specific epitope and not to any other epitopes on the same polypeptide, and not to a polypeptide that does not comprise the epitope.

The invention also provides monoclonal antibodies and MGD-CSF or NP_689669 protein binding fragments thereof. Monoclonal antibodies of the invention can be prepared using hybridoma technology, for example, Kohler et al., *Nature*, 256:495 (1975); Kohler et al., *Eur. J. Immunol.*, 6:511 (1976); Kohler et. al., *Eur. J. Immunol.*, 6:292 (1976); Hammerling et al., in: *Monoclonal Antibodies and T-Cell Hybridomas*, Elsevier, N.Y., (1981) pp. 563-681. In general, such procedures involve immunizing an animal (for example, a mouse) with an MGD-CSF protein antigen or with an MGD-CSF protein-expressing cell. Suitable cells can be recognized by their capacity to bind anti-MGD-CSF protein antibody. Such cells may be cultured in any suitable tissue culture medium; for example, in Earle's modified Eagle's medium supplemented with 10% fetal bovine serum (inactivated at about 56° C.), and supplemented with about 10 grams/liter of nonessential amino acids, about 1,000 U/ml of penicillin, and about 100 µg/ml of streptomycin. The splenocytes of such mice are extracted and fused with a suitable myeloma cell line. Any suitable myeloma cell line may be employed in accordance with the present invention; e.g., the parent myeloma cell line (SP20), available from the American Type Culture Collection (ATCC), Manassas, Va. After fusion, the resulting hybridoma cells are selectively maintained in HAT medium, and then cloned by limiting dilution, for example, as described by Wands et al., *Gastroenterology*, 80:225-232 (1981).

Alternatively, antibodies capable of binding to the MGD-CSF or NP_689669 protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, specific antibodies are used to immunize an animal such as a mouse. The splenocytes of such an animal are then used to produce hybridoma cells, and the hybridoma cells are screened to identify clones which produce an antibody whose ability to bind to the specific antibody can be blocked by the antigen. Such antibodies comprise anti-idiotypic antibodies to the MGD-CSF or NP_689669 protein-specific antibody and can be used to immunize an animal to induce formation of further specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, MGD-CSF protein-binding fragments can be produced through the application of recombinant DNA technology or through synthetic chemistry. Humanized chimeric monoclonal antibodies are suitable for in vivo use of anti-MGD-CSF in humans. Such humanized antibodies can be produced using genetic constructs derived from hybridoma cells producing the monoclonal antibodies described above. Methods for producing chimeric antibodies are known in the art. See, for review, Morrison, *Science*, 229:1202 (1985); Oi et al., *BioTechniques*, 4:214 (1986); Cabilly et al., U.S. Pat. No. 4,816,567; Taniguchi et al., EP 0 171 496; Morrison et al., EP 0 173 494; Neuberger et al., WO 8601533; Robinson et al., WO 8702671; Boulianne et al., *Nature*, 312:643 (1984); Neuberger et al., *Nature*, 314:268 (1985).

Vaccines

The invention provides a method for prophylactic or therapeutic treatment of a subject needing or desiring such treatment by providing a vaccine, that can be administered to the subject. It also provides a method for enhancing immune response to a subject by providing a substantially purified polypeptide from SEQ. ID. NOS.:7-12 or an active fragment;

providing a vaccine composition, and administering the polypeptide and vaccine compositions to the subject. The vaccine may comprise one or more of a polynucleotide, polypeptide, or modulator of the invention, for example an antibody vaccine composition, a polypeptide vaccine composition, or a polynucleotide vaccine composition, useful for treating cancer, proliferative, inflammatory, immune, metabolic, bacterial, or viral disorders.

For example, the vaccine can be a cancer vaccine, and the polypeptide can concomitantly be a cancer antigen. The vaccine may be an anti-inflammatory vaccine, and the polypeptide can concomitantly be an inflammation-related antigen. The vaccine may be a viral vaccine, and the polypeptide can concomitantly be a viral antigen. In some embodiments, the vaccine comprises a polypeptide fragment, comprising at least one extracellular fragment of a polypeptide of the invention, and/or at least one extracellular fragment of a polypeptide of the invention minus the signal peptide, for the treatment, for example, of proliferative disorders, such as cancer. In certain embodiments, the vaccine comprises a polynucleotide encoding one or more such fragments, administered for the treatment, for example, of proliferative disorders, such as cancer. Further, the vaccine can be administered with or without an adjuvant. The vaccine can be administered with polypeptides shown in the Tables and Sequence Listing; it may be administered prior to, substantially contemporaneously with, or after administering the polypeptides.

Vaccine therapy involves the use of polynucleotides, polypeptides, or agents of the invention as immunogens for tumor antigens (Machiels et al., *Semin. Oncol.* 29: 494-502, 2002). For example, peptide-based vaccines of the invention include unmodified subject polypeptides, fragments thereof, and MHC class I and class II-restricted peptide (Knutson et al., *J. Clin. Invest.* 07:477-484, 2001), comprising, for example, the disclosed sequences with universal, nonspecific MHC class II-restricted epitopes. Peptide-based vaccines comprising a tumor antigen can be given directly, either alone or in conjunction with other molecules. The vaccines can also be delivered orally by producing the antigens in transgenic plants that can be subsequently ingested (U.S. Pat. No. 6,395, 964).

In some embodiments, antibodies themselves can be used as antigens in anti-idiotype vaccines. That is, administering an antibody to a tumor antigen stimulates B cells to make antibodies to that antibody, which in turn recognize the tumor cells Nucleic acid-based vaccines can deliver tumor antigens as polynucleotide constructs encoding the antigen. Vaccines comprising genetic material, such as DNA or RNA, can be given directly, either alone or in conjunction with other molecules. Administration of a vaccine expressing a molecule of the invention, e.g., as plasmid DNA, leads to persistent expression and release of the therapeutic immunogen over a period of time, helping to control unwanted tumor growth.

In some embodiments, nucleic acid-based vaccines encode subject antibodies. In such embodiments, the vaccines (e.g., DNA vaccines) can include post-transcriptional regulatory elements, such as the post-transcriptional regulatory acting RNA element (WPRE) derived from Woodchuck Hepatitis Virus. These post-transcriptional regulatory elements can be used to target the antibody, or a fusion protein comprising the antibody and a co-stimulatory molecule, to the tumor microenvironment (Pertl et al., *Blood*, 101:649-654, 2003).

Besides stimulating anti-tumor immune responses by inducing humoral responses, vaccines of the invention can also induce cellular responses, including stimulating T-cells that recognize and kill tumor cells directly. For example, nucleotide-based vaccines of the invention encoding tumor antigens can be used to activate the $CD8^+$ cytotoxic T lymphocyte arm of the immune system.

In some embodiments, the vaccines activate T-cells directly, and in others they enlist antigen-presenting cells to activate T-cells. Killer T-cells are primed, in part, by interacting with antigen-presenting cells, for example, dendritic cells. In some embodiments, plasmids comprising the nucleic acid molecules of the invention enter antigen-presenting cells, which in turn display the encoded tumor-antigens that contribute to killer T-cell activation. Again, the tumor antigens can be delivered as plasmid DNA constructs, either alone or with other molecules.

Since MGD-CSF and NP_689669 can promote dendritic cell differentiation in vitro from either human bone marrow $CD34^+$ stem cells or peripheral blood monocytes, molecules of the invention can be used to expand dendritic cells ex vivo. The expanded cell population can then be returned to the patient, for example, as a dendritic cell vaccine. Furthermore, molecules of the invention may promote dendritic cell differentiation from autologous hematopoietic stem cells and/or monocytes in vivo in the patient, which will enhance the patient's antigen presenting capability, and contribute to the ability to combat certain diseases, such as cancer.

In further embodiments, RNA can be used in vaccine production. For example, dendritic cells can be transfected with RNA encoding tumor antigens (Heiser et al., *J. Clin. Invest.* 109:409-417, 2002; Mitchell and Nair, *J. Clin. Invest.* 106: 1065-1069, 2000). This approach overcomes the limitations of obtaining sufficient quantities of tumor material, extending therapy to patients otherwise excluded from clinical trials. For example, a subject RNA molecule isolated from tumors can be amplified using RT-PCR. In some embodiments, the RNA molecule of the invention is directly isolated from tumors and transfected into dendritic cells with no intervening cloning steps.

In some embodiments the molecules of the invention are altered such that the peptide antigens are more highly antigenic than in their native state. These embodiments address the need in the art to overcome the poor in vivo immunogenicity of most tumor antigens by enhancing tumor antigen immunogenicity via modification of epitope sequences (Yu and Restifo, *J. Clin. Invest.* 110:289-294, 2002).

Another recognized problem of cancer vaccines is the presence of preexisting neutralizing antibodies. Some embodiments of the present invention overcome this problem by using viral vectors from non-mammalian natural hosts, for example, avian pox viruses. Alternative embodiments that also circumvent preexisting neutralizing antibodies include genetically engineered influenza viruses, and the use of naked plasmid DNA vaccines that contain DNA with no associated protein (Yu and Restifo, *J. Clin. Invest.* 110:289-294, 2002).

All of the immunogenic methods of the invention can be used alone or in combination with other conventional or unconventional therapies. For example, immunogenic molecules can be combined with other molecules that have a variety of antiproliferative effects, or with additional substances that help stimulate the immune response, i.e., adjuvants or cytokines.

For example, in some embodiments, nucleic acid vaccines encode an alphaviral replicase enzyme, in addition to tumor antigens. This approach to vaccine therapy successfully combines therapeutic antigen production with the induction of the apoptotic death of the tumor cell (Yu and Restifo, *J. Clin. Invest.* 110:289-294, 2002).

In some embodiments, a molecule of the invention is involved in the control of cell proliferation, and an agent of the invention inhibits undesirable cell proliferation. Such agents are useful for treating disorders that involve abnormal cell proliferation, including, but not limited to, cancer, psoriasis, and scleroderma. Whether a particular agent and/or therapeutic regimen of the invention is effective in reducing unwanted cellular proliferation, e.g., in the context of treating cancer, can be determined using standard methods. For example, the number of cancer cells in a biological sample (e.g., blood, a biopsy sample, and the like), can be determined. The tumor mass can be determined using standard radiological or biochemical methods.

The molecules of the invention find use in immunotherapy of hyperproliferative disorders, including cancer, neoplastic, and paraneoplastic disorders. That is, the subject molecules can correspond to tumor antigens, of which over 1770 have been identified to date (Yu and Restifo, *J. Clin. Invest.* 110: 289-294, 2002). Immunotherapeutic approaches include passive immunotherapy and vaccine therapy and can accomplish both generic and antigen-specific cancer immunotherapy.

Passive immunity approaches involve antibodies of the invention that are directed toward specific tumor-associated antigens. Such antibodies can eradicate systemic tumors at multiple sites, without eradicating normal cells. In some embodiments, the antibodies are combined with radioactive components, as provided above, for example, combining the antibody's ability to specifically target tumors with the added lethality of the radioisotope to the tumor DNA.

Useful antibodies comprise a discrete epitope or a combination of nested epitopes, i.e., a 10-mer epitope and associated peptide multimers incorporating all potential 8-mers and 9-mers, or overlapping epitopes (Dutoit et al., *J. Clin. Invest.* 110:1813-1822, 2002). Thus a single antibody can interact with one or more epitopes. Further, the antibody can be used alone or in combination with different antibodies, that all recognize either a single or multiple epitopes.

Neutralizing antibodies can provide therapy for cancer and proliferative disorders. Neutralizing antibodies that specifically recognize a protein or peptide of the invention can bind to the protein or peptide, e.g., in a bodily fluid or the extracellular space, thereby modulating the biological activity of the protein or peptide. For example, neutralizing antibodies specific for proteins or peptides that play a role in stimulating the growth of cancer cells can be useful in modulating the growth of cancer cells. Similarly, neutralizing antibodies specific for proteins or peptides that play a role in the differentiation of cancer cells can be useful in modulating the differentiation of cancer cells.

MGD-CSF "Knock-Outs" and Homologous Recombination

Endogenous gene expression can be reduced by inactivating or "knocking out" a gene of interest and/or its promoter using targeted homologous recombination, for example, Smithies et al., *Nature,* 317:230-234 (1985); Thomas et al., *Cell,* 51:503-512 (1987); and Thompson et al., *Cell,* 5:313-321 (1989). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express, the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene, for example, Thomas et al., *Cell* 51:503-512, (1987); Thompson (1989), supra). However, this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention, such as knockouts, are administered to a patient in vivo. Such cells may be obtained from the patient, including humans and non-human animals, or an MHC compatible donor, and can include, but are not limited to, fibroblasts, bone marrow cells, blood cells (for example, lymphocytes), adipocytes, muscle cells, endothelial cells, etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and/or vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and secretion, of the polypeptides of the invention. The engineered cells which express and secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic Non-Human Animals

The polypeptides of the invention can also be expressed in transgenic non-human animals. Animals of any species, including, but not limited to, mice, rats, rabbits, hamsters, guinea pigs, pigs, micro-pigs, goats, sheep, cows, and non-human primates, for example, baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (embodied in polynucleotides shown in the Sequence Listing) into animals to produce a founder lines of transgenic animals. Such techniques include, but are not limited to, pronuclear microinjection (Paterson et al., *Appl. Microbiol. Biotechnol.* 40:691-698 (1994); Carver et al., *Biotechnology* (NY) 11:1263-1270 (1993); Wright et al., *Biotechnology* (NY) 9:830-834 (1991); and Hoppe et al., U.S. Pat. No. 4,873,191 (1989)); retrovirus mediated gene transfer into germ lines (Van der Putten et al., *Proc. Natl. Acad. Sci.* 82:6148-6152 (1985)), blastocysts or embryos; gene targeting in embryonic stem cells (Thompson et al., *Cell* 56:313-321 (1989)); electroporation of cells or embryos (Lo, *Mol. Cell. Biol.* 3:1803-1814 (1983)); introduction of the polynucleotides of the invention using a gene gun (see, for example, Ulmer et al., *Science* 259:1745 (1993); introducing nucleic acid constructs into embryonic pluripotent stem cells and transferring the stem cells back into the blastocyst; and sperm-mediated gene transfer (Lavitrano et al., *Cell* 57:717-723 (1989); etc. For a review of such techniques, see Gordon, *Intl. Rev. Cytol.* 115:171-229 (1989). See also, U.S. Pat. No. 5,464,764 (Capecchi et al., Positive-Negative Selection Methods and Vectors); U.S. Pat. No. 5,631,153 (Capecchi et al., Cells and Non-Human Organisms Containing Predetermined Genomic Modifications and Positive-Negative Selection Methods and Vectors for Making Same); U.S. Pat. No. 4,736,866 (Leder et al., Transgenic Non-Human Animals); and U.S. Pat. No. 4,873,191 (Wagner et al., Genetic Transformation of Zygotes). Any technique known in the art may be used to produce transgenic clones containing polynucleotides of the invention, for example, nuclear transfer into enucleated oocytes of nuclei from cultured embryonic, fetal, or adult cells induced to quiescence (Campbell et al., *Nature* 380:64-66 (1996); Wilmut et al., *Nature* 385:810-813 (1997)).

The invention provides for transgenic animals that carry the transgene in all their cells, as well as animals which carry the transgene in some, but not all their cells, such as mosaic or chimeric animals. The transgene may be integrated as a single transgene or as multiple copies such as in concatamers, for example, head-to-head tandems or head-to-tail tandems. The transgene may also be selectively introduced into and activated in a particular cell type by following, for example, the teaching of Lasko et al. (*Proc. Natl. Acad. Sci.* 89:6232-6236 (1992)). The regulatory sequences required for such a cell-type specific activation will depend upon the particular cell type of interest, and will be apparent to those of skill in the art. It may be desired that the polynucleotide transgene be integrated into the chromosomal site of the endogenous gene, gene targeting is then suitable. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (*Science* 265:103-106 (1994)). The regulatory sequences required for such a cell-type specific inactivation will depend upon the particular cell type of interest, and will be apparent to those of skill in the art.

Once transgenic animals have been generated, the expression of the recombinant gene may be assayed using standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (RT-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of molecules of the invention studying conditions and/or disorders associated with aberrant expression of molecules of the invention, and in screening for compounds effective in ameliorating such conditions and/or disorders.

Kits

The present invention provides kits that can be used in the above methods. In one embodiment, a kit comprises an antibody of the invention, for example, a purified antibody, in one or more containers. In an embodiment, the kits of the invention contain a substantially isolated polypeptide comprising an epitope which is specifically immunoreactive with an antibody included in the kit. The kits of the invention may also comprise a control antibody which does not react with the polypeptide of interest.

In an embodiment, the kits of the present invention comprise a means for detecting the binding of an antibody to a polypeptide of interest. For example, the antibody may be conjugated to a detectable substrate such as a fluorescent compound, an enzymatic substrate, a radioactive compound or a luminescent compound, or a second antibody which recognizes the first antibody may be conjugated to a detectable substrate).

In an embodiment, the kit is a diagnostic kit for use in screening serum containing antibodies specific against MGD-CSF related molecules. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of the antibody to the antigen. The antibody may be conjugated to a fluorescent compound, such as fluorescein or rhodamine, which can be detected by flow cytometry. In an embodiment, the kit may include a recombinantly produced or chemically synthesized polypeptide antigen. The polypeptide antigen of the kit may also be attached to a solid support.

In a further embodiment, the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In an embodiment, the antibody is attached to a solid support. In an embodiment, the antibody is a monoclonal antibody. The detecting means of the kit may include a second, labeled monoclonal antibody. Alternatively, or in addition, the detecting means may include a labeled, competing antigen.

In a diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate.

The solid surface reagent may be prepared by known techniques for attaching protein material to solid support material, such as polymeric beads, dip sticks, 96-well plates, and/or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with a biotinylated antigen.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. Moreover, advantages described in the body of the specification, if not included in the claims, are not per se limitations to the claimed invention.

It is to be understood that both the foregoing general description and the following detailed description are exemplary and explanatory only and are not restrictive of the invention, as claimed. Moreover, it must be understood that the invention is not limited to the particular embodiments described, as such may, of course, vary. Further, the terminology used to describe particular embodiments is not intended to be limiting, since the scope of the present invention will be limited only by its claims. The claims do not encompass embodiments in the public domain.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. Further, all publications mentioned herein are incorporated by reference in their entireties.

It must be noted that, as used herein and in the appended claims, the singular forms "a," "or," and "the" include plural referents unless the context clearly dictates otherwise. Thus, for example, reference to "a subject polypeptide" includes a plurality of such polypeptides and reference to "the agent" includes reference to one or more agents and equivalents thereof known to those skilled in the art, and so forth.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

The specification is most thoroughly understood in light of the references cited herein. Each of these references is hereby incorporated by the reference in its entirety.

EXAMPLES

The examples, which are intended to be exemplary of the invention and should therefore not be considered to limit the invention in any way, also describe and provide detail for aspects and embodiments of the invention discussed above. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Amino Acid Sequence Alignment of MGD-CSF with MCG34647

MGD-CSF and NP_689669 were compared by aligning their amino acids using the program clustal format for T-COFFEE Version 1.37, cpu=0.00 sec., score=72, Nseq=3, len=242. As shown in FIG. 1, the amino acid sequence of MGD-CSF differs from the amino acid sequence of NP_689669 (MCG34647). The latter sequence has a glutamine (Q) residue at amino acid 81. The five flanking amino acid residues adjacent to and on either side of amino acid 81 in the NCBI sequence of MCG34647 are NVTRLQRAQVS (SEQ ID NO.:279). In contrast to this published sequence of MCG34647, MGD-CSF contains the amino acid sequence NVTRLRAQVS (SEQ ID NO.:280). The difference between these sequences results from alternative splicing of the MCG34647 gene between exons 3 and 4. The genome sequences at the exon 3-4 boundary are the codons aac gtc acc agg ctg gtg (SEQ ID NO.:281) and cag cag agg gcc cag gtg agc (SEQ ID NO.:282), wherein the gtg codon (shown in italics) represents the 5' splice donor site at the end of exon 3, and the two cag codons (shown in italics) represent two alternative splice acceptor sites at the beginning of exon 4. Thus, the published MCG34647 sequence represents a transcript resulting from the use of the first cag splice acceptor site, while the MGD-CSF sequence represents a transcript resulting from the use of the second cag splice acceptor site.

The MCG34647 glutamine 81 residue is encoded by the second cag codon, which is not spliced out when the first cag splice acceptor site is used. In contrast, the use of the second cag as the splice acceptor site results in the first cag sequence being spliced out of the resulting RNA transcript, which in turn results in the lack of a corresponding glutamine in the MGD-CSF splice variant. Hence, MGD-CSF is a splice variant and represents RNA and protein species that are distinct from MCG34647.

Example 2

Plasmid Vectors for MGD-CSF Expression

The MGD-CSF gene was cloned into pTT-5 and pTT-2 mammalian expression vectors modified as shown in FIG. 2 and FIG. 3 using standard cloning procedures. The MGD-CSF gene was also cloned into the pIB/V5His-DEST insect cell expression vector (Invitrogen, Carlsbad Calif.) using standard cloning procedures. The resulting constructs are described in Table 1 and Table 5. They include human MGD-CSF untagged in vector pTT5 (MGD-CSF), human MGD-CSF untagged in vector pTT2 (CLN00839395), human MGD-CSF with a C-terminal V5H8 tag in vector pTT5 (CLN00732663), human MGD-CSF tagged with V5H8 (CLN00732663), human MGD-CSF with a C-terminal V5H8 tag in vector pTT2 (CLN00840351), human MGD-CSF with a C-terminal V5H8 tag in vector pIB/V5His-DEST, (CLN00758593), and human MGD-CSF with a collagen secretory leader and a C-terminal Streptag in vector pTT5-G (CLN00816424).

To monitor the expression and secretion of MGD-CSF and to aid in its purification, the construct CLN00821867 was generated with a Tobacco Etch Virus (TEV) protease recognition site engineered between the protein and a C-terminal cleavable tag. The seven amino acid recognition site for TEV protease is Glu-Asn-Leu-Tyr-Phe-Gln-Gly (SEQ ID NO.: 283) with cleavage occurring between Gln and Gly. Construct CLN00821867 was designated MGD-CSF(1 to 241aa)_TEV_V5_Streptag II_H8 and C-tagged in vector pTT5-I.

To improve the secretion of MGD-CSF, its secretory signal peptide, which is encoded by the first 20 amino acids, was replaced by the 23 amino acids that encode the signal peptide of collagen (GenBank® protein accession number NP_001842). This construct, CLN00848149, was designated MGD-CSF collagen SP(1-23aa)_MGD-CSF(21 to 241aa), and is untagged in vector pTT5-G. Another such construct also has a TEV protease recognition site engineered between the protein and the C-terminal cleavable tag. CLN00816424 was designated MGD-CSF collagen SP(1-23aa)_MGD-CSF(21 to 241 aa)_TEV_V5_Streptag II_H8, and is C-tagged in vector pTT5-G. A third such construct was generated with a TEV site engineered between the N-terminal tag and the protein. CLN00816425 was designated MGD-CSF collagenSP(1-23aa)_H8_Streptag II_V5_TEV_MGD-CSF(21 to 241 aa), and is N-tagged in vector pTT5-H.

Deletion constructs were generated in which amino acids were deleted from the N-terminal, C-terminal, or both ends of mature proteins. The MGD-CSF signal peptide of these deletion constructs was replaced with the collagen signal peptide. CLN00848160 has 25 N-terminal amino acids deleted; it was designated MGD-CSF collagenSP(1-23aa)_MGD-CSF(26 to 241 aa), and is untagged in vector pTT5. CLN00848173 has 30 N-terminal amino acids deleted; it was designated MGD-CSF collagenSP(1-23aa)_MGD-CSF(31 to 241aa), and is untagged in vector pTT5. CLN00848209 has 5 C-terminal amino acids and 20 N-terminal amino acids (signal peptide) deleted; it was designated MGD-CSF collagenSP(1-23aa)_MGD-CSF(21 to 236aa), and is untagged in vector pTT5. CLN00848197 has 10 C-terminal amino acids and 20 N-terminal amino acids (signal peptide) deleted; it was designated MGD-CSF collagenSP(1-23aa)_MGD-CSF(21 to 231aa), and is untagged in vector pTT5. CLN00848185 has 28 C-terminal amino acids and 20 N-terminal amino acids (signal peptide) deleted; it was designated MGD-CSF collagenSP(1-23aa)_MGD-CSF(21 to 213aa), and is untagged in vector pTT5. CLN00848220 has 25 N-terminal amino acids and 10 C-terminal amino acids deleted; it was designated MGD-CSF collagenSP(1-23aa)_MGD-CSF(26 to 231aa), and is untagged in vector pTT5.

Two mouse orthologs of MGD-CSF were identified and cloned by standard procedures into untagged pTT5 (CLN00840257 and CLN00847948) and into pTT5-I tagged with a TEV site between the clone and the tag (CLN00840253 and CLN00842712). These orthologues can be used to perform animal studies relating to the biological activity of MGD-CSF in mouse tissues and cells.

The mouse orthologs represented by constructs CLN00840257 and CLN00840235, were derived from *Mus musculus* adult male small intestine cDNA clone 2010004A03 from the RIKEN full-length enriched library; hypothetical protein 12842043; at locus AK008082. The construct CLN00840257 represents the open reading frame (ORF) of the nucleotide sequence of phantom clone 2010004A03, and is a mouse ortholog of human MGD-CSF cloned into vector pTT5. The construct CLN00840253 represents the ORF of the nucleotide sequence of phantom clone 2010004A03, and was cloned into vector pTT5-L.

The mouse orthologs represented by constructs CLN00847948 and CLN00842712 were derived from *Mus musculus* cDNA clone 2010004A03, mRNA (cDNA clone MGC:28891 IMAGE:4912097), complete cds 18921436, from the RIKEN full-length enriched library, at locus BC016254. The construct CLN00847948 (18921436) represents the ORF nucleotide sequence of human MGD-CSF cloned into vector pTT5. The construct CLN00842712 (18921436) represents the ORF nucleotide sequence of human MGD-CSF cloned into vector pTT5.

Example 3

Transient Expression in Mammalian Cells

Complementary DNA encoding the MGD-CSF polypeptide was cloned into the expression vectors pTT5 and pCDNA-pDEST40 and expressed as both a tagged and untagged protein. Protein levels were quantified by measuring the levels of the tag, for example, a V5H is tag, by quantitative Western blot analysis. The expression vectors were transfected into adherent 293T cells using the transfection agent Fugene 6 (Roche, Nutley N.J.) in DMEM with 10% fetal bovine serum (FBS) and penicillin/streptomycin (100 µg/ml, 100 U/ml), and incubated at 37° C. in 5% $CO_2$ for 40 hours, after which the cells were washed with PBS and incubated for an additional 48 hours in complete DMEM. Cell supernatant was harvested, cleared of cell debris by centrifugation, and tested for biological activity (untagged cDNA) and protein expression (V5 tagged cDNA) by Western blot assay using an anti-V5 antibody.

Expression studies were also performed with 293-6E cells transiently expressing tagged MGD-CSF constructs in suspension culture. Cells were diluted to a density of 6×10$^5$ cells/ml in 25 ml FreeStyle medium (Invitrogen, Carlsbad Calif.) 18-24 hours before transfection. Transfection complexes were prepared by adding 25 μg DNA to 1.25 ml PBS, adding 50 μl linear 25 kD polyethylenimine (PEI) (Polysciences, Warrington Pa.) dissolved in water at a concentration of 1 mg/ml, mixing the solutions, and incubating the mixture for 1 hour at room temperature before adding it to the cells to be transfected. Cells and their supernatants were harvested 3-6 days post-transfection and protein expression was evaluated by Western blot analysis.

Cell suspensions (1 ml) were pelleted then mixed with four parts XT sample buffer (Bio-Rad, Hercules Calif.). Following denaturation at 99° C. for 3 minutes, samples were either loaded onto a Criterion XT SDS-PAGE gel (Bio-Rad, Hercules Calif.) or stored at −20° C. Cell pellets were lysed by resuspension in 100 μl lysis buffer (1% NP-40; 50 mM Tris-HCl, pH 8.0; 150 mM NaCl; and one tablet complete protease inhibitors (Roche, Indianapolis Ind.)). Lysed cells were pelleted by centrifugation at 14,000 rpm and the proteins of the resulting cleared lysate, as well as the cell supernatants, were separated by SDS-PAGE and transferred to a nitrocellulose membrane. Western blotting was performed by probing the membrane with a HRP-conjugated monoclonal antibody specific for the V5-epitope (Invitrogen, Carlsbad Calif.) or with a polyclonal rabbit-anti-MGD-CSF antibody (Five Prime Therapeutics, Inc., South San Francisco Calif.). Bound rabbit-anti-MGD-CSF antibody was detected with polyclonal goat-anti-rabbit conjugated to horseradish peroxidase (Jackson Immuno Research, West Grove Pa.). Immunocomplexes were visualized by incubating the membrane in chemiluminescence substrate (SuperSignal West Femto, Pierce, Rockford Ill.) and exposing it to light sensitive film.

Figure 4:
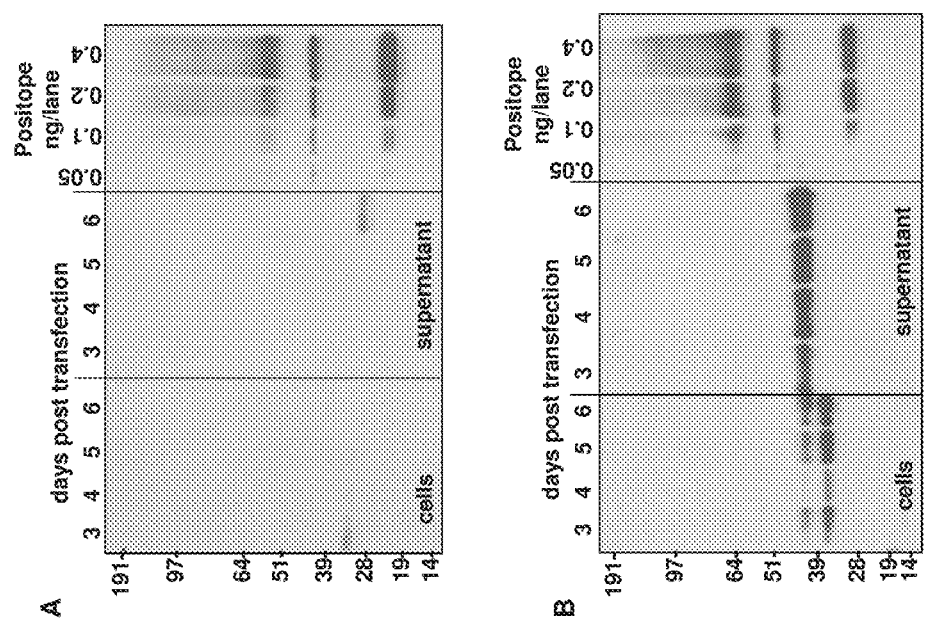
FIG. 4 shows the expression of MGD-CSF with plasmid vectors on days 3 through 6 post-transfection, as further described in Example 3 and Table 1.

As shown in FIGS. 4A and 4B, 293-6E cells expressed tagged MGD-CSF between 3 and 6 days after transfection. FIG. 4A shows the expression of MGD-CSF tagged with V5H8 (CLN00732663) transiently transfected into 293-6E cells. The left panel shows intracellular MGD-CSF. Expression was most prominent at day 3 post-transfection. The middle panel shows MGD-CSF secreted into the supernatant. Expression was most prominent at day 6 post-transfection. The right panel shows a quantitative positive control (Positope, Invitrogen, Carlsbad, Calif.)

FIG. 4B shows the expression of MGD-CSF with a collagen secretory sequence and tagged with V5H8 (CLN00816424). The left panel shows intracellular MGD-CSF. Expression was observed at day 3 and continued to increase through day 6 post-transfection. The middle panel shows MGD-CSF secreted into the supernatant; its expression also increased from day 3 to day 6. The right panel shows a quantitative positive control (Positope, Invitrogen, Carlsbad, Calif.).

In both FIGS. 4A and 4B, the protein loads of the cells and supernatants were matched so that the gel loads of the left and middle panels reflect comparable cell numbers. Thus, the amount of MGD-CSF shown in the middle panels reflects the cells' secretory efficiency. Tagged protein detected in the supernatant had a molecular weight of approximately 40 kD, whereas the intracellular protein had a molecular weight of approximately 37 kD, presumably due to incomplete glycosylation. Yields of the secreted protein differed depending on the construct design. CLN00732663 was expressed intracellularly at a low yield. The 37 kD form, and not the 40 kD form, was detected in cell culture supernatant six days post transfection, also at a low yield (approximately 5-10 ng/ml), possibly due to cell lysis. Replacing the endogenous signal peptide with the exogenous secretion signal and an extended cleavable C-terminal tag increased expression and secretion at least 10-fold (CLN00816424). In addition, only the higher molecular weight protein band was detectable in the supernatant of cell cultures transfected with CLN00816424, indicating the protein was secreted and did not originate from lysed cells.

Example 4

Proliferation and Viability of Transfected Cells

Figure 5:
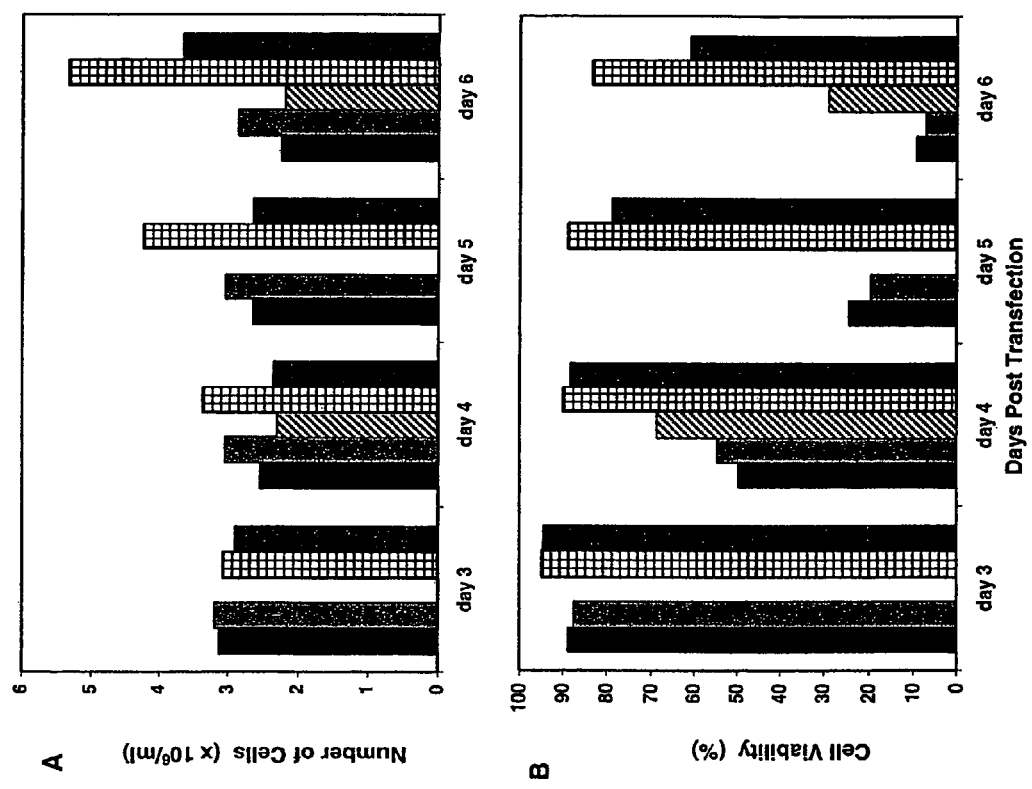
FIG. 5 shows the degree of proliferation and the viability of cells transfected with constructs described in Example 2 and Table 1 from days 3 through 6 post-transfection, as further described in Example 4 and Table 1.

As shown in FIG. 5A and Table 1, 293-6E cells transiently transfected with CLN00816424 continued to proliferate from days 3 through 6 post-transfection. The density of the cells in suspension culture was monitored by counting cells that excluded trypan blue using a hemocytometer from day 3 through day 6 following transfection with CLN00542945 (black), CLN00732663 (light grey), CLN00821867 (diagonal stripe), and CLN00816424 (cross-hatch), and compared to a control gene encoding secreted alkaline phosphatase (SEAP) (dark grey). Both the control SEAP cells and the cells transfected with CLN00816424 (MGD-CSF with a collagen leader) increased in number from day 3 through day 6. Cells transfected with CLN00542945 (untagged MGD-CSF), CLN00732663 (V5H8-tagged MGD-CSF), or CLN00821867 (streptagged MGD-CSF) did not proliferate.

As shown in FIG. 5B, cells transiently transfected with CLN00816424 (MGD-CSF with a collagen leader) remained viable. They maintained greater than 80% viability during 6 days in culture. The viability of the cells in suspension culture was monitored by Trypan Blue exclusion using a hemocytometer from day 3 to day 6 following transfection with CLN00542945 (black), CLN00732663 (light grey), CLN00821867 (diagonal stripe), and CLN00816424 (cross-hatch), and compared to a control gene encoding secreted alkaline phosphatase (SEAP) (dark grey). Cells expressing MGD-CSF, CLN00732663, and CLN00821867, showed increased cell toxicity, evidenced by their decreased viability over time in culture. This toxicity is not specific to MGD-CSF cDNA in host 293 cells, but rather is observed only under certain culture conditions.

Example 5

Stable Transfection in Mammalian Cells

MGD-CSF was stably expressed by transfected adherent 293-T cells. Stable transfection was performed in 293-T cells purchased from ATCC (Manassas Va.) and cultured in complete DMEM medium (DMEM medium supplemented with 10% FBS (Mediatech, Herndon Va.); 100 U/ml penicillin, 100 μg/ml streptomycin, and 2 mM glutamine (Invitrogen, Carlsbad Calif.)). The day before transfection, 1.25×10$^5$ cells were seeded into a T-175 culture flask (Corning, Acton MA) and incubated overnight at 37° C. with 5% CO$_2$. Cells were transfected by mixing 114 μl Fugene6 (Roche, Nutley N.J.) with 1.9 ml RPMI-1640 medium (Mediatech, Herndon Va.) and incubated for 5 minutes at room temperature. Plasmid DNA (19 μg full length MGD-CSF in pIRESpuro3) (BD Biosciences, San Jose, Calif.) was added to the Fugene/media mix and incubated for 15 minutes at room temperature. The lipid/DNA mixture was transferred into the T-175 flask and incubated with the cells for 16 hours. The following day, the cells were detached with 0.25% trypsin (Invitrogen, Carlsbad Calif.) and expanded into three T-175 flasks. After approximately 16 hours, the cells were attached to the culture vessel and the selection reagent puromycin (Invivogen, San Diego Calif.) was added to a final concentration of 10 mg/ml. Selection medium was changed once a week and the cell viability monitored for 4-6 weeks. Expression was validated by Western blot analysis using the polyclonal rabbit-anti-MGD-CSF antibody described above.

Adherent 293-T cells stably expressing MGD-CSF were adapted to suspension culture in low-serum or serum free medium. Cells were resuspended at a concentration of $10^6$/ml in FreeStyle medium (Invitrogen, Carlsbad Calif.) or in HyQ PF CHO LS medium (Hyclone, Logan Utah), respectively, and supplemented with 5% FBS (Mediatech, Herndon, Va.). Suspension cell cultures were maintained at a volume of 50 ml in a 250 ml shake flask and cultured at 37° C. and 5% $CO_2$. The medium was changed twice a week and the cells were maintained at a density at or below approximately $10^6$/ml. Cell viability was measured by Trypan Blue exclusion. When viability exceeded 80%, the serum concentration was progressively reduced to 3%, 2%, 1%, then serum free. Transfected cells adapted to conditions of reduced or absent serum. Cell viability and protein yields of 293-T cells transiently expressing untagged MGD-CSF was considerably higher after four days in culture in HyQ-CHO media with 1% FBS than the viability and yields observed after six days of transient expression in 293-E cells cultured in Free Style media with 3% FBS.

Figure 6:
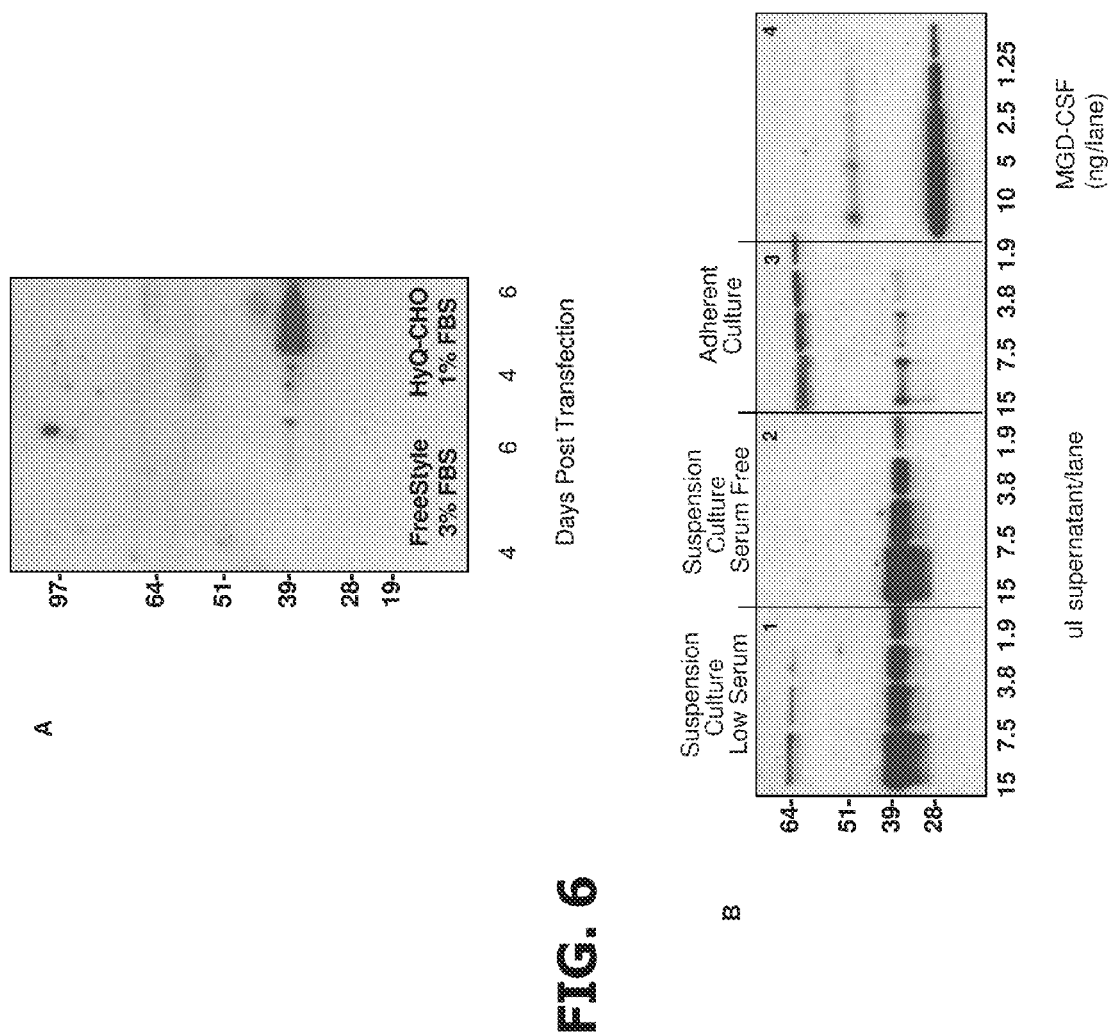
FIG. 6 shows that adherent 293-T cells expressing MGD-CSF can be adapted to culture conditions with low serum concentrations, as further described in Example 5.

Adherent 293-T cells maintained in FreeStyle medium with 3% FBS grew relatively slowly; their viability was 67% after three passages. In comparison, cells maintained in HyQ PF CHO LS medium with 1% FBS grew more quickly; their viability was >85% after four passages. As shown in FIG. 6A, the protein yields of cultures in HyQ PF CHO LS medium and 1% FBS (right panel) were increased more than 10-fold compared to the yields from cells cultured in FreeStyle medium supplemented with 3% FBS (left panel), as determined by quantitative Western blot.

As shown in FIG. 6B, high protein yields were obtained from stably transfected MGD-CSF 293-T cells adapted to grow in suspension culture with low serum or with serum free media, as shown by Western blot analysis. Stably transfected MGD-CSF 293-T cells adapted to grow in suspension culture with low serum secreted 8-fold more (1.3 µg ml) (panel 1). Those grown in serum free media secreted 4-fold more (650 ng/ml) (panel 2) MGD-CSF into the culture supernatant within 6 days than stably transfected MGD-CSF 293-T cells growing adherently as described above for 4 days (approximately 160 ng/ml) (panel 3). MGD-CSF expressed in *E. coli* and then purified served as a quantitative standard (panel 4).

Example 6

Bioreactor Fermentation

Figure 7:
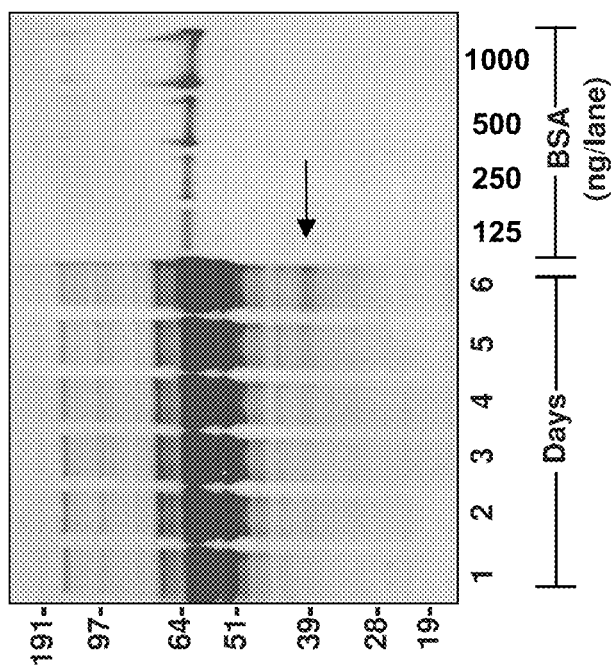
FIG. 7 shows the expression of MGD-CSF in a bioreactor, as further described in Example 6. Fermentation was monitored for 6 days. Samples were examined by gel electrophoresis and stained with Coomassie Blue on days 1-6 post-inoculation. Molecular weights are indicated on the left panels. The position of MGD-CSF is indicated by the arrow. Increasing amounts of bovine serum albumin (BSA) is shown to quantify the amount of protein on the gel.

As shown in FIG. 7, bioreactor fermentation improved MGD-CSF productivity to approximately 10 µg/ml during the course of a 6-7 day fermentation in a 10 liter bioreactor. Cells adapted to grow in low serum were inoculated at a concentration of approximately $5 \times 10^5$/ml into 10 liters of HyQ PF CHO LS medium supplemented with 1% FBS. Fermentation was monitored for 6 days and samples were prepared for gel electrophoresis as described above. The left panel of FIG. 7 shows the presence of MGD-CSF in a gel loaded with 22.5 µl sample per lane and stained with Coomassie Blue on days 1-6 post-inoculation. Bovine serum albumin (BSA) is shown as a quantitative control in the right panel. The arrow indicates the position of MGD-CSF.

Example 7

Protein Isolation

MGD-CSF was isolated from 293T cells grown in suspension cultures stably expressing the protein, as described above and shown in FIG. 8. The culture supernatant was adjusted to 0.5 M NaCl, pH 5.0 (with HCl), then concentrated 5-fold with a cellulose membrane having a 10 kD molecular weight cut-off (Millipore, Billerica Mass.). The concentrate was dialyzed against buffer A (10 mM acetic acid pH 5.0, 110 mM NaCl) and fractionated on a SP-Sepharose® FF (Amersham, Piscataway N.J.) cation exchange column equilibrated with Buffer A. The protein was eluted with a linear gradient to 1.5 M NaCl and the fractions containing MGD-CSF were dialyzed against buffer B (10 mM 1,3 diaminopropane pH 8.9, 30 mM NaCl).

This dialyzed SP-Pool was applied to a heparin Sepharose® HP (Amersham, Piscataway, N.J.) column, equilibrated with buffer B and eluted with a linear gradient to 1.5 M NaCl. Fractions containing MGD-CSF were dialyzed against buffer C (10 mM bis-trispropane pH 7.4, 30 mM NaCl). This dialyzed Hep-Pool was fractionated on a Q-Sepharose® FF (Amersham, Piscataway, N.J.) anion exchange column equilibrated in buffer C, and eluted with a linear gradient to 1.5 M NaCl. The fractions containing MGD-CSF were pooled and this Q-Pool was snap-frozen in liquid nitrogen and stored at −80C. This purification procedure recovered a yield of 12% of the expressed protein at >95% purity.

Example 8

Cysteine to Serine Mutational Analysis

The MGD-CSF sequence includes seven cysteine residues, located at amino acid positions 35, 167, 176, 178, 179, 190, and 198. Based on a comparison of denaturing and nondenaturing gel electrophoresis results under non-reducing conditions, MGD-CSF does not form disulfide-linked oligomers. Therefore, at least one of the cysteine residues in the native protein is expected to be unpaired. Unpaired cysteine residues may lead to improper protein folding and formation of covalent aggregates.

A set of seven muteins of the MGD-CSF protein was constructed, expressed, and characterized, in which each of the cysteines was mutated to serine to understand its disulfide bond pattern. This analysis of the disulfide bond pattern can determine whether eliminating one or more free cysteine residues would produce an MGD-CSF protein with improved properties, for example, improved expression and secretion from mammalian cells, decreased aggregation of the purified protein, and/or the potential to produce active recombinant MGD-CSF when expressed in *E. coli*.

DNA encoding each of the muteins was generated from a construct comprising the collagen signal peptide and the nucleotide sequence encoding mature MGD-CSF (CLN00848149). Protein was expressed in 293-T cells, as described above. The supernatant was harvested and subjected to reducing and nonreducing gel electrophoresis followed by Western blotting with polyclonal antibody raised to the middle peptide epitope in human MGD-CSF.

As shown in FIG. 8B, the Western blot of the reducing gel was analyzed to determine relative expression levels of wild type human MGD-CSF (with native or collagen signal peptide) and each of the Cys to Ser muteins. The secreted protein yield of wild type human MGD-CSF was observed to be higher with the collagen signal peptide than the native signal peptide. All of the muteins were observed to have at least a slightly decreased yield of secreted protein as compared to wild type human MGD-CSF with the collagen signal peptide. The yields of C179S and C190S were significantly decreased and C35S was not detectably expressed. Based on these results, it is likely that C35, C179, and C190 participate in disulfide bonding in native MGD-CSF.

As further shown in FIG. 8B, the Western blot of the nonreducing gel was analyzed for changes in apparent molecular weight, as determined by the relative migration of the MGD-CSF species compared with protein standards. When a disulfide bond is disrupted, the apparent size of the protein will typically increase under the denaturing conditions of SDS-PAGE, and the magnitude of this increase will typically be correlated with the distance between the two cysteine residues in the primary sequence of the protein. The disruption of a disulfide bond may lead to the formation of higher molecular weight aggregated species. C167S is observed to have the same migration time as wild type MGD-CSF, while all of the other muteins have altered migration behavior. This indicates that C167 is likely the only unpaired cysteine in native MGD-CSF. C179S and C190S both primarily form higher molecular weight species. These muteins have the same changes in protein yield and migration, suggesting that they are paired with one another in native MGD-CSF. C176S and C178S show the same slight decrease in migration, suggesting that they may be paired with each other in native MGD-CSF. Finally, C198S has a larger change in migration, suggesting that its partner may be C35, which is located further away in the protein sequence. The fact that C167 is likely the only unpaired cysteine in native MGD-CSF indicates it may be mutated to a serine or an alanine with a resulting improvement in the yield of the expressed protein and a decrease in the heterogeneity of the recovered protein product.

Example 9

MGD-CSF Promotes Hematapoeitic Cell Proliferation

A. MGD-CSF Promotes NK Cell Proliferation

Figure 9:
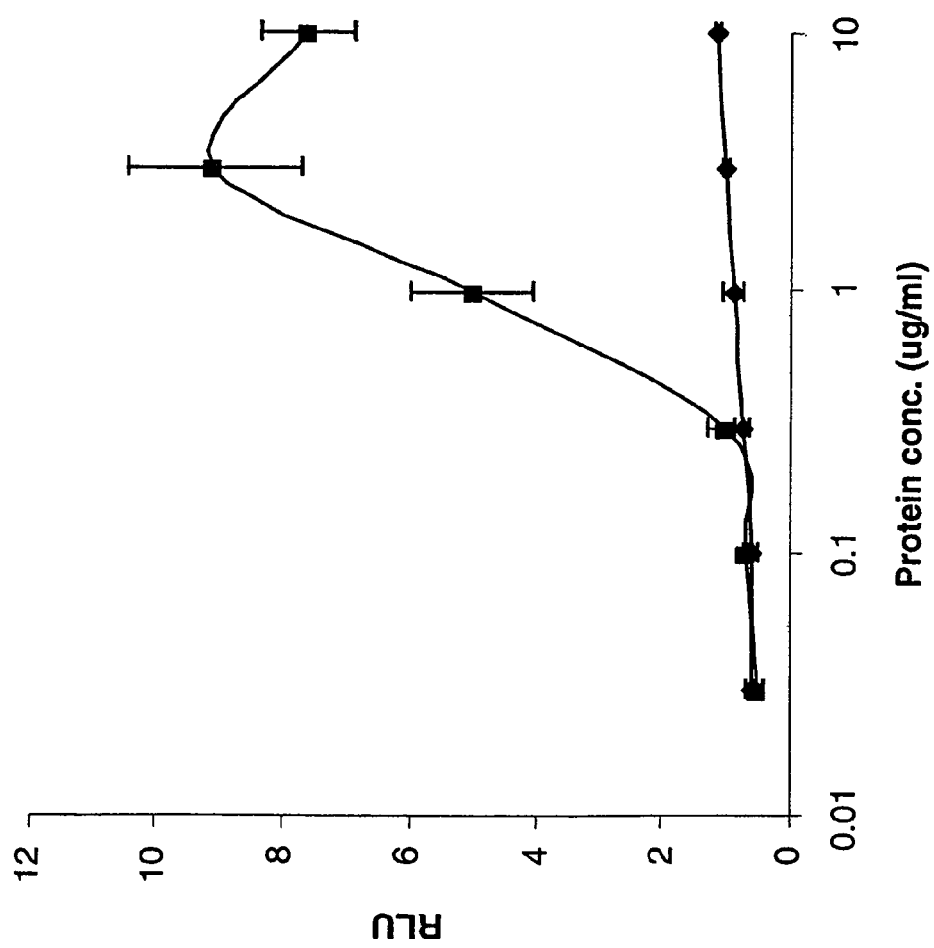
FIG. 9 shows the ability of MGD-CSF to induce NK cell proliferation and/or survival, as further described in Example 9A. NK cell number was expressed in relative luciferase units (RLU) per well following exposure to a negative buffer control (diamonds) or conditioned media from cells transfected with MGD-CSF (squares). MGD-CSF stimulated mouse NK cell proliferation. The control buffer had no effect. The proliferative activity of MGD-CSF on NK cells was specific and dose-dependent.

Mouse NK cells were purified from the spleens of C57BL6 10 week old female mice using the NK cell isolation kit according to the manufacturer's instructions (Miltenyi Biotechnology Inc., Auburn Calif.). Approximately 30,000 purified NK cells were incubated with purified MGD-CSF at concentrations from 0.01 to 10 µg/ml. NK cell numbers were determined using the CellTiter-Glo Luminescent Cell Viability Assay Kit (Promega #G7571). As shown in FIG. 9, after four days of incubation in RPMI with 5% FBS, MGD-CSF specifically increased the proliferation and/or survival of NK cell numbers in a dose-dependent manner.

Human NK cells were isolated and purified from blood enriched in buffy coat cells obtained from the Stanford Blood Center (Palo Alto, Calif.). The blood was diluted approximately 1:5 with PBS and Ficoll (Ficoll-Paque Plus, Amersham Biosciences; Piscataway, N.J.) added (12.5 ml/tube) to multiple 50 ml conical tubes, each with 25 ml of diluted blood. The Ficoll/blood mixture was centrifuged at 450×g for 30 minutes. The peripheral blood mononuclear cell (PBMC) layers were removed, washed with DPBS 1× without calcium and magnesium (Mediatech, Inc., Prince William Co. VA) and pelleted at 1000 RPM for 10 minutes. The PBMCs were washed three times in PBS by centrifugation at 1350 RPM for 10 minutes and resuspended in 40 ml PBS with 0.5% fetal calf serum (Gibco (Invitrogen), Carlsbad Calif.) and 2 mM EDTA (Sigma Aldrich, St. Louis Mo.) (PBSFE).

NK cells were enriched from the PBMCs with a human NK Cell Isolation Kit II (Miltenyi Biotechnology Inc., Auburn Calif.), as recommended by the manufacturer. This enrichment step utilized the "deplete" program of an autoMACST™ Separator (Miltenyi Biotechnology Inc., Auburn Calif.); the negative fraction, representing enriched NK cells, was collected from outlet port "neg1." These cells were centrifuged at 1350 RPM for 10 minutes, the cell pellets resuspended in DMEM with 10% fetal calf serum, and diluted to a concentration of $1\times10^6$ cells/ml. The cells were incubated with the control and test agents described below for four days at 37° C. in an atmosphere of 7% $CO_2$ in 96 well round bottom plates at a cell concentration of $5\times10^4$ cells in 50 µl DMEM with 10% fetal calf serum per well.

The effect of control and test agents on the proliferation of human NK cells prepared in this manner was determined in a screening assay by measuring the number of viable cells in the culture based on quantitation of ATP by measuring luciferase activity as described in Promega CellTitreGlo Technical Bulletin No. 288 (Promega, Madison Wis.). Quantitative results were read on an Lmax plate reader (Molecular Devices, Sunnyvale Calif.) at room temperature for 0.6 second/well. The ATP content of the wells was measured four days after plating.

Figure 10:
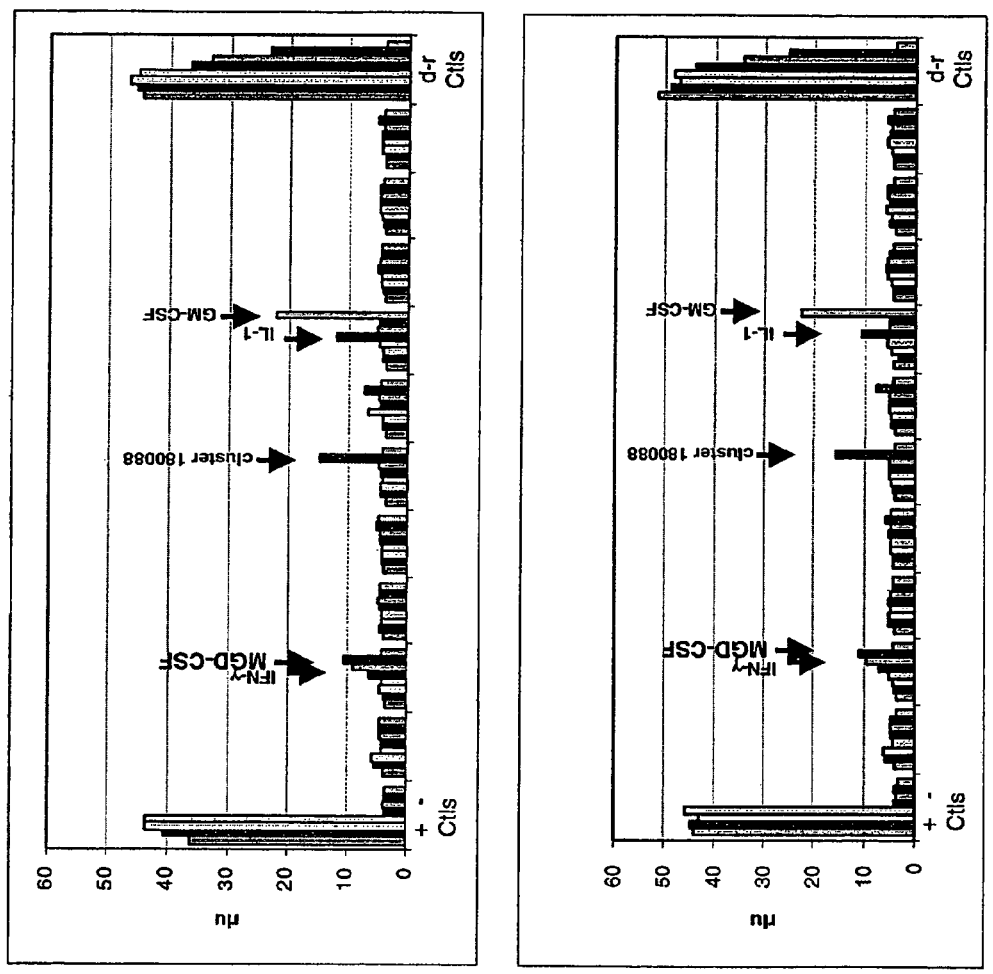
FIG. 10 shows the results of a screening assay for agents that induce NK cell proliferation and/or survival, as further described in Example 9A. The top and bottom panels represent two identical experiments, performed independently. The number of human NK cells is expressed in relative luciferase units (flu), following exposure to a test agent. Conditioned media from cells transfected with MGD-CSF or with plasmid DNA from the cluster 190647, the source of MGD-CSF, stimulated human NK cell survival and/or proliferation. The positive controls IFNγ, IL-1, and GM-CSF also stimulated NK cell proliferation.

As shown in FIG. 10, conditioned media from cells transfected with MGD-CSF and with cells transfected with plasmid DNA from cluster 190647, the source of the MGD-CSF clones, stimulated NK cell production. Interferon gamma (IFN-γ), interleukin 1 (IL-1), and GM-CSF were used as internal positive controls. External positive controls, which include recombinant interleukin 15, and external negative controls, which include culture medium, are shown on the right and the left of FIG. 10. This screening assay identified MGD-CSF as an agent that stimulated the production of and/or stabilized the number of NK cells. This result was seen in four independent repetitions of the screening assay. MGD-CSF did not consistently induce the production of cytokines from NK cells. It increased or stabilized monocyte cell number but did not induce the production of cytokines from monocytic cells. MGD-CSF had no effect on the number of activated T cells or B cells.

B. MGD-CSF Promotes Hematapoeitic Stem Cell Proliferation

Figure 11:
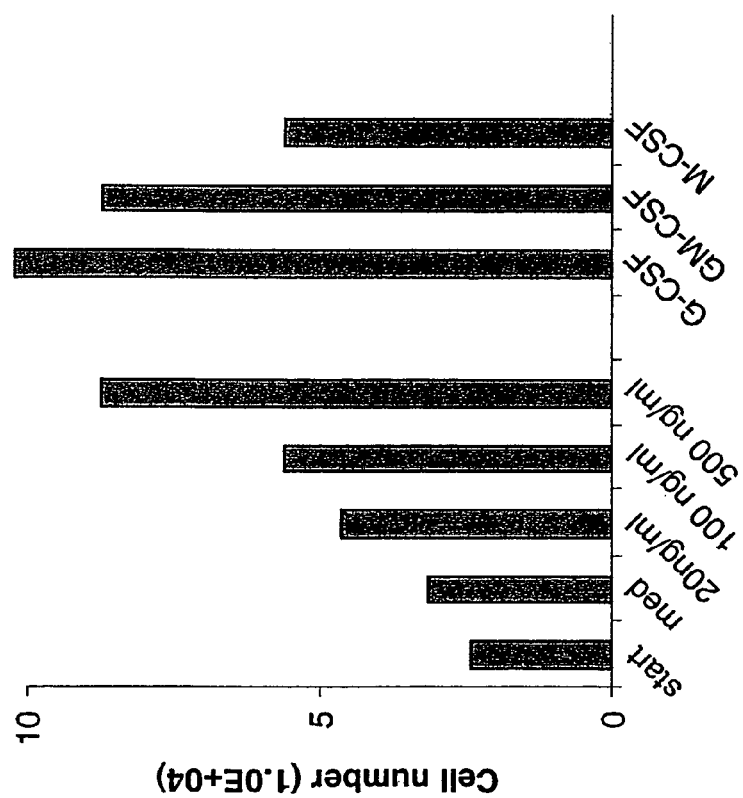
FIG. 11 shows the ability of MGD-CSF to induce hematopoietic stem cell proliferation, as further described in Example 9B. The number of stem cells was determined by counting the cells with a hemocytometer. MGD-CSF increased proliferation in a dose dependent manner. MGD-CSF (500 ng/ml) induced stem cell proliferation to a greater extent than M-CSF and to a similar extent as G-CSF and GM-CSF.

MGD-CSF also stimulated the proliferation of bone marrow CD34+ hematopoietic stem cells (HSC cells) (Cambrex, Inc., Baltimore Md.) in culture. As shown in FIG. 11, MGD-CSF increased proliferation in a dose dependent manner. HSC cells were grown in culture under stromal free conditions at a density of $2.4\times10^4$ cells per well in 12-well tissue culture dishes containing 1 ml/well RPMI (ATCC) supplemented with 5% heat inactivated fetal bovine serum (ATCC) and 10 ng/ml recombinant human stem cell factor (SCF), 10 ng/ml Flt3 ligand (Flt3L) (R&D Systems, Minneapolis Minn.) in a 5% $CO_2$ incubator at 37° C. for 1-2 weeks, washed with PBS, lifted with 0.5 ml Versene (Gibco BRL, Gaithersburg Md.), washed again with PBS, resuspended in 1 ml PBS/0.1% BSA (Sigma, St. Louis Mo.) and counted with a hematocytometer. Purified MGD-CSF increased their growth in a dose dependent manner from 20 ng/ml to 500 ng/ml. MGD-CSF induced stem cell proliferation to a greater extent than M-CSF and to a similar extent as G-CSF and GM-CSF.

C. MGD-CSF Promotes Myelocytic Cell Proliferation In Vitro

Human primary monocytes were purified from PBMC using a protocol modified from a previously-described method (de Almeida, et al., *Mem. Inst Oswaldo Cruz* 95:221-223, 2000). To isolate human PBMC from blood, the buffy coat was diluted in a six-fold volume of PBS, then overlain onto 20-ml Ficoll in a 50 ml tube. The tubes were centrifuged at 2,000 rpm at 22° C. for 20 minutes without the use of the centrifuge brake. The PMBC cells were collected from the interface, washed with PBS twice then resuspended in RPMI 5% FBS and filtered through a BD Falcon cell strainer. To purify the primary untouched monocytes from PBMC, six ml of the PBMC suspension (containing 70-120×$10^6$ cells) was carefully and slowly overlain onto 10 ml hyperosmotic Percoll. The cells were centrifuged at a speed of 580×g for 15 minutes without the use of the centrifuge brake. Cells at the interface were collected and washed with 50 ml of RPMI 5% FBS. This purified monocyte cell pellet was resuspended in 50 ml RPMI 5% FBS.

The monocyte assay was performed by incubating approximately 30,000 purified monocytes with MGD-CSF purified as described above. After four days of incubation in RPMI with 5% FBS, monocyte proliferation was determined using the CellTiter-Glo Luminescent Cell Viability Assay Kit (Promega #G7571).

Conditioned medium from MGD-CSF transfected 293-T cells (MGD-CSF CM) promoted monocyte proliferation. The screening assay was performed in duplicate plates in a 96-well plate format on monocytes activated by mouse IgG2a. Table 6 shows semiquantitative descriptions of the potency of the activity of each clone to stimulate monocyte proliferation and the degree of expression of each construct. MGD-CSF CM stimulated monocyte proliferation to approximately the same extent as GM-CSF. Results were considered significant when at least two standard deviations from the median. The observed $ED_{50}$ was 3-5 ng/ml. Mutant MGD-CSF proteins were also tested in this assay. The mutant clone CLN00848185 demonstrated activity (potency) comparable to the wild type protein, and other mutant clones had slightly lower activities than the wild type protein, suggesting that some mutant proteins can be used as therapeutic proteins.

Figure 12A:
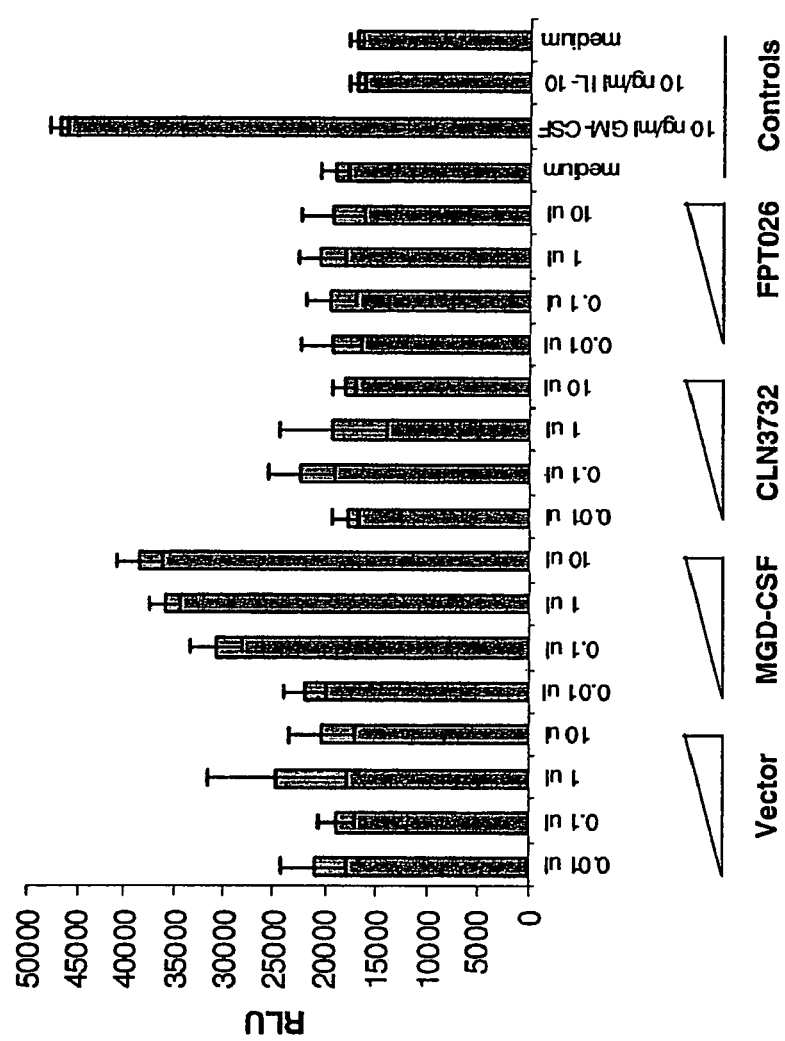
FIG. 12A compares the ability of conditioned media containing MGD-CSF to induce myelocyte proliferation with the negative controls of the empty vector (Vector) and the irrelevant compounds CLN3732, FPT026, IL-10, and unconditioned media; and with the positive control GM-CSF. Monocyte number was expressed in relative luciferase units (RLU) per well following exposure to the test agent.

As shown in FIG. 12A, the stimulatory effect of MGD-CSF CM on monocyte proliferation was dose-dependent over a 10,000-fold range. The lowest dose of MGD-CSF CM tested, 0.01 μl, had no significant effect on monocyte proliferation. Increasing the dose 10-fold to 0.1 μl MGD-CSF CM induced cell proliferation to a significant level compared to controls. Further increasing the dose to 1 μl MGD-CSF CM and 10 μl MGD-CSF CM further increased monocyte proliferation in a dose-dependent manner. No dose dependency was observed with the empty vector or the negative controls CLN003732 or FPT026. The effect of a single dose of 10 ng/ml GM-CSF, a stimulatory positive control, is shown, as well as the effect of the negative control IL-10, and of unconditioned medium.

Figure 12B:
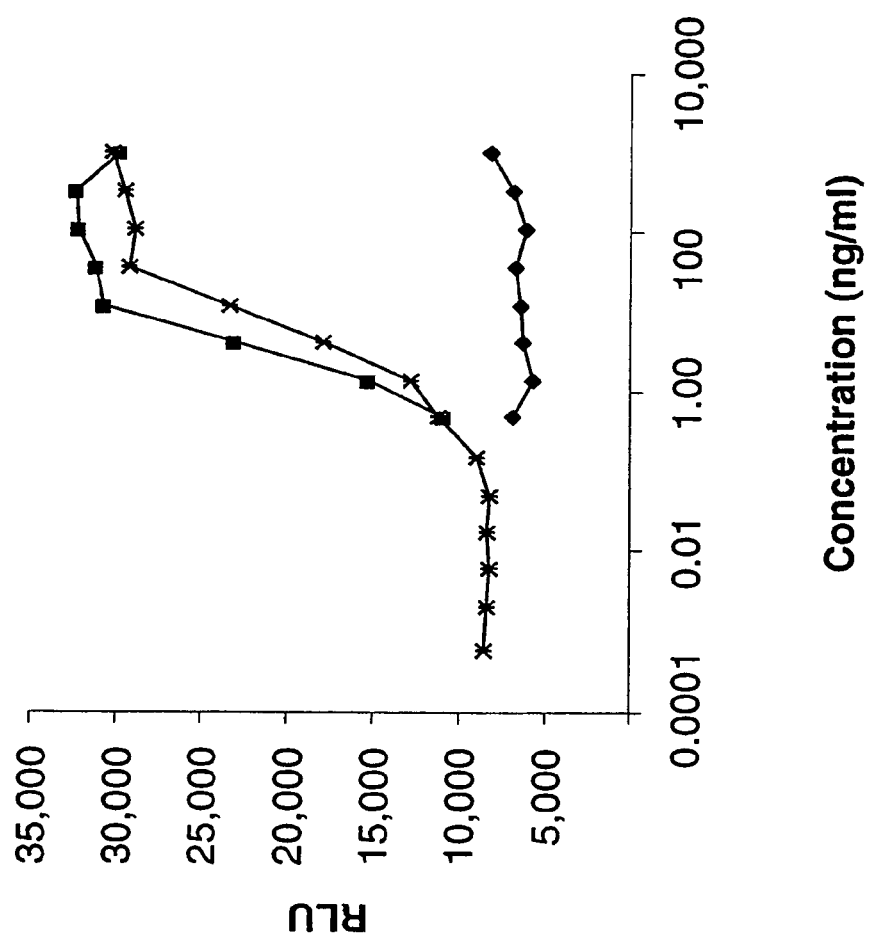
FIG. 12B shows that both purified GM-CSF (stars) and conditioned media from cells transfected with MGD-CSF (squares) stimulated human monocyte proliferation. The control vector (diamonds) had no effect. The proliferative activity of MGD-CSF on monocytes was specific and dose-dependent.

As shown in FIG. 12B, both purified GM-CSF and conditioned media from cells transfected with MGD-CSF stimulated human monycyte proliferation. Thus, MGD-CSF functions as an agonist of monocyte proliferation, in addition to its role in the differentiation and growth of myeloid cells and granulocytes. It may be used as a hematopoietic factor to enhance the recovery of hematopoietic cells following chemotherapy or radiation treatment and bone marrow transplantation in cancer patients.

D. MGD-CSF Promotes Myelocytic Cell Proliferation In Vivo

To understand the role of MGD-CSF in vivo, C57BL6 mice were injected with MGD-CSF plasmid DNA using a method described by Wang, et al. *Cancer Res.* 63:9016-9022, 2003). The human cytochrome P450 3A4 promoter was operably linked to a nucleic acid molecule with the nucleotide sequence of MGD-CSF and injected into the tail vein of a mouse in order to transfect the mouse's liver with MGD-CSF. The human 3A4 promoter was used to drive the expression of MGD-CSF in mouse liver. A complete blood count (CBC) and differential analysis was performed on the control and experimental groups in each of two independent experiments using a Serono Baker 9000 hematology analyzer.

The control group (Table 7A, animals 1-3) in the first experiment comprised three uninjected mice age matched to the experimental mice. The experimental group (Table 7A, animals 4-6) in the first experiment comprised three mice injected with naked MGD-CSF DNA via the tail vein. Blood samples were collected on day 14 following injection. As shown in Table 7A, the injected mice had elevated monocyte counts compared to the controls. Control animals 1, 2, and 3 had 94, 84, and 52 monocytes/μl blood, respectively. Experimental animals 4 and 6 had 216 and 268 monocytes/μl blood, respectively. No meaningful monocyte count was obtained for animal 3.

The control group (Table 7B, animals 1-6) in the second experiment comprised six mice age matched to the experimental mice and injected via the tail vein with a LacZ construct. The experimental group (Table 7B, animals 7-12) in the second experiment comprised six mice injected with naked MGD-CSF DNA via the tail vein. Blood samples were collected on day 21 following injection. As shown in Table 7B, the injected mice had elevated monocyte counts compared to the controls. None of the control animals had detectable monocyte levels. Four of the six experimental animals had detectable monocyte levels, ranging from 50-78 monocytes/μl. These results demonstrate that MGD-CSF increased myeloid cell numbers in vivo.

Example 10

FACS Analysis of the Effect of MGD-CSF on Hematopoietic Differentiation

In vitro granulocyte, monocyte, and dendritic cell development assays further revealed the function of MGD-CSF in hematopoeisis. Human bone marrow CD34$^+$ hematopoietic stem cells (HSC cells) (Cambrex, Inc., Baltimore Md.) were cultured as described above.

Differentiation was determined by fluorescence activated cell sorting (FACS) analysis using fluorescently labeled antibodies to detect the differentiation markers on the granulocyte cell surface (Kavathas et al., *Proc. Natl. Acad. Sci.* 80:524-528 (1983)). After one week culture in either the presence or absence of MGD-CSF, G-CSF, GM-CSF, or M-CSF, the BM CD34$^+$ cells were washed once with PBS, lifted with 0.5 ml Versene (Gibco BRL, Gaithersburg Md.), washed with 1 ml PBS/0.1% BSA (Sigma, St. Louis Mo.), resuspended in 0.2 ml PBS/0.1% BSA (Sigma, St. Louis Mo.), and aliquoted (50 μl per well) into a 96-well plate for FACS staining. Cells were incubated with fluorescent-conjugated antibodies for 15 minutes at 4° C. After washing twice with 150 μl PBS/0.1% BSA, the cells were analyzed with a FACS Calibur, per manufacturer's instruction (Becton Dickinson, Franklin Lakes N.J.). 10 ng/ml G-CSF, 10 ng/ml M-CSF, or 30 ng/ml GM-CSF (from R&D Systems, Minneapolis Minn.) served for positive controls of the effects of known growth factors. Fluorescent-conjugated antibodies specific for granulocyte, monocyte, or dendritic lineage-specific surface markers were purchased from BD Biosciences, (San Jose, Calif.) and used to determine the effect of MGD-CSF on differentiation of HSC cells to granulocytic, monocytic, and dendritic lineages.

A. Granulocyte Differentiation

Figure 13:
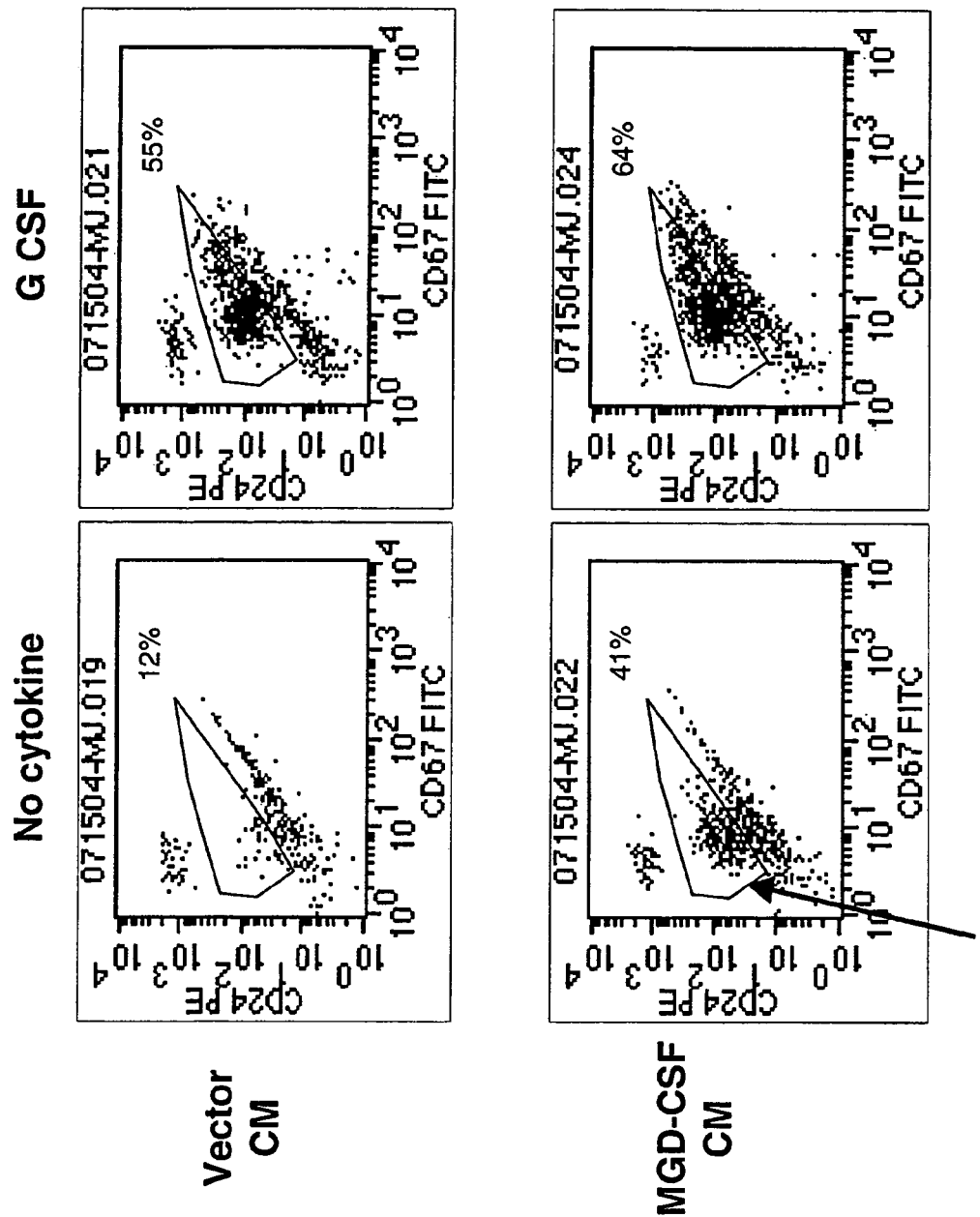
FIG. 13 shows the results of a fluorescent activated cell sorting (FACS) analysis of granulocyte differentiation, as measured by the presence of the differentiation antigens CD67 and CD24 and described in greater detail in Example 10A. The number of hematopoeitic stem cells induced to differentiate into granulocytes in response to media conditioned with negative control vector (Vector CM) and media conditioned with the MGD-CSF vector (MGD-CSF CM) is shown. CD67 FITC (x-axis) indicates the number of CD67 positive cells by the fluorescence intensity of the antibody specific for CD67. CD24PE (y-axis) indicates the number of CD24 positive cells by the fluorescence intensity of the antibody specific for CD24. The outlined triangular area (arrow) indicates the number of cells positive for both of the cell surface differentiation antigens CD67 and CD24 in each of the four panels. MGD-CSF CM stimulated granulocyte differentiation both in the absence (no cytokine) and the presence of G-CSF. This stimulation by MGD-CSF was synergistic with the effects of G-CSF.

As shown in FIG. 13, MGD-CSF stimulated the differentiation of granulocytes from undifferentiated cells to differentiated granulocytes possessing the differentiation markers $CD67^+$ and $CD24^+$. As a negative control, the baseline level of granulocyte differentiation in the presence of empty vector and the absence of cytokine was measured to be 1.2%. The positive control, G-CSF, stimulated 55% of the granulocytes to differentiate. MGD-CSF CM stimulated 41% of the granulocytes to differentiate (arrow). The effect of MGD-CSF was synergistic with that of G-CSF, in the presence of both, 64% of the granulocytes were stimulated to differentiate.

CD24 and CD15 antibodies were used to monitor granulocyte differentiation. The CD24 antibody reacted with a 35-45 kDa two-chain glycoprotein expressed on the surface of B cells and granulocytes. The CD15 antibody reacted with 3-fucosyl-N-acetyllactosamine (3-FAL), a 220 kDa carbohydrate structure, also known as X-hapten. 3-FAL was expressed on 95% of the granulocytes examined, including neutrophils and eosinophils, and to a varying degree on monocytes, but not on lymphocytes or basophils. CD15 plays a role in mediating phagocytosis, bactericidal activity and chemotaxis. Cells positive for both CD24 and CD15 represent granulocytes which have differentiated from the BM $CD34^+$ hematopoietic progenitor cells.

Figure 14:
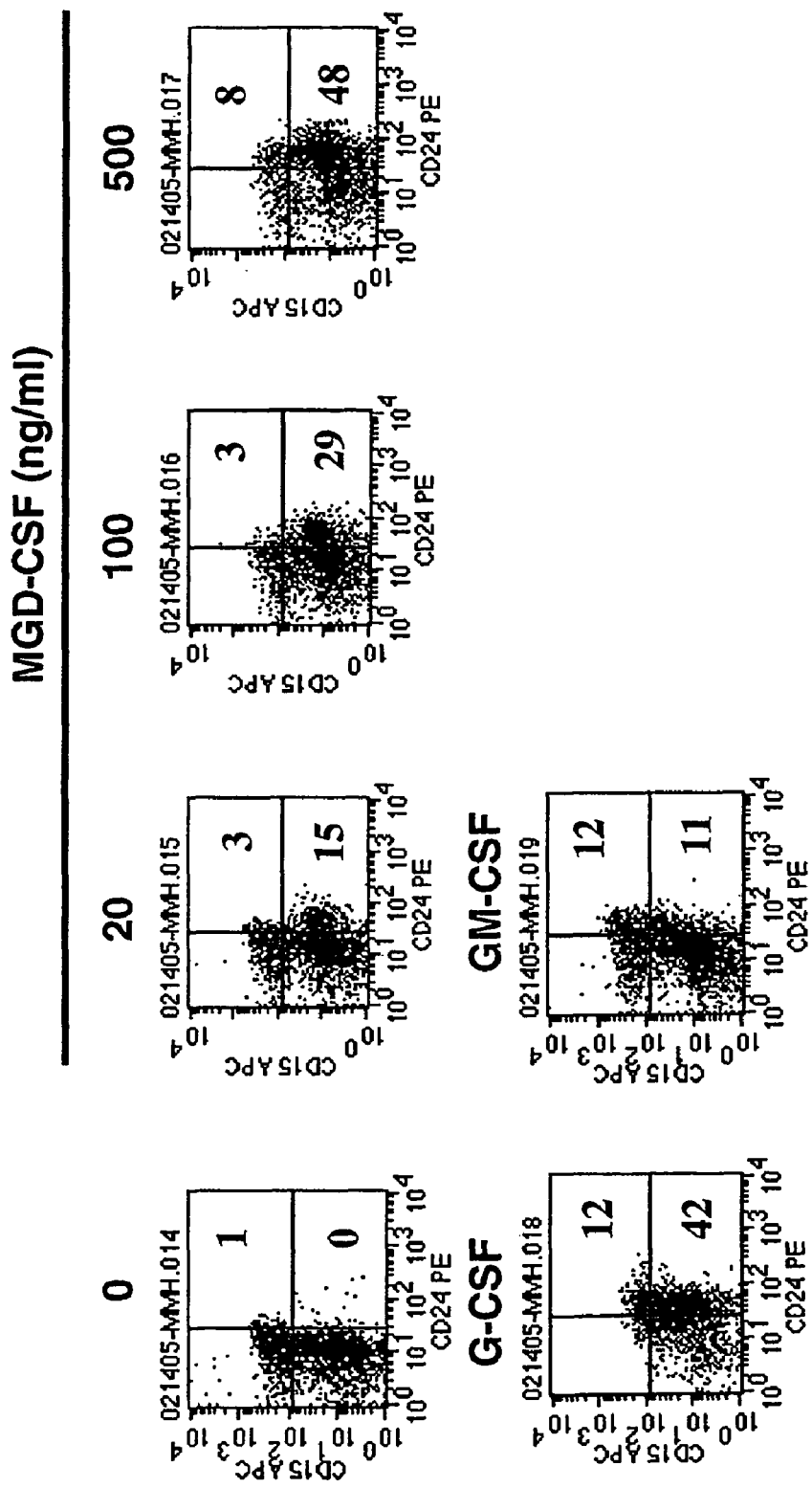
FIG. 14 shows the results of a FACS analysis of granulocyte differentiation, as measured by the presence of the differentiation antigens CD15 and CD24 and described in greater detail in Example 10A. CD24PE (x-axis) indicates the number of CD24 positive cells by the fluorescence intensity of the antibody specific for CD24. CD15APC (y-axis) indicates the number of CD15 positive cells by the fluorescence intensity of the antibody specific for CD15. The box in the upper right of each graph indicates the percent of cells that have both CD15 and CD34 differentiation markers on their cell surface. MGD-CSF induced granulocyte differentiation in a concentration-dependent manner, with a dose of 500 ng/ml resulting in the differentiation of 8% of the bone marrow hematopoeitic stem cells into granulocytes.

As shown in FIG. 14, 20 ng/ml and 100 ng/ml MGD-CSF induced 3% differentiation to $CD15^+/CD24^+$ granulocytes, and 500 ng/ml MGD-CSF induced 8% differentiation to $CD15^+/CD24^+$ granulocytes. The positive controls G-CSF and GM-CSF both induced 12% of bone marrow $CD34^+$ cells to differentiate into CD15/CD24 positive granulocytes.

B. Monocyte Differentiation

Figure 15:
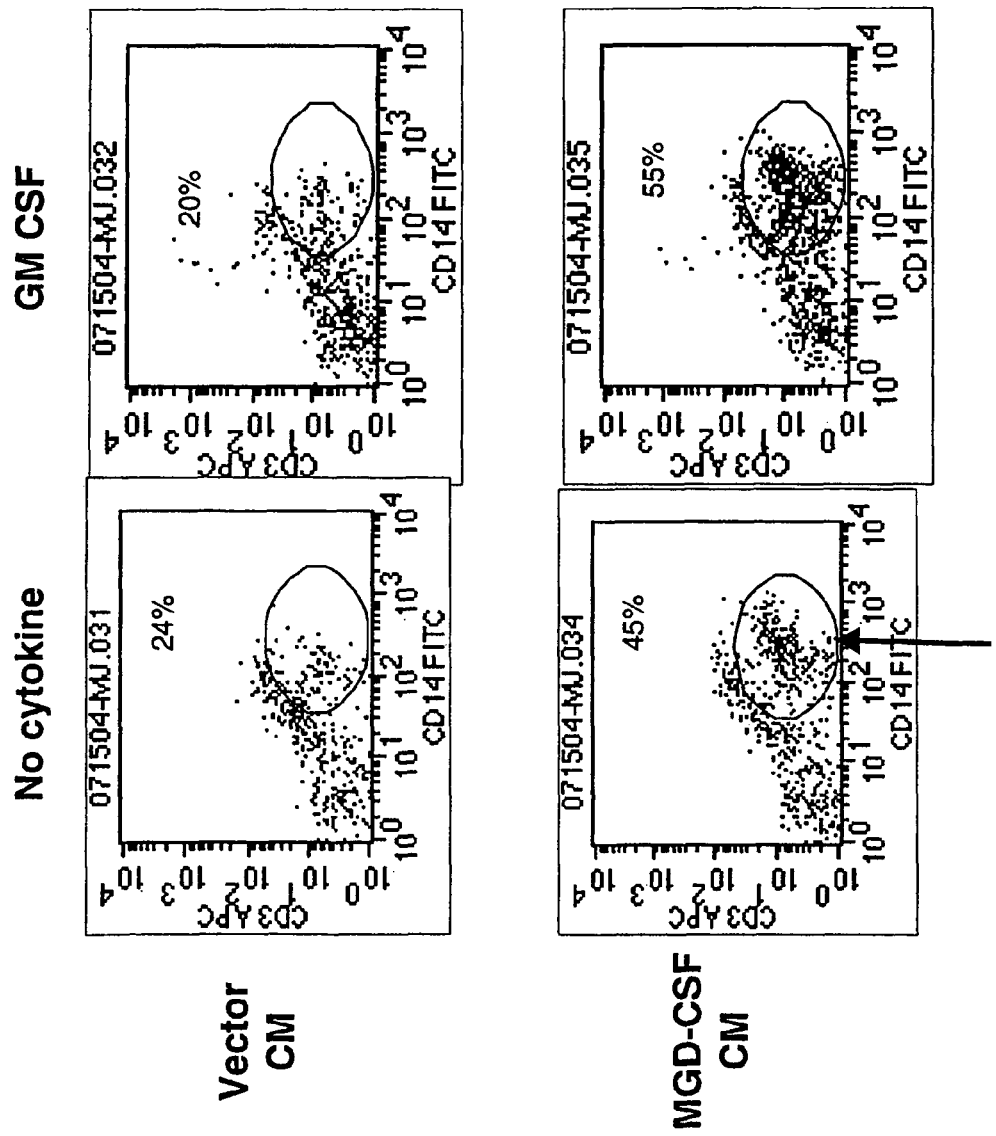
FIG. 15 shows the results of a FACS analysis of monocyte differentiation, as measured by the presence of the differentiation antigens CD14 and CD3 and described in greater detail in Example 10B. The number of hematopoeitic stem cells induced to differentiate into monoocytes in response to media conditioned with negative control vector (Vector CM) and media conditioned with the MGD-CSF vector (MGD-CSF CM) is shown. CD14FITC (x-axis) indicates the number of CD14 positive cells by the fluorescence intensity of the antibody specific for CD14. CD3APC (y-axis) indicates the number of CD3 positive cells by the fluorescence intensity of the antibody specific for CD3. The outlined oval area (arrow) indicates the number of cells positive for both of the cell surface differentiation antigens CD14 and CD3 in each of the four panels. MGD-CSF CM stimulated monocyte differentiation. MGD-CSF CM stimulated monocyte differentiation both in the absence (no cytokine) and the presence (G-CSF) of G-CSF. The ability of MGD-CSF to induce monocyte differentiation was greater than that of GM-CSF. MGD-CSF acted synergistically with GM-CSF.

As shown in FIG. 15, MGD-CSF stimulated the differentiation of monocytes from undifferentiated cells to differentiated monocytes possessing the $CD14^+$ marker. As a negative control, the baseline level of monocyte differentiation in the presence of empty vector and the absence of cytokine was measured to be 24%. GM-CSF stimulated 20% of the monocytes to differentiate. MGD-CSF stimulated 45% of the monocytes to differentiate (arrow). Although GM-CSF alone had no effect on these cells, when combined with MGD-CSF, its effect was synergistic; in the presence of both, 55% of the monocytes were stimulated to differentiate.

Figure 16:
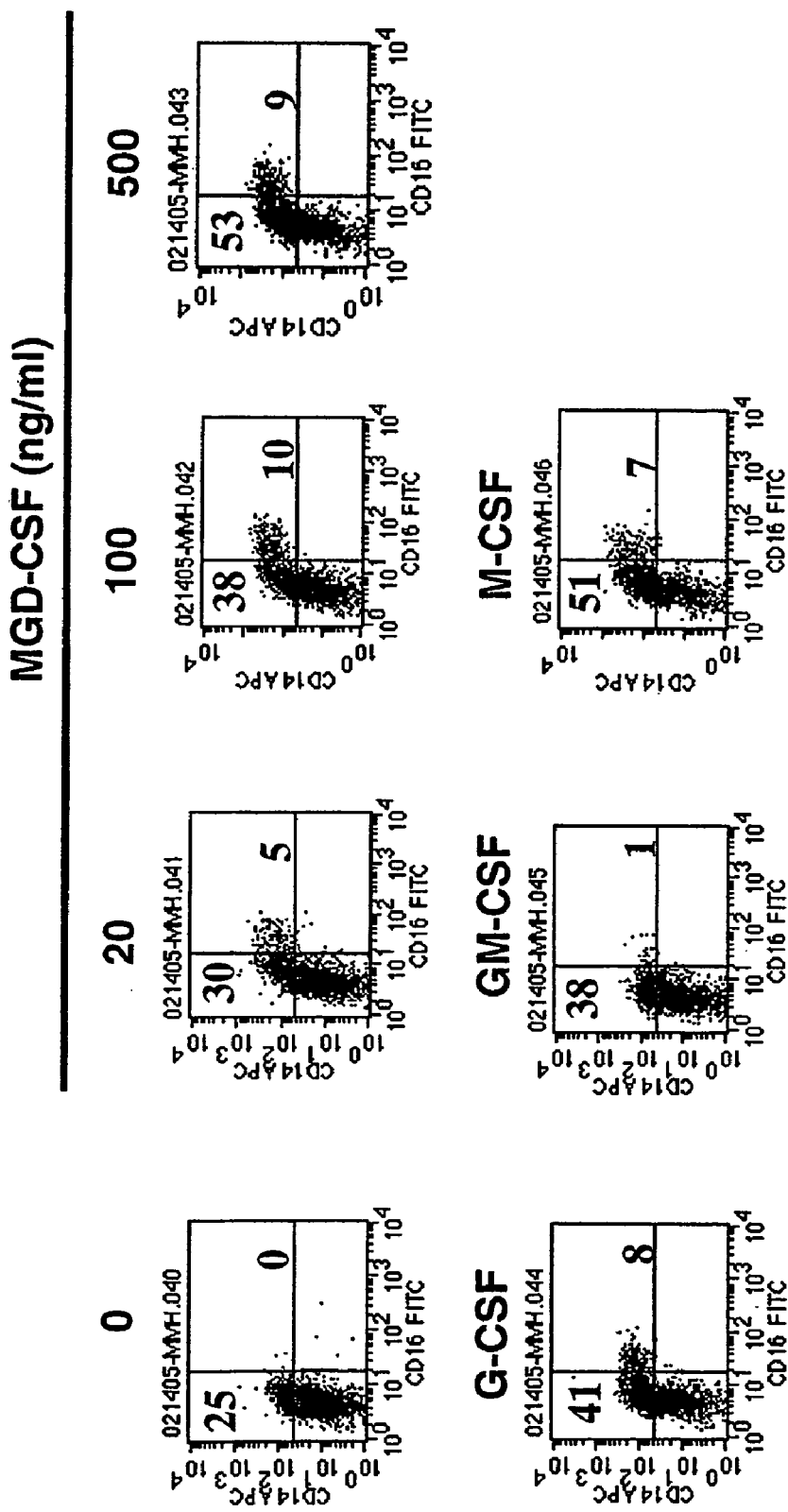
FIG. 16 shows the results of a FACS analysis of monocyte differentiation, as measured by the presence of the differentiation antigens CD14 and CD16 and described in greater detail in Example 10B. CD14APC (y-axis) indicates the number of CD14 positive cells by the fluorescence intensity of the antibody specific for CD14. CD16FITC (x-axis) indicates the number of CD16 positive cells by the fluorescence intensity of the antibody specific for CD16. The box in the upper right of each graph indicates the percent of cells that have both CD14 and CD16 differentiation markers on their cell surface. MGD-CSF induced monocyte differentiation in a concentration-dependent manner, with a dose of 100 ng/ml resulting in the differentiation of 10% of the bone marrow hematopoeitic stem cells into monocytes.

As shown in FIG. 16, CD14 and CD16 antibodies were used to monitor monocyte differentiation. The CD14 antibody reacted with a 53-55 kD glycosylphosphatidylinositol (GPI)-anchored single chain glycoprotein expressed at high levels on monocytes. Additionally, the CD14 antibody reacted with some macrophages. The CD16 antibody reached with the 50-65 kDa transmembrane form of IgG Fc receptor (FcgRIII). CD16 antigen was expressed on monocytes, macrophages, granulocytes, and NK cells. Monocytes can be divided into two subsets according to their CD16 expression; resident monocytes are $CD14^+CD16^-$ and inflammatory monocytes are $CD14^{low}CD16^+$. 20 ng/ml MGD-CSF induced 30% differentiation, 100 ng/ml MGD-CSF induced 30% differentiation, and 500 ng/ml induced 53% differentiation to either $CD14^+CD16^-$ or $CF14^{low}CD16^+$ monocytes. The positive controls G-CSF, GM-CSF, and M-CSF promoted 41%, 38%, and 51% CD14 differentiation, respectively.

C. Dendritic Cell Differentiation

Figure 17:
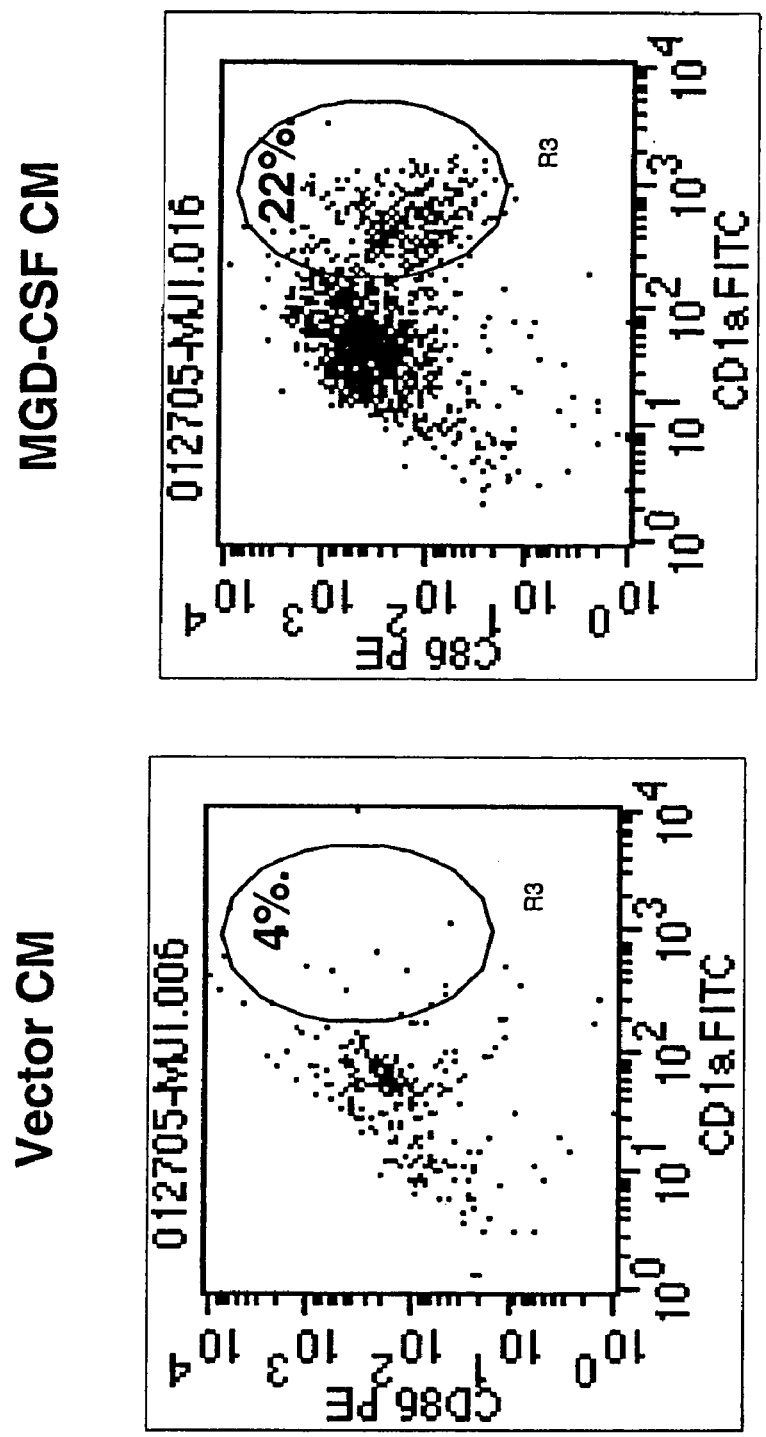
FIG. 17 shows the results of a FACS analysis of dendritic cell differentiation, as measured by the presence of the differentiation antigens CD86 and CD1 and described in greater detail in Example 10C. The number of hematopoeitic stem cells induced to differentiate into dendritic cells in response to media conditioned with negative control vector (Vector CM) and media conditioned with the MGD-CSF vector (MGD-CSF) is shown. CD1aFITC (x-axis) indicates the number of CD1 positive cells by the fluorescence intensity of the antibody specific for CD1. CD86PE (y-axis) indicates the number of CD86 positive cells by the fluorescence intensity of the antibody specific for CD86. The outlined oval area indicates the number of cells positive for both of the cell surface differentiation antigens CD1 and CD86. MGD-CSF CM stimulated dendritic cell differentiation. 4% of the cells transfected with the negative control differentiated into dendritic cells, while 22% of the cells transfected with the MGD-CSF vector differentiated into dendritic cells.

As shown in FIG. 17, MGD-CSF stimulated the differentiation of dendritic cells from undifferentiated cells to differentiated dendritic cells possessing the CD86 and CD1 markers. As a negative control, the baseline level of dendritic cell differentiation in the presence of empty vector was measured to be 4%. MGD-CSF stimulated 22% of the undifferentiated cells to differentiate into dendritic cells.

Example 11

MGD-CSF Promotes Bone Marrow Colony Formation

To assess stimulatory effects of MGD-CSF on human bone marrow derived myeloid (CFU-G, CFU-M, and CFU-GM) progenitor proliferation, colony formation assays were performed. The positive controls for stimulation of myeloid progenitors were the addition of G-CSF at 0.1 ng/ml, 1 ng/ml and 10 ng/ml and GM-CSF at 0.01 ng/ml, 0.1 ng/ml and 3 ng/ml. MGD-CSF protein was diluted into methylcellulose-based media for each test concentration to final concentrations of 20, 100, and 500 ng/ml. Cells were added such that each of three replicate cultures contained $3\times10^4$ cells. The replicate cultures were incubated at 37° C., 5% $CO_2$ for 14 days, then counted, photographed, classified on the basis of morphology as CFU-G, CFU-M, or CFU-GM, and FACS analysis was performed. Statistical analyses were performed to assess changes in colony number, size, and morphology. MGD-CSF promoted formation of CFU-G, CFU-M, CFU-GM, and total colony formation. In addition, as further described below, MGD-CSF promoted large CFU-M colonies distinct from those promoted by G-CSF or GM-CSF. These results suggest that MGD-CSF enhanced early hematopoietic progenitor formation.

Figure 18B:
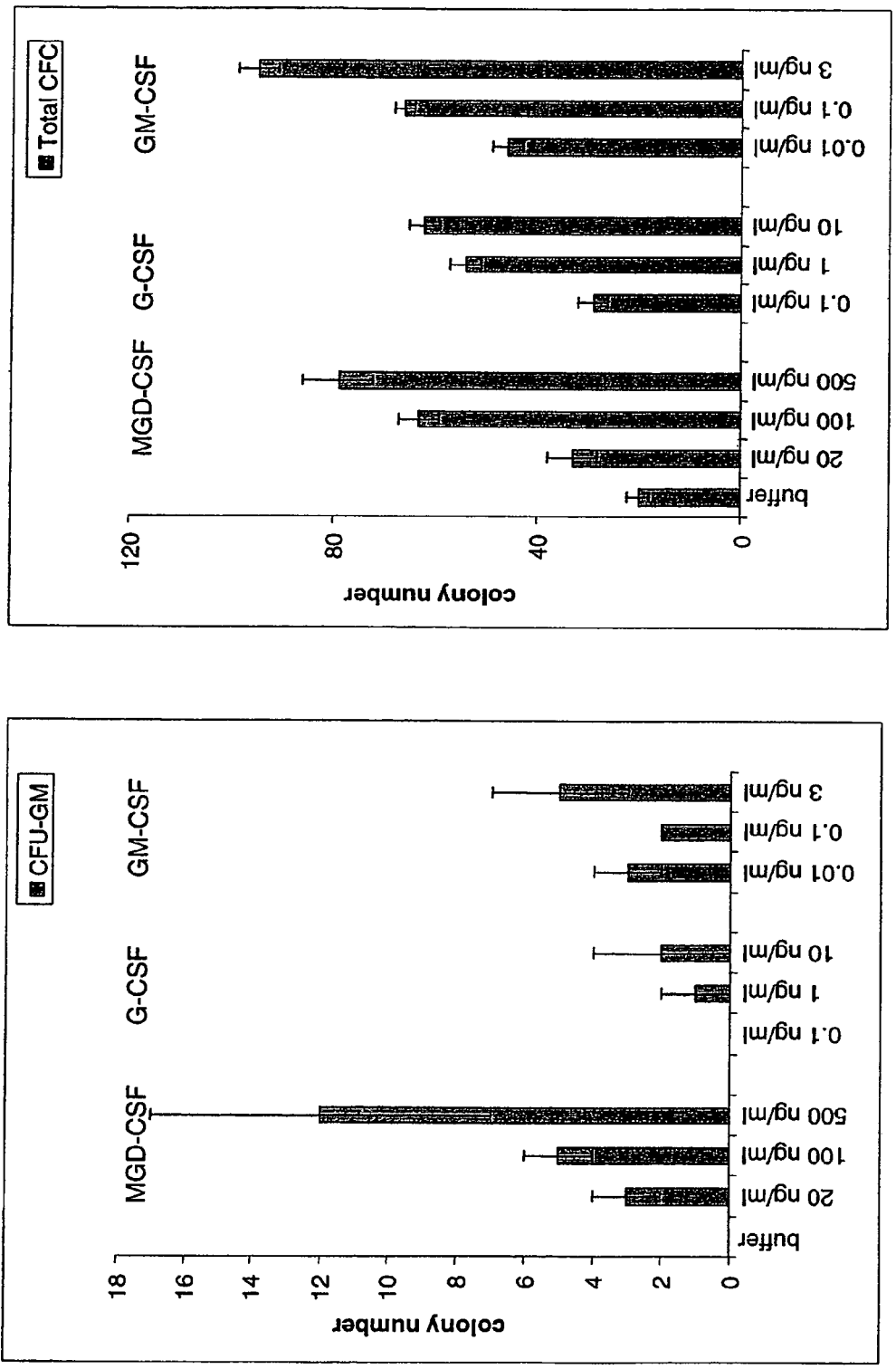
FIG. 18B shows the dose-dependent stimulatory effect of MGD-CSF on the formation of CFU-GM (left panel) and the total colony forming capacity (Total CFC) (right panel) in comparison to the effects of G-CSF and GM-CSF.
Figure 18C:
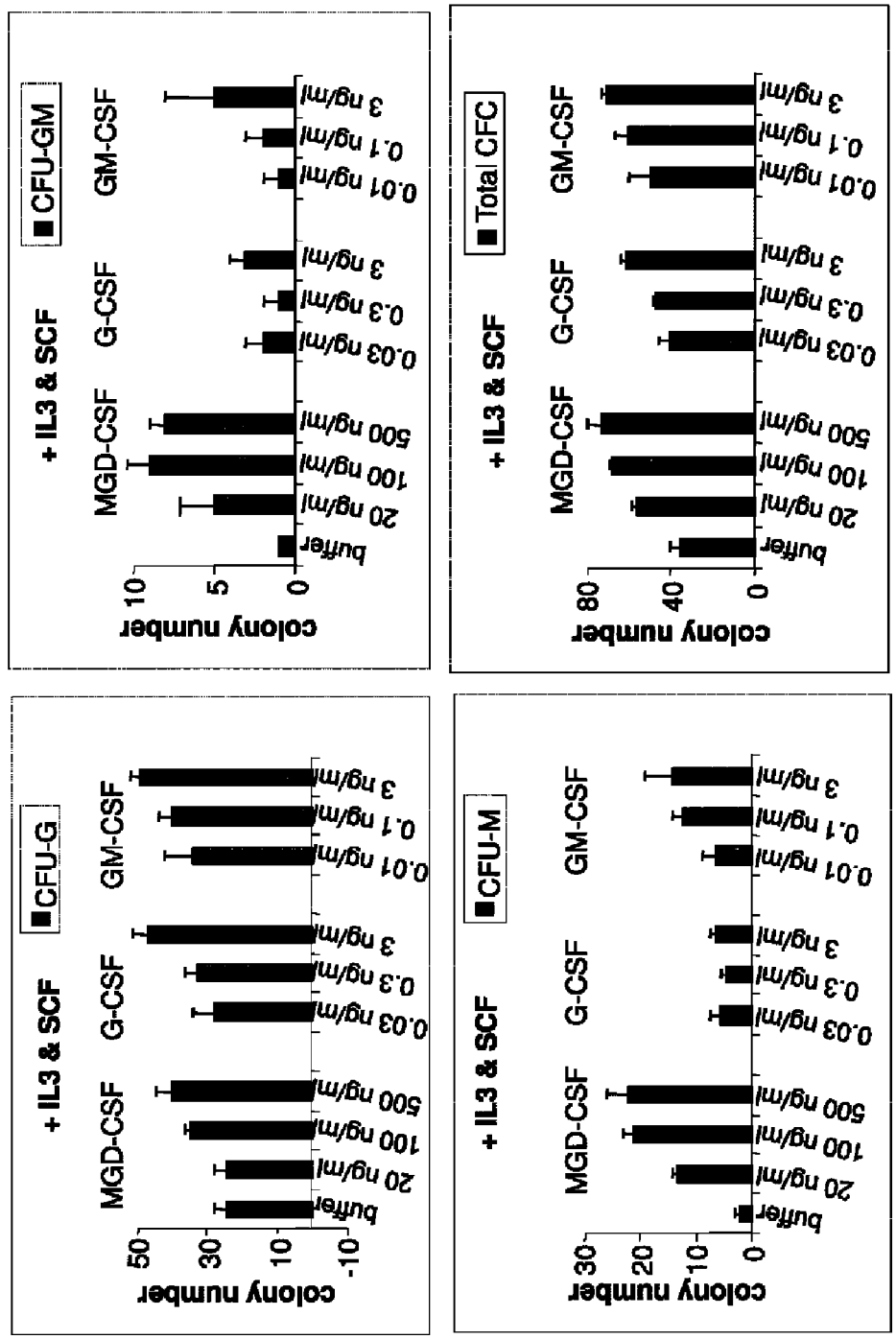
FIG. 18C shows the dose-dependent stimulatory effect of MGD-CSF on the formation of CFU-G (top left panel), CFU-GM (top right panel), CFU-M (bottom left panel), and the total colony forming capacity (Total CFC)

FIG. 18A and FIG. 18B show the effect of MGD-CSF on human bone marrow colony formation in the absence of exogenous cytokines. As shown in FIG. 18A, purified MGD-CSF had little effect on granulocyte colony formation (CFU-G) compared to G-CSF and GM-CSF. MGD-CSF stimulated monocyte colony formation (CFU-M) in a dose-dependent manner. As shown in FIG. 18B, MGD-CSF stimulated granulocyte-monocyte colony formation CFU-GM in a dose-dependent manner. MGD-CSF also stimulated total colony forming capacity (CFC) in a dose-dependent manner. FIG. 18C shows the effect of MGD-CSF on human bone marrow colony formation in the presence of the cytokines IL-3 and stem cell factor (SCF). Under those conditions, purified MGD-CSF stimulated CFU-G, CFU-GM, CFU-M, and total CFC in a dose-dependent manner. The distribution of myeloid progenitors in the presence of MGD-CSF was distinct from that of G-CSF or GM-CSF.

Example 12

Profile of Biological Activities of MGD-CSF

As shown in FIG. 19, MGD-CSF was tested for its biological effects in assays that measure non-activated B cell proliferation (BPro4), ability to stimulate glucose uptake by adipocytes (Gu2Gy3T3), unactivated monocyte proliferation (MonPro4), NK cell proliferation and/or survival (NKGlo), T cell proliferation (TPro4), activated primary B cell proliferation (aBPro4), activated primary monocyte proliferation (aMonPro3), and activated primary T cell proliferation (aTPro4). Results were considered significant if they were at least two standard deviations from the median. MGD-CSF specifically stimulated the proliferation of NK cells and unactivated monocytes, without stimulating the proliferation of activated monocytes or the proliferation of either activated or unactivated B cells or T cells.

Example 13

Profile of MGD-CSF-Induced Cytokine Secretion

As shown in FIG. 20, MGD-CSF was tested for its biological effect on cytokine secretion from NK cells. Assays were performed as described in Example 11. Conditioned medium was removed at the end of the experiment to determine the type and amount of cytokine secretion, using the Luminex cytokine assay kit from Linco, Inc. (St. Charles, Mo.) according to the manufacturer's instructions. Results were considered significant if they were at least two standard deviations from the median. MGD-CSF stimulated the secretion of GM-CSF, IL-12, and IL-13.

Example 14

MGD-CSF Stimulated CFU-M Differentiation from HSC Cells

MGD-CSF increased the size as well as the number of myeloid colonies formed from human bone marrow cells in a dose-dependent manner. The top left panel of FIG. 21 shows a representative photograph of CFU-M colonies observed in bone marrow cells cultured the absence of cytokine (buffer). Evidence of colony formation is weak or absent. The top middle panel shows a representative photograph of CFU-M colonies induced by GM-CSF; colony formation was apparent. The top right panel shows a representative photograph which demonstrates that G-CSF does not stimulate CFU-M formation. The bottom three panels of FIG. 16 show representative photographs of CFU-Ms induced by MGD-CSF. Both the number and the size increased in a dose-dependent manner between 20 ng/ml and 500 ng/ml MGD-CSF. The cells were examined and photographed with an Axiovert 25 microscope and AxioCam HRc (both from Carl Zeiss, Gottingen, Germany) using a 40× lens. Cells were visualized with a Zeiss KS300 3.0 digital imaging system.

The size of the colonies induced by MGD-CSF were larger than those induced by GM-CSF. Approximately 10% of the colonies induced by MGD-CSF were extremely large, in the range of 100-2000 microns. MGD-CSF induced these large colonies both in the presence and absence of the cytokines SCF and IL-3. These data show that MGD-CSF promoted the formation of early myeloid progenitors, including progenitors earlier than GM-CSF or G-CSF. They also suggest that MGD-CSF promotes the differentiation of either or both of the M1 or M2 macrophage lineage.

Example 15

MGD-CSF Stimulated HSC Differentiation to Dendritic Cells

Human bone marrow CD34$^+$ cells (Cambrex, Inc., Baltimore Md.) were plated on 24-well cell culture plates in serum-free X-vivo 20 medium (Cambrex, Inc., Baltimore Md.), and treated with vector control conditioned medium (CM) or MGD-CSF CM. The cells were examined and photographed with an Axiovert 25 microscope and AxioCam HRc (both from Carl Zeiss, Gottingen, Germany) using a 40× lens. Cells were visualized with a Zeiss KS300 3.0 digital imaging system.

As shown in FIG. 22, increasing numbers of elongated cells were observed in the MGD-CSF-treated cultures with increasing MGD-CSF concentrations. Anti-CD1a antibody was used to determine differentiation into dendritic cells. Treating the cultures with MGD-CSF for two weeks induced the differentiation of 20% of the human bone marrow CD34$^+$ into CD1a positive dendritic cells. MGD-CSF induced the differentiation of dendritic cells from human bone marrow cells in a dose-dependent manner (FIG. 22). The cells shown in all four panels were examined and photographed with an Axiovert 25 microscope and AxioCam HRc (both from Carl Zeiss, Gottingen, Germany) using a 40× lens. Cells were visualized with a Zeiss KS300 3.0 digital imaging system.

The top left panel of FIG. 22 shows a representative photograph of bone marrow cells cultured the absence of cytokine (medium). The cells are typically small and rounded. The top right panel shows a representative photograph of the bone marrow cells elongating and flattening to more closely resemble dendritic cells, in response to 20 ng/ml MGD-CSF. The bottom left panel shows a representative photograph which demonstrates that a higher dose of MGD-CSF, 100 ng/ml, has a more pronounced effect on the morphology of the HSC cells. The cells are larger and more elongated. The bottom right panel shows that a concentration of 500 ng/ml MGD-CSF resulted in large, flat, elongated cells with the morphological appearance of dendritic cells.

Example 16

MGD-CSF Gene Expression

The differential level of gene expression was compared in individual human cancer tissue specimens by interrogating a proprietary oncology database from GeneLogic, using the Affymetrix GeneChip® array platform, the Human Genome U133 and U133Plus_2 (Affymetrix, Inc, Santa Clara, Calif.) with probe 237046_x_at. It was also compared by interrogating microarray chips designed by Five Prime Therapeutics, Inc. with probes PRB107386 and PRB107386_at. These probes were used to determine the expression of MGD-CSF in the tissues of patients with hyperproliferative hematologic abnormalities. This analysis identified differential gene expression patterns between different tissue types and different disease stages. Table 8, column 3 lists the number of disease specimens that tested positive for the presence of MGC34647 (MGC34647 Positive). Table 8, column 4 lists the number of specimens examined (Total Gene Logic). MGD-CSF was expressed in most patients with myelodysplastic syndrome. The percent of patients expressing MGD-CSF varied with the observed pathology and was highest in patients with refractory anemia with excess blasts or ringed sideroblasts. Half of the patients with acute B-cell lymphoblastic leukemia expressed MGD-CSF. A subset of patients with acute myeloid leukemia expressed MGD-CSF. The percentage varied from 14-25%, depending on the pathological presentation of the disease. MGD-CSF was generally not expressed in patients with chronic myeloid leukemia, chronic lymphocytic leukemia, or acute promyelocytic leukemia.

SEQUENCE LISTING

A sequence listing transmittal sheet and a sequence listing in paper format accompanies this application.

Tables

TABLE 1

| | | | | SEQ. ID. NOS.: 1-271 | |
|---|---|---|---|---|---|
| FP ID | SEQ. ID. NO.: (N1) | SEQ. ID NO.: (P1) | SEQ. ID. NO.: (N0) | Source ID | Type |
| HG1015544 | SEQ. ID. NO.: 1 | SEQ. ID. NO.: 7 | | CLN00542945 | |
| HG1015545 | SEQ. ID. NO.: 2 | SEQ. ID. NO.: 8 | | CLN00542945_exon4 | |
| HG1015596 | SEQ. ID. NO.: 3 | SEQ. ID. NO.: 9 | | CLN00542945_mature peptide | |
| HG1015546 | SEQ. ID. NO.: 4 | SEQ. ID. NO.: 10 | SEQ. ID. NO.: 13 | NP_689669 | |
| HG1015597 | SEQ. ID. NO.: 5 | SEQ. ID. NO.: 11 | | CLN00542945_fragment | |
| HG1019016 | SEQ. ID. NO.: 6 | SEQ. ID. NO.: 12 | | NP_689669_fragment | |
| HG1018265 | | SEQ. ID. NO.: 14 | | collagen_leader_seq | leader sequence |
| HG1018268 | | SEQ. ID. NO.: 15 | | 112907: 21594845_1-17 | HMM_SP leader sequence |
| HG1018269 | | SEQ. ID. NO.: 16 | | 112907: 21594845_1-13 | leader sequence |
| HG1018270 | | SEQ. ID. NO.: 17 | | 112907: 21594845_1-19 | leader sequence |
| HG1018271 | | SEQ. ID. NO.: 18 | | 112907: 21594845_1-16 | leader sequence |
| HG1018272 | | SEQ. ID. NO.: 19 | | 112907: 21594845_1-15 | leader sequence |
| HG1018274 | | SEQ. ID. NO.: 20 | | 13325208: 13325207_1-30 | HMM_SP leader sequence |
| HG1018275 | | SEQ. ID. NO.: 21 | | 13325208: 13325207_1-25 | leader sequence |
| HG1018276 | | SEQ. ID. NO.: 22 | | 13325208: 13325207_1-33 | leader sequence |
| HG1018277 | | SEQ. ID. NO.: 23 | | 13325208: 13325207_1-24 | leader sequence |
| HG1018278 | | SEQ. ID. NO.: 24 | | 13325208: 13325207_1-26 | leader sequence |
| HG1018279 | | SEQ. ID. NO.: 25 | | 13325208: 13325207_1-32 | leader sequence |
| HG1018280 | | SEQ. ID. NO.: 26 | | 13325208: 13325207_1-27 | leader sequence |
| HG1018281 | | SEQ. ID. NO.: 27 | | 13325208: 13325207_1-23 | leader sequence |
| HG1018282 | | SEQ. ID. NO.: 28 | | 13325208: 13325207_1-35 | leader sequence |
| HG1018284 | | SEQ. ID. NO.: 29 | | 13938307: 13938306_1-24 | HMM_SP leader sequence |
| HG1018285 | | SEQ. ID. NO.: 30 | | 13938307: 13938306_1-21 | leader sequence |
| HG1018287 | | SEQ. ID. NO.: 31 | | 14718453: 14718452_1-19 | HMM_SP leader sequence |
| HG1018288 | | SEQ. ID. NO.: 32 | | 14718453: 14718452_1-15 | leader sequence |
| HG1018289 | | SEQ. ID. NO.: 33 | | 14718453: 14718452_1-17 | leader sequence |
| HG1018291 | | SEQ. ID. NO.: 34 | | 15929966: 15929965_1-23 | HMM_SP leader sequence |
| HG1018293 | | SEQ. ID. NO.: 35 | | 16356651: 16356650_1-21 | leader sequence |
| HG1018294 | | SEQ. ID. NO.: 36 | | 16356651: 16356650_1-17 | leader sequence |
| HG1018296 | | SEQ. ID. NO.: 37 | | 18204192: 18204191_1-19 | HMM_SP leader sequence |
| HG1018297 | | SEQ. ID. NO.: 38 | | 18204192: 18204191_1-22 | leader sequence |
| HG1018298 | | SEQ. ID. NO.: 39 | | 18204192: 18204191_1-18 | leader sequence |
| HG1018299 | | SEQ. ID. NO.: 40 | | 18204192: 18204191_1-16 | leader sequence |
| HG1018300 | | SEQ. ID. NO.: 41 | | 18204192: 18204191_1-14 | leader sequence |

TABLE 1-continued

SEQ. ID. NOS.: 1-271

| FP ID | SEQ. ID. NO.: (N1) | SEQ. ID NO.: (P1) | SEQ. ID. NO.: (N0) | Source ID | Type |
|---|---|---|---|---|---|
| HG1018302 | | SEQ. ID. NO.: 42 | | 23503038: 15778555_1-20 | leader sequence |
| HG1018303 | | SEQ. ID. NO.: 43 | | 23503038: 15778555_1-16 | leader sequence |
| HG1018304 | | SEQ. ID. NO.: 44 | | 23503038: 15778555_1-21 | leader sequence |
| HG1018306 | | SEQ. ID. NO.: 45 | | 27479535: 27479534_1-24 | HMM_SP leader sequence |
| HG1018307 | | SEQ. ID. NO.: 46 | | 27479535: 27479534_1-20 | leader sequence |
| HG1018308 | | SEQ. ID. NO.: 47 | | 27479535: 27479534_1-26 | leader sequence |
| HG1018309 | | SEQ. ID. NO.: 48 | | 27479535: 27479534_1-21 | leader sequence |
| HG1018310 | | SEQ. ID. NO.: 49 | | 27479535: 27479534_1-23 | leader sequence |
| HG1018312 | | SEQ. ID. NO.: 50 | | 37182960: 37182959_1-24 | HMM_SP leader sequence |
| HG1018313 | | SEQ. ID. NO.: 51 | | 37182960: 37182959_1-19 | leader sequence |
| HG1018314 | | SEQ. ID. NO.: 52 | | 37182960: 37182959_1-22 | leader sequence |
| HG1018315 | | SEQ. ID. NO.: 53 | | 37182960: 37182959_1-20 | leader sequence |
| HG1018316 | | SEQ. ID. NO.: 54 | | 37182960: 37182959_1-26 | leader sequence |
| HG1018317 | | SEQ. ID. NO.: 55 | | 37182960: 37182959_1-21 | leader sequence |
| HG1018319 | | SEQ. ID. NO.: 56 | | 7437388: 1208426_1-24 | HMM_SP leader sequence |
| HG1018320 | | SEQ. ID. NO.: 57 | | 7437388: 1208426_1-23 | leader sequence |
| HG1018322 | | SEQ. ID. NO.: 58 | | NP_000286: NM_000295_1-24 | HMM_SP leader sequence |
| HG1018323 | | SEQ. ID. NO.: 59 | | NP_000286: NM_000295_1-18 | leader sequence |
| HG1018324 | | SEQ. ID. NO.: 60 | | NP_000286: NM_000295_1-23 | leader sequence |
| HG1018325 | | SEQ. ID. NO.: 61 | | NP_000286: NM_000295_1-17 | leader sequence |
| HG1018327 | | SEQ. ID. NO.: 62 | | NP_000396: NM_000405_1-23 | HMM_SP leader sequence |
| HG1018328 | | SEQ. ID. NO.: 63 | | NP_000396: NM_000405_1-18 | leader sequence |
| HG1018329 | | SEQ. ID. NO.: 64 | | NP_000396: NM_000405_1-25 | leader sequence |
| HG1018330 | | SEQ. ID. NO.: 65 | | NP_000396: NM_000405_1-20 | leader sequence |
| HG1018331 | | SEQ. ID. NO.: 66 | | NP_000396: NM_000405_1-21 | leader sequence |
| HG1018333 | | SEQ. ID. NO.: 67 | | NP_000495: NM_000504_1-23 | HMM_SP leader sequence |
| HG1018334 | | SEQ. ID. NO.: 68 | | NP_000495: NM_000504_1-19 | leader sequence |
| HG1018335 | | SEQ. ID. NO.: 69 | | NP_000495: NM_000504_1-20 | leader sequence |
| HG1018336 | | SEQ. ID. NO.: 70 | | NP_000495: NM_000504_1-15 | leader sequence |
| HG1018337 | | SEQ. ID. NO.: 71 | | NP_000495: NM_000504_1-21 | leader sequence |
| HG1018338 | | SEQ. ID. NO.: 72 | | NP_000495: NM_000504_1-17 | leader sequence |
| HG1018340 | | SEQ. ID. NO.: 73 | | NP_000573: NM_000582_1-18 | HMM_SP leader sequence |
| HG1018341 | | SEQ. ID. NO.: 74 | | NP_000573: NM_000582_1-16 | leader sequence |
| HG1018342 | | SEQ. ID. NO.: 75 | | NP_000573: NM_000582_1-15 | leader sequence |
| HG1018344 | | SEQ. ID. NO.: 76 | | NP_000574: NM_000583_1-16 | HMM_SP leader sequence |
| HG1018345 | | SEQ. ID. NO.: 77 | | NP_000574: NM_000583_1-14 | leader sequence |
| HG1018347 | | SEQ. ID. NO.: 78 | | NP_000591: NM_000600_1-25 | HMM_SP leader sequence |

TABLE 1-continued

SEQ. ID. NOS.: 1-271

| FP ID | SEQ. ID. NO.: (N1) | SEQ. ID NO.: (P1) | SEQ. ID. NO.: (N0) | Source ID | Type |
|---|---|---|---|---|---|
| HG1018348 | | SEQ. ID. NO.: 79 | | NP_000591: NM_000600_1-24 | leader sequence |
| HG1018349 | | SEQ. ID. NO.: 80 | | NP_000591: NM_000600_1-27 | leader sequence |
| HG1018351 | | SEQ. ID. NO.: 81 | | NP_000598: NM_000607_1-18 | HMM_SP leader sequence |
| HG1018353 | | SEQ. ID. NO.: 82 | | NP_000604: NM_000613_1-19 | leader sequence |
| HG1018354 | | SEQ. ID. NO.: 83 | | NP_000604: NM_000613_1-25 | leader sequence |
| HG1018355 | | SEQ. ID. NO.: 84 | | NP_000604: NM_000613_1-21 | leader sequence |
| HG1018356 | | SEQ. ID. NO.: 85 | | NP_000604: NM_000613_1-23 | leader sequence |
| HG1018357 | | SEQ. ID. NO.: 86 | | NP_000604: NM_000613_1-31 | leader sequence |
| HG1018359 | | SEQ. ID. NO.: 87 | | NP_000726: NM_000735_1-26 | HMM_SP leader sequence |
| HG1018360 | | SEQ. ID. NO.: 88 | | NP_000726: NM_000735_1-24 | leader sequence |
| HG1018362 | | SEQ. ID. NO.: 89 | | NP_000884: NM_000893_1-18 | HMM_SP leader sequence |
| HG1018363 | | SEQ. ID. NO.: 90 | | NP_000884: NM_000893_1-19 | leader sequence |
| HG1018364 | | SEQ. ID. NO.: 91 | | NP_000884: NM_000893_1-16 | leader sequence |
| HG1018365 | | SEQ. ID. NO.: 92 | | NP_000884: NM_000893_1-23 | leader sequence |
| HG1018367 | | SEQ. ID. NO.: 93 | | NP_000909: NM_000918_1-17 | HMM_SP leader sequence |
| HG1018369 | | SEQ. ID. NO.: 94 | | NP_000930: NM_000939_1-23 | HMM_SP leader sequence |
| HG1018370 | | SEQ. ID. NO.: 95 | | NP_000930: NM_000939_1-26 | leader sequence |
| HG1018372 | | SEQ. ID. NO.: 96 | | NP_000945: NM_000954_1-23 | HMM_SP leader sequence |
| HG1018373 | | SEQ. ID. NO.: 97 | | NP_000945: NM_000954_1-22 | leader sequence |
| HG1018374 | | SEQ. ID. NO.: 98 | | NP_000945: NM_000954_1-18 | leader sequence |
| HG1018376 | | SEQ. ID. NO.: 99 | | NP_001176: NM_001185_1-18 | leader sequence |
| HG1018377 | | SEQ. ID. NO.: 100 | | NP_001176: NM_001185_1-20 | leader sequence |
| HG1018378 | | SEQ. ID. NO.: 101 | | NP_001176: NM_001185_1-21 | leader sequence |
| HG1018379 | | SEQ. ID. NO.: 102 | | NP_001176: NM_001185_1-17 | leader sequence |
| HG1018381 | | SEQ. ID. NO.: 103 | | NP_001266: NM_001275_1-18 | HMM_SP leader sequence |
| HG1018382 | | SEQ. ID. NO.: 104 | | NP_001266: NM_001275_1-15 | leader sequence |
| HG1018383 | | SEQ. ID. NO.: 105 | | NP_001266: NM_001275_1-14 | leader sequence |
| HG1018385 | | SEQ. ID. NO.: 106 | | NP_001314: NM_001323_1-26 | HMM_SP leader sequence |
| HG1018386 | | SEQ. ID. NO.: 107 | | NP_001314: NM_001323_1-18 | leader sequence |
| HG1018387 | | SEQ. ID. NO.: 108 | | NP_001314: NM_001323_1-20 | leader sequence |
| HG1018388 | | SEQ. ID. NO.: 109 | | NP_001314: NM_001323_1-28 | leader sequence |
| HG1018389 | | SEQ. ID. NO.: 110 | | NP_001314: NM_001323_1-21 | leader sequence |
| HG1018390 | | SEQ. ID. NO.: 111 | | NP_001314: NM_001323_1-23 | leader sequence |
| HG1018392 | | SEQ. ID. NO.: 112 | | NP_001822: NM_001831_1-22 | leader sequence |
| HG1018393 | | SEQ. ID. NO.: 113 | | NP_001822: NM_001831_1-18 | leader sequence |
| HG1018394 | | SEQ. ID. NO.: 114 | | NP_001822: NM_001831_1-14 | leader sequence |
| HG1018396 | | SEQ. ID. NO.: 115 | | NP_002206: NM_002215_1-24 | leader sequence |

TABLE 1-continued

SEQ. ID. NOS.: 1-271

| FP ID | SEQ. ID. NO.: (N1) | SEQ. ID NO.: (P1) | SEQ. ID. NO.: (N0) | Source ID | Type |
|---|---|---|---|---|---|
| HG1018397 | | SEQ. ID. NO.: 116 | | NP_002206: NM_002215_1-29 | leader sequence |
| HG1018398 | | SEQ. ID. NO.: 117 | | NP_002206: NM_002215_1-30 | leader sequence |
| HG1018399 | | SEQ. ID. NO.: 118 | | NP_002206: NM_002215_1-23 | leader sequence |
| HG1018400 | | SEQ. ID. NO.: 119 | | NP_002206: NM_002215_1-31 | leader sequence |
| HG1018402 | | SEQ. ID. NO.: 120 | | NP_002300: NM_002309_1-22 | HMM_SP leader sequence |
| HG1018403 | | SEQ. ID. NO.: 121 | | NP_002300: NM_002309_1-23 | leader sequence |
| HG1018405 | | SEQ. ID. NO.: 122 | | NP_002336: NM_002345_1-18 | HMM_SP leader sequence |
| HG1018406 | | SEQ. ID. NO.: 123 | | NP_002336: NM_002345_1-15 | leader sequence |
| HG1018407 | | SEQ. ID. NO.: 124 | | NP_002336: NM_002345_1-17 | leader sequence |
| HG1018408 | | SEQ. ID. NO.: 125 | | NP_002336: NM_002345_1-14 | leader sequence |
| HG1018410 | | SEQ. ID. NO.: 126 | | NP_002402: NM_002411_1-18 | HMM_SP leader sequence |
| HG1018412 | | SEQ. ID. NO.: 127 | | NP_002505: NM_002514_1-30 | HMM_SP leader sequence |
| HG1018413 | | SEQ. ID. NO.: 128 | | NP_002505: NM_002514_1-32 | leader sequence |
| HG1018414 | | SEQ. ID. NO.: 129 | | NP_002505: NM_002514_1-28 | leader sequence |
| HG1018415 | | SEQ. ID. NO.: 130 | | NP_002505: NM_002514_1-27 | leader sequence |
| HG1018416 | | SEQ. ID. NO.: 131 | | NP_002505: NM_002514_1-31 | leader sequence |
| HG1018418 | | SEQ. ID. NO.: 132 | | NP_002892: NM_002901_1-26 | HMM_SP leader sequence |
| HG1018419 | | SEQ. ID. NO.: 133 | | NP_002892: NM_002901_1-22 | leader sequence |
| HG1018420 | | SEQ. ID. NO.: 134 | | NP_002892: NM_002901_1-29 | leader sequence |
| HG1018421 | | SEQ. ID. NO.: 135 | | NP_002892: NM_002901_1-24 | leader sequence |
| HG1018422 | | SEQ. ID. NO.: 136 | | NP_002892: NM_002901_1-23 | leader sequence |
| HG1018424 | | SEQ. ID. NO.: 137 | | NP_002893: NM_002902_1-25 | HMM_SP leader sequence |
| HG1018425 | | SEQ. ID. NO.: 138 | | NP_002893: NM_002902_1-19 | leader sequence |
| HG1018426 | | SEQ. ID. NO.: 139 | | NP_002893: NM_002902_1-22 | leader sequence |
| HG1018427 | | SEQ. ID. NO.: 140 | | NP_002893: NM_002902_1-18 | leader sequence |
| HG1018428 | | SEQ. ID. NO.: 141 | | NP_002893: NM_002902_1-20 | leader sequence |
| HG1018429 | | SEQ. ID. NO.: 142 | | NP_002893: NM_002902_1-21 | leader sequence |
| HG1018430 | | SEQ. ID. NO.: 143 | | NP_002893: NM_002902_1-23 | leader sequence |
| HG1018432 | | SEQ. ID. NO.: 144 | | NP_005133: NM_005142_1-19 | HMM_SP leader sequence |
| HG1018433 | | SEQ. ID. NO.: 145 | | NP_005133: NM_005142_1-18 | leader sequence |
| HG1018434 | | SEQ. ID. NO.: 146 | | NP_005133: NM_005142_1-20 | leader sequence |
| HG1018435 | | SEQ. ID. NO.: 147 | | NP_005133: NM_005142_1-24 | leader sequence |
| HG1018436 | | SEQ. ID. NO.: 148 | | NP_005133: NM_005142_1-16 | leader sequence |
| HG1018437 | | SEQ. ID. NO.: 149 | | NP_005133: NM_005142_1-17 | leader sequence |
| HG1018438 | | SEQ. ID. NO.: 150 | | NP_005133: NM_005142_1-14 | leader sequence |
| HG1018440 | | SEQ. ID. NO.: 151 | | NP_005445: NM_005454_1-17 | HMM_SP leader sequence |
| HG1018442 | | SEQ. ID. NO.: 152 | | NP_005555: NM_005564_1-18 | HMM_SP leader sequence |

TABLE 1-continued

SEQ. ID. NOS.: 1-271

| FP ID | SEQ. ID. NO.: (N1) | SEQ. ID NO.: (P1) | SEQ. ID. NO.: (N0) | Source ID | Type |
|---|---|---|---|---|---|
| HG1018443 | | SEQ. ID. NO.: 153 | | NP_005555: NM_005564_1-20 | leader sequence |
| HG1018444 | | SEQ. ID. NO.: 154 | | NP_005555: NM_005564_1-15 | leader sequence |
| HG1018446 | | SEQ. ID. NO.: 155 | | NP_005690: NM_005699_1-29 | HMM_SP leader sequence |
| HG1018447 | | SEQ. ID. NO.: 156 | | NP_005690: NM_005699_1-24 | leader sequence |
| HG1018448 | | SEQ. ID. NO.: 157 | | NP_005690: NM_005699_1-28 | leader sequence |
| HG1018450 | | SEQ. ID. NO.: 158 | | NP_006560: NM_006569_1-19 | HMM_SP leader sequence |
| HG1018451 | | SEQ. ID. NO.: 159 | | NP_006560: NM_006569_1-18 | leader sequence |
| HG1018452 | | SEQ. ID. NO.: 160 | | NP_006560: NM_006569_1-21 | leader sequence |
| HG1018454 | | SEQ. ID. NO.: 161 | | NP_006856: NM_006865_1-15 | HMM_SP leader sequence |
| HG1018456 | | SEQ. ID. NO.: 162 | | NP_036577: NM_012445_1-26 | HMM_SP leader sequence |
| HG1018457 | | SEQ. ID. NO.: 163 | | NP_036577: NM_012445_1-25 | leader sequence |
| HG1018458 | | SEQ. ID. NO.: 164 | | NP_036577: NM_012445_1-24 | leader sequence |
| HG1018459 | | SEQ. ID. NO.: 165 | | NP_036577: NM_012445_1-28 | leader sequence |
| HG1018461 | | SEQ. ID. NO.: 166 | | NP_055070: NM_014255_1-20 | HMM_SP leader sequence |
| HG1018462 | | SEQ. ID. NO.: 167 | | NP_055070: NM_014255_1-18 | leader sequence |
| HG1018463 | | SEQ. ID. NO.: 168 | | NP_055070: NM_014255_1-16 | leader sequence |
| HG1018465 | | SEQ. ID. NO.: 169 | | NP_055582: NM_014767_1-24 | HMM_SP leader sequence |
| HG1018466 | | SEQ. ID. NO.: 170 | | NP_055582: NM_014767_1-19 | leader sequence |
| HG1018467 | | SEQ. ID. NO.: 171 | | NP_055582: NM_014767_1-22 | leader sequence |
| HG1018468 | | SEQ. ID. NO.: 172 | | NP_055582: NM_014767_1-20 | leader sequence |
| HG1018469 | | SEQ. ID. NO.: 173 | | NP_055582: NM_014767_1-26 | leader sequence |
| HG1018470 | | SEQ. ID. NO.: 174 | | NP_055582: NM_014767_1-21 | leader sequence |
| HG1018472 | | SEQ. ID. NO.: 175 | | NP_055697: NM_014882_1-18 | HMM_SP leader sequence |
| HG1018474 | | SEQ. ID. NO.: 176 | | NP_056965: NM_015881_1-18 | HMM_SP leader sequence |
| HG1018475 | | SEQ. ID. NO.: 177 | | NP_056965: NM_015881_1-19 | leader sequence |
| HG1018476 | | SEQ. ID. NO.: 178 | | NP_056965: NM_015881_1-22 | leader sequence |
| HG1018477 | | SEQ. ID. NO.: 179 | | NP_056965: NM_015881_1-16 | leader sequence |
| HG1018478 | | SEQ. ID. NO.: 180 | | NP_056965: NM_015881_1-21 | leader sequence |
| HG1018480 | | SEQ. ID. NO.: 181 | | NP_057603: NM_016519_1-26 | leader sequence |
| HG1018481 | | SEQ. ID. NO.: 182 | | NP_057603: NM_016519_1-28 | leader sequence |
| HG1018483 | | SEQ. ID. NO.: 183 | | NP_149439: NM_033183_1-18 | HMM_SP leader sequence |
| HG1018484 | | SEQ. ID. NO.: 184 | | NP_149439: NM_033183_1-20 | leader sequence |
| HG1018485 | | SEQ. ID. NO.: 185 | | NP_149439: NM_033183_1-16 | leader sequence |
| HG1018487 | | SEQ. ID. NO.: 186 | | NP_644808: NM_139279_1-18 | leader sequence |
| HG1018488 | | SEQ. ID. NO.: 187 | | NP_644808: NM_139279_1-20 | leader sequence |
| HG1018489 | | SEQ. ID. NO.: 188 | | NP_644808: NM_139279_1-26 | leader sequence |
| HG1018490 | | SEQ. ID. NO.: 189 | | NP_644808: NM_139279_1-23 | leader sequence |

TABLE 1-continued

SEQ. ID. NOS.: 1-271

| FP ID | SEQ. ID. NO.: (N1) | SEQ. ID NO.: (P1) | SEQ. ID. NO.: (N0) | Source ID | Type |
|---|---|---|---|---|---|
| HG1018492 | | SEQ. ID. NO.: 190 | | NP_660295: NM_145252_1-13 | leader sequence |
| HG1018493 | | SEQ. ID. NO.: 191 | | NP_660295: NM_145252_1-16 | leader sequence |
| HG1018494 | | SEQ. ID. NO.: 192 | | NP_660295: NM_145252_1-14 | leader sequence |
| HG1018495 | | SEQ. ID. NO.: 193 | | NP_660295: NM_145252_1-17 | leader sequence |
| HG1018497 | | SEQ. ID. NO.: 194 | | NP_689534: NM_152321_1-25 | HMM_SP leader sequence |
| HG1018498 | | SEQ. ID. NO.: 195 | | NP_689534: NM_152321_1-21 | leader sequence |
| HG1018500 | | SEQ. ID. NO.: 196 | | NP_689848: NM_152635_1-18 | HMM_SP leader sequence |
| HG1018501 | | SEQ. ID. NO.: 197 | | NP_689848: NM_152635_1-16 | leader sequence |
| HG1018502 | | SEQ. ID. NO.: 198 | | NP_689848: NM_152635_1-15 | leader sequence |
| HG1018504 | | SEQ. ID. NO.: 199 | | NP_689968: NM_152755_1-21 | HMM_SP leader sequence |
| HG1018506 | | SEQ. ID. NO.: 200 | | NP_766630: NM_173042_1-29 | HMM_SP leader sequence |
| HG1018507 | | SEQ. ID. NO.: 201 | | NP_766630: NM_173042_1-24 | leader sequence |
| HG1018508 | | SEQ. ID. NO.: 202 | | NP_766630: NM_173042_1-28 | leader sequence |
| HG1018510 | | SEQ. ID. NO.: 203 | | NP_776214: NM_173842_1-23 | HMM_SP leader sequence |
| HG1018511 | | SEQ. ID. NO.: 204 | | NP_776214: NM_173842_1-25 | leader sequence |
| HG1018513 | | SEQ. ID. NO.: 205 | | NP_783165: NM_175575_1-32 | HMM_SP leader sequence |
| HG1018514 | | SEQ. ID. NO.: 206 | | NP_783165: NM_175575_1-34 | leader sequence |
| HG1018515 | | SEQ. ID. NO.: 207 | | NP_783165: NM_175575_1-29 | leader sequence |
| HG1018516 | | SEQ. ID. NO.: 208 | | NP_783165: NM_175575_1-30 | leader sequence |
| HG1018517 | | SEQ. ID. NO.: 209 | | NP_783165: NM_175575_1-27 | leader sequence |
| HG1018857 | | SEQ. ID. NO.: 210 | | 27482680: 27482679_1-26 | HMM_SP leader sequence |
| HG1018858 | | SEQ. ID. NO.: 211 | | 27482680: 27482679_1-24 | leader sequence |
| HG1015544 | SEQ. ID. NO.: 212 | SEQ. ID. NO.: 235 | | CLN00542945 | hypothetical protein MGD-CSF [Homo sapiens] untagged in vector pTT5. |
| HG1019453 | SEQ. ID. NO.: 213 | SEQ. ID. NO.: 236 | | CLN00839395 | hypothetical protein MGD-CSF [Homo sapiens] untagged in vector pTT2 |
| HG1019454 | SEQ. ID. NO.: 214 | SEQ. ID. NO.: 237 | | CLN00732663 | hypothetical protein MGD-CSF [Homo sapiens] C-terminus V5H8 tagged in vector pTT5 |
| HG1019455 | SEQ. ID. NO.: 215 | SEQ. ID. NO.: 238 | | CLN00840351 | hypothetical protein MGD-CSF [Homo sapiens] C-terminus V5H8 tagged in vector pTT2 |
| HG1019456 | SEQ. ID. NO.: 216 | SEQ. ID. NO.: 239 | | CLN00758593 | hypothetical protein MGD-CSF [Homo sapiens] C-terminus V5H8 tagged in pIB/V5His-DEST vector (Invitrogen). |
| HG1019457 | SEQ. ID. NO.: 217 | SEQ. ID. NO.: 240 | | CLN00848149 | hypothetical protein MGD-CSF [Homo sapiens]. Collagen SP(1-23aa)_MGD-CSF(21 to 241aa). Untagged in vector pTT5-G. |
| HG1019458 | SEQ. ID. NO.: 218 | SEQ. ID. NO.: 241 | | CLN00821867 | hypothetical protein MGD-CSF [Homo sapiens]. MGD-CSF (1-241aa)_TEV_V5_StreptagII_H8. C- tagged in vector pTT5-I. |

TABLE 1-continued

SEQ. ID. NOS.: 1-271

| FP ID | SEQ. ID. NO.: (N1) | SEQ. ID NO.: (P1) | SEQ. ID. NO.: (N0) | Source ID | Type |
|---|---|---|---|---|---|
| HG1019459 | SEQ. ID. NO.: 219 | SEQ. ID. NO.: 242 | | CLN00816424 | hypothetical protein MGD-CSF [Homo sapiens] Collagen SP (1-23aa)_MGD-CSF(21 to 241aa)_TEV_V5_StreptagII_H8. C- tagged in vector pTT5-G |
| HG1019460 | SEQ. ID. NO.: 220 | SEQ. ID. NO.: 243 | | CLN00816425 | hypothetical protein MGD-CSF [Homo sapiens] Collagen SP(1-23aa)_H8_StreptagII_V5_TEV_MGD-CSF (21 to 241aa). N- tagged in vector pTT5-H |
| HG1019461 | SEQ. ID. NO.: 221 | SEQ. ID. NO.: 244 | | CLN00848160 | hypothetical protein MGD-CSF [Homo sapiens]. Collagen SP(1-23aa)_MGD-CSF(26 to 241aa). Untagged in vector pTT5. |
| HG1019462 | SEQ. ID. NO.: 222 | SEQ. ID. NO.: 245 | | CLN00848173 | hypothetical protein MGD-CSF [Homo sapiens]. Collagen SP(1-23aa)_MGD-CSF(31 to 241aa). Untagged in vector pTT5. |
| HG1019463 | SEQ. ID. NO.: 223 | SEQ. ID. NO.: 246 | | CLN00848185 | hypothetical protein MGD-CSF [Homo sapiens] Collagen SP(1-23aa)_MGD-CSF(21 to 213aa). Untagged in vector pTT5. |
| HG1019464 | SEQ. ID. NO.: 224 | SEQ. ID. NO.: 247 | | CLN00848197 | hypothetical protein MGD-CSF [Homo sapiens] Collagen SP(1-23aa)_MGD-CSF(21 to 231aa). Untagged in vector pTT5. |
| HG1019465 | SEQ. ID. NO.: 225 | SEQ. ID. NO.: 248 | | CLN00848209 | hypothetical protein MGD-CSF [Homo sapiens] Collagen SP(1-23aa)_MGD-CSF(21 to 236aa). Untagged in vector pTT5. |
| HG1019466 | SEQ. ID. NO.: 226 | SEQ. ID. NO.: 249 | | CLN00848220 | hypothetical protein MGD-CSF [Homo sapiens] Collagen SP(1-23aa)_MGD-CSF(26 to 231aa). Untagged in vector pTT5. |
| HG1019467 | SEQ. ID. NO.: 227 | SEQ. ID. NO.: 250 | | CLN00840257 | Phantom Clone 2010004A03 mouse ortholog of human MGC34647 cloned in vector pTT5. |
| HG1019468 | SEQ. ID. NO.: 228 | SEQ. ID. NO.: 251 | | CLN00840253 | Phantom Clone 2010004A03 mouse ortholog of human MGC34647. 12842044(1 to 219aa)_TEV_V5_StreptagII_H8. cloned in vector pTT5-I |
| HG1019469 | SEQ. ID. NO.: 229 | SEQ. ID. NO.: 252 | | CLN00847948 | mouse ortholog of human MGC34647 cloned in vector pTT5 235aa |
| HG1019470 | SEQ. ID. NO.: 230 | SEQ. ID. NO.: 253 | | CLN00842712 | mouse ortholog of human MGC34647. 18921437(1-235aa)_TEV_V5_StreptagII_H8. cloned in pTT5-I |
| HG1019471 | SEQ. ID. NO.: 231 | SEQ. ID. NO.: 254 | | NP_689669_maturepeptide | |
| HG1019472 | SEQ. ID. NO.: 232 | SEQ. ID. NO.: 255 | SEQ. ID. NO.: 257 | WO02048337_seq49 | Incyte patent WO 02/048337 (seqs 49/103) |
| HG1019473 | SEQ. ID. NO.: 233 | SEQ. ID. NO.: 256 | | WO02048337_seq49_maturepeptide | |
| HG1019474 | SEQ. ID. NO.: 234 | | | Kozak_sequence | GCCGCCACC |

TABLE 1-continued

SEQ. ID. NOS.: 1-271

| FP ID | SEQ. ID. NO.: (N1) | SEQ. ID. NO.: (P1) | SEQ. ID. NO.: (N0) | Source ID | Type |
|---|---|---|---|---|---|
| HG1019600 | SEQ. ID. NO.: 258 | SEQ. ID. NO.: 265 | | CLN00872284_20-241 | CollagenSP_C35S-MGC34647(20 to 241aa)_STP |
| HG1019601 | SEQ. ID. NO.: 259 | SEQ. ID. NO.: 266 | | CLN00872342_20-241 | CollagenSP_C179S-MGC34647(20 to 241aa)_STP |
| HG1019602 | SEQ. ID. NO.: 260 | SEQ. ID. NO.: 267 | | CLN00873848_20-241 | CollagenSP_C176S-MGC34647(20 to 241aa)_STP |
| HG1019603 | SEQ. ID. NO.: 261 | SEQ. ID. NO.: 268 | | CLN00873864_20-241 | CollagenSP_C190S-MGC34647(20 to 241aa)_STP |
| HG1019604 | SEQ. ID. NO.: 262 | SEQ. ID. NO.: 269 | | CLN00873948_20-241 | CollagenSP_C167S-MGC34647(20 to 241aa)_STP |
| HG1019605 | SEQ. ID. NO.: 263 | SEQ. ID. NO.: 270 | | CLN00873956_20-241 | CollagenSP_C178S-MGC34647(20 to 241aa)_STP |
| HG1019606 | SEQ. ID. NO.: 264 | SEQ. ID. NO.: 271 | | CLN00873970_20-241 | CollagenSP_C198S-MGC34647(20 to 241aa)_STP |

TABLE 2

Annotation of MGD-CSF

| | | | |
|---|---|---|---|
| FP ID | HG1015544 | HG1015545 | HG1015546 |
| Clone ID | MGD-CSF | MGD-CSF_exon4 | NP_689669 |
| Pred Prot Len | 241 | 53 | 242 |
| Top Human Hit Accession No | gi\|22748957\|ref\|NP_689669.1\| | gi\|22748957\|ref\|NP_689669.1\| | gi\|22748957\|ref\|NP_689669.1\| |
| Top Human Hit Annotation | hypothetical protein MGC34647 [Homo sapiens] | hypothetical protein MGC34647 [Homo sapiens] | hypothetical protein MGC34647 [Homo sapiens] |
| Top Human Hit Len | 242 | 242 | 242 |
| Match Len | 241 | 53 | 242 |
| Top Human Hit % ID Over Query Len | 100 | 100 | 100 |
| % ID Over Human Hit Len | 100 | 22 | 100 |

TABLE 3

Protein Coordinates of MGD-CSF

| | | | |
|---|---|---|---|
| FP ID | HG1015544 | HG1015545 | HG1015546 |
| Clone ID | MGD-CSF | MGD-CSF_exon4 | NP_689669 |
| Cluster | 190647 | 190647 | 190647 |
| Classification | Secreted | Secreted | Secreted |
| Pred Prot Len | 241 | 53 | 242 |
| Treevote | 0.93 | 0.75 | 0.92 |
| Signal Peptide Coords | (1-20) | (9-23) | (1-20) |
| Mature Protein Coords | (21-241) | (24-53) | (21-241) |

TABLE 4

Secretory Leader Sequence Annotations

| FP ID | Source ID | Annotation |
|---|---|---|
| HG1018265 | collagen_leader_seq | collagen alpha 1(IX) chain precursor, long splice form - human |
| HG1018268 | 112907: 21594845_1-17 | Alpha-2-antiplasmin precursor (Alpha-2-plasmin inhibitor) |
| HG1018269 | 112907: 21594845_1-13 | Alpha-2-antiplasmin precursor (Alpha-2-plasmin inhibitor) |
| HG1018270 | 112907: 21594845_1-19 | Alpha-2-antiplasmin precursor (Alpha-2-plasmin inhibitor) |
| HG1018271 | 112907: 21594845_1-16 | Alpha-2-antiplasmin precursor (Alpha-2-plasmin inhibitor) |
| HG1018272 | 112907: 21594845_1-15 | Alpha-2-antiplasmin precursor (Alpha-2-plasmin inhibitor) |
| HG1018274 | 13325208: 13325207_1-30 | Trinucleotide repeat containing 5 [Homo sapiens] |
| HG1018275 | 13325208: 13325207_1-25 | Trinucleotide repeat containing 5 [Homo sapiens] |
| HG1018276 | 13325208: 13325207_1-33 | Trinucleotide repeat containing 5 [Homo sapiens] |
| HG1018277 | 13325208: 13325207_1-24 | Trinucleotide repeat containing 5 [Homo sapiens] |

TABLE 4-continued

Secretory Leader Sequence Annotations

| FP ID | Source ID | Annotation |
|---|---|---|
| HG1018278 | 13325208: 13325207__1-26 | Trinucleotide repeat containing 5 [*Homo sapiens*] |
| HG1018279 | 13325208: 13325207__1-32 | Trinucleotide repeat containing 5 [*Homo sapiens*] |
| HG1018280 | 13325208: 13325207__1-27 | Trinucleotide repeat containing 5 [*Homo sapiens*] |
| HG1018281 | 13325208: 13325207__1-23 | Trinucleotide repeat containing 5 [*Homo sapiens*] |
| HG1018282 | 13325208: 13325207__1-35 | Trinucleotide repeat containing 5 [*Homo sapiens*] |
| HG1018284 | 13938307: 13938306__1-24 | ARMET protein [*Homo sapiens*] |
| HG1018285 | 13938307: 13938306__1-21 | ARMET protein [*Homo sapiens*] |
| HG1018287 | 14718453: 14718452__1-19 | calumenin [*Homo sapiens*] |
| HG1018288 | 14718453: 14718452__1-15 | calumenin [*Homo sapiens*] |
| HG1018289 | 14718453: 14718452__1-17 | calumenin [*Homo sapiens*] |
| HG1018291 | 15929966: 15929965__1-23 | COL9A1 protein [*Homo sapiens*] |
| HG1018293 | 16356651: 16356650__1-21 | NBL1 [*Homo sapiens*] |
| HG1018294 | 16356651: 16356650__1-17 | NBL1 [*Homo sapiens*] |
| HG1018296 | 18204192: 18204191__1-19 | PACAP protein [*Homo sapiens*] |
| HG1018297 | 18204192: 18204191__1-22 | PACAP protein [*Homo sapiens*] |
| HG1018298 | 18204192: 18204191__1-18 | PACAP protein [*Homo sapiens*] |
| HG1018299 | 18204192: 18204191__1-16 | PACAP protein [*Homo sapiens*] |
| HG1018300 | 18204192: 18204191__1-14 | PACAP protein [*Homo sapiens*] |
| HG1018302 | 23503038: 15778555__1-20 | Alpha-1B-glycoprotein precursor (Alpha-1-B glycoprotein) |
| HG1018303 | 23503038: 15778555__1-16 | Alpha-1B-glycoprotein precursor (Alpha-1-B glycoprotein) |
| HG1018304 | 23503038: 15778555__1-21 | Alpha-1B-glycoprotein precursor (Alpha-1-B glycoprotein) |
| HG1018306 | 27479535: 27479534__1-24 | similar to Brain-specific angiogenesis inhibitor 2 precursor [*Homo sapiens*] |
| HG1018307 | 27479535: 27479534__1-20 | similar to Brain-specific angiogenesis inhibitor 2 precursor [*Homo sapiens*] |
| HG1018308 | 27479535: 27479534__1-26 | similar to Brain-specific angiogenesis inhibitor 2 precursor [*Homo sapiens*] |
| HG1018309 | 27479535: 27479534__1-21 | similar to Brain-specific angiogenesis inhibitor 2 precursor [*Homo sapiens*] |
| HG1018310 | 27479535: 27479534__1-23 | similar to Brain-specific angiogenesis inhibitor 2 precursor [*Homo sapiens*] |
| HG1018312 | 37182960: 37182959__1-24 | SPOCK2 [*Homo sapiens*] |
| HG1018313 | 37182960: 37182959__1-19 | SPOCK2 [*Homo sapiens*] |
| HG1018314 | 37182960: 37182959__1-22 | SPOCK2 [*Homo sapiens*] |
| HG1018315 | 37182960: 37182959__1-20 | SPOCK2 [*Homo sapiens*] |
| HG1018316 | 37182960: 37182959__1-26 | SPOCK2 [*Homo sapiens*] |
| HG1018317 | 37182960: 37182959__1-21 | SPOCK2 [*Homo sapiens*] |
| HG1018319 | 7437388: 1208426__1-24 | protein disulfide-isomerase (EC 5341) ER60 precursor - human |
| HG1018320 | 7437388: 1208426__1-23 | protein disulfide-isomerase (EC 5341) ER60 precursor - human |
| HG1018322 | NP_000286: NM_000295__1-24 | serine (or cysteine) proteinase inhibitor, clade A (alpha-1 |
| HG1018323 | NP_000286: NM_000295__1-18 | serine (or cysteine) proteinase inhibitor, clade A (alpha-1 |
| HG1018324 | NP_000286: NM_000295__1-23 | serine (or cysteine) proteinase inhibitor, clade A (alpha-1 |
| HG1018325 | NP_000286: NM_000295__1-17 | serine (or cysteine) proteinase inhibitor, clade A (alpha-1 |
| HG1018327 | NP_000396: NM_000405__1-23 | GM2 ganglioside activator precursor [*Homo sapiens*] |
| HG1018328 | NP_000396: NM_000405__1-18 | GM2 ganglioside activator precursor [*Homo sapiens*] |
| HG1018329 | NP_000396: NM_000405__1-25 | GM2 ganglioside activator precursor [*Homo sapiens*] |
| HG1018330 | NP_000396: NM_000405__1-20 | GM2 ganglioside activator precursor [*Homo sapiens*] |
| HG1018331 | NP_000396: NM_000405__1-21 | GM2 ganglioside activator precursor [*Homo sapiens*] |
| HG1018333 | NP_000495: NM_000504__1-23 | coagulation factor X precursor [*Homo sapiens*] |
| HG1018334 | NP_000495: NM_000504__1-19 | coagulation factor X precursor [*Homo sapiens*] |
| HG1018335 | NP_000495: NM_000504__1-20 | coagulation factor X precursor [*Homo sapiens*] |
| HG1018336 | NP_000495: NM_000504__1-15 | coagulation factor X precursor [*Homo sapiens*] |
| HG1018337 | NP_000495: NM_000504__1-21 | coagulation factor X precursor [*Homo sapiens*] |
| HG1018338 | NP_000495: NM_000504__1-17 | coagulation factor X precursor [*Homo sapiens*] |
| HG1018340 | NP_000573: NM_000582__1-18 | secreted phosphoprotein 1 (osteopontin, bone sialoprotein I, early |
| HG1018341 | NP_000573: NM_000582__1-16 | secreted phosphoprotein 1 (osteopontin, bone sialoprotein I, early |
| HG1018342 | NP_000573: NM_000582__1-15 | secreted phosphoprotein 1 (osteopontin, bone sialoprotein I, early |
| HG1018344 | NP_000574: NM_000583__1-16 | vitamin D-binding protein precursor [*Homo sapiens*] |
| HG1018345 | NP_000574: NM_000583__1-14 | vitamin D-binding protein precursor [*Homo sapiens*] |
| HG1018347 | NP_000591: NM_000600__1-25 | interleukin 6 (interferon, beta 2) [*Homo sapiens*] |
| HG1018348 | NP_000591: NM_000600__1-24 | interleukin 6 (interferon, beta 2) [*Homo sapiens*] |
| HG1018349 | NP_000591: NM_000600__1-27 | interleukin 6 (interferon, beta 2) [*Homo sapiens*] |
| HG1018351 | NP_000598: NM_000607__1-18 | orosomucoid 1 precursor [*Homo sapiens*] |
| HG1018353 | NP_000604: NM_000613__1-19 | hemopexin [*Homo sapiens*] |
| HG1018354 | NP_000604: NM_000613__1-25 | hemopexin [*Homo sapiens*] |
| HG1018355 | NP_000604: NM_000613__1-21 | hemopexin [*Homo sapiens*] |
| HG1018356 | NP_000604: NM_000613__1-23 | hemopexin [*Homo sapiens*] |
| HG1018357 | NP_000604: NM_000613__1-31 | hemopexin [*Homo sapiens*] |
| HG1018359 | NP_000726: NM_000735__1-26 | glycoprotein hormones, alpha polypeptide precursor [*Homo sapiens*] |
| HG1018360 | NP_000726: NM_000735__1-24 | glycoprotein hormones, alpha polypeptide precursor [*Homo sapiens*] |
| HG1018362 | NP_000884: NM_000893__1-18 | kininogen 1 [*Homo sapiens*] |
| HG1018363 | NP_000884: NM_000893__1-19 | kininogen 1 [*Homo sapiens*] |
| HG1018364 | NP_000884: NM_000893__1-16 | kininogen 1 [*Homo sapiens*] |
| HG1018365 | NP_000884: NM_000893__1-23 | kininogen 1 [*Homo sapiens*] |

TABLE 4-continued

Secretory Leader Sequence Annotations

| FP ID | Source ID | Annotation |
|---|---|---|
| HG1018367 | NP_000909: NM_000918_1-17 | prolyl 4-hydroxylase, beta subunit [*Homo sapiens*] |
| HG1018369 | NP_000930: NM_000939_1-23 | proopiomelanocortin [*Homo sapiens*] |
| HG1018370 | NP_000930: NM_000939_1-26 | proopiomelanocortin [*Homo sapiens*] |
| HG1018372 | NP_000945: NM_000954_1-23 | prostaglandin D2 synthase 21 kDa [*Homo sapiens*] |
| HG1018373 | NP_000945: NM_000954_1-22 | prostaglandin D2 synthase 21 kDa [*Homo sapiens*] |
| HG1018374 | NP_000945: NM_000954_1-18 | prostaglandin D2 synthase 21 kDa [*Homo sapiens*] |
| HG1018376 | NP_001176: NM_001185_1-18 | alpha-2-glycoprotein 1, zinc [*Homo sapiens*] |
| HG1018377 | NP_001176: NM_001185_1-20 | alpha-2-glycoprotein 1, zinc [*Homo sapiens*] |
| HG1018378 | NP_001176: NM_001185_1-21 | alpha-2-glycoprotein 1, zinc [*Homo sapiens*] |
| HG1018379 | NP_001176: NM_001185_1-17 | alpha-2-glycoprotein 1, zinc [*Homo sapiens*] |
| HG1018381 | NP_001266: NM_001275_1-18 | chromogranin A [*Homo sapiens*] |
| HG1018382 | NP_001266: NM_001275_1-15 | chromogranin A [*Homo sapiens*] |
| HG1018383 | NP_001266: NM_001275_1-14 | chromogranin A [*Homo sapiens*] |
| HG1018385 | NP_001314: NM_001323_1-26 | cystatin M precursor [*Homo sapiens*] |
| HG1018386 | NP_001314: NM_001323_1-18 | cystatin M precursor [*Homo sapiens*] |
| HG1018387 | NP_001314: NM_001323_1-20 | cystatin M precursor [*Homo sapiens*] |
| HG1018388 | NP_001314: NM_001323_1-28 | cystatin M precursor [*Homo sapiens*] |
| HG1018389 | NP_001314: NM_001323_1-21 | cystatin M precursor [*Homo sapiens*] |
| HG1018390 | NP_001314: NM_001323_1-23 | cystatin M precursor [*Homo sapiens*] |
| HG1018392 | NP_001822: NM_001831_1-22 | clusterin isoform 1 [*Homo sapiens*] |
| HG1018393 | NP_001822: NM_001831_1-18 | clusterin isoform 1 [*Homo sapiens*] |
| HG1018394 | NP_001822: NM_001831_1-14 | clusterin isoform 1 [*Homo sapiens*] |
| HG1018396 | NP_002206: NM_002215_1-24 | inter-alpha (globulin) inhibitor H1 [*Homo sapiens*] |
| HG1018397 | NP_002206: NM_002215_1-29 | inter-alpha (globulin) inhibitor H1 [*Homo sapiens*] |
| HG1018398 | NP_002206: NM_002215_1-30 | inter-alpha (globulin) inhibitor H1 [*Homo sapiens*] |
| HG1018399 | NP_002206: NM_002215_1-23 | inter-alpha (globulin) inhibitor H1 [*Homo sapiens*] |
| HG1018400 | NP_002206: NM_002215_1-31 | inter-alpha (globulin) inhibitor H1 [*Homo sapiens*] |
| HG1018402 | NP_002300: NM_002309_1-22 | leukemia inhibitory factor (cholinergic differentiation factor) |
| HG1018403 | NP_002300: NM_002309_1-23 | leukemia inhibitory factor (cholinergic differentiation factor) |
| HG1018405 | NP_002336: NM_002345_1-18 | lumican [*Homo sapiens*] |
| HG1018406 | NP_002336: NM_002345_1-15 | lumican [*Homo sapiens*] |
| HG1018407 | NP_002336: NM_002345_1-17 | lumican [*Homo sapiens*] |
| HG1018408 | NP_002336: NM_002345_1-14 | lumican [*Homo sapiens*] |
| HG1018410 | NP_002402: NM_002411_1-18 | secretoglobin, family 2A, member 2 [*Homo sapiens*] |
| HG1018412 | NP_002505: NM_002514_1-30 | nov precursor [*Homo sapiens*] |
| HG1018413 | NP_002505: NM_002514_1-32 | nov precursor [*Homo sapiens*] |
| HG1018414 | NP_002505: NM_002514_1-28 | nov precursor [*Homo sapiens*] |
| HG1018415 | NP_002505: NM_002514_1-27 | nov precursor [*Homo sapiens*] |
| HG1018416 | NP_002505: NM_002514_1-31 | nov precursor [*Homo sapiens*] |
| HG1018418 | NP_002892: NM_002901_1-26 | reticulocalbin 1 precursor [*Homo sapiens*] |
| HG1018419 | NP_002892: NM_002901_1-22 | reticulocalbin 1 precursor [*Homo sapiens*] |
| HG1018420 | NP_002892: NM_002901_1-29 | reticulocalbin 1 precursor [*Homo sapiens*] |
| HG1018421 | NP_002892: NM_002901_1-24 | reticulocalbin 1 precursor [*Homo sapiens*] |
| HG1018422 | NP_002892: NM_002901_1-23 | reticulocalbin 1 precursor [*Homo sapiens*] |
| HG1018424 | NP_002893: NM_002902_1-25 | reticulocalbin 2, EF-hand calcium binding domain [*Homo sapiens*] |
| HG1018425 | NP_002893: NM_002902_1-19 | reticulocalbin 2, EF-hand calcium binding domain [*Homo sapiens*] |
| HG1018426 | NP_002893: NM_002902_1-22 | reticulocalbin 2, EF-hand calcium binding domain [*Homo sapiens*] |
| HG1018427 | NP_002893: NM_002902_1-18 | reticulocalbin 2, EF-hand calcium binding domain [*Homo sapiens*] |
| HG1018428 | NP_002893: NM_002902_1-20 | reticulocalbin 2, EF-hand calcium binding domain [*Homo sapiens*] |
| HG1018429 | NP_002893: NM_002902_1-21 | reticulocalbin 2, EF-hand calcium binding domain [*Homo sapiens*] |
| HG1018430 | NP_002893: NM_002902_1-23 | reticulocalbin 2, EF-hand calcium binding domain [*Homo sapiens*] |
| HG1018432 | NP_005133: NM_005142_1-19 | gastric intrinsic factor (vitamin B synthesis) [*Homo sapiens*] |
| HG1018433 | NP_005133: NM_005142_1-18 | gastric intrinsic factor (vitamin B synthesis) [*Homo sapiens*] |
| HG1018434 | NP_005133: NM_005142_1-20 | gastric intrinsic factor (vitamin B synthesis) [*Homo sapiens*] |
| HG1018435 | NP_005133: NM_005142_1-24 | gastric intrinsic factor (vitamin B synthesis) [*Homo sapiens*] |
| HG1018436 | NP_005133: NM_005142_1-16 | gastric intrinsic factor (vitamin B synthesis) [*Homo sapiens*] |
| HG1018437 | NP_005133: NM_005142_1-17 | gastric intrinsic factor (vitamin B synthesis) [*Homo sapiens*] |
| HG1018438 | NP_005133: NM_005142_1-14 | gastric intrinsic factor (vitamin B synthesis) [*Homo sapiens*] |
| HG1018440 | NP_005445: NM_005454_1-17 | cerberus 1 [*Homo sapiens*] |
| HG1018442 | NP_005555: NM_005564_1-18 | lipocalin 2 (oncogene 24p3) [*Homo sapiens*] |
| HG1018443 | NP_005555: NM_005564_1-20 | lipocalin 2 (oncogene 24p3) [*Homo sapiens*] |
| HG1018444 | NP_005555: NM_005564_1-15 | lipocalin 2 (oncogene 24p3) [*Homo sapiens*] |
| HG1018446 | NP_005690: NM_005699_1-29 | interleukin 18 binding protein isoform C precursor [*Homo sapiens*] |
| HG1018447 | NP_005690: NM_005699_1-24 | interleukin 18 binding protein isoform C precursor [*Homo sapiens*] |
| HG1018448 | NP_005690: NM_005699_1-28 | interleukin 18 binding protein isoform C precursor [*Homo sapiens*] |
| HG1018450 | NP_006560: NM_006569_1-19 | cell growth regulator with EF hand domain 1 [*Homo sapiens*] |

TABLE 4-continued

Secretory Leader Sequence Annotations

| FP ID | Source ID | Annotation |
|---|---|---|
| HG1018451 | NP_006560: NM_006569_1-18 | cell growth regulator with EF hand domain 1 [*Homo sapiens*] |
| HG1018452 | NP_006560: NM_006569_1-21 | cell growth regulator with EF hand domain 1 [*Homo sapiens*] |
| HG1018454 | NP_006856: NM_006865_1-15 | leukocyte immunoglobulin-like receptor, subfamily A (without TM |
| HG1018456 | NP_036577: NM_012445_1-26 | spondin 2, extracellular matrix protein [*Homo sapiens*] |
| HG1018457 | NP_036577: NM_012445_1-25 | spondin 2, extracellular matrix protein [*Homo sapiens*] |
| HG1018458 | NP_036577: NM_012445_1-24 | spondin 2, extracellular matrix protein [*Homo sapiens*] |
| HG1018459 | NP_036577: NM_012445_1-28 | spondin 2, extracellular matrix protein [*Homo sapiens*] |
| HG1018461 | NP_055070: NM_014255_1-20 | transmembrane protein 4 [*Homo sapiens*] |
| HG1018462 | NP_055070: NM_014255_1-18 | transmembrane protein 4 [*Homo sapiens*] |
| HG1018463 | NP_055070: NM_014255_1-16 | transmembrane protein 4 [*Homo sapiens*] |
| HG1018465 | NP_055582: NM_014767_1-24 | sparc/osteonectin, cwcv and kazal-like domains proteoglycan |
| HG1018466 | NP_055582: NM_014767_1-19 | sparc/osteonectin, cwcv and kazal-like domains proteoglycan |
| HG1018467 | NP_055582: NM_014767_1-22 | sparc/osteonectin, cwcv and kazal-like domains proteoglycan |
| HG1018468 | NP_055582: NM_014767_1-20 | sparc/osteonectin, cwcv and kazal-like domains proteoglycan |
| HG1018469 | NP_055582: NM_014767_1-26 | sparc/osteonectin, cwcv and kazal-like domains proteoglycan |
| HG1018470 | NP_055582: NM_014767_1-21 | sparc/osteonectin, cwcv and kazal-like domains proteoglycan |
| HG1018472 | NP_055697: NM_014882_1-18 | Rho GTPase activating protein 25 isoform b [*Homo sapiens*] |
| HG1018474 | NP_056965: NM_015881_1-18 | dickkopf homolog 3 [*Homo sapiens*] |
| HG1018475 | NP_056965: NM_015881_1-19 | dickkopf homolog 3 [*Homo sapiens*] |
| HG1018476 | NP_056965: NM_015881_1-22 | dickkopf homolog 3 [*Homo sapiens*] |
| HG1018477 | NP_056965: NM_015881_1-16 | dickkopf homolog 3 [*Homo sapiens*] |
| HG1018478 | NP_056965: NM_015881_1-21 | dickkopf homolog 3 [*Homo sapiens*] |
| HG1018480 | NP_057603: NM_016519_1-26 | ameloblastin precursor [*Homo sapiens*] |
| HG1018481 | NP_057603: NM_016519_1-28 | ameloblastin precursor [*Homo sapiens*] |
| HG1018483 | NP_149439: NM_033183_1-18 | chorionic gonadotropin, beta polypeptide 8 recursor [*Homo sapiens*] |
| HG1018484 | NP_149439: NM_033183_1-20 | chorionic gonadotropin, beta polypeptide 8 recursor [*Homo sapiens*] |
| HG1018485 | NP_149439: NM_033183_1-16 | chorionic gonadotropin, beta polypeptide 8 recursor [*Homo sapiens*] |
| HG1018487 | NP_644808: NM_139279_1-18 | multiple coagulation factor deficiency 2 [*Homo sapiens*] |
| HG1018488 | NP_644808: NM_139279_1-20 | multiple coagulation factor deficiency 2 [*Homo sapiens*] |
| HG1018489 | NP_644808: NM_139279_1-26 | multiple coagulation factor deficiency 2 [*Homo sapiens*] |
| HG1018490 | NP_644808: NM_139279_1-23 | multiple coagulation factor deficiency 2 [*Homo sapiens*] |
| HG1018492 | NP_660295: NM_145252_1-13 | similar to common salivary protein 1 [*Homo sapiens*] |
| HG1018493 | NP_660295: NM_145252_1-16 | similar to common salivary protein 1 [*Homo sapiens*] |
| HG1018494 | NP_660295: NM_145252_1-14 | similar to common salivary protein 1 [*Homo sapiens*] |
| HG1018495 | NP_660295: NM_145252_1-17 | similar to common salivary protein 1 [*Homo sapiens*] |
| HG1018497 | NP_689534: NM_152321_1-25 | hypothetical protein FLJ32115 [*Homo sapiens*] |
| HG1018498 | NP_689534: NM_152321_1-21 | hypothetical protein FLJ32115 [*Homo sapiens*] |
| HG1018500 | NP_689848: NM_152635_1-18 | oncoprotein-induced transcript 3 [*Homo sapiens*] |
| HG1018501 | NP_689848: NM_152635_1-16 | oncoprotein-induced transcript 3 [*Homo sapiens*] |
| HG1018502 | NP_689848: NM_152635_1-15 | oncoprotein-induced transcript 3 [*Homo sapiens*] |
| HG1018504 | NP_689968: NM_152755_1-21 | hypothetical protein MGC40499 [*Homo sapiens*] |
| HG1018506 | NP_766630: NM_173042_1-29 | interleukin 18 binding protein isoform A precursor [*Homo sapiens*] |
| HG1018507 | NP_766630: NM_173042_1-24 | interleukin 18 binding protein isoform A precursor [*Homo sapiens*] |
| HG1018508 | NP_766630: NM_173042_1-28 | interleukin 18 binding protein isoform A precursor [*Homo sapiens*] |
| HG1018510 | NP_776214: NM_173842_1-23 | interleukin 1 receptor antagonist isoform 1 precursor [*Homo sapiens*] |
| HG1018511 | NP_776214: NM_173842_1-25 | interleukin 1 receptor antagonist isoform 1 precursor [*Homo sapiens*] |
| HG1018513 | NP_783165: NM_175575_1-32 | WFIKKN2 protein [*Homo sapiens*] |
| HG1018514 | NP_783165: NM_175575_1-34 | WFIKKN2 protein [*Homo sapiens*] |
| HG1018515 | NP_783165: NM_175575_1-29 | WFIKKN2 protein [*Homo sapiens*] |
| HG1018516 | NP_783165: NM_175575_1-30 | WFIKKN2 protein [*Homo sapiens*] |
| HG1018517 | NP_783165: NM_175575_1-27 | WFIKKN2 protein [*Homo sapiens*] |
| HG1018857 | 27482680: 27482679_1-26 | similar to hypothetical protein 9330140G23 [*Homo sapiens*] |
| HG1018858 | 27482680: 27482679_1-24 | similar to hypothetical protein 9330140G23 [*Homo sapiens*] |

TABLE 5

MGD-CSF Construct Annotations

| Clone ID | Annotation | Vector Description | Tag |
|---|---|---|---|
| CLN00542945 | hypothetical protein MGD-CSF [*Homo sapiens*] | pTT5-Gateway | no tag |
| CLN00732663 | hypothetical protein MGD-CSF [*Homo sapiens*] | pTT5-Gateway | C-Tagged (V5H8) |

TABLE 5-continued

MGD-CSF Construct Annotations

| Clone ID | Annotation | Vector Description | Tag |
|---|---|---|---|
| CLN00839395 | hypothetical protein MGD-CSF [Homo sapiens] | pTT2-Gateway | C-Tagged (V5H8) |
| CLN00840351 | hypothetical protein MGD-CSF [Homo sapiens] | pTT2-Gateway | C-Tagged (V5H8) |
| CLN00843208 | hypothetical protein MGD-CSF [Homo sapiens] | ptt2-I | no tag |
| CLN00758593 | hypothetical protein MGD-CSF [Homo sapiens] | pIB | C-Tagged (V5H8) |
| CLN00848149 | SP_MGD-CSF(21 to 241aa) | pTT5-G | no tag |
| *Cleavable C-Tagged and N-Tagged Constructs* | | | |
| CLN00816424 | SP_MGD-CSF(21 to 241aa)_TEV_V5_StrecTagII_H8 | pTT5-G | C-Tagged (TEV_V5_StrecTagII_H8) |
| CLN00816425 | SP_TEV_V5_StrecTagII_H8_MGD-CSF(21 to 241aa) | pTT5-H | N-Tagged (SP_TEV_V5_StrecTagII_H8) |
| CLN00821867 | MGD-CSF(1-241)_TEV_V5_StrecTagII_H8 | pTT5-I | C-Tagged (TEV_V5_StrecTagII_H8) |
| *Mouse Orthologues* | | | |
| CLN00840253 | hypothetical protein MGC34647 [mouse 660 bp] | pTT5-I | C-Tagged (TEV_V5_StrecTagII_H8) |
| CLN00840257 | hypothetical protein MGC34647 [mouse 660 bp] | pTT5-I | no tag |
| CLN00842712 | hypothetical protein MGC34647 [mouse 708 bp] | pTT5-I | C-Tagged (TEV_V5_StrecTagII_H8) |
| CLN00847948 | hypothetical protein MGC34647 [mouse 708 bp] | pTT5-I | no tag |
| *Deletion mutants* | | | |
| CLN00848160 | SP_MGD-CSF(26 to 241aa) | pTT5-G | no tag |
| CLN00848173 | MGD-CSF(31 to 241aa) | pTT5-G | no tag |
| CLN00848185 | SP_MGD-CSF(21 to 213aa) | pTT5-G | no tag |
| CLN00848197 | SP_MGD-CSF(21 to 231aa) | pTT5-G | no tag |
| CLN00848209 | SP_MGD-CSF(21 to 236aa) | pTT5-G | no tag |
| CLN00848220 | SP_MGD-CSF(26 to 231aa) | pTT5-G | no tag |

TABLE 6

MGD-CSF Promotes Myelocytic Cell Proliferation In Vitro

| Clone ID | Description | Potency | Expression |
|---|---|---|---|
| CLN00542945 | MGD-CSF (1-241 aa) | +++ | +++ |
| CLN00848149 | CSP-025 (20 to 241aa) | ++ | ++ |
| CLN00848160 | CSP-025 (25 to 241aa) | + | + |
| CLN00848173 | CSP-025 (30 to 241aa) | ++ | ++ |
| CLN00848185 | CSP-025 (20 to 213 aa) | +++ | ++ |
| CLN00848197 | CSP-025 (20 to 231aa) | ++ | +++ |
| CLN00848209 | CSP-025 (20 to 236 aa) | + | + |
| CLN00848220 | CSP-025 (25 to 231aa) | ++ | ++ |
| | Vector Control | − | |

TABLE 7

MGD-CSF Promotes Myelocytic Proliferation In Vivo

| Animal ID | Description | Monocytes/ul |
|---|---|---|
| A: Human MGD-CSF Promotes Myelocytic Cell Proliferation in Mice In Vivo | | |
| 1 | Vector control | 94.0 |
| 2 | Vector control | 84.0 |
| 3 | Vector control | 52.0 |
| 4 | human MGD-CSF | 216.0 |
| 5 | human MGD-CSF | 0.0 |
| 6 | human MGD-CSF | 268.0 |
| B: Mouse MGD-CSF Promotes Myelocytic Cell Proliferation in Mice In Vivo | | |
| 1 | Vector control | 0.0 |
| 2 | Vector control | 0.0 |
| 3 | Vector control | 0.0 |
| 4 | Vector control | 0.0 |
| 5 | Vector control | 0.0 |
| 6 | Vector control | 0.0 |
| 7 | mouse MGD-CSF | 50.0 |
| 8 | mouse MGD-CSF | 0.0 |
| 9 | mouse MGD-CSF | 61.0 |
| 10 | mouse MGD-CSF | 78.0 |
| 11 | mouse MGD-CSF | 0.0 |
| 12 | mouse MGD-CSF | 77.0 |

TABLE 8

MGD-CSF Gene Expression

| Disease | Pathology | MGC34647 Positive | Total Gene Logic | % Total |
|---|---|---|---|---|
| Myelodysplastic syndrome | Refractory anemia with excess blasts | 4 | 4 | 100% |
| Myelodysplastic syndrome | Refractory anemia with ringed sideroblasts | 1 | 1 | 100% |
| Myelodysplastic syndrome | Refractory anemia with excess blasts in transformation | 2 | 3 | 67% |
| Myelodysplastic syndrome | Myelodysplastic syndrome (morphologic abnormality) | 1 | 2 | 50% |
| Acute B-cell lymphoblastic leukemia | Precursor B-cell lymphoblastic leukemia | 3 | 6 | 50% |
| Acute myeloid leukemia | Acute myeloid leukemia, with maturation | 1 | 4 | 25% |
| Acute myeloid leukemia | Acute myeloid leukemia, without maturation | 2 | 11 | 18% |
| Acute myeloid leukemia | Acute myeloid leukemia, minimal differentiation | 1 | 7 | 14% |
| Chronic myeloid leukemia | Chronic myeloid leukemia | 2 | 45 | 4% |
| Chronic lymphocytic leukemia | Chronic lymphocytic leukemia | 1 | 40 | 3% |
| Acute promyelocytic leukemia | Acute promyelocytic leukemia | 1 | 36 (3 from bone marrow) | 3% (33% from bone marrow) |

The invention claimed is:

1. A method of increasing the number of human monocytes comprising contacting human monocytes with a recombinant polypeptide comprising the amino acid sequence of SEQ ID NO:9, wherein the polypeptide increases the number of monocytes in a mouse model of monocyte proliferation.

2. The method of claim 1, wherein the polypeptide further comprises a fusion partner.

3. The method of claim 2, wherein the fusion partner is a succinyl group.

4. The method of claim 2, wherein the fusion partner is selected from a polymer and a second polypeptide.

5. The method of claim 4, wherein the polymer is polyethylene glycol.

6. The method of claim 4, wherein the second polypeptide is selected from a serum albumin, a fetuin A, a fetuin B, a leucine zipper domain, a tetranectin trimerization domain, a mannose binding protein, and an Fc.

7. The method of claim 6, wherein the fusion partner is an Fc.

8. The method of claim 1, wherein the polypeptide is produced in host cells that comprise a polynucleotide encoding the polypeptide.

9. The method of claim 8, wherein the host cells are a 293 cell line.

10. The method of claim 8, wherein the host cells are a 293-6E cell line.

11. The method of claim 8, wherein the host cells are a Chinese hamster ovary (CHO) cell line.

12. The method of claim 8, wherein the polynucleotide comprises the nucleic acid sequence of SEQ ID NO:3.

* * * * *